US011377638B2

(12) United States Patent
Baeuerle et al.

(10) Patent No.: US 11,377,638 B2
(45) Date of Patent: Jul. 5, 2022

(54) COMPOSITIONS AND METHODS FOR TCR REPROGRAMMING USING FUSION PROTEINS

(71) Applicant: TCR2 Therapeutics Inc., Cambridge, MA (US)

(72) Inventors: Patrick Baeuerle, Gauting (DE); Gregory Sieczkiewicz, Cambridge, MA (US); Robert Hofmeister, Scituate, MA (US)

(73) Assignee: TCR2 Therapeutics Inc., Cambridge, MA (US)

( * ) Notice: Subject to any disclaimer, the term of this patent is extended or adjusted under 35 U.S.C. 154(b) by 615 days.

(21) Appl. No.: 16/222,846

(22) Filed: Dec. 17, 2018

(65) Prior Publication Data

US 2019/0177694 A1 Jun. 13, 2019

Related U.S. Application Data

(60) Division of application No. 15/888,897, filed on Feb. 5, 2018, now Pat. No. 10,208,285, which is a continuation of application No. PCT/US2017/055628, filed on Oct. 6, 2017.

(60) Provisional application No. 62/510,108, filed on May 23, 2017, provisional application No. 62/405,551, filed on Oct. 7, 2016.

(51) Int. Cl.

| | |
|---|---|
| ***C07K 16/28*** | (2006.01) |
| ***C12N 5/0783*** | (2010.01) |
| ***A61P 35/00*** | (2006.01) |
| ***C07K 14/47*** | (2006.01) |
| ***C07K 16/18*** | (2006.01) |
| *A61K 39/00* | (2006.01) |

(52) U.S. Cl.

CPC ............ *C12N 5/0638* (2013.01); *A61P 35/00* (2018.01); *C07K 14/4748* (2013.01); *C07K 16/18* (2013.01); *C07K 16/28* (2013.01); *C12N 5/0646* (2013.01); *A61K 2039/505* (2013.01); *A61K 2039/572* (2013.01); *A61K 2039/585* (2013.01); *A61K 2039/6006* (2013.01); *C07K 2317/70* (2013.01); *C07K 2319/02* (2013.01); *C07K 2319/03* (2013.01); *C07K 2319/30* (2013.01); *C07K 2319/33* (2013.01); *C07K 2319/70* (2013.01)

(58) Field of Classification Search

None

See application file for complete search history.

(56) References Cited

U.S. PATENT DOCUMENTS

| | | |
|---|---|---|
| 4,816,567 A | 3/1989 | Cabilly et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,766,886 A | 6/1998 | Studnicka et al. |
| 5,858,358 A | 1/1999 | June et al. |
| 5,883,223 A | 3/1999 | Gray |
| 6,120,766 A | 9/2000 | Hale et al. |
| 6,326,193 B1 | 12/2001 | Liu et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,534,055 B1 | 3/2003 | June et al. |
| 6,548,640 B1 | 4/2003 | Winter |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,081,518 B1 | 7/2006 | Pastan et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,572,631 B2 | 8/2009 | Berenson et al. |
| 7,695,936 B2 | 4/2010 | Carter et al. |
| 7,741,465 B1 | 6/2010 | Eshhar et al. |
| 8,206,710 B2 | 6/2012 | Ebel et al. |

(Continued)

FOREIGN PATENT DOCUMENTS

| | | |
|---|---|---|
| EP | 0239400 A2 | 9/1987 |
| EP | 0519596 A1 | 12/1992 |

(Continued)

OTHER PUBLICATIONS

Lamberts et al. (Oncotarget. Sep. 29, 2015;6(29):28164-72). (Year: 2015).*

"Haas, et al., "Phase I study of lentiviral-transduced chimeric antigen receptor modified T cells recognizing mesothelin in advanced solid cancers" (2019) Molecular Therapy pp. 1-40".

"Lantis, et al., "Redirected Antitumor Activity of Primary Human Lymphocytes Transduced With a Fully Human Anti-mesothelin Chimeric Receptor" Molecular Therapy (2012) vol. 20, No. 3, pp. 633-643".

(Continued)

*Primary Examiner* — Zachary S Skelding

(74) *Attorney, Agent, or Firm* — Wilson Sonsini Goodrich & Rosati

(57) ABSTRACT

Provided herein are T-cell receptor (TCR) fusion proteins (TFPs), T-cells engineered to express one or more TFPs, and methods of use thereof for the treatment of diseases, including cancer.

19 Claims, 46 Drawing Sheets

Specification includes a Sequence Listing.

(56) References Cited

U.S. PATENT DOCUMENTS 8,389,282 B2 3/2013 Sadelain et al.
8,697,359 B1 4/2014 Zhang
8,911,732 B2 12/2014 Dennis et al.
9,023,351 B2 5/2015 Kahnert et al.
9,062,127 B2 6/2015 Voss et al.
9,102,736 B2 8/2015 Hofmeister et al.
9,115,197 B2 8/2015 Ebel et al.
9,181,527 B2 11/2015 Sentman
9,217,040 B2 12/2015 Kipps et al.
9,220,728 B2 12/2015 Sadelain et al.
9,272,002 B2 3/2016 Powell, Jr. et al.
9,316,646 B2 4/2016 Rader et al.
9,365,641 B2 6/2016 June et al.
9,393,257 B2 7/2016 Osborn et al.
9,416,190 B2 8/2016 Ho et al.
9,422,351 B2 8/2016 Scholler et al.
9,447,194 B2 9/2016 Jensen et al.
9,464,140 B2 10/2016 June et al.
9,758,586 B2 9/2017 Rader et al.
10,093,900 B2 10/2018 Jantz et al.
10,208,285 B2 2/2019 Baeuerle et al.
2002/0110855 A1 8/2002 Sheppard et al.
2004/0266390 A1 12/2004 Faucher et al.
2005/0042664 A1 2/2005 Wu et al.
2005/0048617 A1 3/2005 Wu et al.
2005/0100543 A1 5/2005 Hansen et al.
2005/0175606 A1 8/2005 Huang et al.
2006/0062780 A1 3/2006 Zocher et al.
2006/0121005 A1 6/2006 Berenson et al.
2007/0014794 A1 1/2007 Carter et al.
2008/0294058 A1 11/2008 Shklarski
2009/0047211 A1 2/2009 Pastan et al.
2009/0322513 A1 12/2009 Hwang et al.
2010/0003249 A1 1/2010 Silence et al.
2010/0122358 A1 5/2010 Bruggemann et al.
2011/0189141 A1 8/2011 Kieback et al.
2013/0066283 A1 3/2013 Alster et al.
2013/0251642 A1 9/2013 Rader et al.
2013/0266551 A1 10/2013 Campana et al.
2013/0273073 A1 10/2013 Kipps et al.
2013/0280220 A1 10/2013 Ahmed et al.
2013/0295011 A1 11/2013 Guise et al.
2013/0315884 A1 11/2013 Galetto et al.
2013/0323214 A1 12/2013 Gottschalk et al.
2013/0323247 A1 12/2013 Zugmaier et al.
2014/0004132 A1 1/2014 Brenner et al.
2014/0050708 A1 2/2014 Powell et al.
2014/0099340 A1 4/2014 June et al.
2014/0227237 A1 8/2014 June et al.
2014/0242075 A1 8/2014 Parren et al.
2014/0271635 A1 9/2014 Brogdon et al.
2014/0286973 A1 9/2014 Powell, Jr. et al.
2014/0301993 A1 10/2014 Powell, Jr. et al.
2014/0308259 A1 10/2014 Scholler et al.
2014/0322212 A1 10/2014 Brogdon et al.
2014/0322216 A1 10/2014 Kaplan
2014/0370045 A1 12/2014 June et al.
2015/0031624 A1 1/2015 Feldman et al.
2015/0051266 A1 2/2015 Kochenderfer
2015/0093822 A1 4/2015 June et al.
2015/0190428 A1 7/2015 June et al.
2015/0203817 A1 7/2015 Galetto et al.
2015/0238631 A1 8/2015 Kim et al.
2015/0252110 A1 9/2015 Hansen et al.
2015/0274836 A1 10/2015 Ho et al.
2015/0284475 A1 10/2015 Zhou et al.
2015/0297640 A1 10/2015 Cooper et al.
2015/0306141 A1 10/2015 Jensen et al.
2015/0307564 A1 10/2015 Young et al.
2015/0322169 A1 11/2015 June et al.
2015/0329640 A1 11/2015 Finer
2015/0342993 A1 12/2015 Kloss et al.
2015/0344573 A1 12/2015 Chang et al.
2015/0344844 A1 12/2015 Better et al.
2015/0368360 A1 12/2015 Liang et al.
2015/0376287 A1 12/2015 Vu et al.
2015/0376296 A1 12/2015 Fedorov et al.
2016/0008398 A1 1/2016 Sadelain et al.
2016/0009813 A1 1/2016 Themeli et al.
2016/0015749 A1 1/2016 Gottschalk et al.
2016/0030479 A1 2/2016 Abbot et al.
2016/0039903 A1 2/2016 Ring et al.
2016/0040127 A1 2/2016 Leventhal et al.
2016/0045551 A1 2/2016 Brentjens et al.
2016/0046678 A1 2/2016 Roschke et al.
2016/0046724 A1 2/2016 Brogdon et al.
2016/0052990 A1 2/2016 Ring et al.
2016/0120906 A1 5/2016 Galetto et al.
2016/0120907 A1 5/2016 Sentman
2016/0122782 A1 5/2016 Crisman et al.
2016/0144026 A1 5/2016 Lutteropp et al.
2016/0145354 A1 5/2016 Bacac et al.
2016/0158359 A1 6/2016 Gilbert
2016/0168262 A1 6/2016 Spriggs et al.
2016/0176973 A1 6/2016 Kufer et al.
2016/0184362 A1 6/2016 Duchateau et al.
2016/0185861 A1 6/2016 Bedoya et al.
2016/0185862 A1 6/2016 Wu et al.
2016/0186165 A1 6/2016 Dose et al.
2016/0194375 A1 7/2016 Kitchen et al.
2016/0206656 A1 7/2016 Gilbert
2016/0207989 A1 7/2016 Short
2016/0208018 A1 7/2016 Chen et al.
2016/0215051 A1 7/2016 Sharma et al.
2016/0228547 A1 8/2016 Wagner et al.
2016/0235787 A1 8/2016 June et al.
2016/0237139 A1 8/2016 Pulé et al.
2016/0237407 A1 8/2016 Wagner et al.
2016/0256488 A1 9/2016 Wu
2016/0257762 A1 9/2016 Kwon et al.
2016/0264665 A1 9/2016 Lim et al.
2016/0272999 A1 9/2016 Duchateau et al.
2016/0289343 A1 10/2016 Wu
2016/0296633 A1 10/2016 Goldenberg et al.
2016/0340406 A1 11/2016 Zhao et al.
2017/0029502 A1 2/2017 Raum et al.
2017/0081405 A1 3/2017 Adusumilli et al.
2017/0166622 A1 6/2017 Baeuerle et al.
2017/0355766 A1 12/2017 Zack et al.
2018/0134789 A1 5/2018 Baeuerle et al.
2018/0170992 A1 6/2018 Balyasnikova et al.
2018/0230419 A1 8/2018 Dines et al.
2018/0244747 A1 8/2018 Baeuerle et al.
2018/0251514 A1 9/2018 Baeuerle et al.
2019/0256571 A1 8/2019 Baeuerle et al.
2019/0276540 A1 9/2019 Baeuerle et al.
2020/0207828 A1 7/2020 Baeuerle et al.
2020/0289646 A1 9/2020 Wesche et al.
2020/0362011 A1 11/2020 Baeuerle et al.
2020/0362306 A1 11/2020 Baeuerle et al.

FOREIGN PATENT DOCUMENTS

EP 0592106 A1 4/1994
EP 0638119 A1 2/1995
EP 1075517 B1 7/2006
EP 2258719 A1 12/2010
EP 2258720 A1 12/2010
EP 2894164 A1 7/2015
EP 2342227 B1 10/2015
EP 2632954 B1 11/2015
EP 2953974 A1 12/2015
EP 2970472 A1 1/2016
EP 2982692 A1 2/2016
EP 2982696 A2 2/2016
EP 2361936 B1 4/2016
EP 3006459 A1 4/2016
EP 3018145 A1 5/2016
EP 3019622 A2 5/2016
EP 3023437 A1 5/2016
EP 2686417 B1 6/2016
EP 2982694 B1 6/2016
EP 3025719 A1 6/2016
EP 3029067 A1 6/2016

(56) References Cited

FOREIGN PATENT DOCUMENTS

EP 3029068 A1 6/2016
EP 3057991 A1 8/2016
EP 3057994 A1 8/2016
EP 2370467 B1 9/2016
EP 3087101 A1 11/2016
FR 901228 A 7/1945
JP H07505282 A 6/1995
JP 2012508164 A 4/2012
KR 20090092900 A 9/2009
WO WO-9109967 A1 7/1991
WO WO-9317105 A1 9/1993
WO WO-0129058 A1 4/2001
WO WO-0196584 A2 12/2001
WO WO-2006020258 A2 2/2006
WO WO-2007024715 A2 3/2007
WO WO-2010052014 A1 5/2010
WO WO-2010104949 A2 9/2010
WO WO-2012076066 A1 6/2012
WO WO-2012138475 A1 10/2012
WO WO-2013040557 A2 3/2013
WO WO-2013063419 A2 5/2013
WO WO-2013072415 A1 5/2013
WO WO-2013126712 A1 8/2013
WO WO-2013154760 A1 10/2013
WO WO-2013176916 A1 11/2013
WO WO-2014052064 A1 4/2014
WO WO-2014153270 A1 9/2014
WO WO-2014184143 A1 11/2014
WO WO-2014190273 A1 11/2014
WO WO-2015090230 A1 6/2015
WO WO-2015092024 A2 6/2015
WO WO-2015095895 A1 6/2015
WO WO-2015107075 A1 7/2015
WO WO-2015112800 A1 7/2015
WO WO-2015112830 A1 7/2015
WO WO-2015121454 A1 8/2015
WO WO-2015123642 A1 8/2015
WO WO-2015124715 A1 8/2015
WO WO-2015142661 A1 9/2015
WO WO-2015142675 A2 9/2015
WO WO-2015158671 A1 10/2015
WO WO-2015164745 A1 10/2015
WO WO-2015168613 A2 11/2015
WO WO-2015177349 A1 11/2015
WO WO-2015179801 A1 11/2015
WO WO-2015188141 A2 12/2015
WO WO-2016011210 A2 1/2016
WO WO-2016014789 A2 1/2016
WO WO-2016016344 A1 2/2016
WO WO-2016019969 A1 2/2016
WO WO-2016025454 A2 2/2016
WO WO-2016030691 A1 3/2016
WO WO-2016036678 A1 3/2016
WO WO-2016040441 A1 3/2016
WO WO-2016044853 A1 3/2016
WO WO-2016054520 A2 4/2016
WO WO-2016055551 A1 4/2016
WO WO-2016070061 A1 5/2016
WO WO-2016073381 A1 5/2016
WO WO-2016079081 A1 5/2016
WO WO-2016087245 A1 6/2016
WO WO-2016090034 A2 6/2016
WO WO-2016090312 A1 6/2016
WO WO-2016090320 A1 6/2016
WO WO-2016090327 A2 6/2016
WO WO-2016097231 A2 6/2016
WO WO-2016115274 A1 7/2016
WO WO-2016115482 A1 7/2016
WO WO-2016116601 A1 7/2016
WO WO-2016123675 A1 8/2016
WO WO-2016126608 A1 8/2016
WO WO-2016127043 A1 8/2016
WO WO-2016127257 A1 8/2016
WO WO-2016132366 A1 8/2016
WO WO-2016151315 A1 9/2016
WO WO-2016161415 A2 10/2016
WO WO-2016187349 A1 11/2016
WO WO-2016203048 A1 12/2016
WO WO-2017112741 A1 6/2017
WO WO-2017173256 A1 10/2017
WO WO-2018017863 A1 1/2018
WO WO-2018023025 A1 2/2018
WO WO-2018026953 A1 2/2018
WO WO-2018067993 A1 4/2018
WO WO-2018098365 A2 5/2018
WO WO-2018119298 A1 6/2018
WO WO-2018165619 A1 9/2018
WO WO-2018200583 A1 11/2018
WO WO-2018209298 A1 11/2018
WO WO-2018209304 A1 11/2018
WO WO-2018232020 A1 12/2018
WO WO-2019173693 A1 9/2019
WO WO-2019222275 A2 11/2019
WO WO-2020023888 A2 1/2020
WO WO-2020047501 A1 3/2020
WO WO-2020061526 A1 3/2020

OTHER PUBLICATIONS

"O'Hara, et al., "Mesothelin as a target for chimeric antigen receptor-modified T cells as anticancer therapy" Immunotherapy (2016) 8(4), pp. 449-460".

Ordonez. Application of mesothelin immunostaining in tumor diagnosis. Am J Surg Pathol 27:1418-1428 (2003).

"Pranter, et al., "Anti-Mesothelin Nanobodies for Both Conventional and Nanoparticle-Based Biomedical Applications" Journal of Biomedical Nanotechnology (2015) vol. 11, 1201-1212".

"Zhang, et al., "New High Affinity Monoclonal Antibodies Recognize Non-Overlapping Epitopes on Mesothelin for Monitoring and Treating Mesothelioma" Scientific Reports (2015)".

Abate-Daga et al. CAR models: next-generation CAR modifications for enhanced T-cell function. Mol Ther Oncolytics 3:16014 (2016).

Acuto et al. Tailoring T-cell receptor signals by proximal negative feedback mechanisms. Nat Rev Immunol 8(9):699-712 (2008).

Adusumilli et al. 342: A Phase 1 Clinical Trial of Malignant Pleural Disease Treated with Regionally Delivered Autologous Mesothelin-Targeted CAR T Cells: Safety and Efficacy—A Preliminary Report. Mol Therapy 26(5S1):158-159 (2018).

Adusumilli et al. Regional delivery of mesothelin-targeted CAR T cell therapy generates potent and long-lasting CD4-dependent tumor immunity. Sci Transl Med 6(261):261ra151 (2014) (w/Supplementary Data).

Agata et al. Expression of the PD-1 antigen on the surface of stimulated mouse T and B lymphocytes. Int Immunol 8:765-775 (1996).

Ager et al. Homing to solid cancers: a vascular checkpoint in adoptive cell therapy using CAR T-cells. Biochemical Society transactions. 44(2):377-385 (2016).

Almasbak et al. CAR T Cell Therapy: A Game Changer in Cancer Treatment. Journal of Immunology Research. 2016:1-10 (2016).

Al-Rawi et al. Interleukin-7 (IL-7) and IL-7 receptor (IL-7R) signalling complex in human solid tumours. Hist Histopathol 18:911-923 (2003).

Altschul et al. Basic local alignment search tool. J Mol Biol 215(3):403-410 (1990).

Altschul et al. Gapped BLAST and PSI-BLAST: a new generation of protein database search programs. Nucleic Acids Res 25:3389-3402 (1977).

Angelo et al. Antitumor Activity Associated with Prolonged Persistence of Adoptively Transferred NY-ESO-1c259 T cells in Synovial Sarcoma. Cancer Disov 8(8):944-957 (2018).

Ankri et al. Human T cells engineered to express a programmed death 1/28 costimulatory retargeting molecule display enhanced antitumor activity. J Immunol 191:4121-4129 (2013).

Baca et al. Antibody humanization using monovalent phage display. J Biol Chem 272(16):10678-10684 (1997).

Baeuerle. Abstract No. A058. TRuC-T Cells Targeting CD19 or Mesothelin Demonstrate Superior Antitumor Activity in Preclinical Models Compared to CAR-T Cells (Poster session). Third CRI-CIMT-EATI-AACR International Cancer Immunotherapy Confer-

(56) References Cited

OTHER PUBLICATIONS ence. URL:https://static1.squarespace.com/static/56dee71e555986fb3ae583e2/t/59ad08b1b8a79b086c865d6c/1504512189107/CIMT_Abstracts_170904.pdf (1 pg.) (2017) [retrieved on Jan. 9, 2018].
Baeuerle et al. A Novel T Cell Therapy Engaging the Complete T Cell Receptor. (45 pgs) (2016).
Barretina et al. The Cancer Cell Line Encyclopedia enables predictive modelling of anticancer drug sensitivity. Nature 483:603-607 (2012).
Barrett et al. Eradication of established CD19-positive leukemia using a single injection of chimeric immunoreceptor modified lentiviral-transduced T cells in a xenograft NOG mouse model. Journal of Immunotherapy 32(9):941 (2009).
Barrett et al. Treatment of advanced leukemia in mice with mRNA engineered T cells. Hum Gene Ther 22:1575-1586 (2011).
Batlevi et al. Novel immunotherapies in lymphoid malignancies. Nat Rev Clin Oncol 13(1):25-40 (2016).
Batzer et al. Enhanced evolutionary PCR using oligonucleotides with inosine at the 3'-terminus. Nucleic Acid Res 19:5081 (1991).
Beatty et al. Activity of Mesothelin-specific Chimeric Antigen Receptor T cells Against Pancreatic Carcinoma Metastases in a Phase 1 Trial. Gastroenterology 5085(18)30323-30328 (accepted manuscript).
Beatty et al. Mesothelin-Specific Chimeric Antigen Receptor mRNA-Engineered T Cells Induce Antitumor Activity in Solid Malignancies. Cancer Immunol 3(2):217 (2015).
Beatty et al. Mesothelin-specific Chimeric Antigen Receptor mRNA-Engineered T cells Induce Anti-Tumor Activity in Solid Malignancies. Cancer Immunol Res 2(2):112-120 (2014).
Bezverbnaya et al. Tumor-targeting domains for chimeric antigen receptor T cells. Immunotherapy 9(1):33-46 (2017).
Billadeau et al. ITAMs versus ITIMs: striking a balance during cell regulation. J Clin Invest 109:161-168 (2002).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bonifant et al. Toxicity and management in CAR T-cell Therapy. Mol Ther Oncolytics 3:16011 (2016).
Brentjens et al. Genetically targeted T cells eradicate systemic acute lymphoblastic leukemia xenograft. Clin Cancer Res13:5426-5435 (2007).
Brentjens. Novel cellular therapies for leukemia: CAR-modified T cells targeted to the CD19 antigen. Hematology Am Soc Hematol Educ Program 2012:143-151 (2012).
Bridgeman et al. Building better chimeric antigen receptors for adoptive T cell therapy. Current Gene Therapy 10:77-90 (2010).
Bridgeman et al. Structural and biophysical determinants of aβ T-cell antigen recognition. Immunology 135(1):9-18 (2012).
Brudno et al. Allogeneic T cells that express an anti-CD19 chimeric antigen receptor induce remissions of B-cell malignancies that progress after allogeneic hematopoietic stem-cell transplantation without causing graft-versus-host disease. J Clin Oncol 34(10):1112-1121 (2016).
Buck et al. Mitochondrial Dynamics Controls T Cell Fate through Metabolic Programming. Cell 166:63-76 (2016).
Budde et al. Combining a CD20 chimeric antigen receptor and an inducible caspase 9 suicide switch to improve the efficacy and safety of T cell adoptive immunotherapy for lymphoma. PLoS One 8(12):e82742 (2013).
Caldas et al. Design and synthesis of germline-based hemi-humanized single-chain Fv against the CD18 surface antigen. Protein Eng 13(5):353-360 (2000).
Call et al. The organizing principle in the formation of the T cell receptor-CD3 complex. Cell 111(7):967-979 (2002).
Carpenito et al. Control of large, established tumor xenografts with genetically retargeted human T cells containing CD28 and CD137 domains. PNAS USA 106(9):3360-3365 (2009).
Carpenter et al. B-cell maturation antigen is a promising target for adoptive T-cell therapy of multiple myeloma. Clin Cancer Res 19(8):2048-2060 (2013).
Cartellieri et al. Switching CAR T cells on and off: a novel modular platform for retargeting of T cells to AML blasts. Blood Cancer J 6(8):e458 (2016).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Chan et al. Chimeric antigen receptor-redirected CD45RA-negative T cells have potent antileukemia and pathogen memory response without graft-versus-host activity. Leukemia 29:387-395 (2015).
Chen et al. Novel anti-CD3 chimeric antigen receptor targeting of aggressive T cell malignancies. Oncotarget 7(35):56219-56232 (2016).
Chen et al. Oncology Meets Immunology: The Cancer-Immunity Cycle. Immunity 39(1):1-10 (2013).
Chhabra et al. TCR-Engineered, Customized, Antitumor T Cells for Cancer Immunotherapy: Advantages and Limitations. Scientific World Journal 11:121-129 (2011).
Chmielewski et al. of CARs and TRUCKS: Chimeric antigen receptor (CAR) T cells engineered with an inducible cytokine to modulate the tumor stroma, Immunological Reviews 257(1):83-90 (2014).
Chothia et al. Canonical structures for the hypervariable regions of immunoglobulins. J Mol Biol. 196(4):901-917 (1987).
Chu et al. Targeting+ CD20 Aggressive B-cell Non-Hodgkin Lymphoma by Anti-CD20 CAR mRNA-Modified Expanded Natural Killer Cells in Vitro and in NSG Mice. Cancer Immunol Res 3(4):333-344 (2015).
Cieri et al. Adoptive immunotherapy with genetically modified lymphocytes in allogeneic stem cell transplantation. Immun Rev 257(1):165-180 (2014).
Cieri et al. IL-7 and IL-15 instruct the generation of human memory stem T cells from naive precursors. Blood 121(4):573-584 (2013).
Cooper. Adoptive transfer of T cells genetically modified using the Sleeping Beauty system. Adoptive Transfer Session. 24th iSBTc Annual Meeting (30 pgs) (Oct. 31, 2009).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Cristaudo et al. Clinical significance of serum mesothelin in patients with mesothelioma and lung cancer. Clin. Cancer Res. 13:5076-5081 (2007).
D'Argouges. Combination of rituximab with blinatumomab (MT103/MEDI-538), a T cellengaging CD19-/CD3-bispecific antibody, for highly efficient lysis of human B lymphoma cells. Leukemia Res 33:465-473 (2009).
Davila. Efficacy and toxicity management of 19-28z CAR T cell therapy in B cell acute lymphoblastic leukemia. Sci Transl Med 6(224):224ra25 (2014).
Davila et al. How do CARs work? Early insights from recent clinical studies targeting CD19. Oncoimmunology 1(9):1577-1583 (2012).
Desmyter et al. Crystal structure of a camel single-domain VH antibody fragment in complex with lysozyme. Nat Struct Biol 3(9):803-811 (1996).
Dong et al. B7-H1 pathway and its role in the evasion of tumor immunity. J Mol Med 81:281-287 (2003).
Dopfer et al. The CD3 conformational change in the Gamma Delta T cell receptor is not triggered by antigens but can be enforced to enhance tumor killing. Cell Reports 7(5):1704-1715 (2014).
Dotti et al. Design and Development of Therapies using Chimeric Antigen Receptor-Expressing T cells. Immunol Rev. 257(1):35 pgs (2014).

(56) References Cited

OTHER PUBLICATIONS

Elango et al. Optimized transfection of mRNA transcribed from a d(A/T)100 tail-containing vector. Biochim Biophys Res Commun 330:958-966 (2005).
Eshhar et al. Chimeric T cell receptor which incorporates the anti-tumour specificity of a monoclonal antibody with the cytolytic activity of T cells: a model system for immunotherapeutical approach. Br J Cancer 62:27-29 (1990).
Eshhar et al., Design of cytotoxic T lymphocytes with antibody-type specificity against tumor cells using chimeric PCR. Journal of Cellular Biochemistry, A.R. Liss, Suppl. 14B: 70 (1990).
Fang et al. Immunotherapy for advanced melanoma. J Invest Derm 128(11):2596-2605 (2008).
Feng et al. A novel human monoclonal antibody that binds with high affinity to mesothelin-expressing cells and kills them by antibody-dependent cell-mediated cytotoxicity. Mol Cancer Ther 8(5):1113-1118.
Finney et al. Activation of resting human primary T cells with chimeric receptors: costimulation from CD28, inducible costimulator, CD134, and CD137 in series with signals from the TCR zeta chain. J Immunol 172:104-113 (2004).
Finney et al. Chimeric Receptors Providing Both Primary and Costimulatory Signaling in T Cells from a Single Gene Product. J Immunol 161:2791-2797 (1998).
Fraieilla et al. Ibrutinib enhances chimeric antigen receptor T-cell engraftment and efficacy in leukemia. Blood 127(9):1117-1127 (2016).
Freeman et al. Engagement of the PD-1 immunoinhibitory receptor by a novel B7 family member leads to negative regulation of lymphocyte activation. J Exp Med 192:1027-1034 (2000).
Frigault et al. Chimeric antigen receptor-modified T cells strike back. Int Immunol 28(7):355-363 (2016).
Gabrilovich et al. Myeloid-derived-suppressor cells as regulators of the immune system Nat Rev Immunol 9(3):162-174 (2009).
Garfall. Chimeric Antigen Receptor T Cells against CD19 for Multiple Myeloma. N Engl J Med 373(11):1040-1047 (2015).
Gargett et al. Different cytokine and stimulation conditions influence the expansion and immune phenotype of third-generation chimeric antigen receptor T cells specific for tumor antigen GD2. Cytotherapy 17(4):487-495 (2015).
Garland et al. The use of Teflon cell culture bags to expand functionally active CD8+ cytotoxic T lymphocytes. J Immunol Meth 227(1-2):53-63 (1999).
Garrido et al. The urgent need to recover MHC class I in cancers for effective immunotherapy. Current Opinion in Immunology 39:44-51 (2016).
Gattinoni et al. Paths to stemness: building the ultimate antitumour T cell. Nature Reviews Cancer 12(10):671-684 (2012) .
Ghosh et al. Donor CD19 CAR T cells exert potent graft-versus-lymphoma activity with diminished graft-versus-host activity. Nature Medicine 23:242-249 (2017).
Gorochov et al. Functional assembly of chimeric T-cell receptor chains. Int J Cancer Supp 7:53-57 (1992).
Govers et al. TCRs Genetically Linked to CD28 and CD3ϵ Do Not Mispair with Endogenous TCR Chains and Mediate Enhanced T Cell Persistence and Anti-Melanoma Activity. J Immunol 193:5315-5326 (2014).
Griffin et al. Antibody fragments as tools in crystallography. Clin Exp Immunol 165(3):285-291 (2011).
Gross et al. Generation of effector T cells expressing chimeric T cell receptor with antibody type-specificity. Transplant Proc. 21(1 Pt 1):127-130 (1989).
Grupp et al. Chimeric antigen receptor-modified T cells for acute lymphoid leukemia. NEJM 368:1509-1518 (2013).
Guedan et al. ICOS-based chimeric antigen receptors program bipolar TH17/TH1 cells. Blood 124(7):1070-1080 (2014).
Guest et al. The role of extracellular spacer regions in the optimal design of chimeric immune receptors: evaluation of four different scFvs and antigens. J Immunother28(3):203-211 (2005).
Guy et al. Distinct T cell receptor signaling pathways drive proliferation and cytokine production in T cells. Nat Immunol 14(3):262-270 (2013).
Haanen et al. Selective expansion of cross-reactive CD8(+) memory T cells by viral variants. J Exp Med 190(9):1319-1328 (1999).
Hassan et al. Major Cancer Regressions in Mesothelioma After Treatment with an Anti-Mesothelin Immunotoxin and Immune Suppression. Sci Transl Med 5:208ra147 (2013).
Hassan et al. Mesothelin: a new target for immunotherapy. Clin Cancer Res 10:3937-3942 (2004).
Hatzoglou et al. TNF receptor family member BCMA (B cell maturation) associates with TNF receptor-associated factor (TRAF) 1, TRAF2, and TRAF3 and activates NF-kappa B, elk-1, c-Jun N-terminal kinase, and p38 mitogen-activated protein kinase. Immunology 165(3):1322-1330 (2000).
Hicklin et al. HLA class I antigen downregulation in human cancers: T-cell immunotherapy revives and old story. Mol Med Today 5(4):178-186 (1999).
Ho et al. Mesothelin expression in human lung cancer. Clin Cancer Res 13:1571-1575 (2007).
Hollinger et al. "Diabodies": Small bivalent and bispeific antibody fragments. PNAS USA 90:6444 6448 (1993).
Holzinger et al. The growing world of CAR T cell trials: a systematic review, Cancer Immunology. Immunotherapy 65(12):1433-1450 (2016).
Hombach et al. T cell activation by antibody-like immunoreceptors: the position of the binding epitope within the target molecule determines the efficiency of activation of redirected T cells. J Immunol 178:4650-4657 (2007).
Huang et al. Driving an improved CAR for cancer immunotherapy. J Clin Invest 126(8):2795-2798 (2016).
Hudecek et al. The Nonsignaling Extracellular Spacer Domain of Chimeric Antigen Receptors is Decisive for in Vivo Antitumor Activity. Cancer Immunol Res 3(2):125-135 (2015).
Huston et al. Protein engineering of antibody binding sites: recovery of specific activity in an anti-digoxin single-chain Fv analogue produced in *Escherichia coli*. PNAS USA 85(16):5879-5883 (1988).
Hwan et al. Universal Chimeric Antigen Receptors for Multiplexed and Logical Control of T Cell Responses. Cell 173(6):1426-1438. e11 (2018).
Hwu et al., The genetic modification of T cells for cancer therapy: an overview of laboratory and clinical trials. Cancer Detect Prev. 18(1):43-50 (1994).
Illei et al. Mesothelin Expression in Advanced Gastroesophageal Cancer Represents a Novel Target for Immunotherapy. Appl Immunohistochem Mol Morphol 24(4):246-252 (2016).
Institute for Clinical and Economic review (ICER). Chimeric Antigen Receptor T-Cell Therapy for B-Cell Cancers: Effectiveness and Value. Final Evidence Report dated Mar. 23, 2018 (185 pgs).
Iwahori et al. Engager T cells: a new class of antigen-specific T cells that redirect bystander T cells. Mol Ther 23(1):171-178 (2015).
Izumoto et al. Phase II clinical trial of Wilms tumor 1 peptide vaccination for patients with recurrent glioblastoma multiforme. J Neurosurg 108:963-971 (2008).
Jackson et al. Driving CAR T-cells forward. Nat Rev Clin Oncol 13(6):370-383 (2016).
Jacoby. CD19 CAR immune pressure induces B-precursor acute lymphoblastic leukaemia lineage switch exposing inherent leukaemic plasticity. Nat Commun 7:12320 (2016).
Jacoby et al. Murine models of acute leukemia: important tools in current pediatric leukemia research. Front Oncol 4:95 (2014).
James et al. Antigen sensitivity of CD22-specific chimeric TCR is modulated by target epitope distance from the cell membrane. J Immunol 180:7028-7038 (2008).
Jamnani et al. T cells expressing VHH-directed oligoclonal chimeric HER2 antigen receptors: towards tumor-directed oligoclonal T cell therapy. Biochim Biophys Acta 1840(1):378-386 (2014).
Jena et al. Chimeric antigen receptor (CAR)-specific monoclonal antibody to detect CD19-specific T cells in clinical trials. PLoS One. 8(3):e57838 (2013).
Jin et al. Safe engineering of CAR T cells for adoptive cell therapy of cancer using long- term episomal gene transfer. EMBO Mol Med 8(7):702-711 (2016).

(56) References Cited

OTHER PUBLICATIONS

John et al. Anti-PD-1 antibody therapy potently enhances the eradication of established tumors by gene-modified T cells. Clin Cancer Res 19(20):5636-5646 (2013).
Johnson et al. Rational development and characterization of humanized anti-EGFR variant III chimeric antigen receptor T cells for glioblastoma. Immunotherapy 7(275):275ra22 (2015).
Jones et al. Replacing the complementarity-determining regions in a human antibody with those from a mouse. Nature 321:522-525 (1986).
Jonnalagadda et al. Chimeric Antigen Receptors With Mutated IgG4 Fc Spacer Avoid Fc Receptor Binding and Improve T Cell Persistence and Antitumor Efficacy. Mol Ther 23(4):757-768 (2015).
June et al. Chimeric Antigen Receptor Therapy. N Engl J Med 379:64-73 (2018).
June et al. Engineering lymphocyte subsets: tools, trials and tribulations. Nat Rev Immunol 9.10:704-716 (2009).
June et al. Is autoimmunity the Achilles' heel of cancer immunotherapy? Nat Med 23(5):540-547 (2017).
Junghans. The challenges of solid tumor for designer CAR-T therapies: a 25-year perspective. Cancer Gene Ther 24(3):89-99 (2017).
Kabat et al. Sequences of Proteins of Immunological Interest. NIH Pub. No. 91-3242. Public Health Service, National Institutes of Health. 1:647-669 (1991).
Kachala et al. Mesothelin Overexpression is a Marker of Tumor Aggressiveness and is Associated with Reduced Recurrence-Free and Overall Survival in Early-Stage Lung Adenocarcinoma. Clin Cancer Res 20(4):1020-1028 (2013).
Kaiser. Towards a commercial process for the manufacture of genetically modified T cells for therapy. Cancer Gene Thera 22(2):72-78 (2015).
Kalos et al. T cells with chimeric antigen receptors have potent antitumor effects and can establish memory in patients with advanced leukemia. Sci Transl Med 3(95):95ra73 (2011).
Karlsson et al. Evaluation of Intracellular Signaling Downstream Chimeric Antigen Receptors. PLoS One 10(12):e0144787 (2015).
Kawalekar et al. Distinct Signaling of Coreceptors Regulates Specific Metabolism Pathways and Impacts Memory Development in CAR T Cells. Immunity 44(2):380-390 (2016).
Kawalekar et al. Supplemental Information. Distinct Signaling of Coreceptors Regulates Specific Metabolism Pathways and Impacts Memory Development in CAR T Cells. Immunity 44(2):380-390 (2016).
Kebriaei et al. Phase I trials using Sleeping Beauty to generate CD19-specific CAR T cells. J Clin Invest 126(9):3363-3376 (2016).
Kershaw et al. Gene-engineered T cells for cancer therapy. Nat Rev Cancer 13(8):525-541 (2013).
Klebanoff et al. Memory T cell-driven differentiation of naive cells impairs adoptive immunotherapy. J Clin Invest 126(1):318-334 (2016).
Klebanoff et al. Prospects for gene-engineered T cell immunotherapy for solid cancers. Nat Med 22(1):26-36(2016).
Knies et al. An optimized single chain TCR scaffold relying on the assembly with the native CD3-complex prevents residual mispairing with endogenous TCRs in human T-cells. Oncotarget 7(16):21199-211221 (2016).
Kochenderfer et al. B-cell depletion and remissions of malignancy along with cytokine-associated toxicity in a clinical trial of anti-CD19 chimeric-antigen-receptor-transduced T cells. Blood 119(12):2709-2720 (2012).
Kochenderfer et al. Construction and Pre-clinical Evaluation of an Anti-CD19 Chimeric Antigen Receptor. Immunotherapy 32(7):689-702 (2010).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Kowolik et al. CD28 costimulation provided through a CD19-specific chimeric antigen receptor enhances in vivo persistence and antitumor efficacy of adoptively transferred T cells. Cancer Res 66(22):10995-11004 (2006).
Krenciute et al. Characterization and Functional Analysis of scFv-based Chimeric Antigen Receptors to Redirect T Cells to IL13Rα2-positive Glioma. Mol Ther 24(2):354-363 (2016).
Kuhns et al. TCR Signaling Emerges from the Sum of Many Parts. Front. Immunol. 3:159 (2012).
Kunert et al. TCR-engineered T cells meet new challenges to treat solid tumors: Choice of antigen, T cell fitness, and sensitization of tumor milieu. Front Immun 4:363 (2013).
Kunkele et al. Functional Tuning of CARs Reveals Signaling Threshold above Which CD8+ CTL Antitumor Potency is Attenuated due to Cell Fas-FasL-Dependent AICD. Cancer Immunol Res 3(4):368-379 (2015).
Laabi et al. A new gene, BCM, on chromosome 16 is fused to the interleukin 2 gene by a t(4;16)(q26;p13) translocation in a malignant T cell lymphoma. EMBO 11 (11):3897-3904 (1992).
Laabi et al. The BCMA gene, preferentially expressed during B lymphoid maturation, is bidirectionally transcribed. Nucleic Acids Res 22(7):1147-1154 (1994).
Langer. Comparative Evaluation of Peripheral Blood T Cells and Resultant Engineered Anti-CD19 CAR T-Cell Products From Patients With Relapsed / Refractory Non-Hodgkin Lymphoma (NHL). Abstract 2305 AACR Apr. 16-20, 2016 (1 pg.).
Lanier. NKG2D Receptor and its Ligands in Host Defense. Cancer Immunol Res. 3(6):575-582 (2015).
Lanitis et al. Chimeric antigen receptor T Cells with dissociated signaling domains exhibit focused antitumor activity with reduced potential for toxicity in vivo. Cancer Immunol Res 1(1):45-53 (2013).
Lanitis et al. Redirected Antitumor Activity of Primary Human Lymphocytes Transduced With a Fully Human Anti-mesothelin Chimeric Receptor. Mol Ther 20(3):633-643 (2012).
Lanzavecchia et al. The use of hybrid hybridomas to target human cytotoxic T lymphocytes. Eur J Immunol. 17(1):105-111 (1987).
Latchman et al. PD-L2 is a second ligand for PD-1 and inhibits T cell activation. Nat Immunol 2:261-268 (2001).
Lee et al. Current concepts in the diagnosis and management of cytokine release syndrome. Blood 124(2):188-196 (2014).
Lee et al. T cells expressing CD19 chimeric antigen receptors for acute lymphoblastic leukaemia in children and young adults: A phase 1 dose-escalation trial. The Lancet 385(9967):517-528 (2014).
Lee. Solid-state target CAR-T, 'TRUC platform' (KR). Biol.co.kr Retrieved from the Internet: URL:http://www.biospectator.com/view/news_ print.php?varAtcld=4037 (7 pgs.) (2017) [retrieved on Jan. 9, 2018] (Machine translation).
Leone et al. MHC Class I Antigen Processing and Presenting Machinery: Organization, Function, and Defects in Tumor Cells. J Natl Cancer Inst 105:1172-1187 (2013).
Li et al. Adoptive immunotherapy using T lymphocytes redirected to glypican-3 for the treatment of lung squamous cell carcinoma. Oncotarget 7(3):2496-2507 (2015).
Li et al. Enhanced Cancer Immunotherapy by Chimeric Antigen Receptor-Modified T Cells Engineered to Secrete Checkpoint Inhibitors. Clin Cancer Res 23(22):6982-6992 (2017).
Lipowska-Bhalla et al. Targeted immunotherapy of cancer with CAR T cells: Achievements and challenges. Cancer Immunol Immuno 61(7):953-962 (2012).
Liu et al. A Chimeric Switch-Receptor Targeting PD1 Augments the Efficacy of Second-Generation CAR T Cells in Advanced Solid Tumors. Cancer Res 76(6):1578-1590 (2016).
Liu et al. Affinity-Tuned ErbB2 or EGFR Chimeric Antigen Receptor T Cells Exhibit an Increased Therapeutic Index against Tumors in Mice. Cancer Res 75(17):3596-3607 (2015).
Liu et al. Improved anti-leukemia activities of adoptively transferred T cells expressing bispecific T-cell engager in mice. Blood Cancer J 6:e430 (2016).
Liu et al. Supplemental Information. A Chimeric Switch-Receptor Targeting PD1 Augments the Efficacy of Second-Generation CAR T Cells in Advanced Solid Tumors. Cancer Res 76(6):1578-1590 (2016).

(56) References Cited

OTHER PUBLICATIONS

Long et al. 4-1BB Costimulation Ameliorates T Cell Exhaustion Induced by Tonic Signaling of Chimeric Antigen Receptors. Nat Med 21(6):581-590 (2015).
Lu et al. Treatment of Patients With Metastatic Cancer Using a Major Histocompatibility Complex Class II-Restricted T-Cell Receptor Targeting the Cancer Germline Antigen MAGE-A3. J Clin Oncol 35(29):3322-3329.
Ma et al. Recognition of mesothelin by the therapeutic antibody MORAb-009: structural and mechanistic insights. J Biol Chem 287:33123-33131(2012).
Ma et al. Versatile strategy for controlling the specificity and activity of engineered T cells. PNAS 113(4):E450-E458 (2016).
Maher et al. Human T-lymphocyte cytotoxicity and proliferation directed by a single chimeric TCRzeta /CD28 receptor. Nat Biotech 20(1):70-75 (2002).
Mahmoud et al. Enforced CD19 expression leads to growth inhibition and reduced tumorigenicity. Blood 94(10):3551-3558 (1999).
Maude et al. CD19-targeted chimeric antigen receptor T-cell therapy for acute lymphoblastic leukemia. Blood 125(26):4017-4024 (2015).
Maus et al. Adoptive immunotherapy for cancer of viruses. Annual Review of Immunology 32:189-225 (2014).
Maus et al. Ex vivo expansion of polyclonal and antigen-specific cytotoxic T lymphocytes by artificial APCs expressing ligands for the T-cell receptor, CD28 and 4-1BB. Nature Biotech 20(2):143-148 (2002).
Maus et al. Making Better Chimeric Antigen Receptors for Adoptive T-cell Therapy. Clin Cancer Res 22(8):1875-1884 (2016).
Maus et al. T Cells Expressing Chimeric Antigen Receptors Can Cause Anaphylaxis in Humans. Cancer Immunol Res. 1:26-31 (2013).
Maus et al. Zoom zoom: Racing CARs for multiple myeloma. Clin Cancer Res 19(8):1917-1919 (2013).
Menk et al. 4-1BB costimulation induces T cell mitochondrial function and biogenesis enabling cancer immunotherapeutic responses. J Exp Med 215(4):1091-1100 (2018).
Merry et al. O-glycan sialylation and the structure of the stalk-like region of the T cell coreceptor CD8. J Biol Chem 278(29):27119-27128 (2003).
Miller et al. CD19-Targeted CAR T Cells: A New Tool in the Fight against B Cell Malignancies. Oncol Res Treat 38(12):683-690 (2015).
Milone et al. Chimeric receptors containing CD137 signal transduction domains mediate enhanced survival of T cells and increased antileukemic efficacy in vivo. Mol Ther 17(8):1453-1464 (2009).
Minguet et al. A permissive geometry model for TCR-CD3 activation. Trends in Biochemical Sciences 33(2):51-57 (2008).
Minguet et al. Full Activation of the T Cell Receptor Requires Both Clustering and Conformational Changes at CD3. Immunity 26(1):43-54 (2007).
Moon et al. Expression of a functional CCR2 receptor enhances tumor localization and tumor eradication by retargeted human T cells expressing a mesothelin-specific chimeric antibody receptor. Clin Cancer Res 17(14):4719-4730 (2011).
Morea et al. Antibody modeling: implications for engineering and design. Methods 20(3):267-279 (2000).
Morello et al. Mesothelin-Targeted CARs: Driving T Cells to Solid Tumors. Cancer Discov 6(2):133-146 (2016).
Morton et al. Establishment of human tumor xenografts in immunodeficient mice. Nat Procol 2:247 (2007).
Moynihan et al. Eradication of large established tumors in mice by combination immunotherapy that engages innate and adaptive immune responses. Nat Med 12(22):1402-1410 (2016).
Mumtaz et al. Design of liposomes for circumventing the reticuloendothelial cells. Glycobiology 5:505-510 (1991).
Nacheva et al. Preventing nondesired RNA-primed RNA extension catalyzed by T7 RNA polymerase. Eur J Biochem 270:1458-1465 (2003).
Needleman et al. A general method applicable to the search for similarities in the amino acid sequence of two proteins. J. Mol. Biol. 48:443-453 (1970).
Newick et al. Chimeric antigen receptor T-cell therapy for solid tumors. Molecular Therapy—Oncolytics 3:16006 (2016).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nolan et al. Bypassing immunization: optimized design of "designer T cells" against carcinoembryonic antigen (CEA)-expressing tumors, and lack of suppression by soluble CEA. Clin Cancer Res 5:3928-3941 (1999).
Oden et al. Potent anti-tumor response by targeting B cell maturation antigen (BCMA) in a mouse model of multiple myeloma. Mole Oncol 9(7):1348-1358 (2015).
O'Hare et al. Mesothelin as a target for chimeric antigen receptor-modified T cells as anticancer therapy. Immunotherapy 8(4):449-460 (2016).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Onda et al. Megakaryocyte potentiation factor cleaved from mesothelin precursor is a useful tumor marker in the serum of patients with mesothelioma. Clin Cancer Res. 12:4225-4231 (2006).
Onda et al. New Monoclonal Antibodies to Mesothelin Useful for Immunohistochemistry, Fluorescence-Activated Cell Sorting, Western Blotting, and ELISA. Clin Cancer Res 11(16):5840-5846 (2005).
Padlan. A possible procedure for reducing the immunogenicity of antibody variable domains while preserving their ligand-binding properties. Mol Immunol 28(4-5):489-498 (1991).
Park et al. Adoptive Immunotherapy for B-cell Malignancies with Autologous Chimeric Antigen Receptor Modified Tumor Targeted T Cells. Disc Med 9(47)277-288 (2010).
Pastan et al. Discovery of Mesothelin and Exploiting it as a Target for Immunotherapy. Cancer Res 74(11):2907-2912 (2014).
Patel et al. Engineering an APRIL-specific B Cell Maturation Antigen. J Bio Chem 279(16):16727-16735 (2004).
Patel et al. PDL-1 Expression as a Predictive Biomarker in cancer Immunotherapy. Mol Cancer Ther 14(4):847-856 (2015).
PCT/US2016/033146 International Preliminary Report on Patentability dated Nov. 30, 2017.
PCT/US2016/033146 International Search Report and Written Opinion dated Oct. 20, 2016.
PCT/US2017/045159 International Search Report and Written Opinion dated Nov. 3, 2017.
PCT/US2017/055628 International Search Report and Written Opinion dated Jan. 24, 2018.
PCT/US2017/063137 International Search Report and Written Opinion datedJune 14, 2018.
PCT/US2017/068002 International Search Report and Written Opinion dated Apr. 12, 2018.
PCT/US2018/037387 International Search Report and Written Opinion dated Sep. 17, 2018.
Pearson, et al. Improved Tools for Biological Sequence Comparison. Proc. Nat'l Acad. Sci. USA. 85 (1988): 2444-48.
Pedersen et al. Comparison of surface accessible residues in human and murine immunoglobulin Fv domains. Implication for humanization of murine antibodies. J Mol Biol 235(3):959-973 (1994).
Philip et al. A highly compact epitope-based marker suicide gene for safer and easier adoptive T-cell gene therapy. Blood 124:1277-1287 (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Porter et al. Pilot study of redirected autologous t cells engineered to contain anti-CD19 attached to TCRZ and 4-1BB signaling domains in patients with chemotherapy resistant or refractory

(56) References Cited

OTHER PUBLICATIONS

CD19+ leukemia and lymphoma. NCT02374333. Available at https://www.clinicaltrials.gov/ct2/show/NCT023743337term-13BT022 (3 pgs.) (2016).
Posey et al. Engineered CAR T Cells Targeting the Cancer-Associated Tn-Glycoform of theMembraneMucinMUCI Control Adenocarcinoma. Immunity 44:1444-1454 (2016).
Presta. Antibody Engineering. Curr Op Struct Biol 2:593-596 (1992).
Presta et al. Humanization of an antibody directed against IgE. J Immunol 151:2623-2632 (1993).
Pule et al. A chimeric T cell antigen receptor that augments cytokine release and supports clonal expansion of primary human T cells. Mol Ther 12(5):933-941 (2005).
Punt et al. Stoichiometry of the T cell antigen receptor (TCR) complex: each TCR/CD3 complex contains one TCR alpha, one TCR beta, and two CD3 epsilon chains. J Exp Med 180(2):587-593 (1994).
Riechmann et al. Reshaping human antibodies for therapy. Nature, 332.6162 (1988): 323-7.
Rivadeneira et al. Antitumor T cell reconditioning: improving metabolic fitness for optimal cancer immunotherapy. Clin Cancer Res 24(11):2473-2481 (2018).
Rodgers et al. Switch-mediated activation and retargeting of CAR-T cells for B-cell malignancies. PNAS USA 113(4):E459-E468 (2016).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg. Cell transfer immunotherapy for metastatic solid cancer—what clinicians need to know. Nat Rev Clin Oncol 8(10):577-585 (2011).
Rosenberg et al. Adoptive cell transfer as personalized immunotherapy for human cancer. Science 348(6230):62-68 (2015).
Rosenberg et al. Use of tumor-infiltrating lymphocytes and interleukin-2 in the immunotherapy of patients with metastatic melanoma. A preliminary report. NEJM 319:1676 (1988).
Rossolini et al. Use of deoxyinosine-containing primers vs degenerate primers for polymerase chain reaction based on ambiguous sequence information. Mol Cell Probes 8(2):91-98 (1994).
Roybal et al. Precision Tumor Recognition by T Cells With Combinatorial Antigen-Sensing Circuits. Cell 164:1-10 (2016).
Ruella et al. Smart CARS: optimized development of a chimeric antigen receptor (CAR) T cell targeting epidermal growth factor receptor variant III (EGFRvIII) for glioblastoma. Ann Transl Med 4(1):13 (2016).
Rump et al. Binding of ovarian cancer antigen CA125/MUC16 to mesothelin mediates cell adhesion. J Biol Chem 279:9190-9198 (2004).
Rushworth et al. Universal Artificial Antigen Presenting Cells to Selectively Propagate T Cells Expressing Chimeric Antigen Receptor Independent of Specificity. J Immunother 37(4):204-213 (2014).
Sadelain. CAR therapy: The CD19 paradigm. J Clin Invest 135(9):3392-3400 (2015).
Sadelain et al. Tales of Antigen Evasion from CAR Therapy. Cancer Immunol Res 4(6):473 (2016).
Sadelain et al. The Basic Principles of Chimeric Antigen Receptor Design. Cancer Discov 3(4):388-398 (2013).
Sadelain et al. Therapeutic T cell engineering. Nature 545:423-431 (2017).
Sakemura et al. A Tet-On Inducible System for Controlling CD19-Chimeric Antigen Receptor Expression upon Drug Administration. Cancer Immunol Res 4(8):658-668 (2016).
Sander et al. CRISPR-Cas systems for editing, regulating and targeting genomes. Nat. Biotechnol 32:347-355 (2014).
Sandhu. A rapid procedure for the humanization of monoclonal antibodies. Gene 150(2):409-410 (1994).
Sapede et al. Aberrant splicing and protease involvement in mesothelin release from epithelioid mesothelioma cells. Cancer Sci 99(3):590-594 (2008).
Schenborn et al. A novel transcription property of SP6 and T7 RNA polymerases: dependence on template structure. Nuc Acids Res 13:6223-6236 (1985).
Servais et al. An in Vivo Platform for Tumor Biomarker Assessment. PloS One 6(10):e26772.
Sharpe et al. Genetically modified T cells in cancer therapy: opportunities and challenges. Dis Model Mech 8(4):337-350 (2015).
Shin et al. Positive conversion of negative signaling of CTLA4 potentiates antitumor efficacy of adoptive T-cell therapy in murine tumor models. Blood 119(24):5678-5687 (2012).
Simon et al. PD-1 expression conditions T cell avidity within an antigen-specific repertoire. Oncoimmunology 5(1):e1104448 (2015).
Sims et al. A humanized CD18 antibody can block function without cell destruction. J Immunol., 151 (1993): 2296-2308.
Smith, et al. Comparison of Biosequences. Advances in Applied Mathematics. 1981;2: 482-489.
Sommers et al. Function of CD3ϵ-mediated Signals in T Cell Development. J Exper Med 192(6):913-920 (2000).
Song et al. CD27 costimulation augments the survival and antitumor activity of redirected human T cells in vivo. Blood 119(3):696-706 (2012).
Song et al. In Vivo Persistence, Tumor Localization, and Antitumor Activity of CAR-Engineered T Cells is Enhanced by Costimulatory Signaling through CD137 (4-1BB). Cancer Res 71(13):4617-4627 (2011).
Spear et al. Collaboration of chimeric antigen receptor (CAR)-expressing T cells and host T cells for optimal elimination of established ovarian tumors. Oncoimmunology 2(4):e23564 (2013).
Srivastava et al. Engineering CAR-T cells: Design concepts. Trends Immunol 36(8):494-502 (2015).
Stepinski et al. Synthesis and properties of mRNAs containing the novel ‘anti-reverse’ cap analogs 7-methyl(3'0-methyl)GpppG and 7-methyl(e'-deoxy)GpppG. RNA 7:1486-1495 (2001).
Stone et al. A novel T cell receptor single-chain signaling complex mediates antigen-specific T cell activity and tumor control. Cancer Immunol Immunother 63(11):1163-1176 (2014).
Stromnes et al. T Cells Engineered against a Native Antigen Can Surmount Immunologic and Physical Barriers to Treat Pancreatic Ductal Adenocarcinoma. Cancer Cell 28:638-652 (2015).
Studnicka et al. Human-engineered monoclonal antibodies retain full specific binding activity by preserving non-CDR complementarity-modulating residues. Pro Eng 7(6):805-814 (1994).
Sun et al. The quest for spatio-temporal control of CAR T cells. Cell Res 25(12):1281-1282 (2015).
Tan et al. “Superhumanized” antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tanyi et al. Possible Compartmental Cytokine Release Syndrome in a Patient With Recurrent Ovarian Cancer After Treatment With Mesothelin-targeted CAR-T Cells. J Immunother 40(3):104-107 (2017).
Tchou et al. Safety and efficacy of intratumoral injections of chimeric antigen receptor (CAR) T cells in metastatic breast cancer. Cancer Immunol Res 5(12):1152-1161 (2017).
TCR2 Therapeutics Presents Positive Solid Tumor Data for its Novel TRuC™ Engineered T Cell Therapies at the World Preclinical Congress. PRNewswire. Available at http://www.prnewswire.com/news-releases/tcr2-therapeutics-presents-positive-solid-tumor-data-for-its-novel-truc-engineered-t-cell-therapies-at-the-world-preclinical-congress-300472629.html (Jun. 13, 2017) (2 pgs.).
Teachey. Identification of Predictive Biomarkers for Cytokine Release Syndrome after Chimeric Antigen Receptor T cell Therapy for Acute Lymphoblastic Leukemia. Cancer Disc 6(6):664-679 (2016).
Ten Berg et al. Selective expansion of a peripheral blood CD8+ memory T cell subset expressing both granzyme B and L-selectin

(56) References Cited

OTHER PUBLICATIONS during primary viral infection in renal allograft recipients. Transplant Proc 30(8):3975-3977 (1998).
Themeli et al. Generation of tumor-targeted human T lymphocytes from induced pluripotent stem cells for cancer therapy. Nat Biotech 31:928-933 (2013).
Themeli et al. New cell sources for T cell engineering and adoptive immunotherapy. Cell Stem Cell 16(4):357-366 (2015).
Thokala et al. Redirecting Specificity of T cells Using the Sleeping Beauty System to Express Chimeric Antigen Receptors by Mix-and-Matching of VLand VHDomains Targeting CD123+ Tumors. PLoS One 11 (8):e0159477 (2016).
Torikai et al. A foundation for universal T-cell based immunotherapy: T cells engineered to express a CD19-specific chimeric-antigen-receptor and eliminate expression of endogenous TCR. Blood 119(24):5697-5705 (2012).
Torikai et al. Translational Implications for Off-the-shelf Immune Cells Expressing Chimeric Antigen Receptors. Mol Ther24(7):1178-1186 (2016).
Tran et al. Cancer Immunotherapy Based on Mutation-Specific CD4+ T Cells in a Patient with Epithelial Cancer. Science 9:641-645 (2014).
Tsai et al. Producer T cells: Using genetically engineered T cells as vehicles to generate and deliver therapeutics to tumors. Oncoimmunol 5(5):e1122158 (2016).
Tumaini et al. Simplified process for the production of anti-CD19-CAR engineered T cells. Cytotherapy 15(11):1406-1415 (2014).
Turtle et al. CD19 CAR-T cells of defined CD4+:CD8+ composition in adult B cell ALL patients. J Clin Invest 126(6):2123-2138 (2016).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/419,398 1st Action Interview dated Jul. 3, 2017.
U.S. Appl. No. 15/419,398 Office Action dated Mar. 7, 2018.
U.S. Appl. No. 15/419,398 Office Action dated Nov. 9, 2017.
U.S. Appl. No. 15/965,738 Preinterview First Action dated Nov. 15, 2018.
U.S. Appl. No. 15/965,739 Preinterview First Action dated Nov. 15, 2018.
Valton et al. A Multidrug-resistant Engineered Car T Cell for Allogeneic Combination Immunotherapy. Mol Ther 23(9):1507-1518 (2015).
Van Der Stegen et al. The pharmacology of second-generation chimeric antigen receptors. Nat Rev Drug Discov 14(7):499-509 (2015).
Velasquez. T cells expressing CD19-specific Engager Molecules for the Immunotherapy of CD19-positive Malignancies. Sci Rep 6:27130 (2016).
Verhoeyen et al. Reshaping human antibodies: grafting an antilysozyme activity. Science 239:1534-1536 (1988).
Wang et al. Generation of Potent T-cell Immunotherapy for Cancer Using DAP12-Based, Multichain, Chimeric Immunoreceptors. Cancer Immunol Res 3(7):815-826 (2015).
Wang et al. Manufacture of tumor- and virus-specific T lymphocytes for adoptive cell therapies. Cancer Gene Therapy 22(2):85-94 (2015).
Wang et al. VISTA, a novel mouse Ig superfamily ligand that negatively regulates T cell responses. J Exp Med 208(3):577-592 (2011).
Watanabe et al. Fine-tuning the CAR spacer improves T-cell potency. Oncoimmunology. 5(2):e1253656 (2016).
Weekes et al. Phase I Study of DMOT4039A, an Antibody-Drug Conjugate Targeting Mesothelin, in Patients with Unresectable Pancreatic or Platinum-Resistant Ovarian Cancer. Mol Cancer Ther 15(3):439-447 (2016).
Wegener et al. The T cell receptor/CD3 complex is composed of at least two autonomous transduction modules. Cell 68:83-95 (1992).
Whittington et al. Accounting for All Costs in the Total Cost of Chimeric Antigen Receptor T-Cell Immunotherapy. JAMA Oncol. Published online Oct. 11, 2018 (1 pg.).
Wilkie et al. Selective Expansion of Chimeric Antigen Receptor-targeted T-cells with Potent Effector Function using Interleukin-4. J Biol Chem 285(33):25538-25544 (2010).
Wu et al. Protein design of IgG/TCR chimeras for the co-expression of Fab-like moieties within bispecific antibodies. MABS 7(2):364-376 (2015).
Wucherpfennig et al. Structural Biology of the T-cell Receptor: Insights into Receptor Assembly, Ligand Recognition, and Initiation of Signaling. Cold Spring Harb Perspect Biol 2(4):a005140 (2010).
Xu et al. The basics of CAR T design and challenges in immunotherapy of solid tumors—Ovarian cancer as a model. Hum Vaccin Immunother 13(7): 1548-1555 (2017).
Yun et al. Targeting of T Lymphocytes to Melanoma Cells Through Chimeric Anti-GD3 Immunoglobulin T-Cell Receptors. Neoplasia 2(5):449-459 (2000).
Zah et al. T cells expressing CD19/CD20 bi-specific chimeric antigen receptors prevent antigen escape by malignant B cells. Cancer Immunol Res 4(6)498-509 (2016) .
Zhang et al. 4-1BB is superior to CD28 costimulation for generating CD8+ cytotoxic lymphocytes for adoptive immunotherapy. J Immunol 179:4910-4918 (2007).
Zhang et al. New High Affinity Monoclonal Antibodies Recognize Non-Overlapping Epitopes on Mesothelin For Monitoring and Treating Mesothelioma. Sci Rep 5:9928 (2015).
Zhang et al. Phase I Escalating-Dose Trial of CAR-T Therapy Targeting CEA+ Metastatic Colorectal Cancers. Mol Ther 25:1248-1258 (2017).
Zhao et al. A herceptin-based chimeric antigen receptor with modified signaling domains leads to enhanced survival of transduced T lymphocytes and antitumor activity. J Immunol 183:5563-5574 (2009).
Zhao et al. Multiple injections of electroporated autologous T cells expressing a chimeric antigen receptor mediate regression of human disseminated tumor. Cancer Res 70(22):9053-9061 w/Supplemental Information (2010).
Zhao et al. Structural Design of Engineered Costimulation Determines Tumor Rejection Kinetics and Persistence of CAR T cells. Cancer Cell 28(4):415-428 (2015).
Zhou et al. Exclusive Transduction of Human CD4+ T Cells upon Systemic Delivery of CD4-Targeted Lentiviral Vectors. J Immunol 195:2493-2501 (2015).
Abate-Daga et al. Expression profiling of TCR-engineered T cells demonstrates overexpression of multiple inhibitory receptors in persisting lymphocytes. Blood 122(8):1 399-410(2013).
Badoual et al. PD-1-expressing tumor-infiltrating T cells are a favorable prognostic biomarker in HPV-associated head and neck cancer. Cancer Res. 73(1):128-138 (2013).
Bahram et al. A second lineage of mammalian major histocompatibility complex class I genes. PNAS USA 91:6259-6263 (1994).
Bauer et al. Activation of NK cells and T cells by NKG2D, a receptor for stress-inducible MICA. Science 285(5428):727-9 (1999).
Borcherding et al. ROR1, an embryonic protein with an emerging role in cancer biology. Protein Cell 5(7):496-502 (2014).
Borroto et al. Crammed signaling motifs in the T-cell receptor. Immunol Lett 161:113-117 (2014).
Brahmer et al. Safety and activity of anti-PD-L1 antibody in patients with advanced cancer. N Engl J Med 366(26):2455-2465 (2012).
Bruhns et al. Specificity and Affinity of Human Fc Receptors and Their Polymorphic Variants for Human IgG Subclasses. Blood 113(16):3716-3725 (2009).
Chen et al. In situ expression and significance of B7 costimulatory molecules within tissues of human gastric carcinoma. World J Gastroenterol. 9(6):1370-1373 (2003).
Chen et al. Mesothelin Binding to CA125/MUC16 Promotes Pancreatic Cancer Cell Motility and Invasion via MMP-7 Activation. Scientific Reports 3(1):4-8 (2013).
Choi et al. Pre-clinical Specificity and Safety of UC-961, a First-In-Class Monoclonal Antibody Targeting ROR1 Clinical Lymphoma, Myeloma & Leukemia 15(Supp):SI67-S169 (2015).
Cui et al. Targeting ROR1 inhibits epithelial-mesenchymal transition and metastasis. Cancer Research 73(12):3649-3660 (2015).

(56) References Cited

OTHER PUBLICATIONS

D'Aloia et al. T Lymphocytes Engineered to Express a CD16-Chimeric Antigen Receptor Redirect T-cell Immune Responses Against Immunoglobulin G-Opsonized Target Cells. Cytotherapy 18(2):278-290 (2016).
Dangaj et al. In vivo blocking of CA125/mesothelin-dependent cell adhesion prevents ovarian cancer peritoneal metastasis. Gynecologic Oncology 116(3):S2-S169 (2010).
Darce et al. Regulated expression of BAFF-binding receptors during human B cell differentiation. J Immunol 179(11):7276-7286 (2007).
Deniger et al. Sleeping Beauty Transposition of Chimeric Antigen Receptors Targeting Receptor Tyrosine Kinase-Like Orphan Receptor-1 (ROR1) into Diverse Memory T-Cell Populations. PLoS ONE 10(6):e0128151 (2015).
Ding et al. CBP loss cooperates with PTEN haploinsufficiency to drive prostate cancer: implications for epigenetic therapy. Cancer Res 74(7):2050-2061 (2014).
Dong et al. Tumor-associated B7-H1 promotes T-cell apoptosis: a potential mechanism of immune evasion. Nat Med 8:793-800 (2002).
Dudley et al. Adoptive cell therapy for patients with metastatic melanoma: evaluation of intensive myeloablative chemoradiation preparative regimens. J Clin Oncol 26(32):5233-5239 (2008).
Eagle et al. Cellular expression, trafficking, and function of two isoforms of human ULBP5/RAET1G. PLoS One 4:e4503 (2009).
Eagle et al. ULBP6/RAET1L is an additional human NKG2D ligand. Eur J Immunol 39:3207-3216 (2009).
Ellyard et al. Antigen-selected, immunoglobulin-secreting cells persist in human spleen and bone marrow. Blood 103(10):3805-3812 (2004).
Gao et al. Overexpression of PD-L1 significantly associates with tumor aggressiveness and postoperative recurrence in human hepatocellular carcinoma. Clin Cancer Res. 15(3):971-979 (2009).
Gattinoni et al. Adoptive immunotherapy for cancer: building on success. Nature Reviews Immunology 6(5):383-393 (2006).
Geng et al. B7-H1 up-regulated expression in human pancreatic carcinoma tissue associates with tumor progression. J Cancer Res Clin Oncol. 134(9):1021-1027 (2008).
Ghebeh et al. The B7-H1 (PD-L1) T Lymphocyte-Inhibitory Molecule Is Expressed in Breast Cancer Patients with Infiltrating Ductal Carcinoma: Correlation with Important High-Risk Prognostic Factors. Neoplasia 8(3):190-198 (2006).
Goding et al. Restoring immune function of tumor-specific CD4+ T cells during recurrence of melanoma. J Immunol 190(9):4899-4909 (2013).
Gros et al. PD-1 identifies the patient-specific CD8+ tumor-reactive repertoire infiltrating human tumors. The Journal of clinical investigation, 124(5):2246-2259 (2014).
Guy et al. Distinct T cell receptor signaling pathways drive proliferation and cytokine production in T cells. Nat Immunol 14(3):262-270 and Supp pp. 1-9 (2013).
Han et al. Masked Chimeric Antigen Receptor for Tumor-Specific Activation. Molecular Therapy 25(1):274-284 (2017).
Holst et al. Scalable signaling mediated by T cell antigen receptor-CD3 ITAMs ensures effective negative selection and prevents autoimmunity. Nat Immunol 9(6):658-666 and Supp pp. 1-21 (2008).
Hudecek et al. Receptor affinity and extracellular domain modifications affect tumor recognition by ROR1-specific chimeric antigen receptor T cells. Clin Cancer Res 19(12):3153-3164 (2013).
Hudecek et al. The B-cell tumor-associated antigen ROR1 can be targeted with T cells modified to express a ROR1-specific chimeric antigen receptor. Blood 116(22):4532-4541 (2010).
James et al. Antibody-mediated B-cell depletion before adoptive immunotherapy with T cells expressing CD20-specific chimeric T-cell receptors facilitates eradication of leukemia in immunocompetent mice. Blood 114(27):5454-5463 (2009).
Karim et al. Tumor-expressed B7-H1 and B7-DC in relation to PD-1 + T-cell infiltration and survival of patients with cervical carcinoma. Clin Cancer Res. 15(20):6341-6347 (2009).
Karyampudi et al. Accumulation of Memory Precursor CD8 T Cells in Regressing Tumors following Combination Therapy with Vaccine and Anti-PD-1 Antibody. Cancer Res 74(11):2974-85 (2014.
Kozako et al. PD-1/PD-L1 expression in human T-cell leukemia virus type 1 carriers and adult T-cell leukemia/lymphoma patients. Leukemia 23(2):375-382 (2009).
Kudo et al. T lymphocytes expressing a CD16 signaling receptor exert antibody-dependent cancer cell killing. Cancer Res 74(1):93-103 (2013).
Leen et al. Improving T cell therapy for cancer. Annu Rev Immunol 25:243-265 (2007).
Liu et al. Plasma cells from multiple myeloma patients express B7-H1 (PD-L1) and increase expression after stimulation with IFN-{gamma} and TLR ligands via a MyD88-, TRAF6-, and MEK-dependent pathway. Blood 110(1):296-304 (2007).
Love et al. ITAM-mediated signaling by the T-cell antigen receptor. Cold Spring Harb Perspect Biol. 2(6):a002485 (2010).
Malaspina et al. Enhanced programmed death 1 (PD-1) and PD-1 ligand (PD-L1) expression in patients with actinic cheilitis and oral squamous cell carcinoma. Cancer Immunol Immunother. 60(7):965-974 (2011).
Mansfield et al. B7-H1 expression in malignant pleural mesothelioma is associated with sarcomatoid histology and poor prognosis. J Thorac Oncol. 9(7):1036-1040 (2014).
Mato et al. A drive through cellular therapy for CLL in 2015: allogeneic cell transplantation and CARS. Blood 126(4):478-485 (2015).
Nakanishi et al. Overexpression of B7-H1 (PD-L1) significantly associates with tumor grade and postoperative prognosis in human urothelial cancers. Cancer Immunol Immunother. 56(8):1173-1182 (2007).
Nicolaides et al. CA125 suppresses amatuximab immune-effector function and elevated serum levels are associated with reduced clinical response in first line mesothelioma patients. Cancer Biology & Therapy 19(7):622-630 (2018).
Nimmerjahn et al. FcγRIV: a Novel FcR with Distinct IgG Subclass Specificity. Immunity 23(1):41-51 (2005).
Novak et al. Expression of BCMA, TACI, and BAFF-R in multiple myeloma: a mechanism for growth and survival. Blood 103(2):689-94 (2004).
Novak et al. Expression of BLyS and its receptors in B-cell non-Hodgkin lymphoma: correlation with disease activity and patient outcome. Blood 104(8):2247-53 (2004).
NP 000064, human T-cell surface glycoprotein CD3 gamma chain precursor, NCBI, pp. 1-4, May 4, 2019.
NP 000724, human T-cell surface glycoprotein CD3 epsilon chain precursor, NCBI, pp. 1-4, May 4, 2019.
O'Connor et al. BCMA is Essential for the Survival of Long-lived Bone Marrow Plasma Cells. J Exp Med 199(1):91-8 (2004).
Ohigashi et al. Clinical significance of programmed death-1 ligand-1 and programmed death-1 ligand-2 expression in human esophageal cancer. Clin Cancer Res 11(8):2947-2953 (2005).
PCT/US2019/021315 International Search Report and Written Opinion dated Jun. 13, 2019.
PCT/US2019/032298 International Search Report and Written Opinion dated Nov. 21, 2019.
PCT/US2019/043690 Invitation to Pay Additional Fees dated Nov. 4, 2019.
Poirot et al. Multiplex Genome-Edited T-cell Manufacturing Platform for Off-the-ShelfAdoptive T-cell Immunotherapies. Cancer Research 75(18):3853-3864 (2015).
Rodriguez-Garcia et al. T-cell target antigens across major gynecologic cancers. Gynecologic Oncology 145(3):426-435 (2017).
Rosenberg et al. Durable complete responses in heavily pretreated patients with metastatic melanoma using T-cell transfer immunotherapy. Clin Cancer Res 17(13):4550-4557 (2011).
Shimabukuro-Vornhagen et al. Cytokine release syndrome. J Immunother Cancer 6:56 (2018).
Spear et al. NKG2D ligands as therapeutic targets. Cancer Immunity 13:8 (2013).
Thompson et al. Costimulatory molecule B7-H1 in primary and metastatic clear cell renal cell carcinoma. Cancer 104(10):2084-2091 (2005).

(56) References Cited

OTHER PUBLICATIONS

Topalian et al. Safety, Activity, and Immune Correlates of Anti-PD-1 Antibody in Cancer. N Engl J Med 366:2443-2454 (2012).
Urnov et al. Genome editing with engineered zinc finger nucleases. Nature Reviews Genetics 11:636-646 (2010).
U.S. Appl. No. 15/419,398 Office Action dated Jul. 17, 2019.
U.S. Appl. No. 15/419,398 Office Action dated May 24, 2019.
Usui et al. Expression of costimulatory molecules on human retinoblastoma cells Y-79: functional expression of CD40 and B7H1. Invest Ophthalmol Vis Sci. 47(10):4607-4613 (2006).
Vanseggelen et al. T Cells Engineered With Chimeric Antigen Receptors Targeting NKG2D Ligands Display Lethal Toxicity in Mice. Molecular Therapy 23(10):1600-1610 (2015).
Vermeire et al. Signal peptide-binding drug as a selective inhibitor of co-translational protein translocation. PLoS Biol 12(12):e1002011 (2014).
Wintterle et al. Expression of the B7-related molecule B7-H1 by glioma cells: a potential mechanism of immune paralysis. Cancer Res. 63(21):7462-7467 (2003).
Xerri et al. Programmed death 1 is a marker of angioimmunoblastic T-cell lymphoma and B-cell small lymphocytic lymphoma/chronic lymphocytic leukemia. Hum Pathol. 39(7):1050-1058 (2008).
Yamamoto et al. PD-1-PD-1 ligand interaction contributes to immunosuppressive microenvironment of Hodgkin lymphoma. Blood 111(6):3220-3224 (2008).
Yao et al. CyTOF supports efficient detection of immune cell subsets from small samples. J Immunol Methods 415:1-5 (2014).
Ye et al. Interaction of B7-H1 on intrahepatic cholangiocarcinoma cells with PD-1 on tumorinfiltrating T cells as a mechanism of immune evasion. J Surg Oncol. 100(6):500-504 (2009).
Yokosuka et al. Programmed cell death 1 forms negative costimulatory microclusters that directly inhibit T cell receptor signaling by recruiting phosphatase SHP2. J Exp Med 209(6):1201-1217 (2012).
Yu et al. Wnt5a induces ROR1/ROR2 heterooligomerization to enhance leukemia chemotaxis and proliferation. J Clin Invest 126(2):585-98 (2016).
Zhang et al. The onco-embryonic antigen ROR1 is expressed by a variety of human cancers. Am J Path 181(6):1903-1910 (2012).
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Goldman et al. Enhancing Stability of Camelid and Shark Single Domain Antibodies: An Overview. Front. Immunol. 8:865 (2017).
Hassan et al. Preclinical evaluation of MORAb-009, a chimeric antibody targeting tumor-associated mesothelin. Cancer Immun. 7:20 (2007).
Ho et al. A novel high-affinity human monoclonal antibody to mesothelin. Int J Cancer 128:2020-2030 (2011).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Riechmann et al. Single domain antibodies: comparison of camel VH and camelised human VH domains. J Immunol Methods 231(1-2):25-38 (1999).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Vincke et al. General strategy to humanize a camelid single-domain antibody and identification of a universal humanized nanobody scaffold. J. Biol. Chem. 284(5):3273-3284 (2009).
Yu et al. Rationalization and design of the complementarity determining region sequences in an antibody-antigen recognition interface. PLoS One 7(3):e33340 (2012).
Brocker et al. Redirecting the complete T cell receptor/CD3 signaling machinery towards native antigen via modified T cell receptor. Eur J. Immunol 26:1770-1774 (1996).
Brocker et al. Signals through T cell receptor-zeta chain alone are insufficient to prime resting T lymphocytes. J Med Chem 181:1653-1659 (1995).
Brocker. Chimeric Fv-zeta or Fv-epsilon receptors are not sufficient to induce activation or cytokine production in peripheral T cells. Blood 96(5):1999-2001 (2000).
Mosquera et al. In vitro and in vivo characterization of a novel antibody-like single-chain TCR human IgG1 fusion protein. J Immunol 174(7):4381-4388 (2005).
Sommermeyer et al. Designer T cells by T cell receptor replacement. Eur J Immunol 36(11):3052-3059 (2006).
PCT/US2019/052270 International Search Report and Written Opinion dated Mar. 5, 2020.
PCT/US2019/052270 Invitation to Pay Additional Fees dated Jan. 9, 2020.
PCT/US2020/023928 International Search Report and Written Opinion dated Jun. 26, 2020.
Pipeline. A Broad Pipeline of T Cell Therapies For Solid And Hematologi Cancers. TCR2 Therapeutics. Available at https://www.tcr2.com/pipeline (Accessed Apr. 15, 2020) (5 pgs).
Rafiq et al. Targeted delivery of a PD-1-blocking scFv by CAR-T cells enhances anti-tumor efficacy in vivo. Nat Biotechnol 36(9):847-856 (2018).
Koneru et al. IL-12 secreting tumor-targeted chimeric antigen receptor T cells eradicate ovarian tumors in vivo. OncoImmunology 4(3):e994446 (2015).
PCT/US2019/043690 International Search Report and Written Opinion dated Jan. 17, 2020.
Tully et al. The reconstruction of 2,631 draft metagenome-assembled genomes from the global oceans. Sci Data 5:170203 w/Supp. Information (2018).

* cited by examiner

% of Activation: sum of CD25+, CD69+ and CD25+CD69+ cells

COMPOSITIONS AND METHODS FOR TCR REPROGRAMMING USING FUSION PROTEINS

CROSS REFERENCE

This application is a continuation U.S. application Ser. No. 15/888,897, filed on Feb. 5, 2018, which is a continuation of International Application No. PCT/US2017/55628, filed Oct. 6, 2017, which claims the benefit of U.S. Provisional Application No. 62/405,551, filed Oct. 7, 2016, and U.S. Provisional Application No. 62/510,108, filed May 23, 2017, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 5, 2018, is named "48538702302_SL.txt" and is 113,160 bytes in size.

BACKGROUND OF THE INVENTION

Most patients with late-stage solid tumors are incurable with standard therapy. In addition, traditional treatment options often have serious side effects. Numerous attempts have been made to engage a patient's immune system for rejecting cancerous cells, an approach collectively referred to as cancer immunotherapy. However, several obstacles make it rather difficult to achieve clinical effectiveness. Although hundreds of so-called tumor antigens have been identified, these are often derived from self and thus can direct the cancer immunotherapy against healthy tissue, or are poorly immunogenic. Furthermore, cancer cells use multiple mechanisms to render themselves invisible or hostile to the initiation and propagation of an immune attack by cancer immunotherapies.

Recent developments using chimeric antigen receptor (CAR) modified autologous T-cell therapy, which relies on redirecting genetically engineered T-cells to a suitable cell-surface molecule on cancer cells, show promising results in harnessing the power of the immune system to treat B cell malignancies (see, e.g., Sadelain et al., Cancer Discovery 3:388-398 (2013)). The clinical results with CD-19-specific CAR T-cells (called CTL019) have shown complete remissions in patients suffering from chronic lymphocytic leukemia (CLL) as well as in childhood acute lymphoblastic leukemia (ALL) (see, e.g., Kalos et al., Sci Transl Med 3:95ra73 (2011), Porter et al., NEJM 365:725-733 (2011), Grupp et al., NEJM 368:1509-1518 (2013)). An alternative approach is the use of T-cell receptor (TCR) alpha and beta chains selected for a tumor-associated peptide antigen for genetically engineering autologous T-cells. These TCR chains will form complete TCR complexes and provide the T-cells with a TCR for a second defined specificity. Encouraging results were obtained with engineered autologous T-cells expressing NY-ESO-1-specific TCR alpha and beta chains in patients with synovial carcinoma.

Besides the ability of genetically modified T-cells expressing a CAR or a second TCR to recognize and destroy respective target cells in vitro/ex vivo, successful patient therapy with engineered T-cells requires the T-cells to be capable of strong activation, expansion, persistence over time, and, in case of relapsing disease, to enable a 'memory' response. High and manageable clinical efficacy of CAR T-cells is currently limited to BCMA- and CD-19-positive B cell malignancies and to NY-ESO-1-peptide expressing synovial sarcoma patients expressing HLA-A2. There is a clear need to improve genetically engineered T-cells to more broadly act against various human malignancies. Described herein are novel fusion proteins of TCR subunits, including CD3 epsilon, CD3gamma and CD3 delta, and of TCR alpha and TCR beta chains with binding domains specific for cell surface antigens that have the potential to overcome limitations of existing approaches. Described herein are novel fusion proteins that more efficiently kill target cells than CARs, but release comparable or lower levels of pro-inflammatory cytokines. These fusion proteins and methods of their use represent an advantage for T-cell receptor (TCR) fusion proteins (TFPs) relative to CARs because elevated levels of these cytokines have been associated with dose-limiting toxicities for adoptive CAR-T therapies.

SUMMARY OF THE INVENTION

Provided herein are T-cell receptor (TCR) fusion proteins (TFPs), T-cells engineered to express one or more TFPs, and methods of use thereof for the treatment of diseases.

In one aspect, provided herein is an isolated recombinant nucleic acid molecule encoding a T-cell receptor (TCR) fusion protein (TFP) comprising a TCR subunit and a human or humanized antibody domain comprising an anti-mesothelin binding domain.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 epsilon; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 gamma; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 delta; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of TCR alpha; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of TCR beta; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit and a human or humanized antibody domain comprising an antigen binding domain that is an anti-mesothelin binding domain.

In some instances, the TCR subunit and the antibody domain are operatively linked. In some instances, the TFP incorporates into a TCR when expressed in a T-cell. In some instances, the encoded antigen binding domain is connected to the TCR extracellular domain by a linker sequence. In some instances, the encoded linker sequence comprises $(G_4S)_n$, wherein n=1 to 4. In some instances, the TCR subunit comprises a TCR extracellular domain. In some instances, the TCR subunit comprises a TCR transmembrane domain. In some instances, the TCR subunit comprises a TCR intracellular domain. In some instances, the TCR subunit comprises (i) a TCR extracellular domain, (ii) a TCR transmembrane domain, and (iii) a TCR intracellular domain, wherein at least two of (i), (ii), and (iii) are from the same TCR subunit. In some instances, the TCR subunit comprises a TCR intracellular domain comprising a stimulatory domain selected from an intracellular signaling domain of CD3 epsilon, CD3 gamma or CD3 delta, or an amino acid sequence having at least one, two or three modifications thereto. In some instances, the TCR subunit comprises an intracellular domain comprising a stimulatory domain selected from a functional signaling domain of 4-1BB and/or a functional signaling domain of CD3 zeta, or an amino acid sequence having at least one modification thereto. In some instances, the human or humanized antibody domain comprises an antibody fragment. In some instances, the human or humanized antibody domain comprises a scFv or a $V_H$ domain. In some instances, the isolated nucleic acid molecule encodes (i) a light chain (LC) CDR1, LC CDR2 and LC CDR3 of an anti-mesothelin light chain binding domain amino acid sequence with 70-100% sequence identity to a light chain (LC) CDR1, LC CDR2 and LC CDR3 of an anti-mesothelin light chain binding domain provided herein, respectively, and/or (ii) a heavy chain (HC) CDR1, HC CDR2 and HC CDR3 of an anti-mesothelin heavy chain binding domain amino acid sequence with 70-100% sequence identity to a heavy chain (HC) CDR1, HC CDR2 and HC CDR3 of an anti-mesothelin heavy chain binding domain provided herein, respectively. In some instances, the isolated nucleic acid molecule encodes a light chain variable region, wherein the light chain variable region comprises an amino acid sequence having at least one but not more than 30 modifications of a light chain variable region amino acid sequence of a light chain variable region provided herein, or a sequence with 95-99% identity to a light chain variable region amino acid sequence of a light chain variable region provided herein. In some instances, the isolated nucleic acid molecule encodes a heavy chain variable region, wherein the heavy chain variable region comprises an amino acid sequence having at least one but not more than 30 modifications of a heavy chain variable region amino acid sequence of a heavy chain variable region provided herein, or a sequence with 95-99% identity to a heavy chain variable region amino acid sequence of a heavy chain variable region provided herein. In some instances, the TFP includes an extracellular domain of a TCR subunit that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the encoded TFP includes a transmembrane domain that comprises a transmembrane domain of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the encoded TFP includes a transmembrane domain that comprises a transmembrane domain of a protein selected from the group consisting of a TCR alpha chain, a TCR beta chain, a TCR zeta chain, a CD3 epsilon TCR subunit, a CD3 gamma TCR subunit, a CD3 delta TCR subunit, CD45, CD2, CD4, CD5, CD8, CD9, CD16, CD22, CD33, CD28, CD37, CD64, CD80, CD86, CD134, CD137, CD154, functional fragments thereof, and amino acid sequences thereof having at least one but not more than 20 modifications. In some instances, the isolated nucleic acid molecule further comprises a sequence encoding a costimulatory domain. In some instances, the costimulatory domain is a functional signaling domain obtained from a protein selected from the group consisting of DAP10, DAP12, CD30, LIGHT, OX40, CD2, CD27, CD28, CDS, ICAM-1, LFA-1 (CD11a/CD18), ICOS (CD278), and 4-1BB (CD137), and amino acid sequences thereof having at least one but not more than 20 modifications thereto. In some instances, the isolated nucleic acid molecule further comprises a leader sequence. In some instances, the isolated nucleic acid molecule is mRNA.

In some instances, the TFP includes an immunoreceptor tyrosine-based activation motif (ITAM) of a TCR subunit that comprises an ITAM or portion thereof of a protein selected from the group consisting of CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some instances, the ITAM replaces an ITAM of CD3 gamma, CD3 delta, or CD3 epsilon. In some instances, the ITAM is selected from the group consisting of CD3 zeta TCR subunit, CD3 epsilon TCR subunit, CD3 gamma TCR subunit, and CD3 delta TCR subunit and replaces a different ITAM selected from the group consisting of CD3 zeta TCR subunit, CD3 epsilon TCR subunit, CD3 gamma TCR subunit, and CD3 delta TCR subunit.

In some instances, the nucleic acid comprises a nucleotide analog. In some instances, the nucleotide analog is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA) modified, a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

In one aspect, provided herein is an isolated polypeptide molecule encoded by a nucleic acid molecule provided herein.

In one aspect, provided herein is an isolated TFP molecule comprising a human or humanized anti-mesothelin binding domain, a TCR extracellular domain, a transmembrane domain, and an intracellular domain.

In one aspect, provided herein is an isolated TFP molecule comprising a human or humanized anti-mesothelin binding domain, a TCR extracellular domain, a transmembrane domain, and an intracellular signaling domain, wherein the TFP molecule is capable of functionally interacting with an endogenous TCR complex and/or at least one endogenous TCR polypeptide.

In some embodiments, the human or humanized antibody domain comprising an antigen binding domain that is an anti-mesothelin binding domain encoded by the nucleic acid, or an antibody comprising the anti-mesothelin binding domain, or a cell expressing the anti-mesothelin binding domain encoded by the nucleic acid has an affinity value of at most about 200 nM, 100 nM, 75 nM, a 50 nM, 25 nM, 20 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM; and/or at least about 100 nM, 75 nM, a 50 nM, 25 nM, 20 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM; and or about 200 nM, 100 nM, 75 nM, a 50 nM, 25 nM, 20 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM.

In one aspect, provided herein is an isolated TFP molecule comprising a human or humanized anti-mesothelin binding domain, a TCR extracellular domain, a transmembrane domain, and an intracellular signaling domain, wherein the TFP molecule is capable of functionally integrating into an endogenous TCR complex In some instances, the isolated TFP molecule comprises an antibody or antibody fragment comprising a human or humanized anti-mesothelin binding domain, a TCR extracellular domain, a transmembrane domain, and an intracellular domain. In some instances, the anti-mesothelin binding domain is a scFv, a $V_H$ domain, or a camelid $V_{HH}$ domain. In some instances, the anti-mesothelin binding domain comprises a heavy chain with 95-100% identity to an amino acid sequence of a heavy chain provided herein, a functional fragment thereof, or an amino acid sequence thereof having at least one but not more than 30 modifications. In some instances, the anti-mesothelin binding domain comprises a light chain with 95-100% identity to an amino acid sequence of a light chain provided herein, a functional fragment thereof, or an amino acid sequence thereof having at least one but not more than 30 modifications. In some instances, the isolated TFP molecule comprises a TCR extracellular domain that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the anti-mesothelin binding domain is connected to the TCR extracellular domain by a linker sequence. In some instances, the linker region comprises $(G_4S)_n$, wherein n=1 to 4.

In some instances, the isolated TFP molecule further comprises a sequence encoding a costimulatory domain. In some instances, the isolated TFP molecule further comprises a sequence encoding an intracellular signaling domain. In some instances, the isolated TFP molecule further comprises a leader sequence.

In one aspect, provided herein is a vector comprising a nucleic acid molecule encoding a TFP provided herein. In some instances, the vector is selected from the group consisting of a DNA, a RNA, a plasmid, a lentivirus vector, adenoviral vector, a Rous sarcoma viral (RSV) vector, or a retrovirus vector. In some instances, the vector further comprises a promoter. In some instances, the vector is an in vitro transcribed vector. In some instances, a nucleic acid sequence in the vector further comprises a poly(A) tail. In some instances, a nucleic acid sequence in the vector further comprises a 3'UTR.

In one aspect, provided herein is a cell comprising a vector provided herein. In some instances, the cell is a human T-cell. In some instances, the T-cell is a CD8+ or CD4+ T-cell. In some instances, the T cell is a gamma delta T cell. In some instances, the T cell is an NK-T cell. In some instances, the cell further comprises a nucleic acid encoding an inhibitory molecule that comprises a first polypeptide that comprises at least a portion of an inhibitory molecule, associated with a second polypeptide that comprises a positive signal from an intracellular signaling domain. In some instances, the inhibitory molecule comprise first polypeptide that comprises at least a portion of PD1 and a second polypeptide comprising a costimulatory domain and primary signaling domain.

In one aspect, provided herein is a human CD8+ or CD4+ T-cell comprising at least two TFP molecules, the TFP molecules comprising a human or humanized anti-mesothelin binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In one aspect, provided herein is a protein complex comprising: a TFP molecule comprising a human or humanized anti-mesothelin binding domain, a TCR extracellular domain, a transmembrane domain, and an intracellular domain; and at least one endogenous TCR complex.

In some instances, the TCR comprises an extracellular domain or portion thereof of a protein selected from the group consisting of TCR alpha chain, a TCR beta chain, a CD3 epsilon TCR subunit, a CD3 gamma TCR subunit, and a CD3 delta TCR subunit. In some instances, the anti-mesothelin binding domain is connected to the TCR extracellular domain by a linker sequence. In some instances, the linker region comprises $(G_4S)_n$, wherein n=1 to 4.

In one aspect, provided herein is a human CD8+ or CD4+ T-cell comprising at least two different TFP proteins per a protein complex provided herein.

In one aspect, provided herein is a method of making a cell comprising transducing a T-cell with a vector provided herein.

In one aspect, provided herein is a method of generating a population of RNA-engineered cells comprising introducing an in vitro transcribed RNA or synthetic RNA into a cell, where the RNA comprises a nucleic acid encoding a TFP molecule provided herein.

In one aspect, provided herein is a method of providing an anti-tumor immunity in a mammal comprising administering to the mammal an effective amount of a cell expressing a TFP molecule provided herein, or expressing a polypeptide molecule provided herein.

In some instances, the cell is an autologous T-cell. In some instances, the cell is an allogeneic T-cell. In some instances, the mammal is a human.

In one aspect, provided herein is a method of treating a mammal having a disease associated with expression of mesothelin comprising administering to the mammal an effective amount of a TFP molecule provided herein, a cell provided herein, or a polypeptide molecule provided herein. In some instances, the disease associated with mesothelin expression is selected from the group consisting of a proliferative disease, a cancer, a malignancy, and a non-cancer related indication associated with expression of mesothelin. In some instances, the disease is a cancer selected from the group consisting of mesothelioma, renal cell carcinoma, stomach cancer, breast cancer, lung cancer, ovarian cancer, prostate cancer, colon cancer, cervical cancer, brain cancer, liver cancer, pancreatic cancer, thyroid cancer, bladder cancer, ureter cancer, kidney cancer, endometrial cancer, esophageal cancer, gastric cancer, thymic carcinoma, cholangiocarcinoma and stomach cancer.

In some instances, the disease is cancer. In some instances, the disease is selected from the group consisting of mesothelioma, papillary serous ovarian adenocarcinoma, clear cell ovarian carcinoma, mixed Mullerian ovarian carcinoma, endometroid mucinous ovarian carcinoma, malignant pleural disease, pancreatic adenocarcinoma, ductal pancreatic adenocarcinoma, uterine serous carcinoma, lung adenocarcinoma, extrahepatic bile duct carcinoma, gastric adenocarcinoma, esophageal adenocarcinoma, colorectal adenocarcinoma, breast adenocarcinoma, a disease associated with mesothelin expression, a disease associated with mesothelin expression, non-mucinous ovarian carcinoma, invasive ductal adenocarcinoma, pulmonary adenocarcinoma, gastric/esophageal adenocarcinoma, colorectal adenocarcinoma, leukemia, pediatric acute myeloid leukemia, invasive intraductal papillary mucinous neoplasm (IPMN), endometrial adenocarcinoma, stomach/esophagus adenocarcinoma, pulmonary adenocarcinoma, breast adenocarcinoma, and combinations thereof.

In some instances, the cells expressing a TFP molecule are administered in combination with an agent that increases the efficacy of a cell expressing a TFP molecule. In some instances, less cytokines are released in the mammal compared a mammal administered an effective amount of a T-cell expressing an anti-mesothelin chimeric antigen receptor (CAR). In some instances, the cells expressing a TFP molecule are administered in combination with an agent that ameliorates one or more side effects associated with administration of a cell expressing a TFP molecule. In some instances, the cells expressing a TFP molecule are administered in combination with an agent that treats the disease associated with mesothelin.

In one aspect, an isolated nucleic acid molecule provided herein, an isolated polypeptide molecule provided herein, an isolated TFP provided herein, a complex provided herein, a vector provided herein, or a cell provided herein, is for use as a medicament.

In one aspect, provided herein is a method of treating a mammal having a disease associated with expression of mesothelin comprising administering to the mammal an effective amount of a TFP molecule provided herein, a cell provided herein, or a polypeptide molecule provided herein, wherein less cytokines are released in the mammal compared a mammal administered an effective amount of a T-cell expressing an anti-mesothelin chimeric antigen receptor (CAR).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustration denoted scFv:TCR-Vα illustrates an exemplary reprogrammed TCR containing a TFP that contains an anti-mesothelin scFv and a full-length TCR-Vα polypeptide fused via a $(G_4S)_3$ linker sequence. FIG. 2B illustration denoted scFv:TCR-Vα:TCR-Vβ illustrates an exemplary reprogrammed TCR that contain multiple TFPs including i) an anti-mesothelin scFv and a full-length TCR-Vα polypeptide fused via a $(G_4S)_3$ linker sequence and ii) an anti-mesothelin scFv and a full-length TCR-Vβ polypeptide fused via a $(G_4S)_3$ linker sequence. FIG. 2C illustration denoted scFv:ΔTCR-Vα:CD3ε illustrates an exemplary reprogrammed TCR that contains multiple TFPs including i) an anti-mesothelin scFv and a truncated (Δ) TCR polypeptide fused via a $(G_4S)_3$ linker sequence and ii) an anti-mesothelin scFv and a full-length CD3 epsilon polypeptide fused via a $(G_4S)_3$ linker sequence. The truncated (Δ) TCR polypeptide is truncated by the deletion of the Vα. FIG. 2D illustration denoted scFv:ΔTCR-Vα:ΔTCR-Vβ illustrates an exemplary reprogrammed TCR that contains multiple TFPs including i) an anti-mesothelin scFv and a truncated (Δ)

TCR Vα polypeptide fused via a $(G_4S)_3$ linker sequence and ii) an anti-mesothelin scFv and a truncated (Δ) TCR Vβ polypeptide fused via a $(G_4S)_3$ linker sequence. The truncated (Δ) TCR polypeptide is truncated by the deletion of the Vβ.

Figure 1:
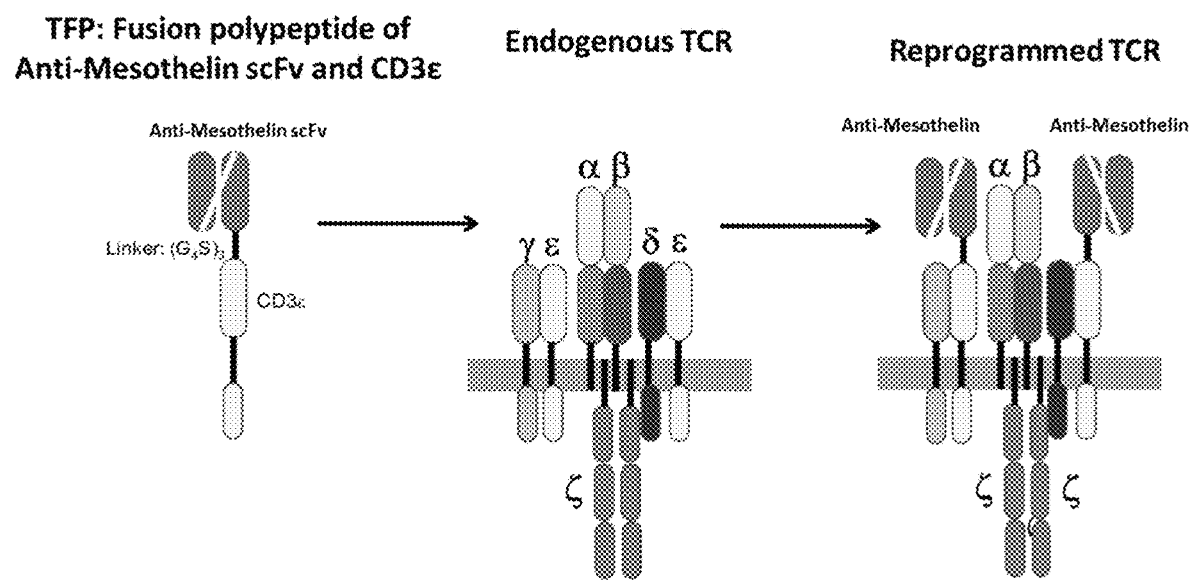
FIG. 1 is a schematic illustration demonstrating the use of T-cell receptor fusion polypeptides (TFPs) of the invention. An exemplary TFP contains an anti-mesothelin scFv and a full-length CD3 epsilon polypeptide fused via a $(G_4S)_3$ linker sequence. When produced by or introduced into a T-cell, the TFP associates with other polypeptides of the endogenous T-cell receptor (TCR) (shown to include two CD3 epsilon polypeptides, one CD3 gamma polypeptide, one CD3 delta polypeptide, two CD3 zeta polypeptides, one TCR alpha subunit and one TCR beta subunit, where the horizontal grey segment represents the plasma membrane) to form a reprogrammed TCR in which one or both of the endogenous CD3 epsilon polypeptides are substituted by the TFP.
Figures 2A, 2B, 2C, 2D:
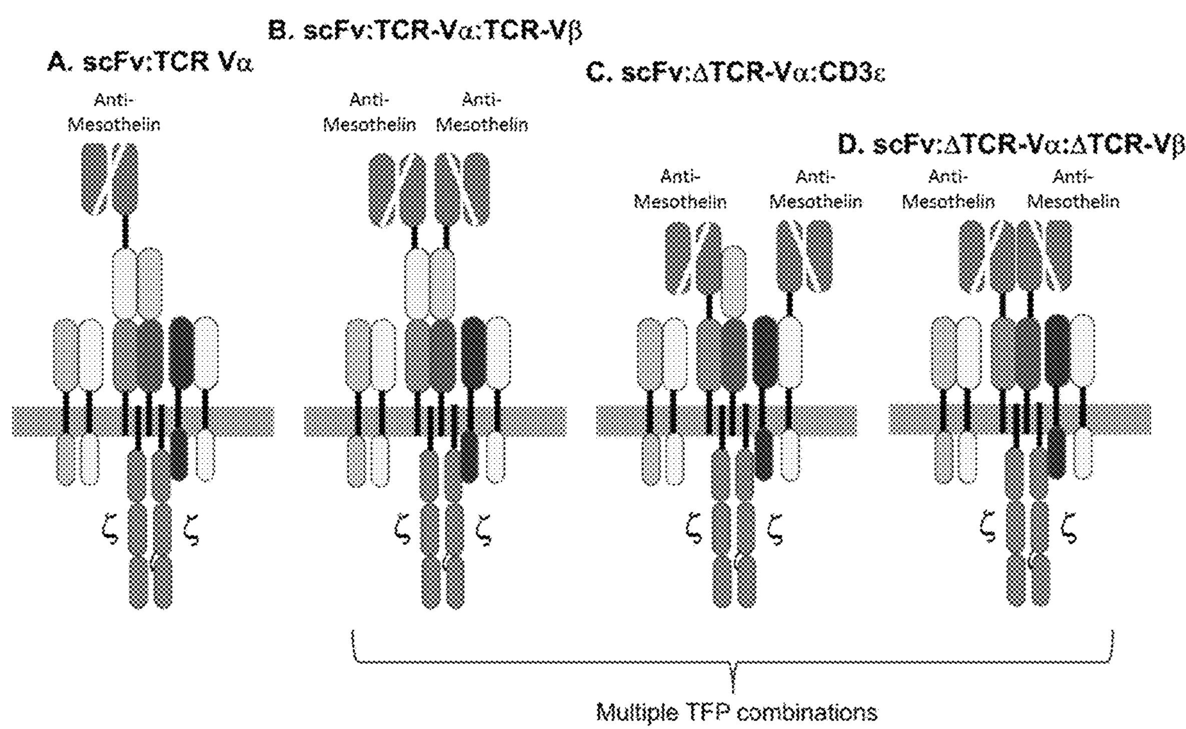
FIGS. 2A-D represents schematic illustrations demonstrating exemplary variations of reprogrammed T-cell receptor fusion polypeptides (TFPs) of the invention.
Figure 3:
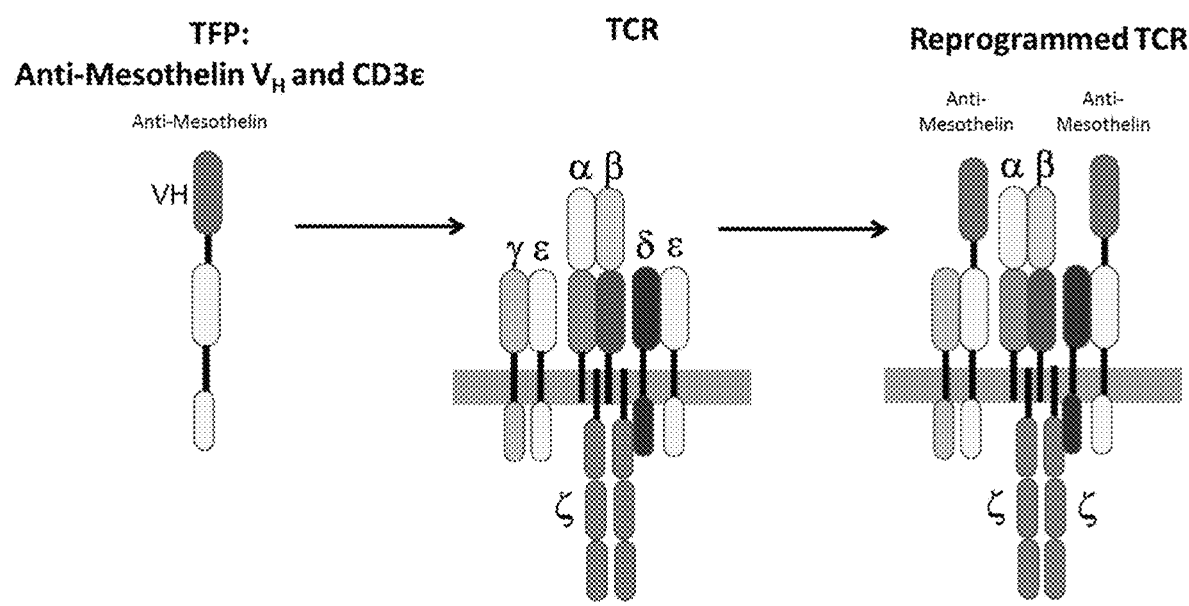

FIG. 3 is a schematic illustration demonstrating the use of T-cell receptor fusion polypeptides (TFPs) of the invention. An exemplary TFP contains an anti-mesothelin $V_H$ domain and a full-length CD3 epsilon polypeptide fused via a $(G_4S)_3$ linker sequence. When produced by a T-cell or introduced into a T-cell, the TFP associates with other polypeptides of the endogenous T-cell receptor (TCR) (shown to include two CD3 epsilon polypeptides, one CD3 gamma polypeptide, one CD3 delta polypeptide, two CD3 zeta polypeptides, one TCR alpha subunit and one TCR beta subunit, where the horizontal grey segment represents the plasma membrane) to form a reprogrammed TCR in which one or both of the endogenous CD3 epsilon polypeptides are substituted by the TFP.

Figure 4:
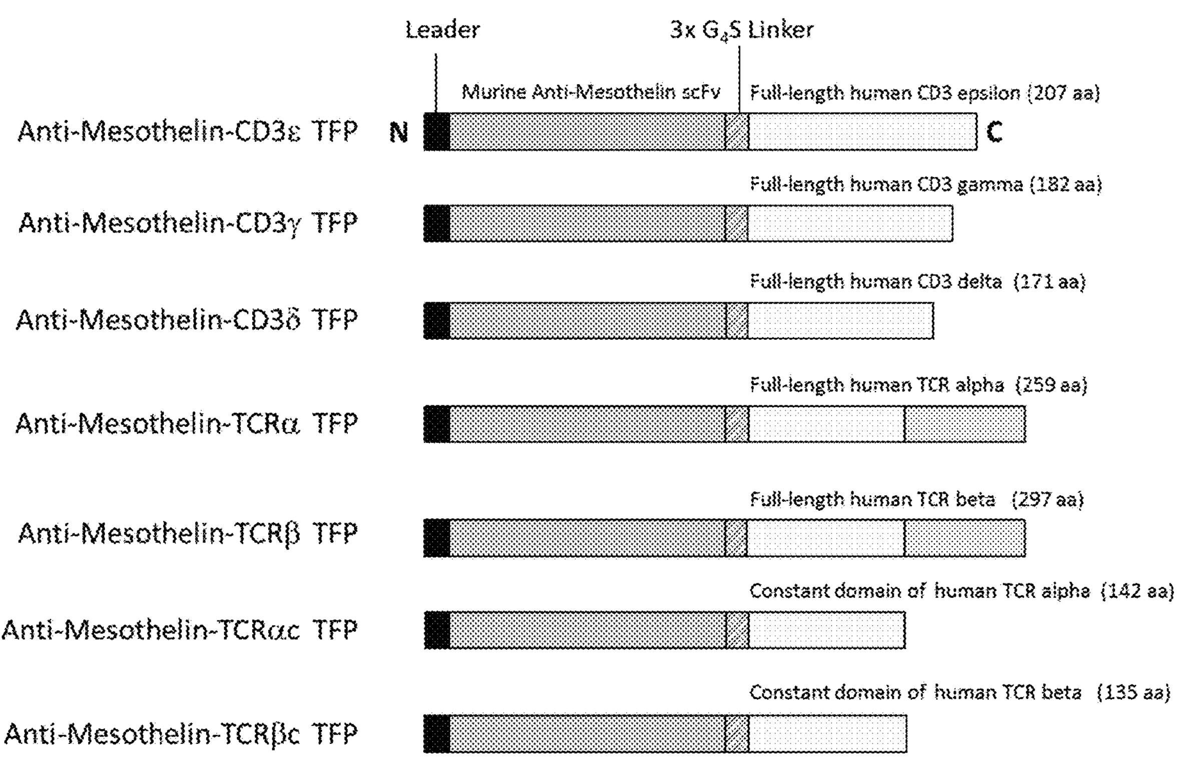

FIG. 4 is a series of schematic illustrations demonstrating DNA constructs encoding various TFPs.

Figure 5A:
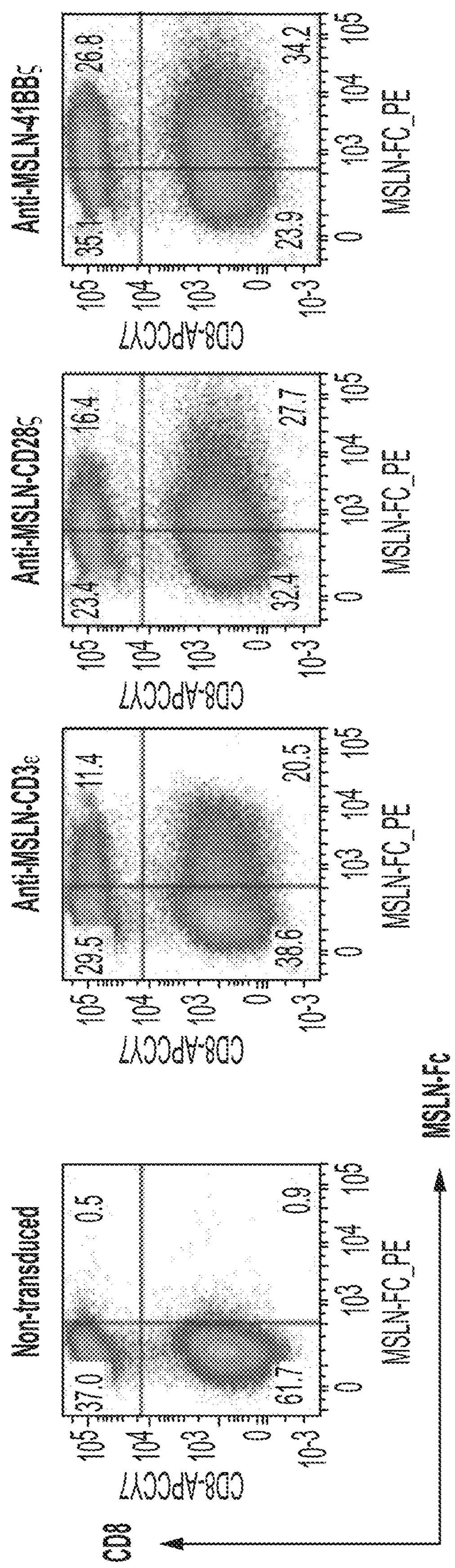

FIG. 5A depicts exemplary surface expression analysis of TFPs on activated PBMC cells and shows $CD3^+$ cells (anti-CD3 APC, gate) activated with MSLN TFPs and stained for CD8 (anti-CD8 APCCy7, y-axes) and mesothelin ("MSLN") (Zenon® R-Phycoerythrin-labeled hMSLN IgG, x-axes). Shown from left to right are cells that were either non-transduced or transduced with anti-MSLN-CD3ε TFP, anti-MSLN-CD28ζ CAR, and anti-MSLN-41BBζ CAR constructs.

Figure 5B:
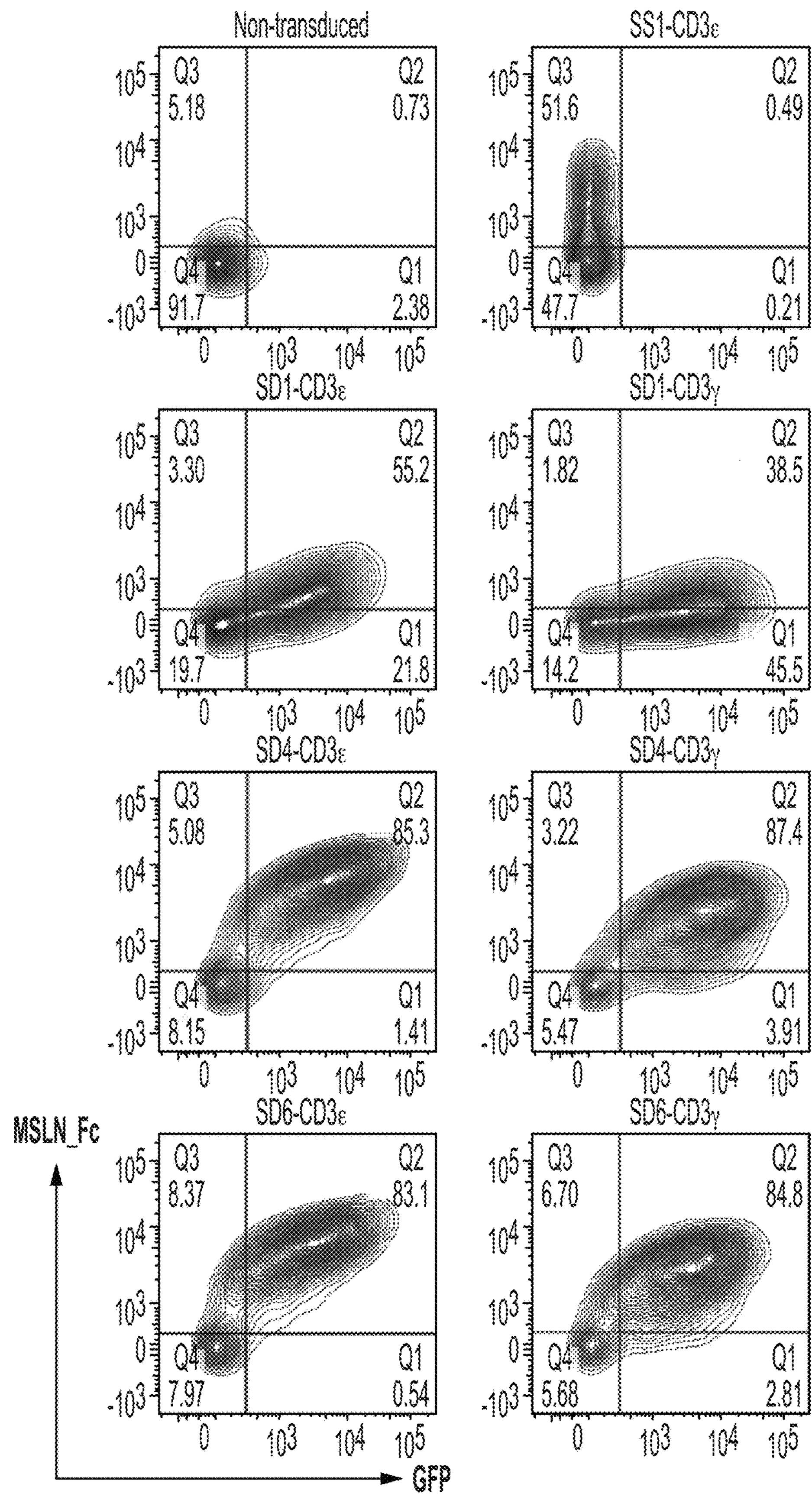
Figure 5B:
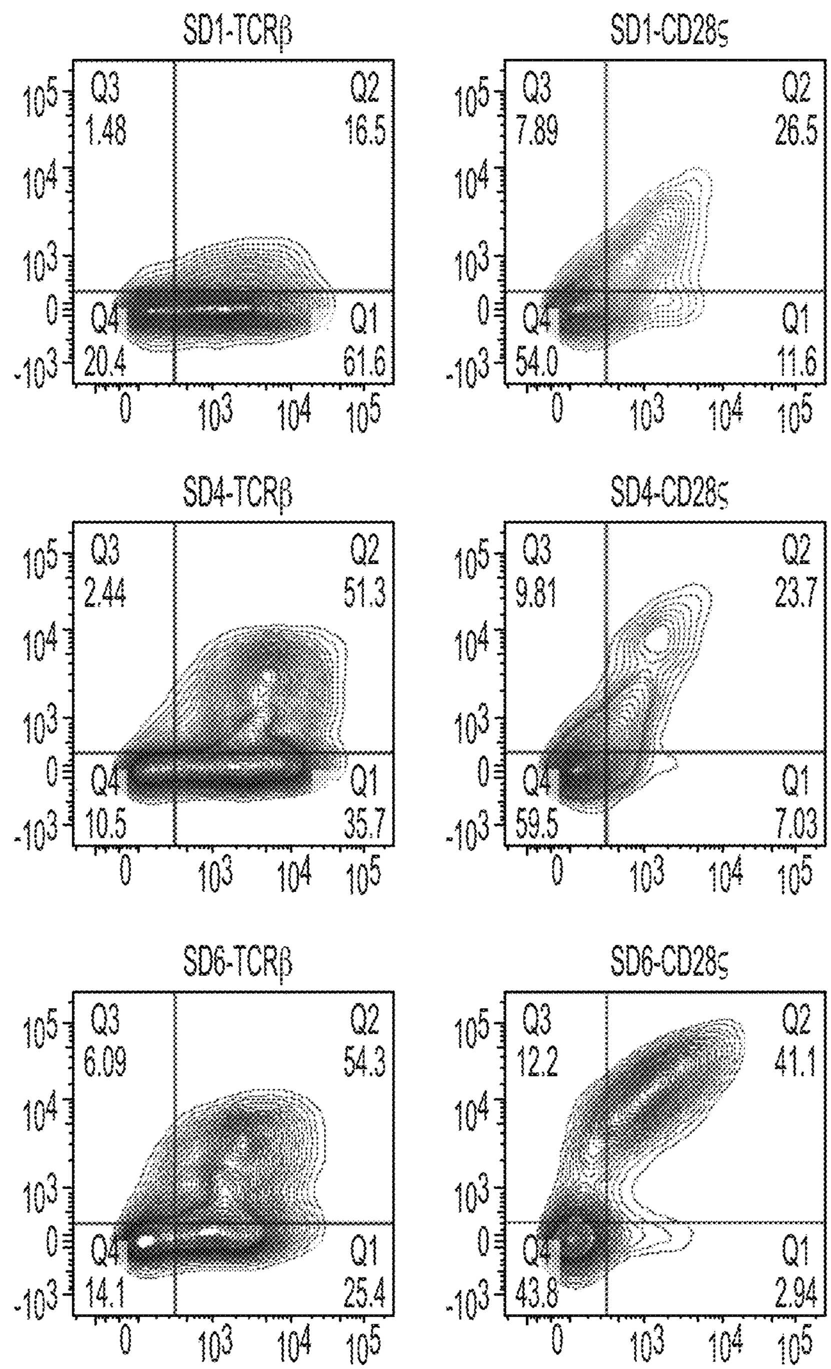

FIG. 5B depicts exemplary surface expression analysis of TFPs on activated PBMC cells and shows cells activated with in-house single domain TFPs and stained for MSLN Fc and and analyzed for GFP. The top row shows (from left to right) non-transduced cells, and cells transduced with a control anti-MSLN-CD3ε TFP ("SS1"). Rows 2-4 show the anti-MSLN binders SD1, SD4, and SD6, respectively, in cells transduced with GFP-tagged (from left to right) CD3ε TFP, CD3γTFP, TCRβ TFP, and CD2ζ CAR constructs.

Figure 6A:
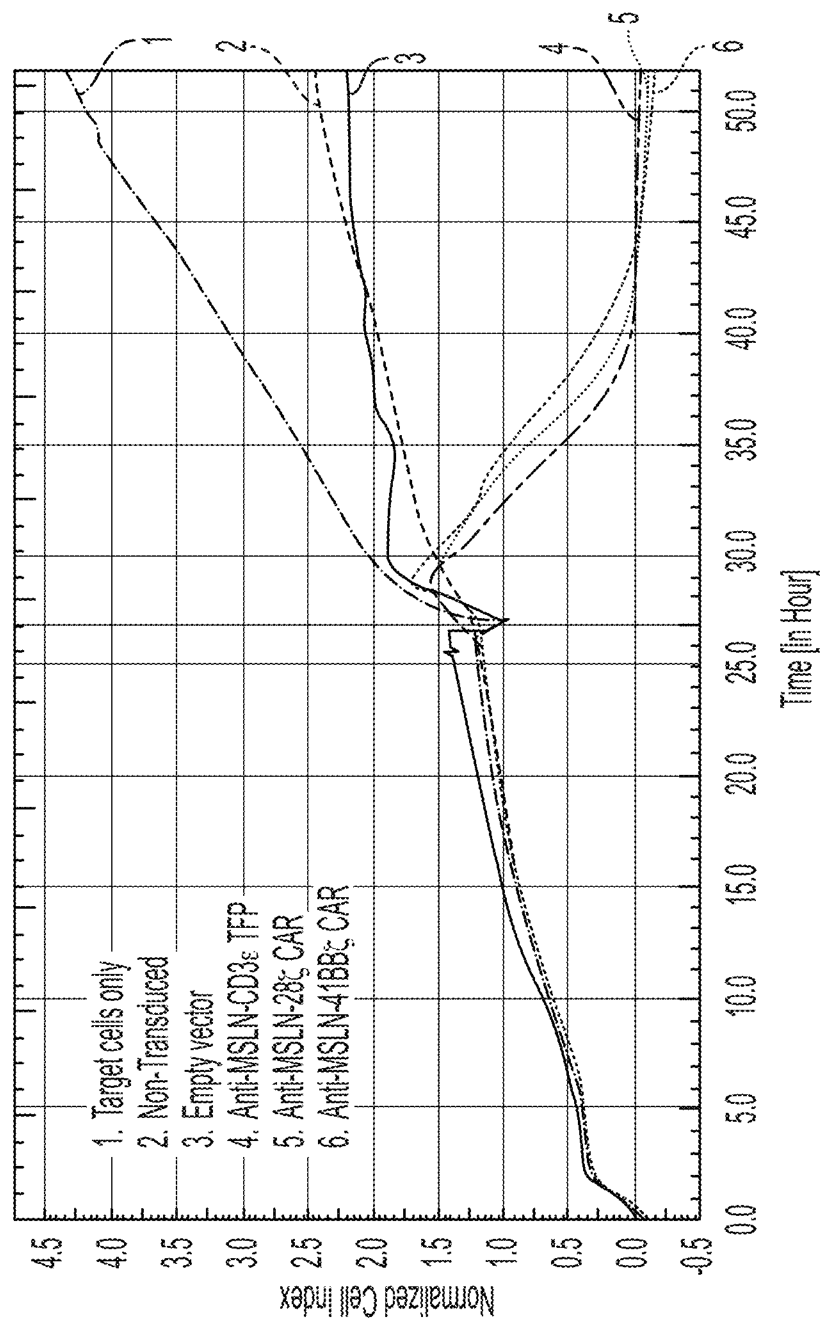

FIG. 6A is an exemplary graph depicting killing of mesothelin (MSLN)-positive HeLa (cervical adenocarcinoma, ATCC® CCL-2™) target cells by anti-MSLN-TFP constructs over time. Activated PBMCs were untreated (trace #1), non-transduced (trace #2), or transduced with empty vector (trace #3), anti-MSLN-CD3ε TFP (trace #4), anti-MSLN-CD28ζ CAR, or anti-MSLN-41BBζ CAR and expanded for 8 days prior to incubation with $1\times10^4$ MSLN-positive HeLa target cells.

Figure 6B:
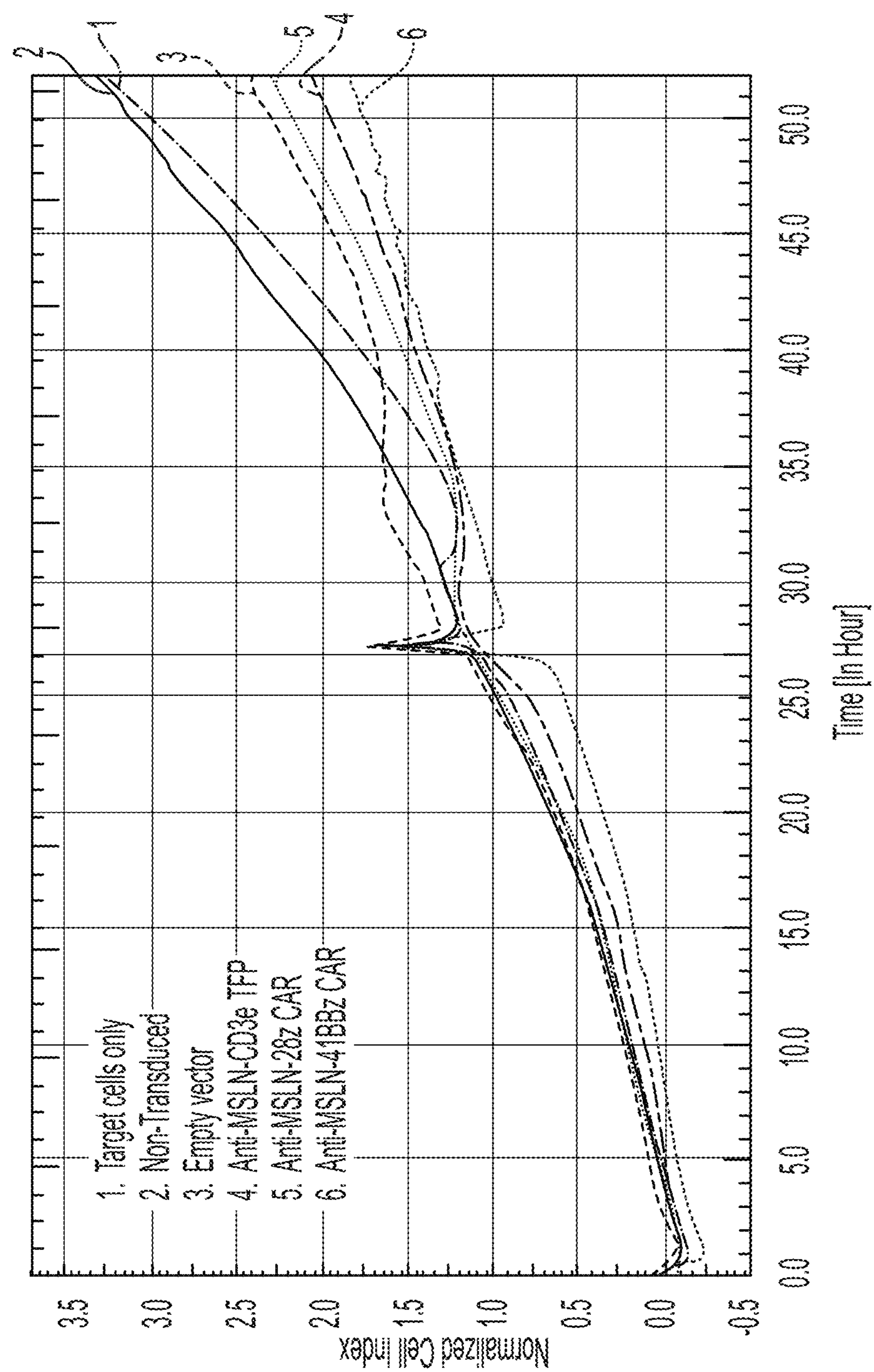

FIG. 6B is an exemplary graph depicting killing of MSLN-negative HeLa (cervical adenocarcinoma, ATCC® CCL-2™) target cells by anti-MSLN-TFP constructs over time. Activated PBMCs were untreated (trace #1), non-transduced (trace #2), or transduced with empty vector (trace #3), anti-MSLN-CD3ε TFP (trace #4), anti-MSLN-CD28ζ CAR, or anti-MSLN-41BBζ CAR and expanded for 8 days prior to incubation with $1\times10^4$ MSLN-positive HeLa target cells.

Figure 6C:
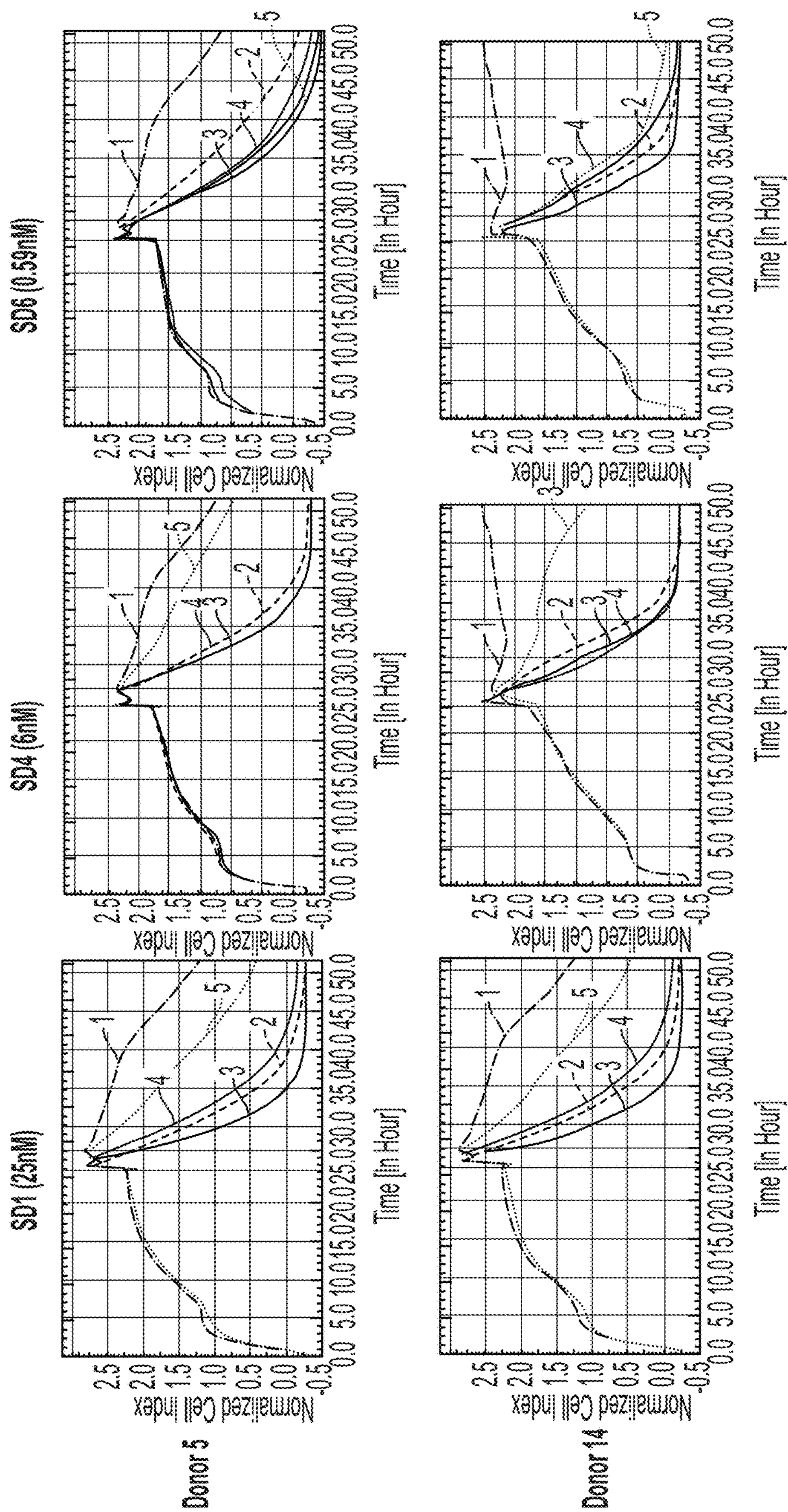

FIG. 6C shows killing of MSLN-positive cells in a high MSLN-expressing cell line (HeLa cells) using T cells from two different human donors (top and bottom). Shown are the cell killing traces for TFP T cells with the in-house anti-MSLN binders SD1 (FIG. 7A), SD4 (middle), and SD6 (right). Activated PBMCs were nontransduced (trace #1), or transduced with CD3ε TFP (trace #2), CD3γ TFP (trace #3), TCRβ TFP (trace #4), or CD28ζ CAR. The normalized cell index, indicative of cytotoxicity, was determined in a real time cell analyzer (RTCA) assay.

Figure 7A:
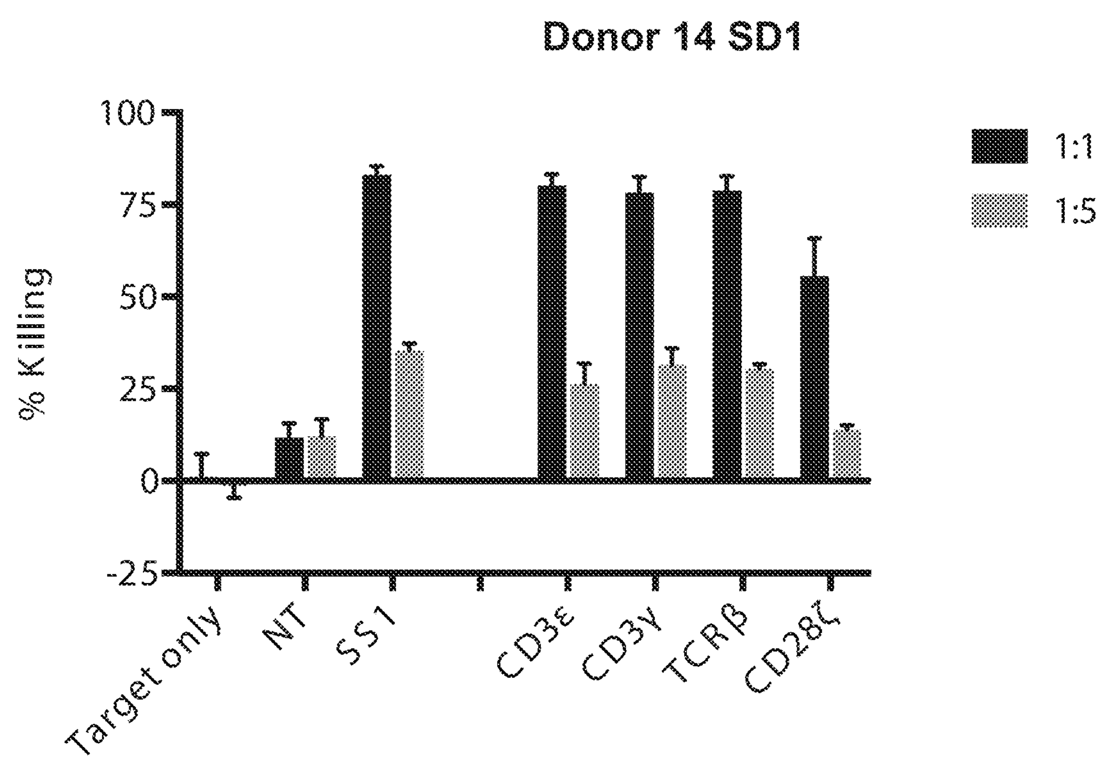
Figure 7B:
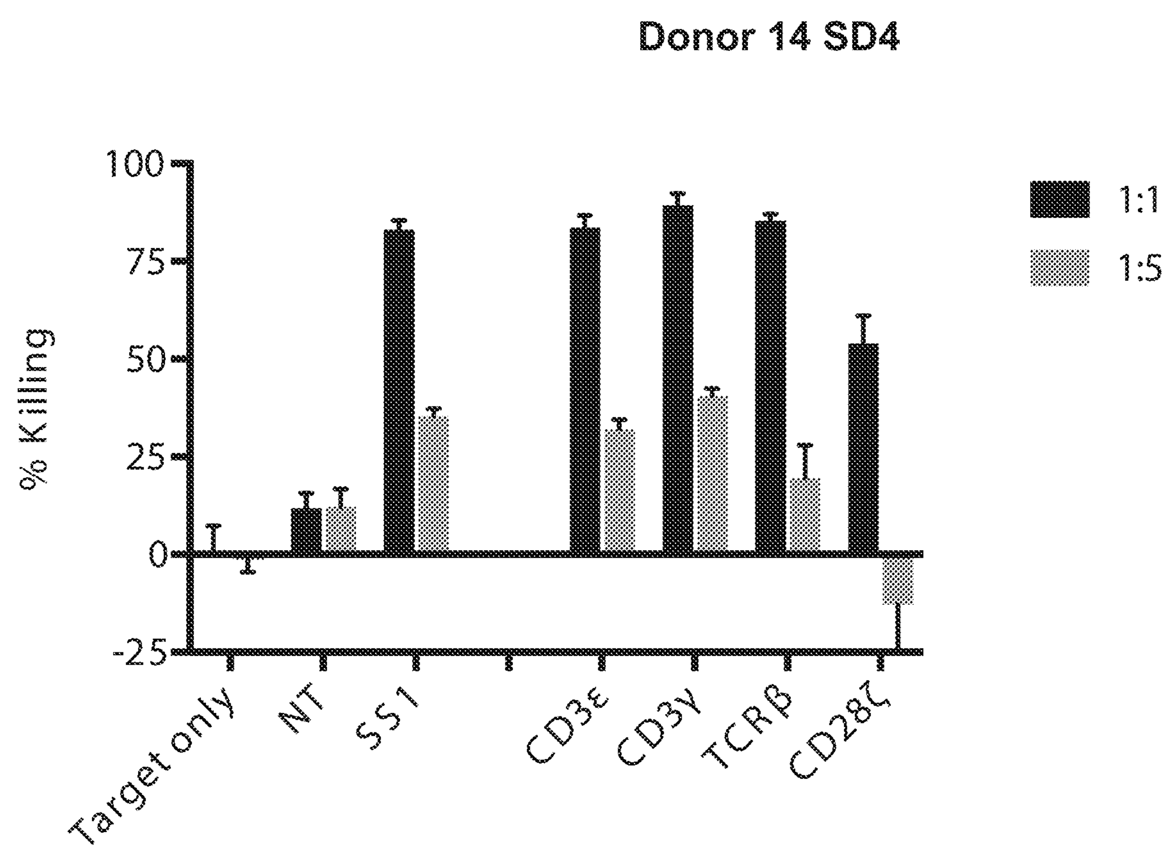
Figure 7C:
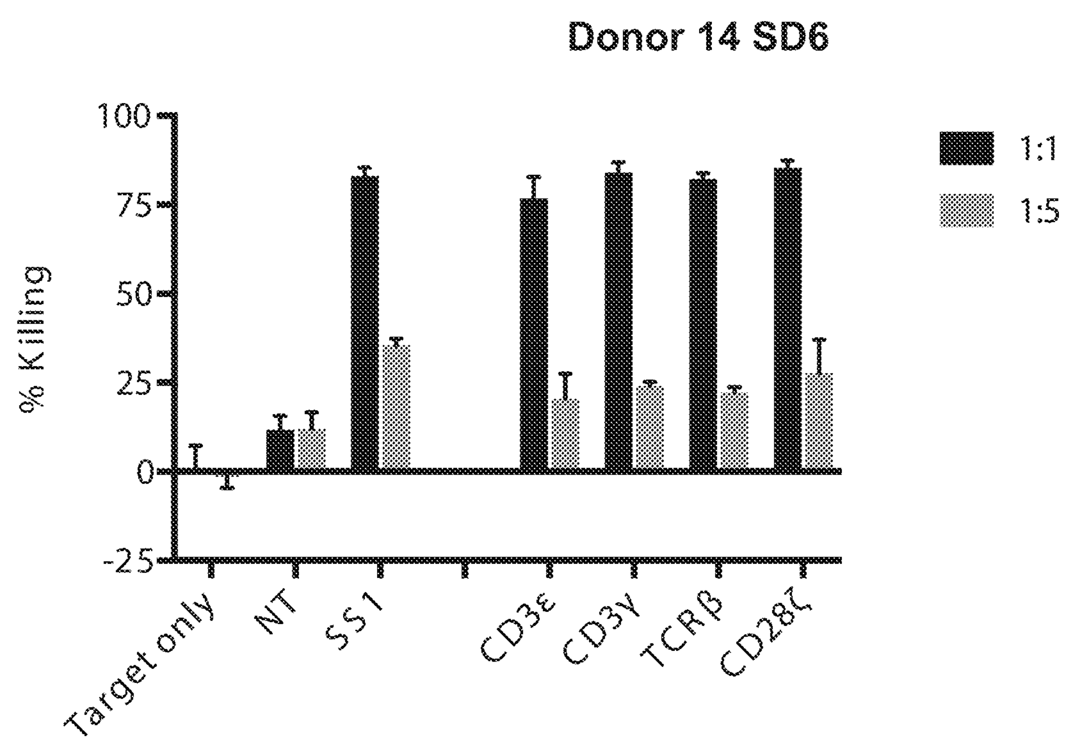

FIGS. 7A-C are a series of graphs showing binding activity of anti-MSLN CAR T cells and TFP T cells against a target cell line expressing high levels of mesothelin (HeLa-Luc($^{MSLN\ high}$)). Shown are the % of cells killed in samples with no T cells ("target only"), empty vector transduced ("NT"), anti-MSLN (positive control), or anti-mesothelin TFP T cells with in-house anti-mesothelin binders SD1 (FIG. 7A), SD4 (FIG. 7B), and SD6 (FIG. 7C), each in each in the format of CD3ε TFP, CD3γ TFP, TCRβ TFP, and CD28ζ CAR. In each graph, black bars represent a 1:1 ratio of T cells to target cells, and gray bars represent a 1:5 ratio of T cells to target cells. Similar results were seen for a second T cell donor.

Figure 8A:
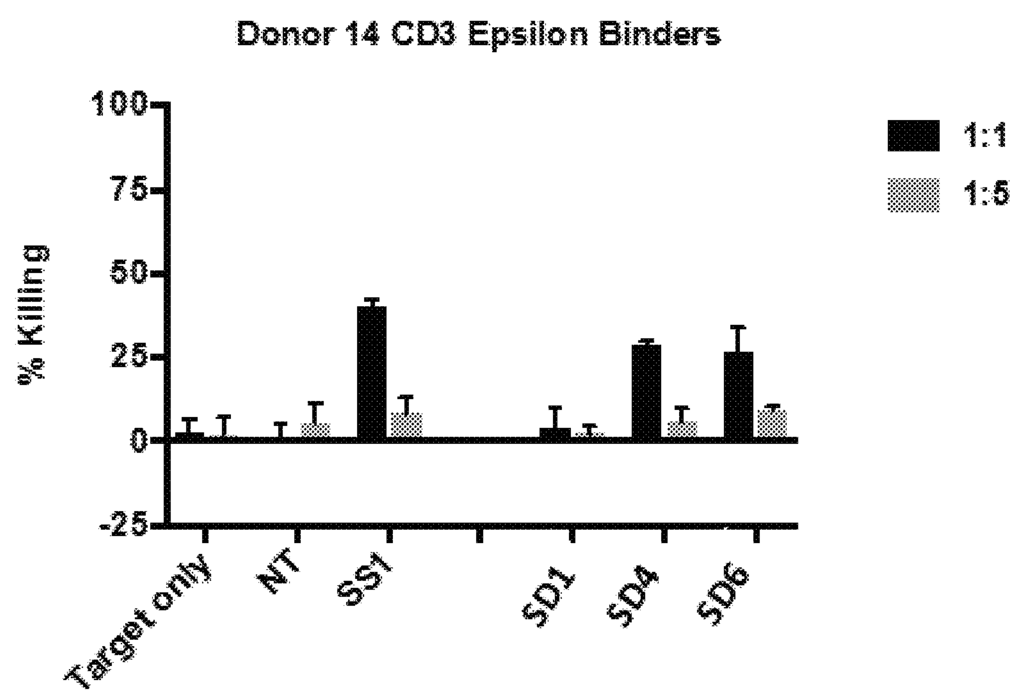
Figure 8B:
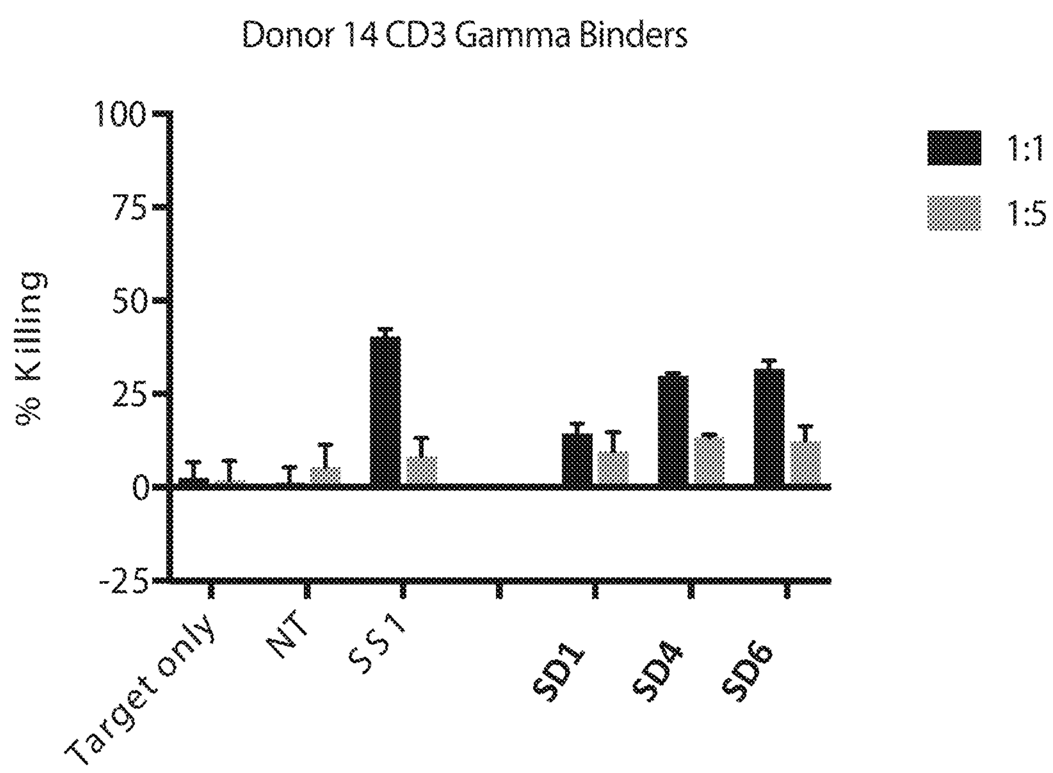
Figure 8C:
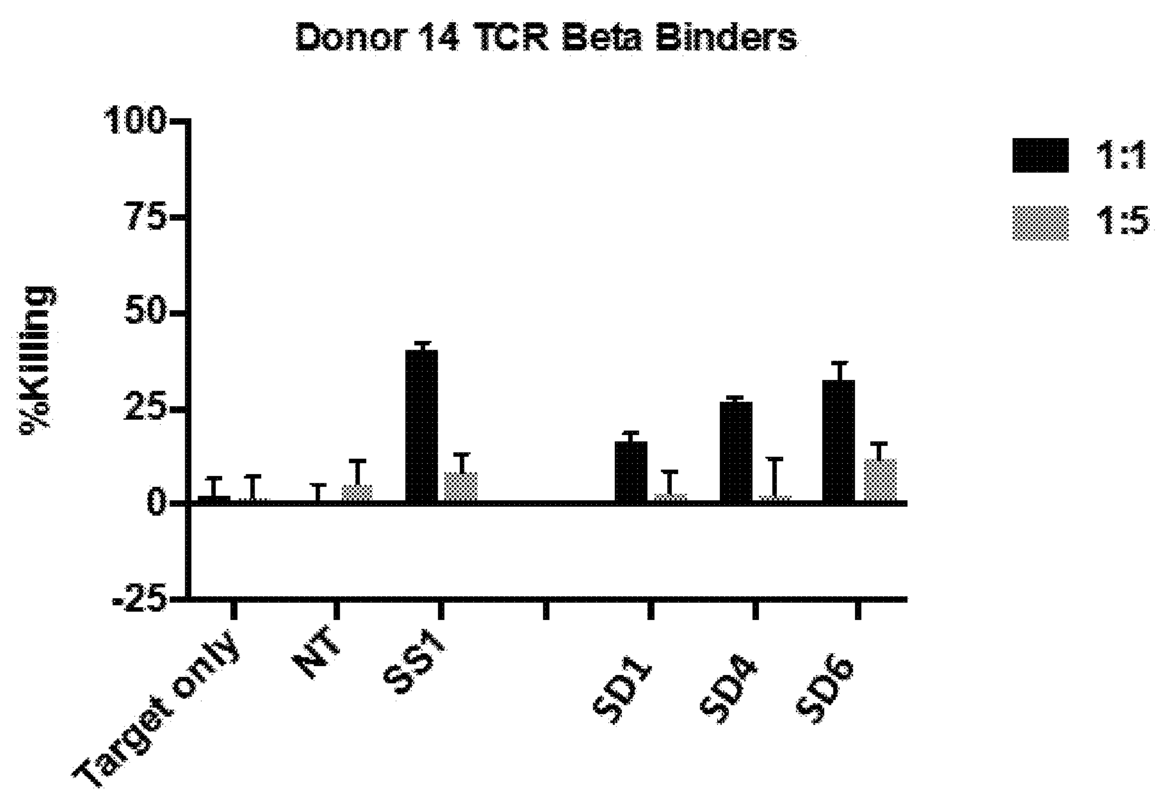
Figure 8D:
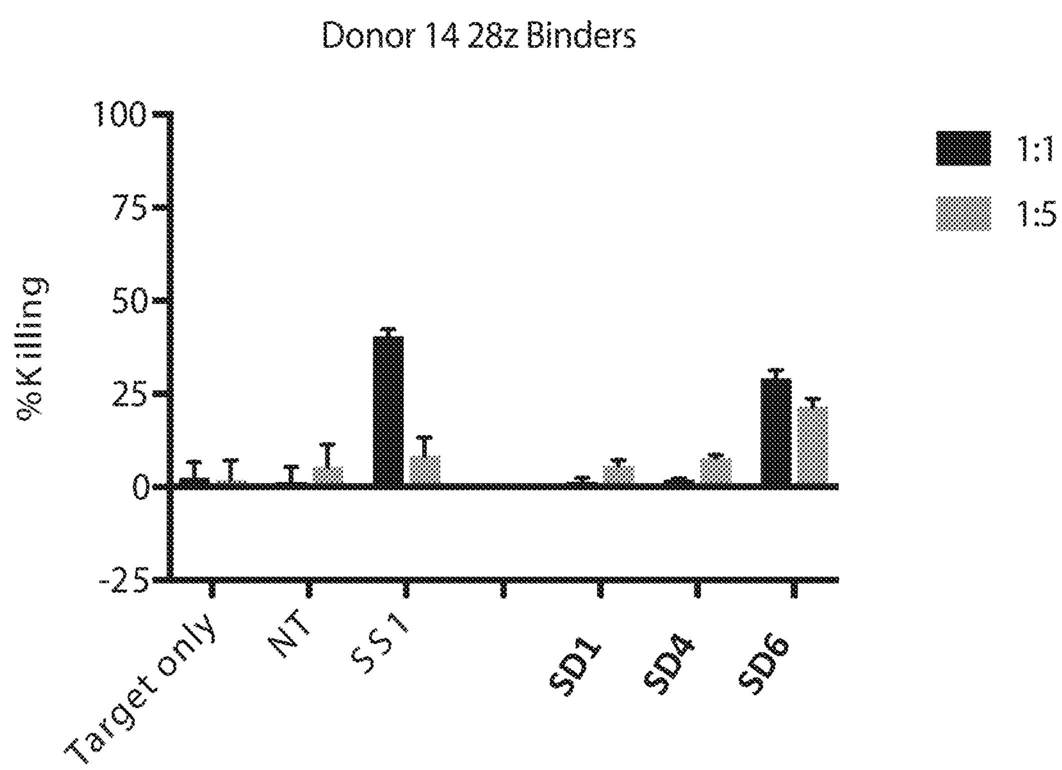

FIGS. 8A-D are a series of graphs showing the activity of anti-MSLN CAR T cells and TFP T cells against a target cell line expressing low levels of mesothelin (PC3-MSLN($^{-/low}$)). Shown are the % of cells killed in samples with no T cells ("target only"), empty vector transduced ("NT"), anti-MSLN (positive control, "SS1"), or in-house anti-mesothelin constructs SD1, SD4, and SD6 in the TFP formats CD3ε (FIG. 8A), CD3γ (FIG. 8B), TCRβ (FIG. 8C), and CD28ζ CAR (FIG. 8D). In each graph, black bars represent a 1:1 ratio of T cells to target cells, and gray bars represent a 1:5 ratio of T cells to target cells. Similar results were seen for a second T cell donor.

Figure 9A:
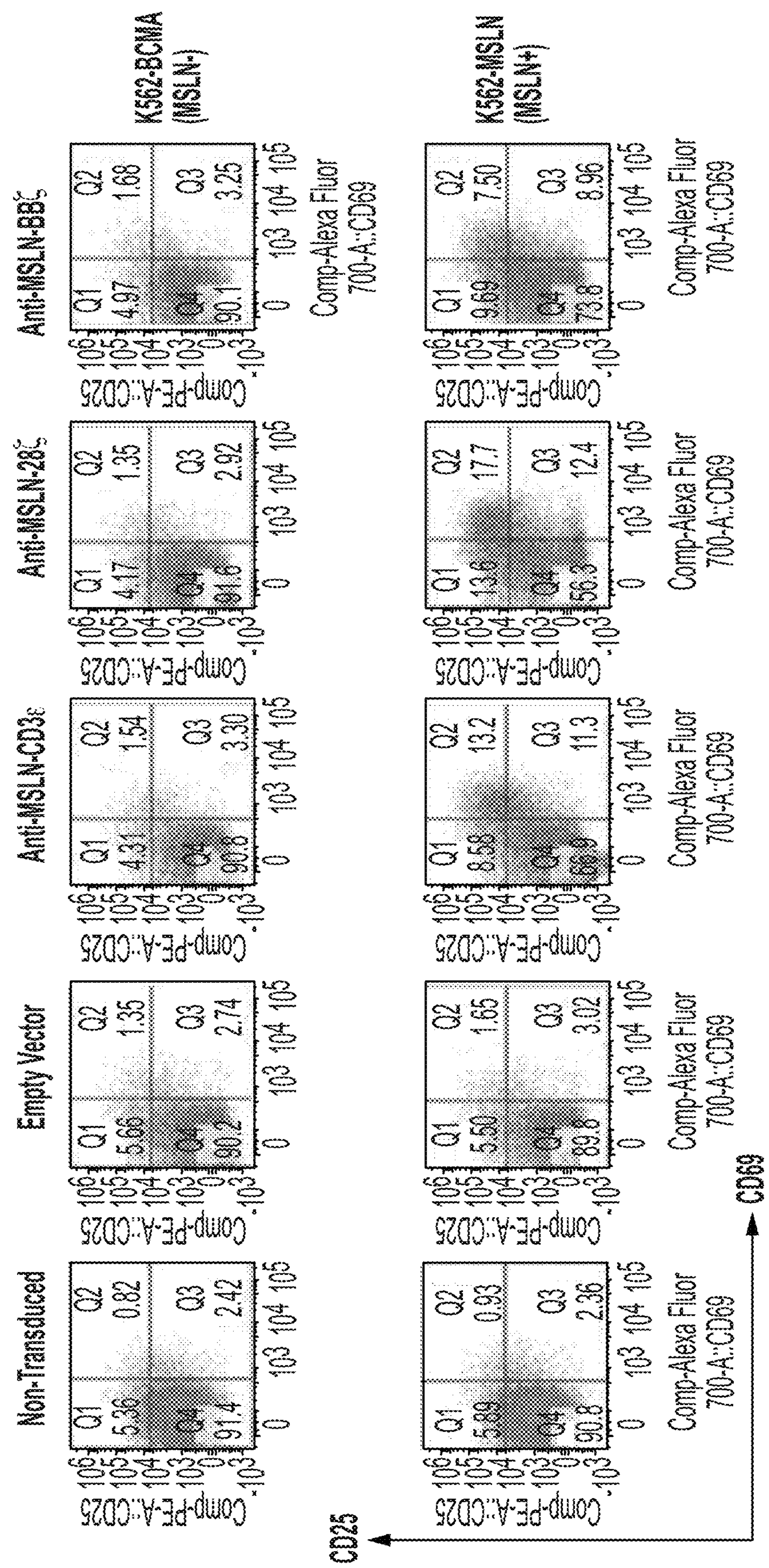
Figure 9B:
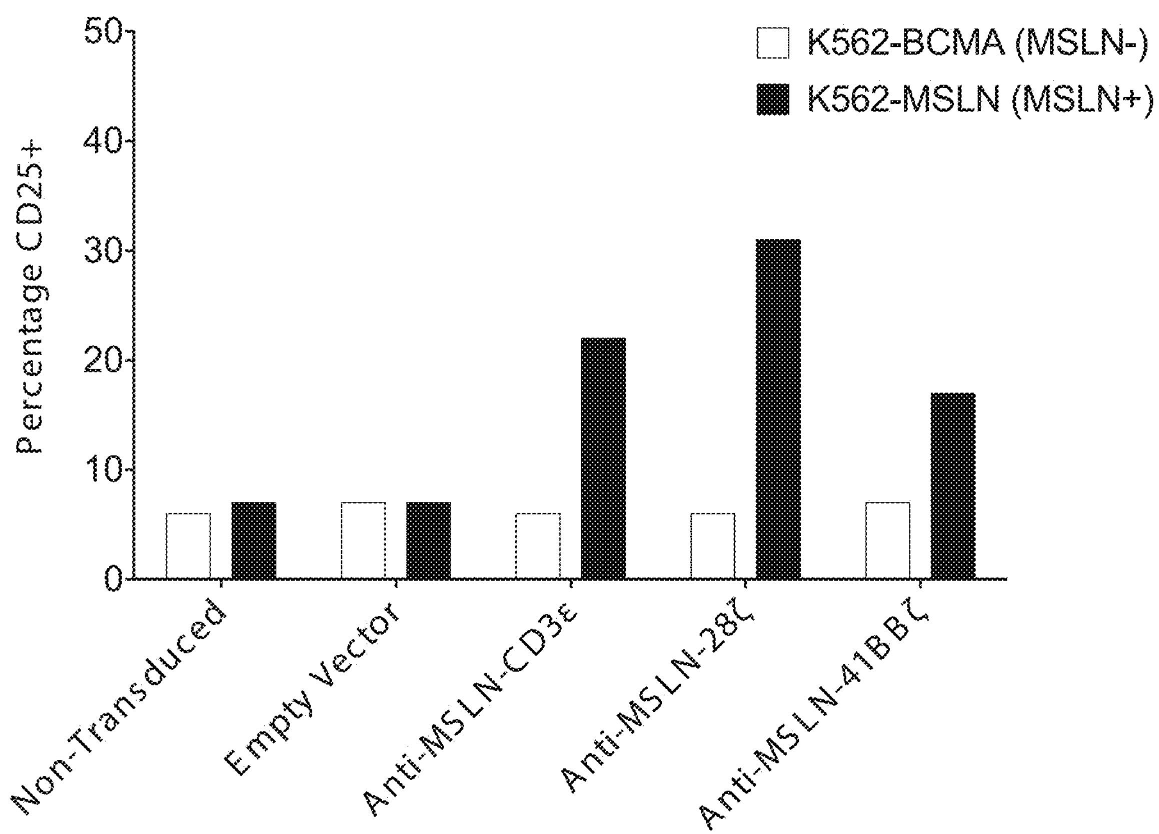
Figure 9C:
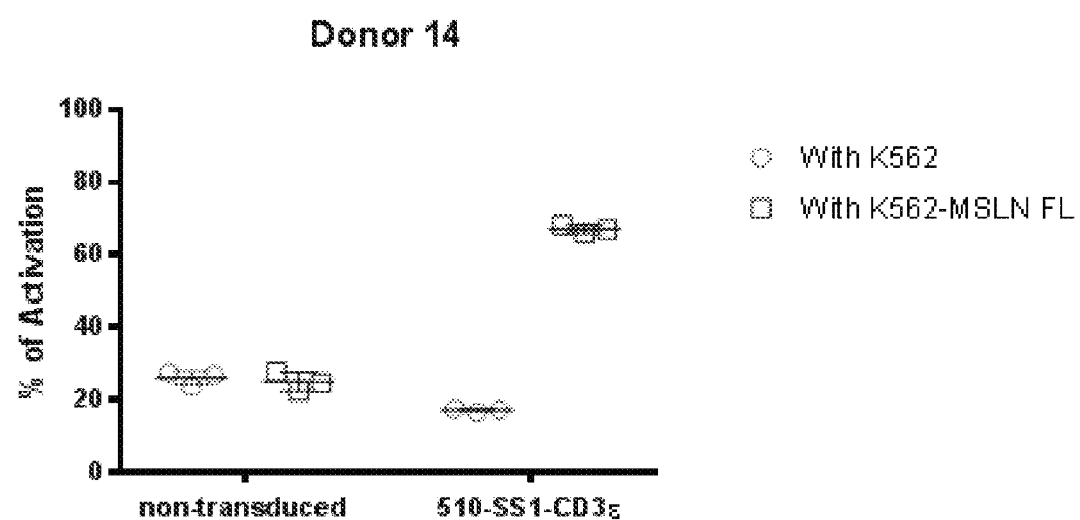
Figure 9D:
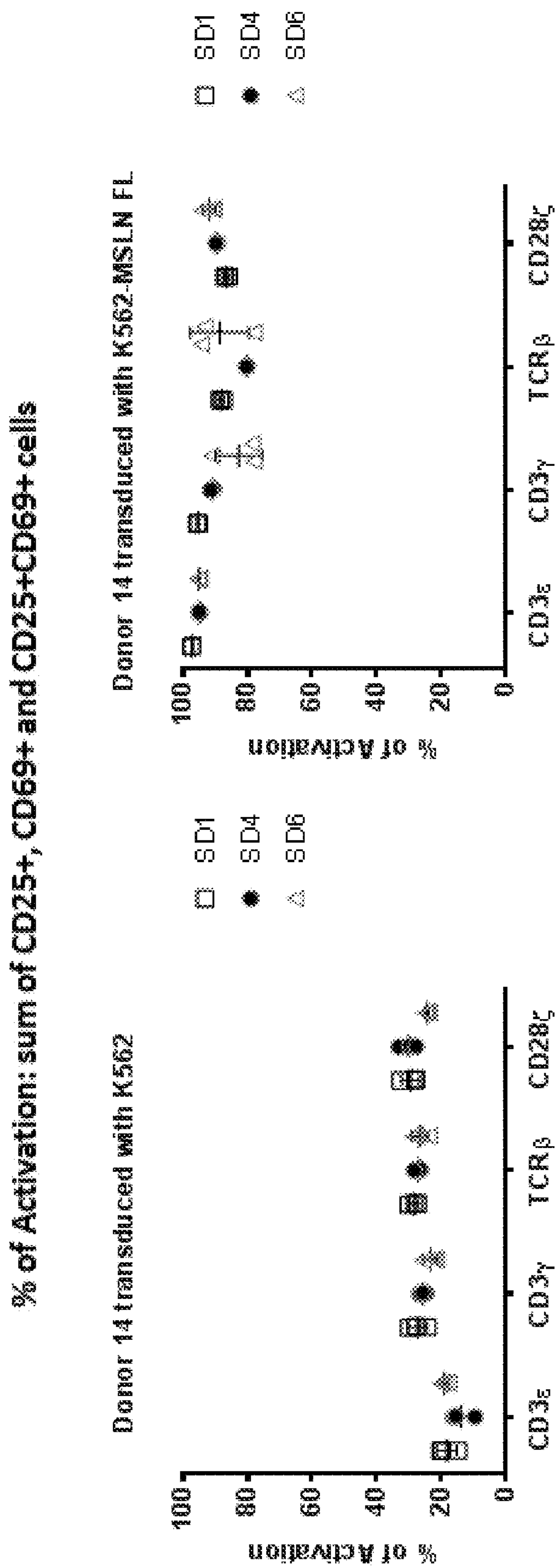

FIGS. 9A-D show the results of FACS analysis demonstrating activation of T-cells expressing anti-MSLN CAR and TFP constructs when co-cultured with MSLN+ cells. As shown in FIG. 9A, from left to right, T cells were either non-transduced, transduced with empty vector, transduced with anti-MSLN-CD3ε TFP, anti-MSLN-28ζ CAR, or anti-MSLN-41BBζ CAR. Cells co-cultured with MSLN-cells are shown in the top row, and those co-cultured with MSLN+ target cells are shown in the bottom row. The cells were then stained with antibodies specific for the surface activation markers CD69 and CD25 or the cytolylic granule component granzyme B (GrB). The numbers of cells stained with anti-CD69 correspond to the x-axes and those stained with anti-CD25 correspond to the y-axes. As shown, T-cells expressing anti-mesothelin CAR and TFP constructs were activated by culturing with MSLN+ cells, as demonstrated by elevated levels of CD69 and CD25 expression, relative to co-culturing with MSLN-cells (FIG. 9B). The percentage of CD25+ cells for each construct in MSLN− (white bars) and MSLN+ (black bars) cells is shown. A similar experiment was done using K562 MSLN− cells (circles) and K562-MSLN+ cells (squares) in either non-transduced T cells or T cells transduced with anti-MSLN positive control binders ("510-SS1-CD3ε) (FIG. 9C). Data represent the sum of CD25+, CD69+, and CD25+/CD69+ cells. In FIG. 9D, data are shown for the in-house anti-MSLN binders SD1 (squares), SD4 (circles), and SD6 (triangles) in K562 MSLN− target cells (left panel) and K562 MSLN+ cells (right panel) combined with donor T cells having TFP formats CD3ε, CD3γ, TCRβ, and CD28ζ CAR Similar results were seen using cells from a second T cell donor.

Figure 10A:
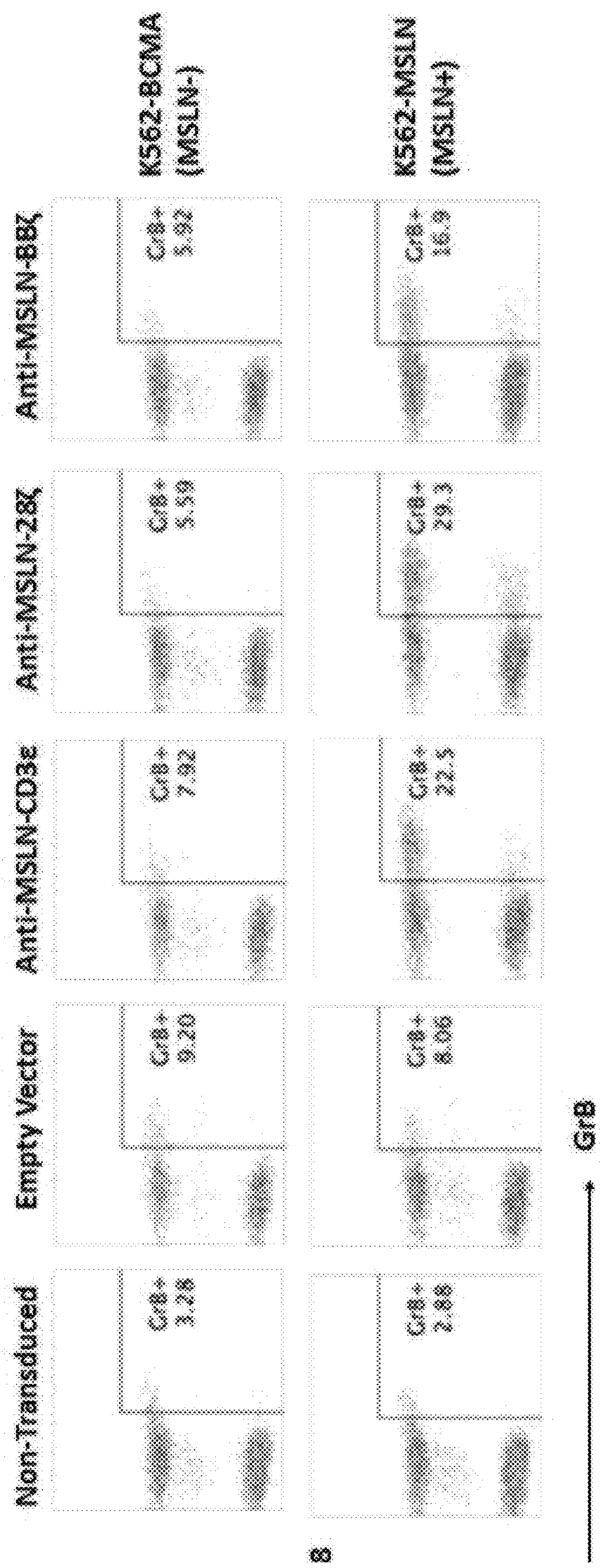
Figure 10B:
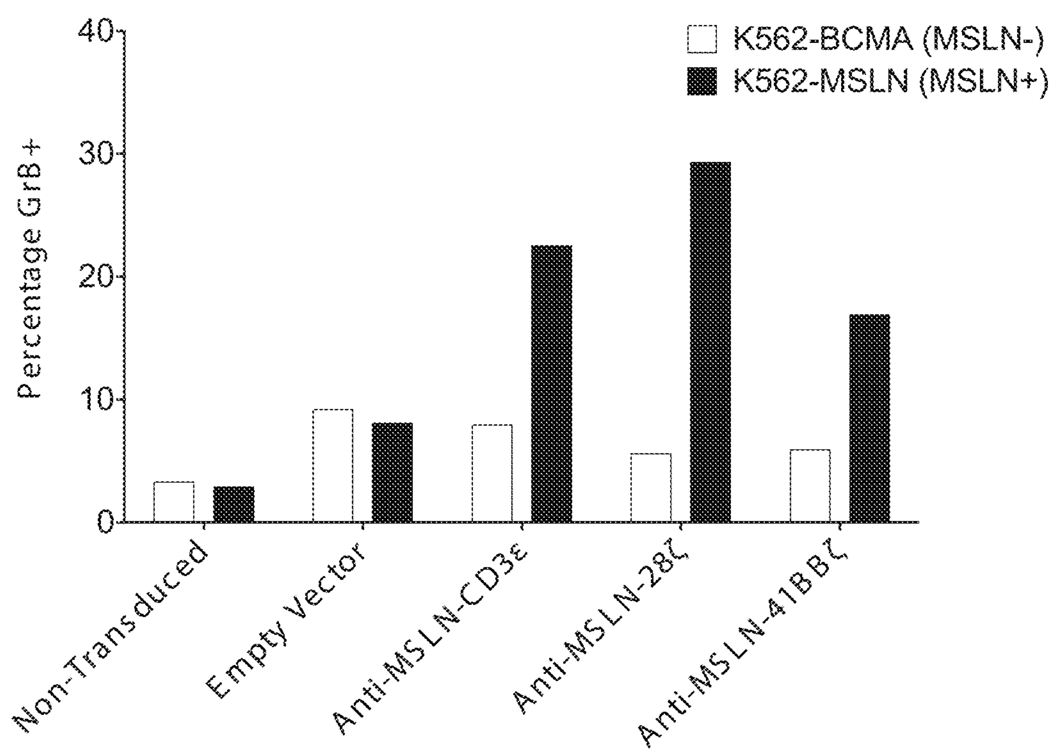

FIGS. 10A-B show the results of FACS analysis demonstrating activation of T-cells expressing anti-MSLN CAR and TFP constructs when co-cultured with MSLN+ cells. Cells were stained for surface antigens with anti-CD3 APC (gate) and anti-CD8 APCcy7 (y-axes) prior to fixation, permealbilzation and staining with anti-Granzyme B Alexafluor700 (x-axes). As shown in FIG. 10A, from left to right, T cells were either non-transduced, transduced with empty vector, transduced with Anti-MSLN-CD3ε TFP, anti-MSLN-28ζ CAR, or anti-MSLN-41BBζ CAR. Cells co-cultured with MSLN− cells are shown in the top row, and those co-cultured with MSLN+ target cells are shown in the bottom row. CD8 T-cells expressing anti-mesothelin CAR and TFP constructs were activated by culturing with MSLN+ cells, as shown by elevated levels of intracellular GrB, compared to co-culturing with MSLN− cells (FIG. 10B). The percentage of granzyme B ("GrB+") cells for each construct, upon coculture with either MSLN− (white bars) or MSLN+ (black bars) cells, is shown.

Figure 11A:
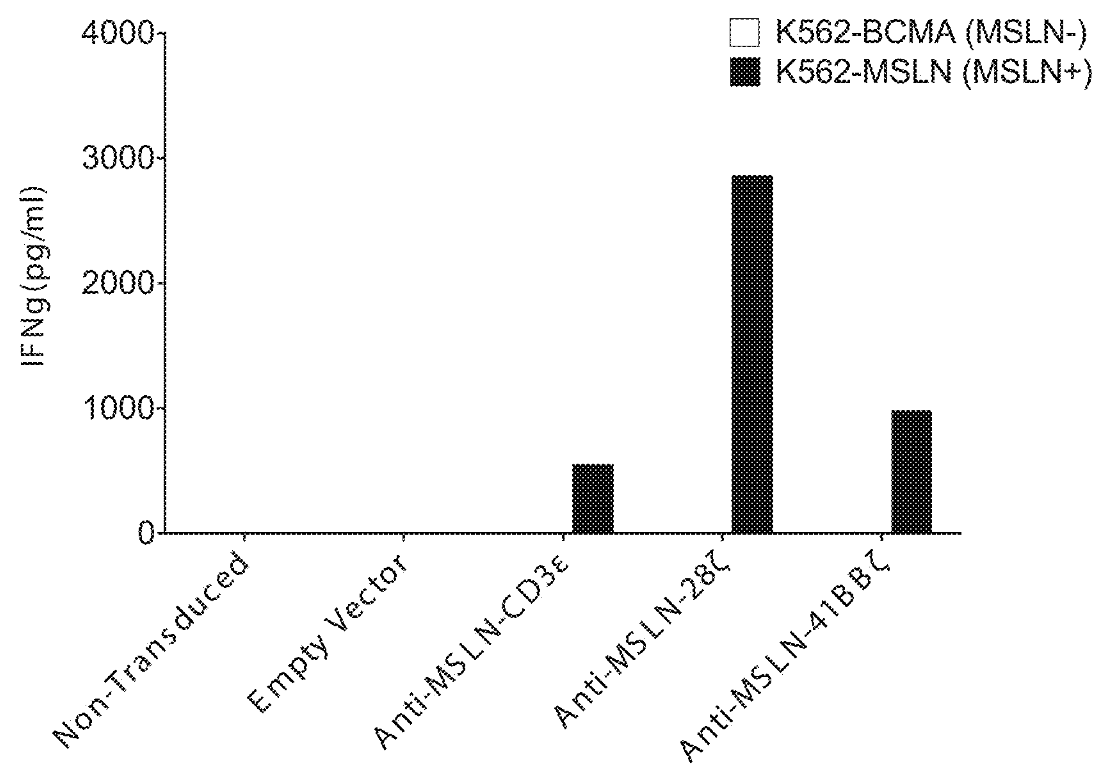
Figure 11B:
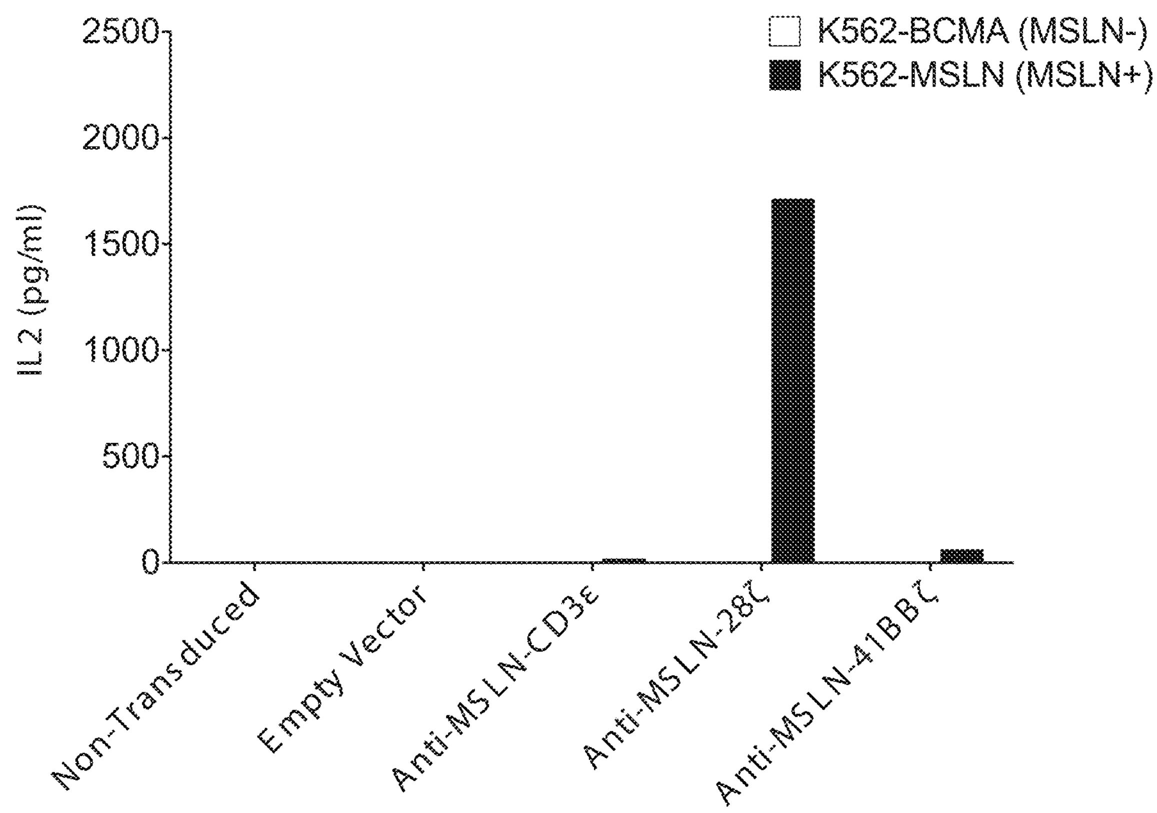

FIGS. 11A-B show the results of ELISA analysis of cytokine production in activated T-cells expressing anti-MSLN CAR and TFP constructs when co-cultured with K562 cells overexpressing MSLN. K562 cells overexpressing BCMA were used as negative controls. After 24 hours cells were analyzed for IFN-γ (FIG. 11A) and IL-2 (FIG. 11B) expression by ELISA. In each FIG., from left to right, T cells were either non-transduced, transduced with empty vector, transduced with Anti-MSLN-CD3ε TFP, anti-MSLN-28ζ CAR, or anti-MSLN-41BBζ CAR. Cells co-cultured with MSLN− cells are represented by white bars, and those co-cultured with MSLN+ target cells are represented by black bars.

Figure 12A:
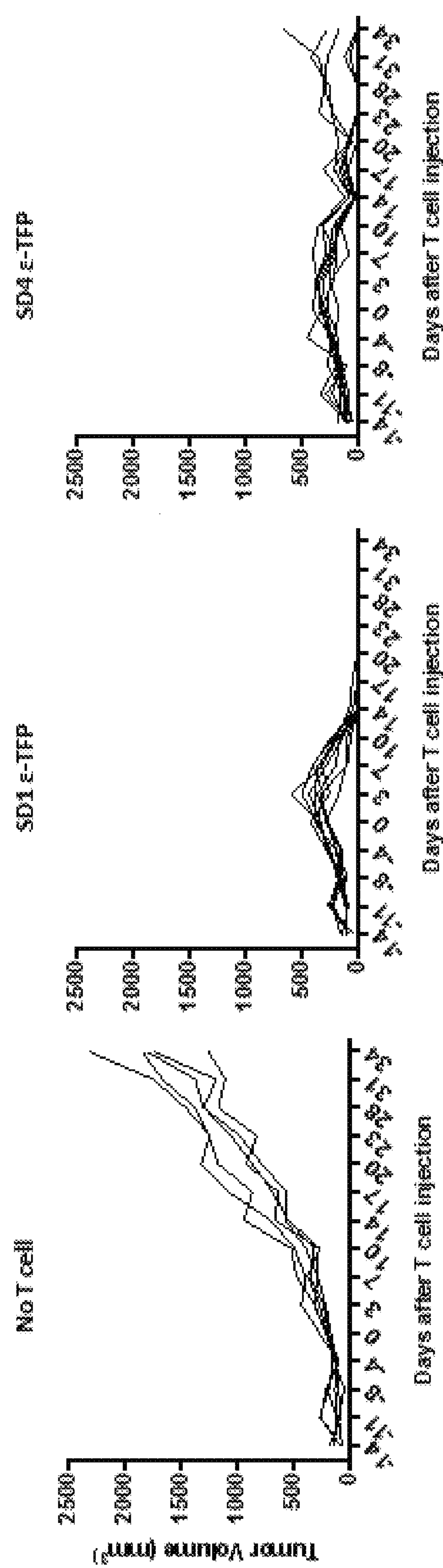
Figure 12B:
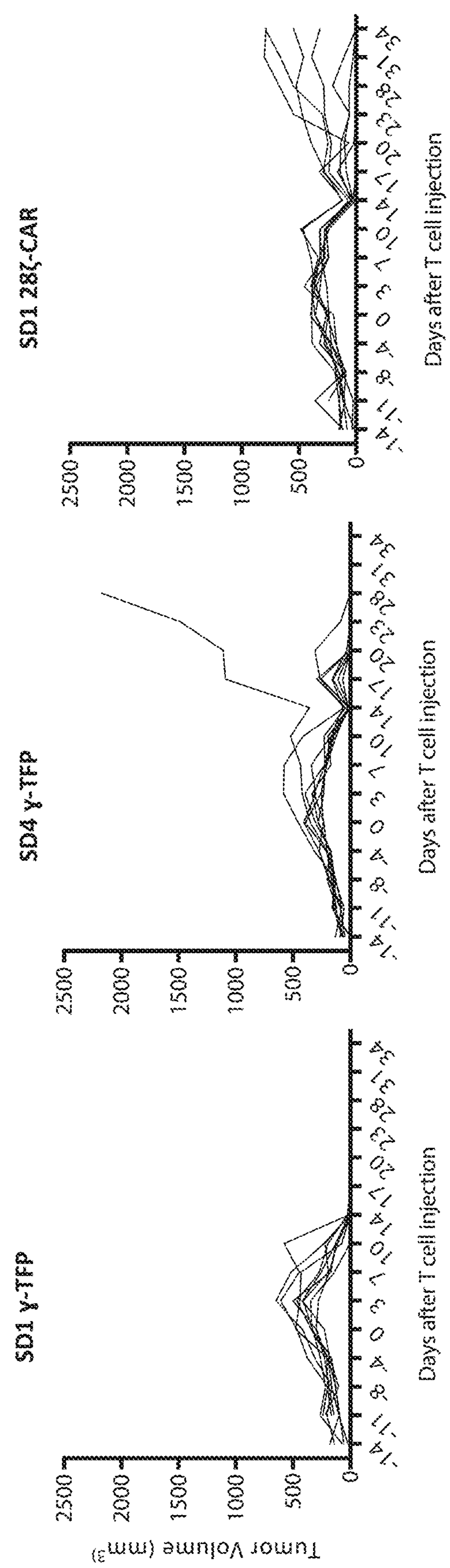
Figure 12C:
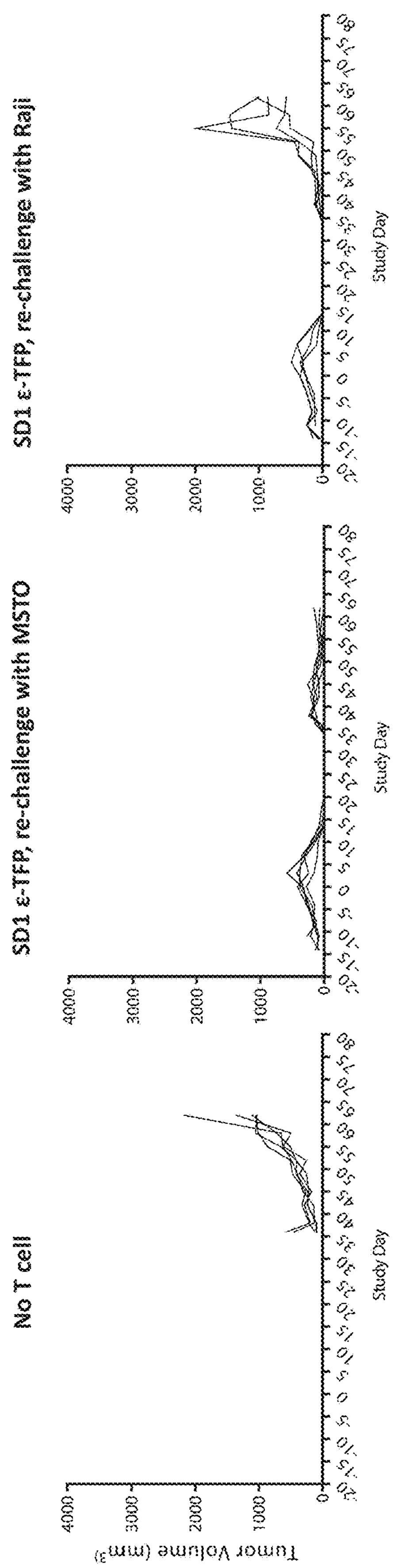
Figure 12D:
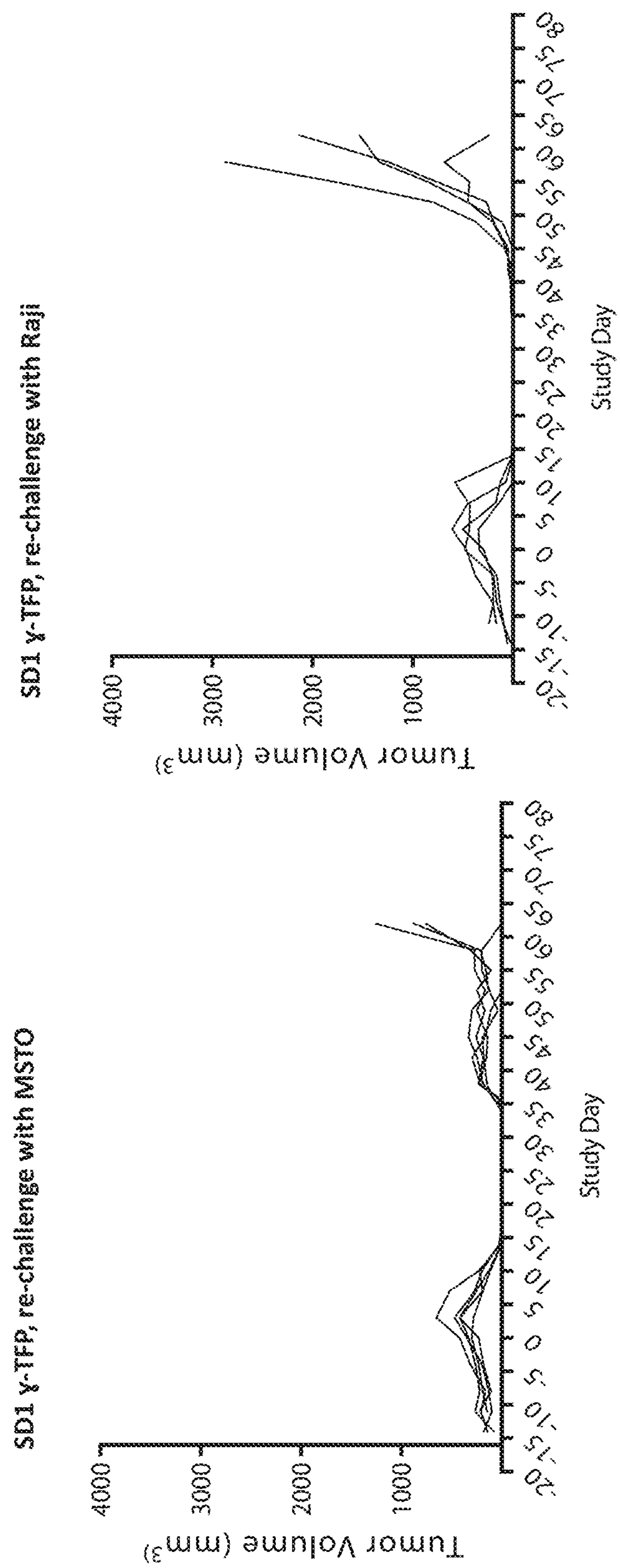

FIGS. 12A-D are a series of graphs showing the efficacy of MSLN-specific sdAb TFP T cells in vivo in a mesothelioma xenograft mouse model. Mice were inoculated with luciferase-labeled MSTO-211H-FL-MSLN-Luc at $1\times10^6$ cells per mouse and tumors were grown until the tumor volume was approximately 300 $mm^3$, $1\times10^7$ T cells were injected intravenously into each animal FIG. 12A shows the tumor volume after injection with T cells including, from left to right, a no T cell control, SD1 CD3ε-TFP, and SD4 CD3ε-TFP. FIG. 12B shows CD3γ-TFPs with SD1 and SD4 binders and SD1 CD28ζ CAR. FIGS. 12C-D shows results from surviving mice from FIGS. 12A-B that were re-challenged with tumor cells in order to determine whether the mice would maintain their anti-MSLN immunity without a second T cell injection. Mice that had been administered SD1 CD3ε-TFP T cells (FIG. 12C) and SD1 CD3γ-TFP T cells (FIG. 12D) and had previously cleared their tumors, were re-inoculated with either MSLN+ (MSTO) or MSLN− (Raji) tumor cell lines. Tumor volume was measured and shown on the x-axis.

Figure 13A:
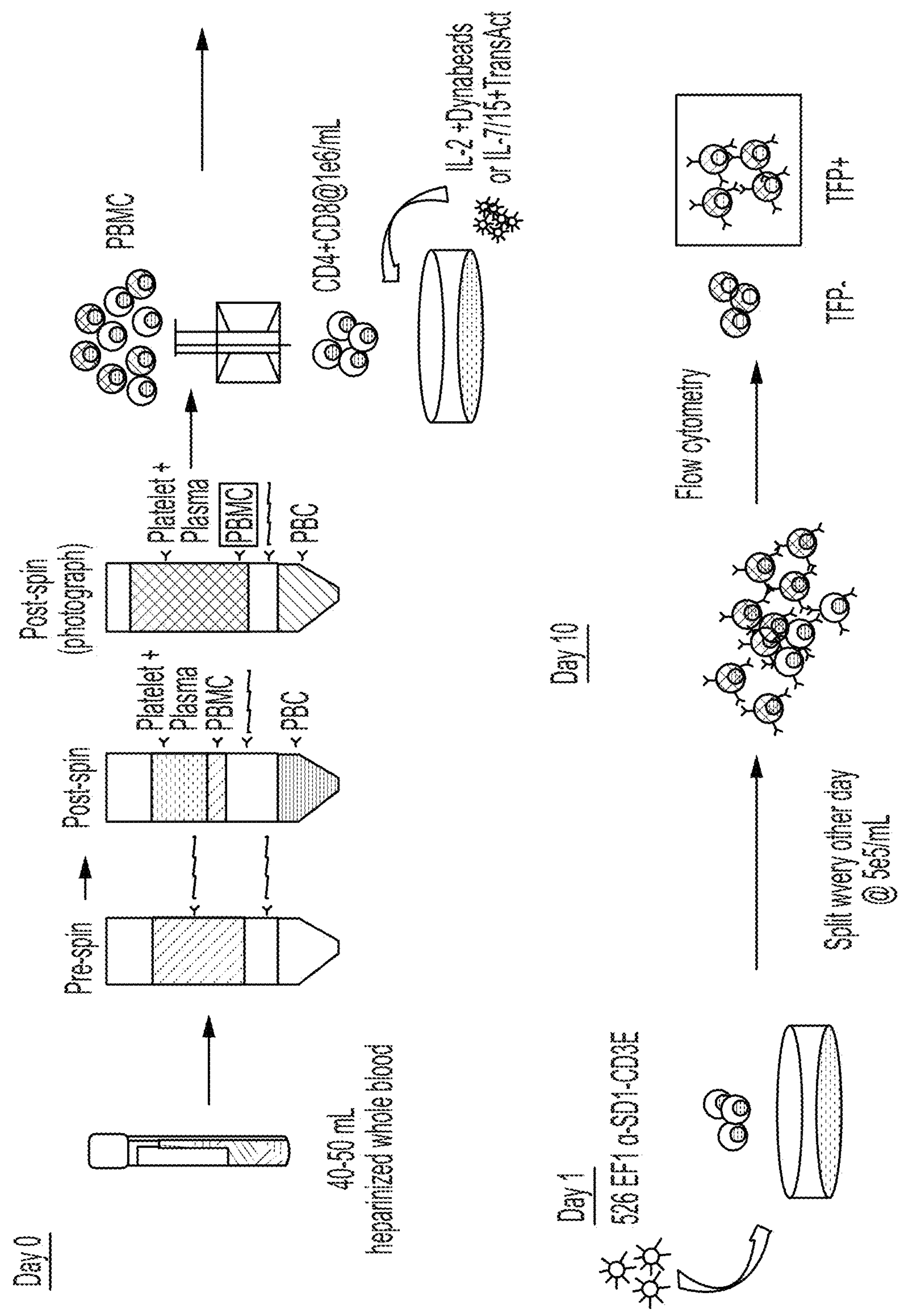
Figure 13B:
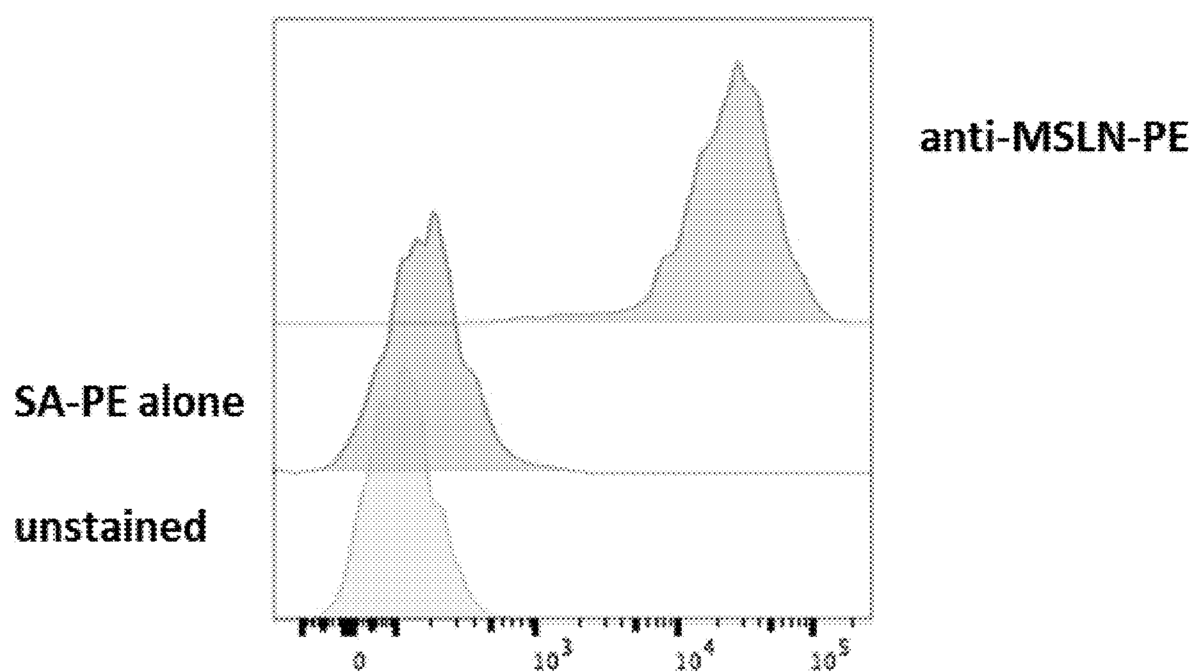
Figure 13C:
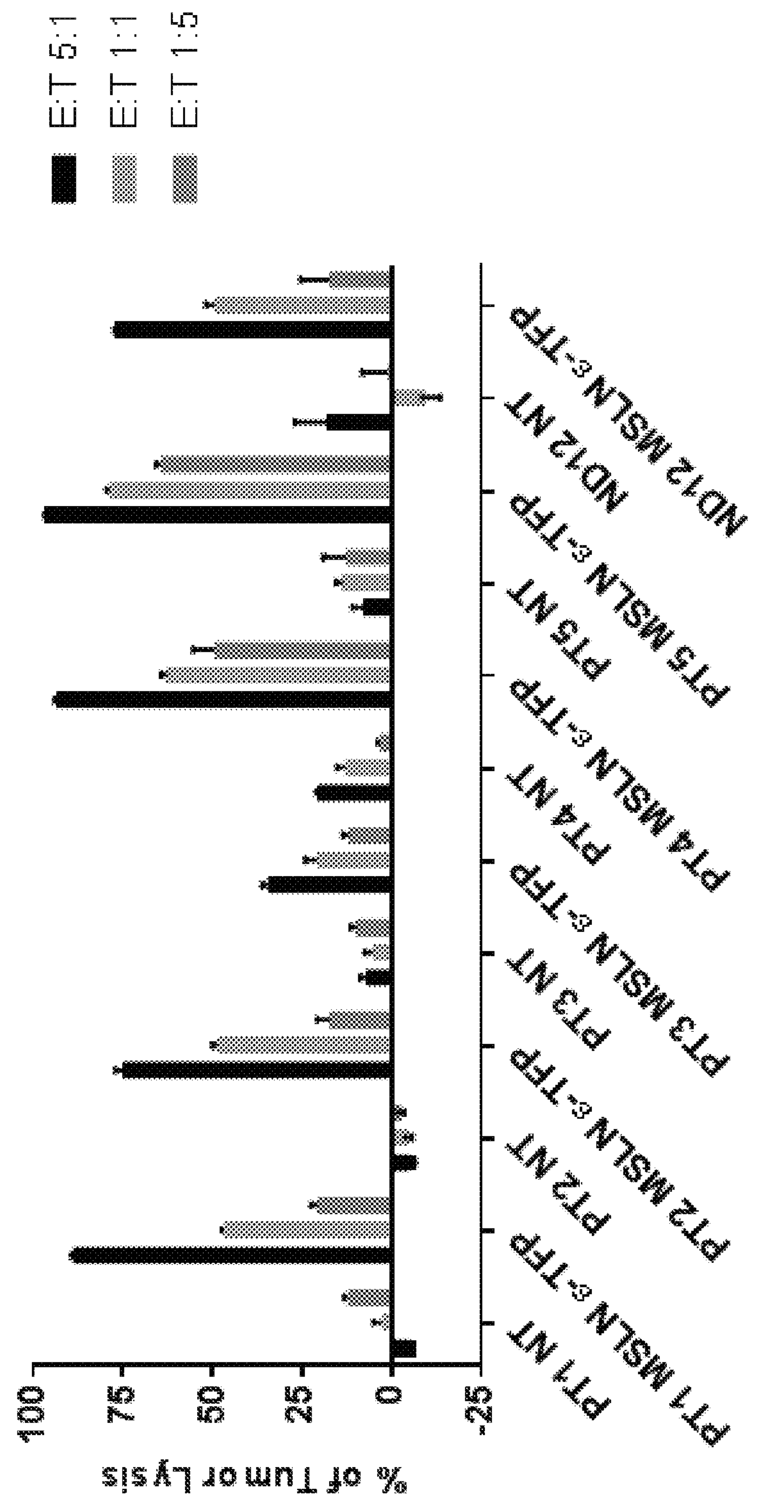
Figure 13D:
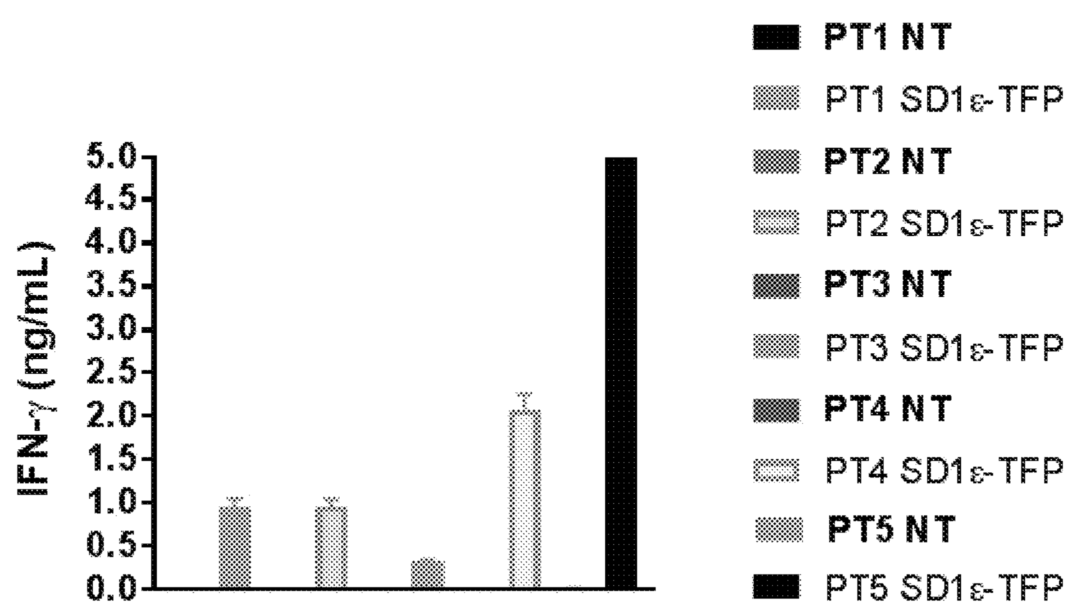
Figure 13E:
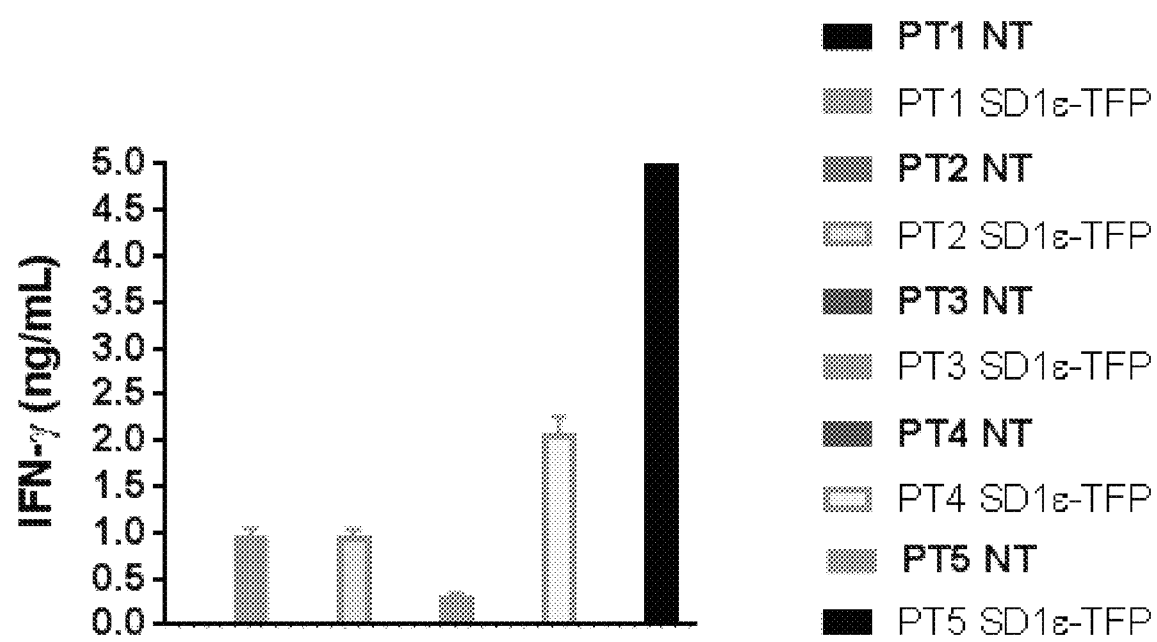
Figure 13F:
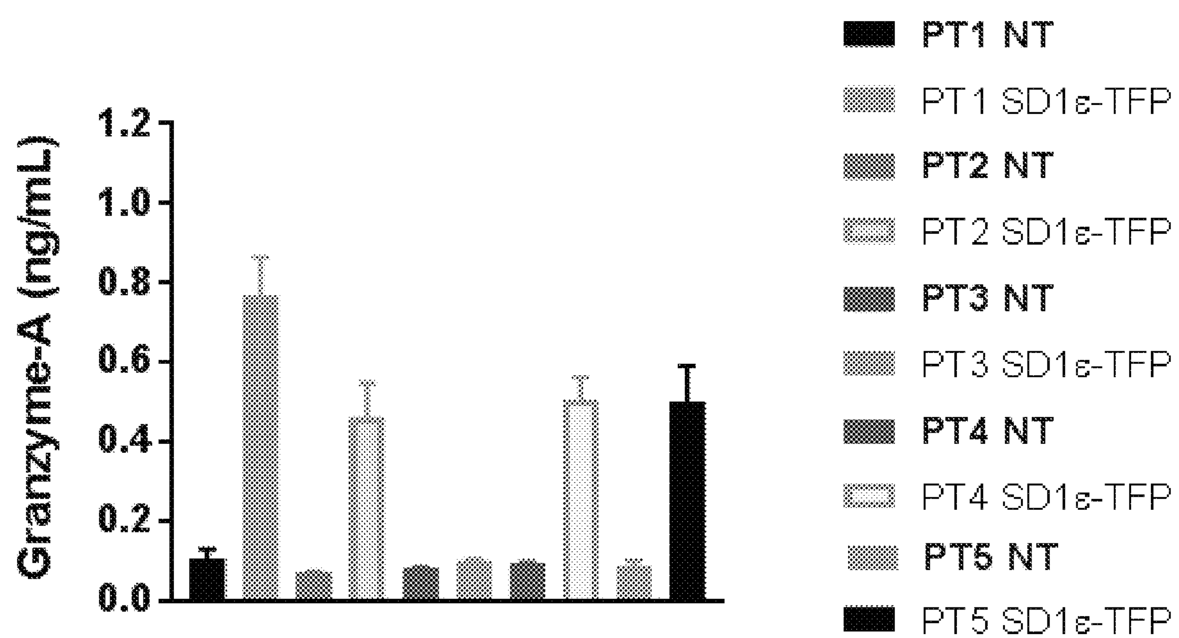
Figure 13G:
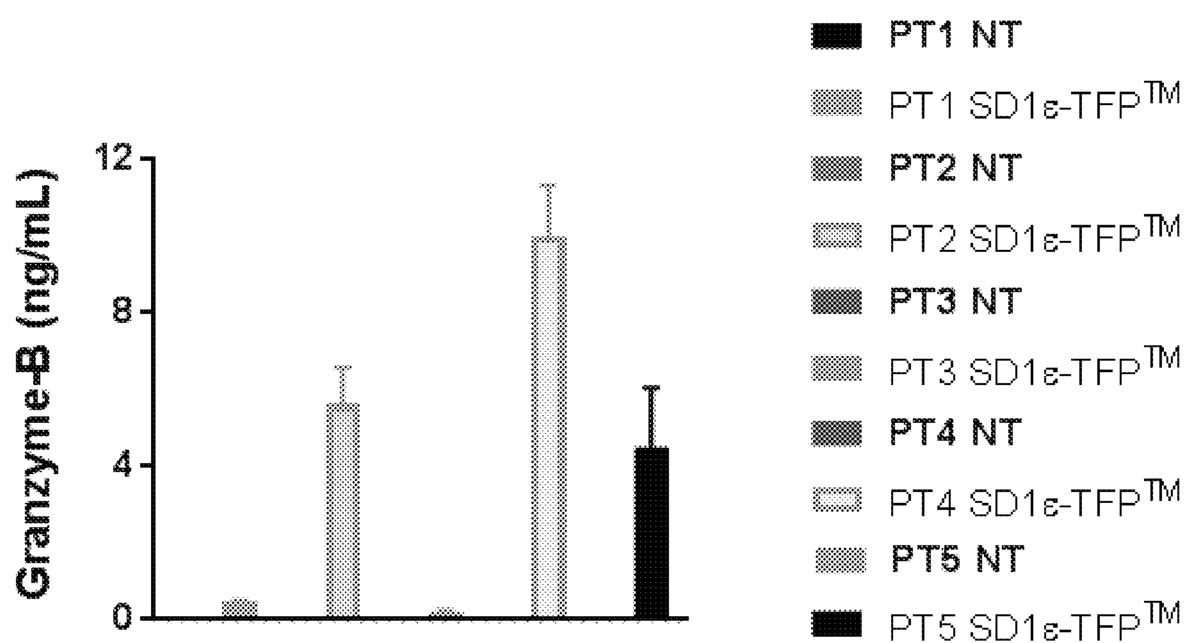
Figure 13H:
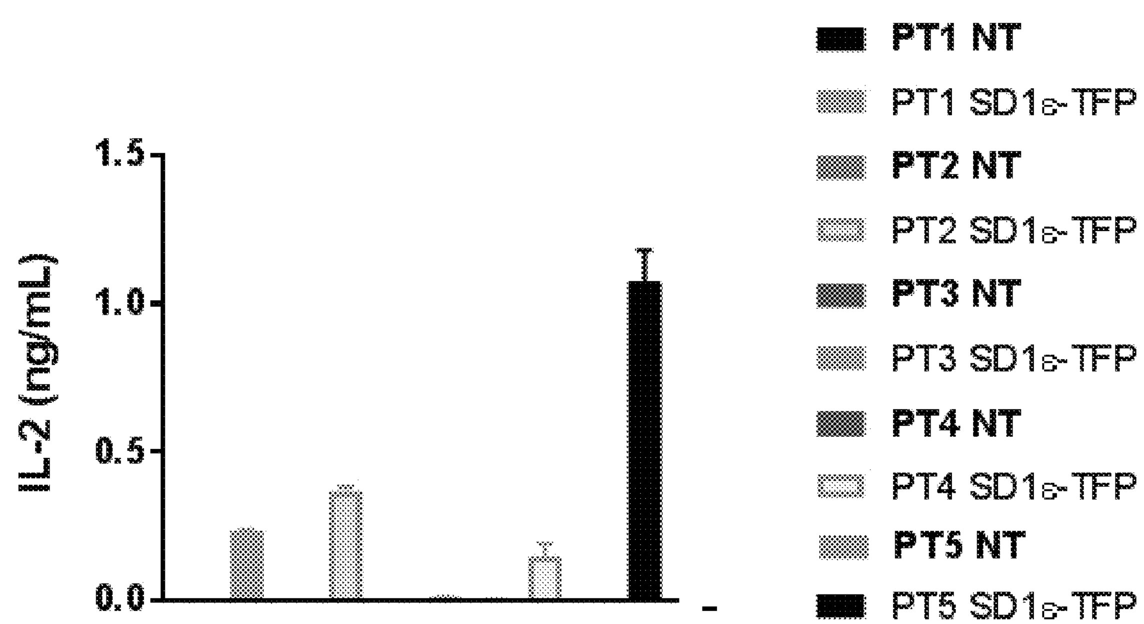
Figure 13I:
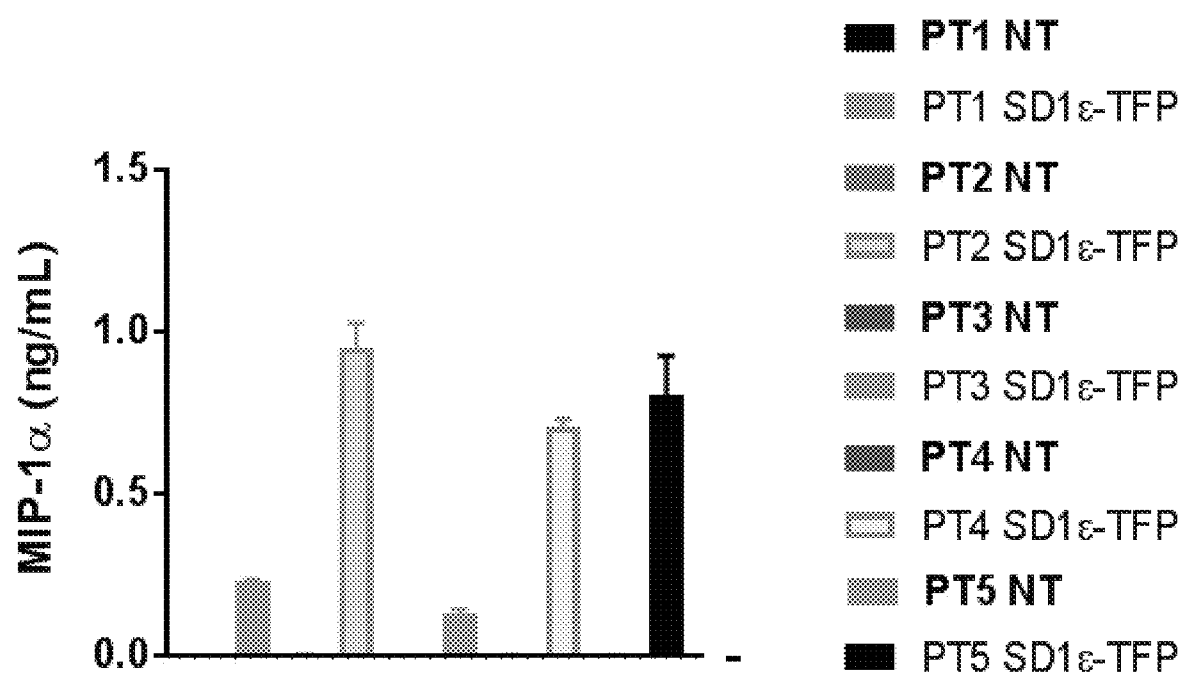
Figure 13J:
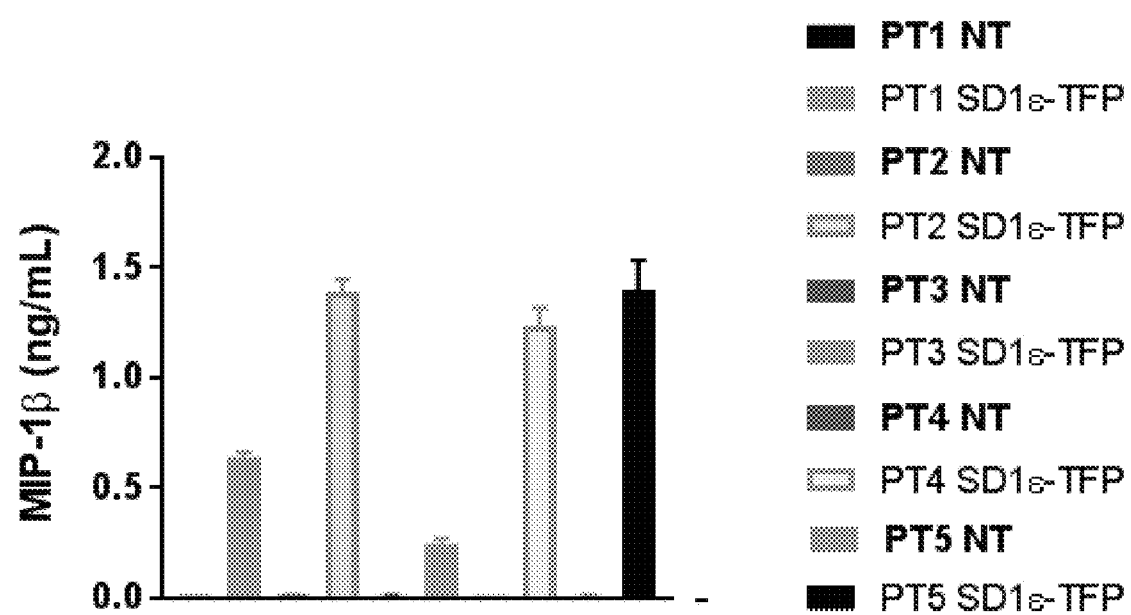
Figure 13K:
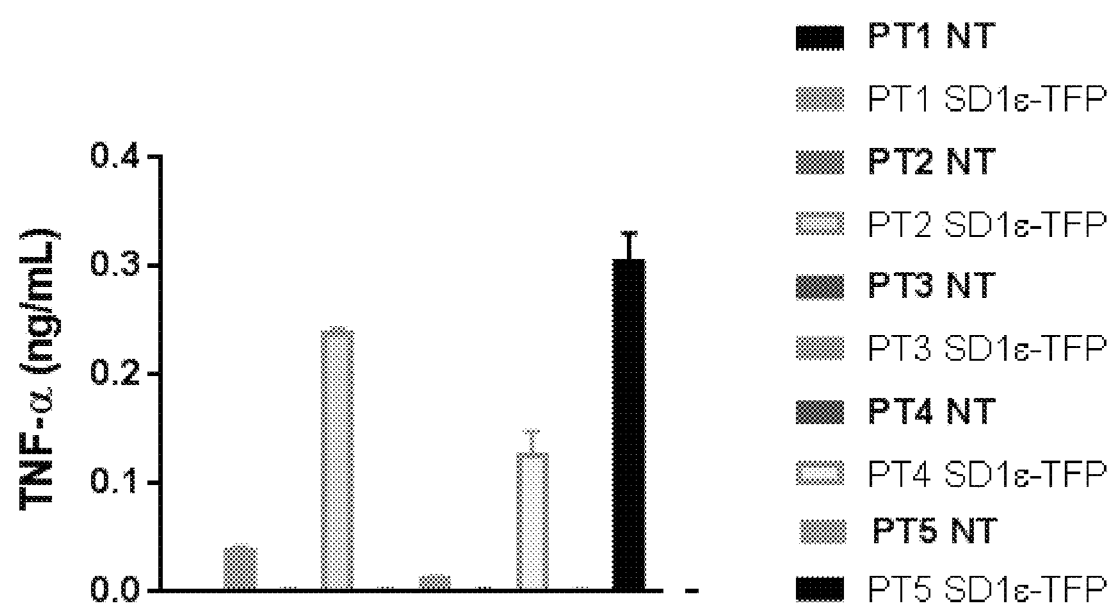
Figure 13L:
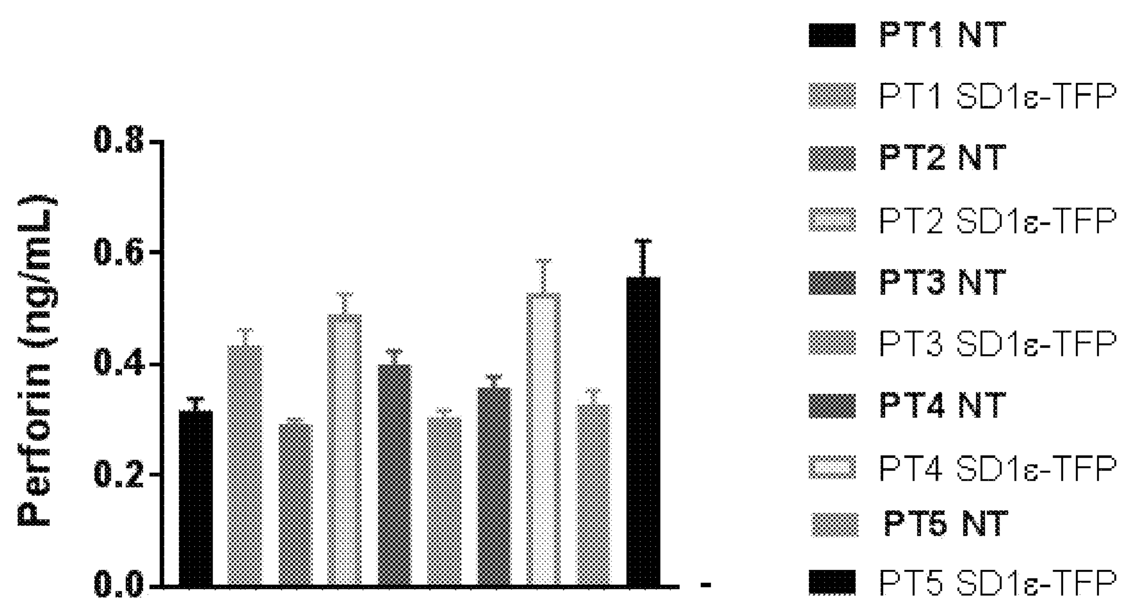

FIGS. 13A-L shows production and functional analysis of MSLN-TFP T cells from ovarian cancer patients. FIG. 13A is a schematic diagram of the experimental design. FIGS. 13B-C show in vitro killing of MSTO-MSLN-Luc tumor cells by patients' SD1 ε-TFP T cells. MSTO-MSLN-Luc tumor cells (target cells) were confirmed for mesothelin expression (FIG. 13B); SD1 ε-TFP T cells (effector cells) and matching non-transduced control were added at E-to-T (effector to target) ratios 5-to-1, 1-to-1, or 1-to-5 for 24 hours. The luminescence of target cells was measured relative luminescence unit (RLU) by SpectraMax® M5 plate reader (Molecular devices). Each line in the figure represents the average of 3 replicates (FIG. 13C). FIGS. 13D-L show measurement of the cytokine profile of SD1 ε-TFP T cells from ovarian cancer patients, including IFNγ (FIG. 13D), GM-CSF (FIG. 13E), Granzyme A (FIG. 13F), Granzyme B (FIG. 13G), IL-2 (FIG. 13H), MIP-1α (FIG. 13I), MIP-1β (FIG. 13J), TNFα (FIG. 13K), and perforin (FIG. 13L). MSTO-MSLN-Luc tumor cells (target cells) were plated at 10000 cells/well in 96 flat bottom plate. SD1 ε-TFP T cells (effector cells) and a matching non-transduced control were added at 1-to-1 ratio for 24 hours. Cell supernatants were collected and cytokines were measured using a Luminex® assay.

Figure 14A:
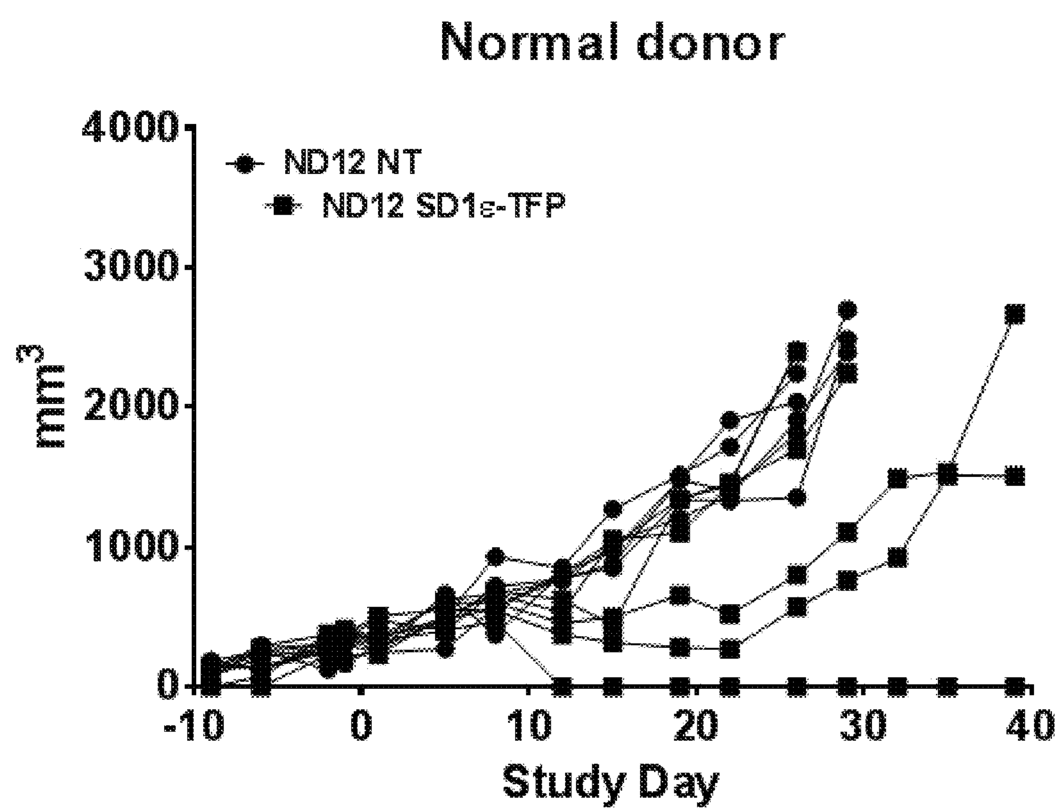
Figure 14B:
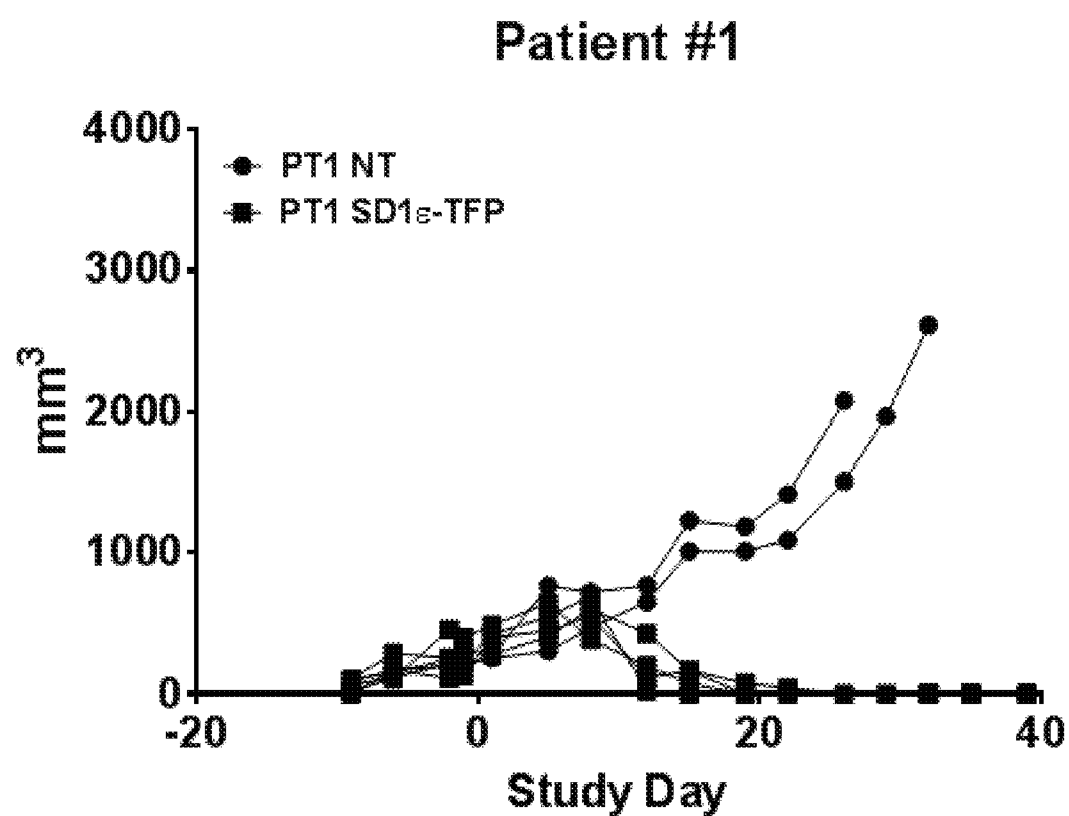
Figure 14C:
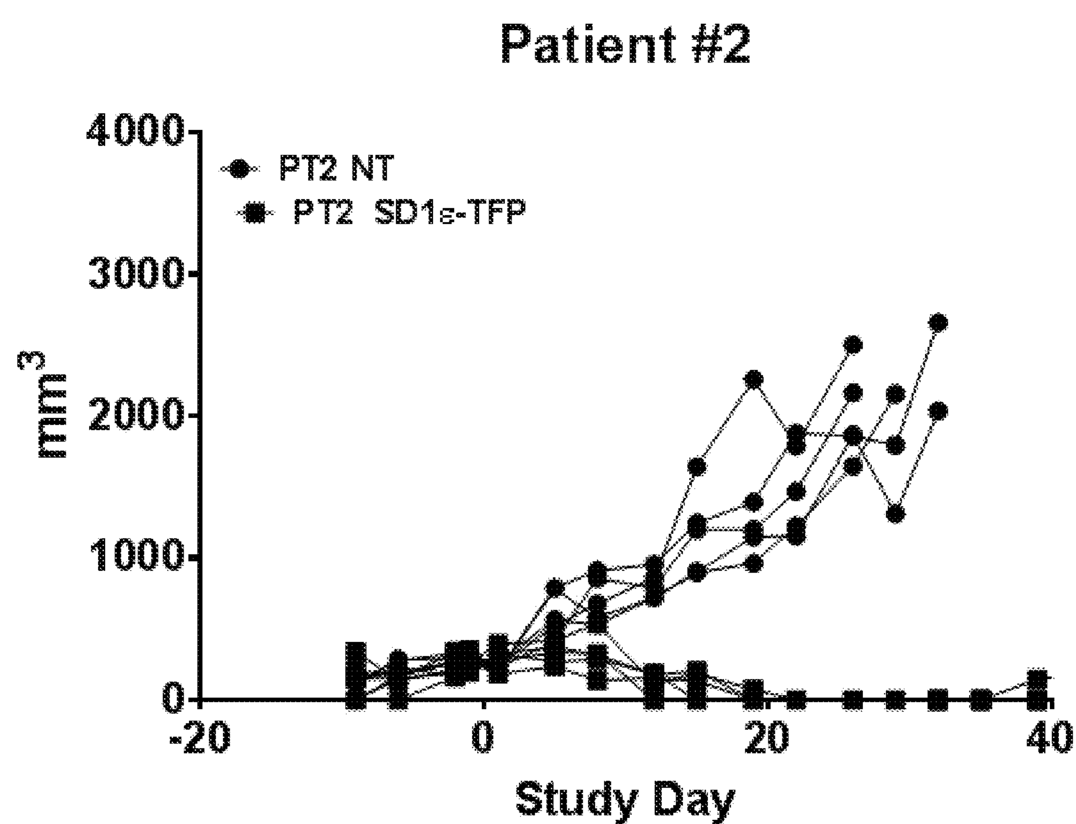
Figure 14D:
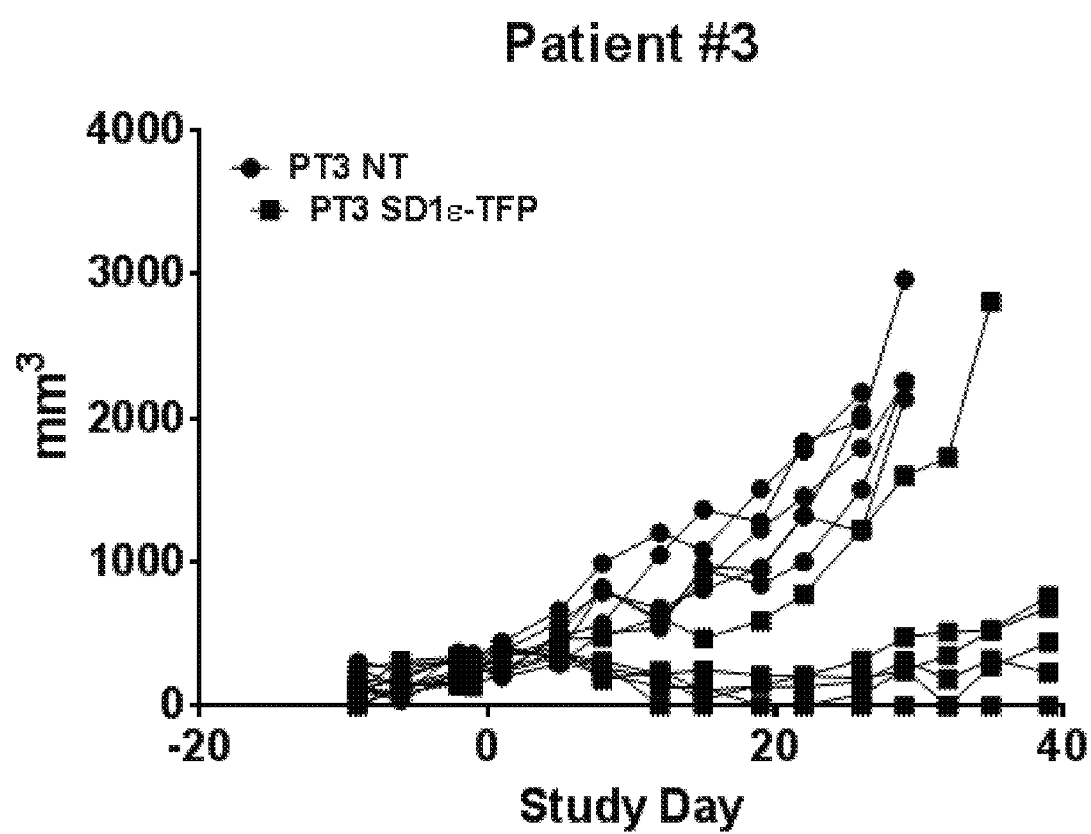
Figure 14E:
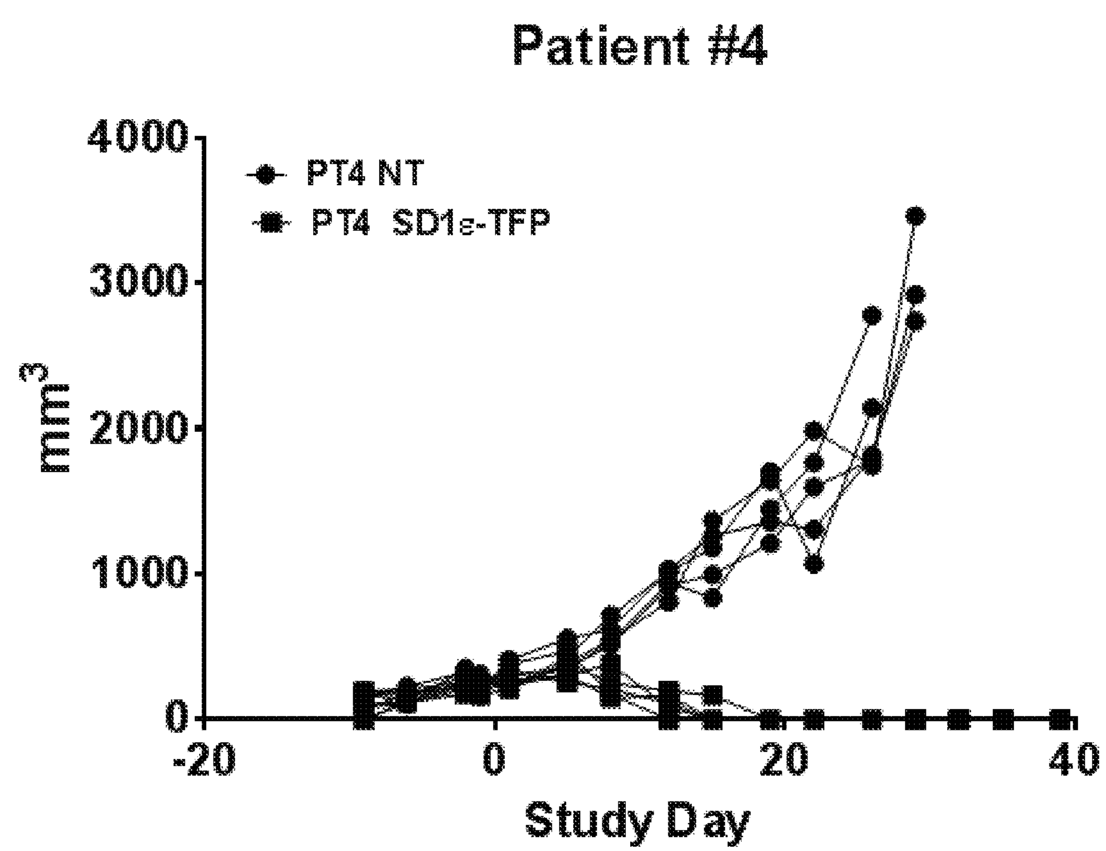

FIGS. 14A-E shows the in vivo efficacy of patient-derived SD1 CD3ε-TFP T cells in MSLN-high xenograft tumor mouse model. MSTO-211H-FL MSLN-Luc cells were inoculated at $1\times10^6$ cells per mouse subcutaneously. Ten days after tumor injection (tumor volume ~200-300 $mm^3$), $5\times10^6$ T cells were injected intravenously into each animal Each line in the figure represents single animal Data are shown for T cells from ND12 (FIG. 14A), Patient 1 (FIG. 14B), Patient 2 (FIG. 14C), Patient 3 (FIG. 14D), and Patient 4 (FIG. 14E). Circles indicate tumor size in mice inoculated with untransduced T cells; squares indicate those inoculated with TFP T cells.

DETAILED DESCRIPTION

In one aspect, described herein are isolated nucleic acid molecules encoding a T-cell Receptor (TCR) fusion protein (TFP) that comprise a TCR subunit and a human or humanized antibody domain comprising an anti-mesothelin binding domain. In some embodiments, the TCR subunit comprises a TCR extracellular domain. In other embodiments, the TCR subunit comprises a TCR transmembrane domain. In yet other embodiments, the TCR subunit comprises a TCR intracellular domain. In further embodiments, the TCR subunit comprises (i) a TCR extracellular domain, (ii) a TCR transmembrane domain, and (iii) a TCR intracellular domain, wherein at least two of (i), (ii), and (iii) are from the same TCR subunit. In yet further embodiments, the TCR subunit comprises a TCR intracellular domain comprising a stimulatory domain selected from an intracellular signaling domain of CD3 epsilon, CD3 gamma or CD3 delta, or an amino acid sequence having at least one, two or three modifications thereto. In yet further embodiments, the TCR subunit comprises an intracellular domain comprising a stimulatory domain selected from a functional signaling domain of 4-1BB and/or a functional signaling domain of CD3 zeta, or an amino acid sequence having at least one, two or three modifications thereto.

In some embodiments, the isolated nucleic acid molecules comprise (i) a light chain (LC) CDR1, LC CDR2 and LC CDR3 of any anti-mesothelin light chain binding domain amino acid sequence provided herein, and/or (ii) a heavy chain (HC) CDR1, HC CDR2 and HC CDR3 of any anti-mesothelin heavy chain binding domain amino acid sequence provided herein.

In some embodiments, the light chain variable region comprises an amino acid sequence having at least one, two or three modifications but not more than 30, 20 or 10 modifications of an amino acid sequence of a light chain variable region provided herein, or a sequence with 95-99% identity to an amino acid sequence provided herein. In other embodiments, the heavy chain variable region comprises an amino acid sequence having at least one, two or three modifications but not more than 30, 20 or 10 modifications of an amino acid sequence of a heavy chain variable region provided herein, or a sequence with 95-99% identity to an amino acid sequence provided herein.

In some embodiments, the TFP includes an extracellular domain of a TCR subunit that comprises an extracellular domain or portion thereof of a protein selected from the group consisting of the alpha or beta chain of the T-cell receptor, CD3 delta, CD3 epsilon, or CD3 gamma, or a functional fragment thereof, or an amino acid sequence having at least one, two or three modifications but not more than 20, 10 or 5 modifications thereto. In other embodiments, the encoded TFP includes a transmembrane domain that comprises a transmembrane domain of a protein selected from the group consisting of the alpha, beta chain of the TCR or TCR subunits CD3 epsilon, CD3 gamma and CD3 delta, or a functional fragment thereof, or an amino acid sequence having at least one, two or three modifications but not more than 20, 10 or 5 modifications thereto.

In some embodiments, the encoded TFP includes a transmembrane domain that comprises a transmembrane domain of a protein selected from the group consisting of the alpha, beta or zeta chain of the TCR or CD3 epsilon, CD3 gamma and CD3 delta CD45, CD2, CD4, CD5, CD8, CD9, CD16, CD22, CD33, CD28, CD37, CD64, CD80, CD86, CD134, CD137 and CD154, or a functional fragment thereof, or an amino acid sequence having at least one, two or three modifications but not more than 20, 10 or 5 modifications thereto.

In some embodiments, the encoded anti-mesothelin binding domain is connected to the TCR extracellular domain by a linker sequence. In some instances, the encoded linker sequence comprises $(G_4S)_n$, wherein n=1 to 4. In some instances, the encoded linker sequence comprises a long linker (LL) sequence. In some instances, the encoded long linker sequence comprises $(G_4S)_n$, wherein n=2 to 4. In some instances, the encoded linker sequence comprises a short linker (SL) sequence. In some instances, the encoded short linker sequence comprises $(G_4S)_n$, wherein n=1 to 3.

In some embodiments, the isolated nucleic acid molecules further comprise a sequence encoding a costimulatory domain. In some instances, the costimulatory domain is a functional signaling domain obtained from a protein selected from the group consisting of DAP10, DAP12, CD30, LIGHT, OX40, CD2, CD27, CD28, CDS, ICAM-1, LFA-1 (CD11a/CD18), ICOS (CD278), and 4-1BB (CD137), or an amino acid sequence having at least one, two or three modifications but not more than 20, 10 or 5 modifications thereto.

In some embodiments, the isolated nucleic acid molecules further comprise a leader sequence.

Also provided herein are isolated polypeptide molecules encoded by any of the previously described nucleic acid molecules.

Also provided herein in another aspect, are isolated T-cell receptor fusion protein (TFP) molecules that comprise a human or humanized anti-mesothelin binding domain, a TCR extracellular domain, a transmembrane domain, and an intracellular domain. In some embodiments, the isolated TFP molecules comprises an antibody or antibody fragment comprising a human or humanized anti-mesothelin binding domain, a TCR extracellular domain, a transmembrane domain, and an intracellular domain.

In some embodiments, the human or humanized antibody domain comprises an antibody fragment. In some embodiments, the human or humanized antibody domain comprises a scFv or a $V_H$ domain.

In some embodiments, the anti-mesothelin binding domain is a scFv or a $V_H$ domain. In other embodiments, the anti-mesothelin binding domain comprises a light chain and a heavy chain of an amino acid sequence provided herein, or a functional fragment thereof, or an amino acid sequence having at least one, two or three modifications but not more than 30, 20 or 10 modifications of an amino acid sequence of a light chain variable region provided herein, or a sequence with 95-99% identity with an amino acid sequence provided herein.

In some embodiments, the isolated TFP molecules comprise a TCR extracellular domain that comprises an extracellular domain or portion thereof of a protein selected from the group consisting of the alpha or beta chain of the T-cell receptor, CD3 delta, CD3 epsilon, or CD3 gamma, or an amino acid sequence having at least one, two or three modifications but not more than 20, 10 or 5 modifications thereto.

In some embodiments, the anti-mesothelin binding domain is connected to the TCR extracellular domain by a linker sequence. In some instances, the linker region comprises $(G_4S)_n$, wherein n=1 to 4. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

In some embodiments, the isolated TFP molecules further comprise a sequence encoding a costimulatory domain. In other embodiments, the isolated TFP molecules further comprise a sequence encoding an intracellular signaling domain. In yet other embodiments, the isolated TFP molecules further comprise a leader sequence.

Also provided herein are vectors that comprise a nucleic acid molecule encoding any of the previously described TFP molecules. In some embodiments, the vector is selected from the group consisting of a DNA, a RNA, a plasmid, a lentivirus vector, adenoviral vector, or a retrovirus vector. In some embodiments, the vector further comprises a promoter. In some embodiments, the vector is an in vitro transcribed vector. In some embodiments, a nucleic acid sequence in the vector further comprises a poly(A) tail. In some embodiments, a nucleic acid sequence in the vector further comprises a 3'UTR.

Also provided herein are cells that comprise any of the described vectors. In some embodiments, the cell is a human T-cell. In some embodiments, the cell is a CD8+ or CD4+ T-cell. In other embodiments, the cells further comprise a nucleic acid encoding an inhibitory molecule that comprises a first polypeptide that comprises at least a portion of an inhibitory molecule, associated with a second polypeptide that comprises a positive signal from an intracellular signaling domain. In some instances, the inhibitory molecule comprise first polypeptide that comprises at least a portion of PD1 and a second polypeptide comprising a costimulatory domain and primary signaling domain.

In another aspect, provided herein are isolated TFP molecules that comprise a human or humanized anti-mesothelin binding domain, a TCR extracellular domain, a transmembrane domain, and an intracellular signaling domain, wherein the TFP molecule is capable of functionally interacting with an endogenous TCR complex and/or at least one endogenous TCR polypeptide.

In another aspect, provided herein are isolated TFP molecules that comprise a human or humanized anti-mesothelin binding domain, a TCR extracellular domain, a transmembrane domain, and an intracellular signaling domain, wherein the TFP molecule is capable of functionally integrating into an endogenous TCR complex.

In another aspect, provided herein are human CD8+ or CD4+ T-cells that comprise at least two TFP molecules, the TFP molecules comprising a human or humanized anti-mesothelin binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In another aspect, provided herein are protein complexes that comprise i) a TFP molecule comprising a human or humanized anti-mesothelin binding domain, a TCR extracellular domain, a transmembrane domain, and an intracellular domain; and ii) at least one endogenous TCR complex.

In some embodiments, the TCR comprises an extracellular domain or portion thereof of a protein selected from the group consisting of the alpha or beta chain of the T-cell receptor, CD3 delta, CD3 epsilon, or CD3 gamma. In some embodiments, the anti-mesothelin binding domain is connected to the TCR extracellular domain by a linker sequence. In some instances, the linker region comprises $(G_4S)_n$, wherein n=1 to 4. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

Also provided herein are human CD8+ or CD4+ T-cells that comprise at least two different TFP proteins per any of the described protein complexes.

In another aspect, provided herein is a population of human CD8+ or CD4+ T-cells, wherein the T-cells of the population individually or collectively comprise at least two TFP molecules, the TFP molecules comprising a human or humanized anti-mesothelin binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In another aspect, provided herein is a population of human CD8+ or CD4+ T-cells, wherein the T-cells of the population individually or collectively comprise at least two TFP molecules encoded by an isolated nucleic acid molecule provided herein.

In another aspect, provided herein are methods of making a cell comprising transducing a T-cell with any of the described vectors.

In another aspect, provided herein are methods of generating a population of RNA-engineered cells that comprise introducing an in vitro transcribed RNA or synthetic RNA into a cell, where the RNA comprises a nucleic acid encoding any of the described TFP molecules.

In another aspect, provided herein are methods of providing an anti-tumor immunity in a mammal that comprise administering to the mammal an effective amount of a cell expressing any of the described TFP molecules. In some embodiments, the cell is an autologous T-cell. In some embodiments, the cell is an allogeneic T-cell. In some embodiments, the mammal is a human.

In another aspect, provided herein are methods of treating a mammal having a disease associated with expression of mesothelin that comprise administering to the mammal an effective amount of the cell of comprising any of the described TFP molecules. In some embodiments, the disease associated with mesothelin expression is selected from a proliferative disease such as a cancer or malignancy or a precancerous condition such as a pancreatic cancer, an ovarian cancer, a stomach cancer, a lung cancer, or an endometrial cancer, or is a non-cancer related indication associated with expression of mesothelin.

In some embodiments, the cells expressing any of the described TFP molecules are administered in combination with an agent that ameliorates one or more side effects associated with administration of a cell expressing a TFP molecule. In some embodiments, the cells expressing any of the described TFP molecules are administered in combination with an agent that treats the disease associated with mesothelin.

Also provided herein are any of the described isolated nucleic acid molecules, any of the described isolated polypeptide molecules, any of the described isolated TFPs, any of the described protein complexes, any of the described vectors or any of the described cells for use as a medicament

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

As used herein, "about" can mean plus or minus less than 1 or 1, 2, 3, 4, 5, 6, 7, 8, 9, 10, 11, 12, 13, 14, 15, 16, 17, 18, 19, 20, 25, 30, or greater than 30 percent, depending upon the situation and known or knowable by one skilled in the art.

As used herein the specification, "subject" or "subjects" or "individuals" may include, but are not limited to, mammals such as humans or non-human mammals, e.g., domesticated, agricultural or wild, animals, as well as birds, and aquatic animals. "Patients" are subjects suffering from or at risk of developing a disease, disorder or condition or otherwise in need of the compositions and methods provided herein.

As used herein, "treating" or "treatment" refers to any indicia of success in the treatment or amelioration of the disease or condition. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. As used herein, "treat or prevent" is sometimes used herein to refer to a method that results in some level of treatment or amelioration of the disease or condition, and contemplates a range of results directed to that end, including but not restricted to prevention of the condition entirely.

As used herein, "preventing" refers to the prevention of the disease or condition, e.g., tumor formation, in the patient. For example, if an individual at risk of developing a tumor or other form of cancer is treated with the methods of the present invention and does not later develop the tumor or other form of cancer, then the disease has been prevented, at least over a period of time, in that individual.

As used herein, a "therapeutically effective amount" is the amount of a composition or an active component thereof sufficient to provide a beneficial effect or to otherwise reduce a detrimental non-beneficial event to the individual to whom the composition is administered. By "therapeutically effective dose" herein is meant a dose that produces one or more desired or desirable (e.g., beneficial) effects for which it is administered, such administration occurring one or more times over a given period of time. The exact dose will depend on the purpose of the treatment, and will be ascertainable by one skilled in the art using known techniques (see, e.g. Lieberman, Pharmaceutical Dosage Forms (vols. 1-3, 1992); Lloyd, *The Art, Science and Technology of Pharmaceutical Compounding* (1999); and Pickar, *Dosage Calculations* (1999))

As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell. A "TFP T cell" is a T cell that has been transduced (e.g., according to the methods disclosed herein) and that expresses a TFP, e.g., incorporated into the natural TCR. In some embodiments, the T cell is a CD4+ T cell, a CD8+ T cell, or a CD4+/CD8+ T cell. In some embodiments, the TFP T cell is an NK cell. In some embodiments, the TFP T cell is agamma-delta T cell.

As used herein, the term "mesothelin" also known as MSLN or CAK1 antigen or Pre-pro-megakaryocyte-potentiating factor, refers to the protein that in humans is encoded by the MSLN (or Megakaryocyte-potentiating factor (MPF)) gene. Mesothelin is a 40 kDa protein present on normal mesothelial cells and overexpressed in several human tumors, including mesothelioma and ovarian and pancreatic adenocarcinoma. The mesothelin gene encodes a precursor protein that is processed to yield mesothelin which is attached to the cell membrane by a glycophosphatidylinositol linkage and a 31-kDa shed fragment named megakaryocyte-potentiating factor (MPF). Mesothelin may be involved in cell adhesion, but its biological function is not known. Mesothelin is a tumour differentiation antigen that is normally present on the mesothelial cells lining the pleura, peritoneum and pericardium. Mesothelin is an antigenic determinant detectable on mesothelioma cells, ovarian cancer cells, pancreatic adenocarcinoma cell and some squamous cell carcinomas (see, e.g., Kojima et al., J. Biol. Chem. 270:21984-21990 (1995) and Onda et al., Clin. Cancer Res. 12:4225-4231 (2006)). Mesothelin interacts with CA125/MUC16 (see, e.g., Rump et al., J. Biol. Chem. 279:9190-9198 (2004) and Ma et al., J. Biol. Chem. 287:33123-33131 (2012)).

The human and murine amino acid and nucleic acid sequences can be found in a public database, such as GenBank, UniProt and Swiss-Prot. For example, the amino acid sequence of human mesothelin can be found as UniProt/Swiss-Prot Accession No. Q13421. The human mesothelin polypeptide canonical sequence is UniProt Accession No. Q13421 (or Q13421-1):

```
                                      (SEQ ID NO: 15)
MALPTARPLLGSCGTPALGSLLFLLFSLGWVQPSRTLAGETGQEAAPLDG

VLANPPNISSLSPRQLLGFPCAEVSGLSTERVRELAVALAQKNVKLSTEQ

LRCLAHRLSEPPEDLDALPLDLLLFLNPDAFSGPQACTRFFSRITKANVD

LLPRGAPERQRLLPAALACWGVRGSLLSEADVRALGGLACDLPGRFVAES

AEVLLPRLVSCPGPLDQDQQEAARAALQGGGPPYGPPSTWSVSTMDALRG

LLPVLGQPIIRSIPQGIVAAWRQRSSRDPSWRQPERTILRPRFRREVEKT

ACPSGKKAREIDESLIFYKKWELEACVDAALLATQMDRVNAIPFTYEQLD

VLKHKLDELYPQGYPESVIQHLGYLFLKMSPEDIRKWNVTSLETLKALLE

VNKGHEMSPQAPRRPLPQVATLIDRFVKGRGQLDKDTLDTLTAFYPGYLC

SLSPEELSSVPPSSIWAVRPQDLDTCDPRQLDVLYPKARLAFQNMNGSEY

FVKIQSFLGGAPTEDLKALSQQNVSMDLATFMKLRTDAVLPLTVAEVQKL

LGPHVEGLKAEERHRPVRDWILRQRQDDLDTLGLGLQGGIPNGYLVLDLS

MQEALSGTPCLLGPGPVLTVLALLLASTLA.
```

The nucleotide sequence encoding human mesothelin transcript variant 1 can be found at Accession No. NM005823. The nucleotide sequence encoding human mesothelin transcript variant 2 can be found at Accession No. NM013404. The nucleotide sequence encoding human mesothelin transcript variant 3 can be found at Accession No. NM001177355. Mesothelin is expressed on mesothelioma cells, ovarian cancer cells, pancreatic adenocarcinoma cell and squamous cell carcinomas (see, e.g., Kojima et al., J. Biol. Chem. 270:21984-21990 (1995) and Onda et al., Clin. Cancer Res. 12:4225-4231 (2006)). Other cells that express mesothelin are provided below in the definition of "disease associated with expression of mesothelin." Mesothelin also interacts with CA125/MUC16 (see, e.g., Rump et al., J. Biol. Chem. 279:9190-9198 (2004) and Ma et al., J. Biol. Chem. 287:33123-33131 (2012)). In one example, the antigen-binding portion of TFPs recognizes and binds an epitope within the extracellular domain of the mesothelin protein as expressed on a normal or malignant mesothelioma cell, ovarian cancer cell, pancreatic adenocarcinoma cell, or squamous cell carcinoma cell.

The term "antibody," as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', $F(ab')_2$, and Fv fragments, single-chain (sc)Fv ("scFv") antibody fragments, linear antibodies, single domain antibodies (abbreviated "sdAb") (either $V_L$ or $V_H$), camelid $V_{HH}$ domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "$V_H$"" (or, in the case of single domain antibodies, e.g., nanobodies, "$V_{HH}$") with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein a scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

The portion of the TFP composition of the invention comprising an antibody or antibody fragment thereof may exist in a variety of forms where the antigen binding domain is expressed as part of a contiguous polypeptide chain including, for example, a single domain antibody fragment (sdAb) or heavy chain antibodies HCAb, a single chain antibody (scFv) derived from a murine, humanized or human antibody (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a TFP composition of the invention comprises an antibody fragment. In a further aspect, the TFP comprises an antibody fragment that comprises a scFv or a sdAb.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa ("•") and lambda ("•") light chains refer to the two major antibody light chain isotypes.

The term "recombinant antibody" refers to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that is capable of being bound specifically by an antibody, or otherwise provokes an immune response. This immune response may involve either antibody production, or the activation of specific immunologically-competent cells, or both.

The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autologous" refers to any material derived from the same individual to whom it is later to be re-introduced into the individual.

The term "allogeneic" refers to any material derived from a different animal of the same species or different patient as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lung cancer, and the like.

The phrase "disease associated with expression of mesothelin" includes, but is not limited to, a disease associated with expression of mesothelin or condition associated with cells which express mesothelin including, e.g., proliferative diseases such as a cancer or malignancy or a precancerous condition In one aspect, the cancer is a mesothelioma. In one aspect, the cancer is a pancreatic cancer. In one aspect, the cancer is an ovarian cancer. In one aspect, the cancer is a stomach cancer. In one aspect, the cancer is a lung cancer. In one aspect, the cancer is an endometrial cancer. Non-cancer related indications associated with expression of mesothelin include, but are not limited to, e.g., autoimmune disease, (e.g., lupus, rheumatoid arthritis, colitis), inflammatory disorders (allergy and asthma), and transplantation.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a TFP of the invention can be replaced with other amino acid residues from the same side chain family and the altered TFP can be tested using the functional assays described herein.

The term "stimulation" refers to a primary response induced by binding of a stimulatory domain or stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, and/or reorganization of cytoskeletal structures, and the like.

The term "stimulatory molecule" or "stimulatory domain" refers to a molecule or portion thereof expressed by a T-cell that provides the primary cytoplasmic signaling sequence(s) that regulate primary activation of the TCR complex in a stimulatory way for at least some aspect of the T-cell signaling pathway. In one aspect, the primary signal is initiated by, for instance, binding of a TCR/CD3 complex with an MHC molecule loaded with peptide, and which leads to mediation of a T-cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or "ITAM". Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the TFP containing cell, e.g., a TFP-expressing T-cell. Examples of immune effector function, e.g., in a TFP-expressing T-cell, include cytolytic activity and T helper cell activity, including the secretion of cytokines. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation.

A primary intracellular signaling domain can comprise an ITAM ("immunoreceptor tyrosine-based activation motif"). Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "costimulatory molecule" refers to the cognate binding partner on a T-cell that specifically binds with a costimulatory ligand, thereby mediating a costimulatory response by the T-cell, such as, but not limited to, proliferation. Costimulatory molecules are cell surface molecules other than antigen receptors or their ligands that are required for an efficient immune response. Costimulatory molecules include, but are not limited to an MHC class 1 molecule, BTLA and a Toll ligand receptor, as well as DAP10, DAP12, CD30, LIGHT, OX40, CD2, CD27, CD28, CDS, ICAM-1, LFA-1 (CD11a/CD18) and 4-1BB (CD137). A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like. The intracellular signaling domain can comprise the entire intracellular portion, or the entire native intracellular signaling domain, of the molecule from which it is derived, or a functional fragment thereof. The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or equivalent residues from non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain one or more introns.

The term "effective amount" or "therapeutically effective amount" are used interchangeably herein, and refer to an amount of a compound, formulation, material, or composition, as described herein effective to achieve a particular biological or therapeutic result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR™ gene delivery technology from Oxford BioMedica, the LENTIMAX™ vector system from Lentigen, and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Human" or "fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the transcription machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "linker" and "flexible polypeptide linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence $(Gly\text{-}Gly\text{-}Gly\text{-}Ser)_n$, where n is a positive integer equal to or greater than 1. For example, n=1, n=2, n=3, n=4, n=5, n=6, n=7, n=8, n=9 and n=10. In one embodiment, the flexible polypeptide linkers include, but are not limited to, $(Gly_4Ser)_4$ or $(Gly_4Ser)_3$. In another embodiment, the linkers include multiple repeats of $(Gly_2Ser)$, (Gly Ser) or $(Gly_3Ser)$. Also included within the scope of the invention are linkers described in WO2012/138475 (incorporated herein by reference). In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, which has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. Poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma mesothelioma, renal cell carcinoma, stomach cancer, breast cancer, lung cancer, ovarian cancer, prostate cancer, colon cancer, cervical cancer, brain cancer, liver cancer, pancreatic cancer, kidney, endometrial, and stomach cancer.

In some instances, the disease is a cancer selected from the group consisting of mesothelioma, papillary serous ovarian adenocarcinoma, clear cell ovarian carcinoma, mixed Mullerian ovarian carcinoma, endometroid mucinous ovarian carcinoma, malignant pleural disease, pancreatic adenocarcinoma, ductal pancreatic adenocarcinoma, uterine serous carcinoma, lung adenocarcinoma, extrahepatic bile duct carcinoma, gastric adenocarcinoma, esophageal adenocarcinoma, colorectal adenocarcinoma, breast adenocarcinoma, a disease associated with mesothelin expression, and combinations thereof, a disease associated with mesothelin expression, and combinations thereof.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, an antibody fragment or a specific ligand, which recognizes and binds a cognate binding partner (e.g., mesothelin) present in a sample, but which does not necessarily and substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Description

Provided herein are compositions of matter and methods of use for the treatment of a disease such as cancer, using T-cell receptor (TCR) fusion proteins. As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell. As provided herein, TFPs provide substantial benefits as compared to Chimeric Antigen Receptors. The term "Chimeric Antigen Receptor" or alternatively a "CAR" refers to a recombinant polypeptide comprising an extracellular antigen binding domain in the form of a scFv, a transmembrane domain, and cytoplasmic signaling domains (also referred to herein as "an intracellular signaling domains") comprising a functional signaling domain derived from a stimulatory molecule as defined below. Generally, the central intracellular signaling domain of a CAR is derived from the CD3 zeta chain that is normally found associated with the TCR complex. The CD3 zeta signaling domain can be fused with one or more functional signaling domains derived from at least one co-stimulatory molecule such as 4-1BB (i.e., CD137), CD27 and/or CD28.

T-Cell Receptor (TCR) Fusion Proteins (TFP)

The present invention encompasses recombinant DNA constructs encoding TFPs, wherein the TFP comprises an antibody fragment that binds specifically to mesothelin, e.g., human mesothelin, wherein the sequence of the antibody fragment is contiguous with and in the same reading frame as a nucleic acid sequence encoding a TCR subunit or portion thereof. The TFPs provided herein are able to associate with one or more endogenous (or alternatively, one or more exogenous, or a combination of endogenous and exogenous) TCR subunits in order to form a functional TCR complex.

In one aspect, the TFP of the invention comprises a target-specific binding element otherwise referred to as an antigen binding domain. The choice of moiety depends upon the type and number of target antigen that define the surface of a target cell. For example, the antigen binding domain may be chosen to recognize a target antigen that acts as a cell surface marker on target cells associated with a particular disease state. Thus, examples of cell surface markers that may act as target antigens for the antigen binding domain in a TFP of the invention include those associated with viral, bacterial and parasitic infections; autoimmune diseases; and cancerous diseases (e.g., malignant diseases).

In one aspect, the TFP-mediated T-cell response can be directed to an antigen of interest by way of engineering an antigen-binding domain into the TFP that specifically binds a desired antigen.

In one aspect, the portion of the TFP comprising the antigen binding domain comprises an antigen binding domain that targets mesothelin. In one aspect, the antigen binding domain targets human mesothelin.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain ($V_H$), a light chain variable domain ($V_L$) and a variable domain ($V_{HH}$) of a camelid derived nanobody, and to an alternative scaffold known in the art to function as antigen binding domain, such as a recombinant fibronectin domain, anticalin, DARPIN and the like. Likewise a natural or synthetic ligand specifically recognizing and binding the target antigen can be used as antigen binding domain for the TFP. In some instances, it is beneficial for the antigen binding domain to be derived from the same species in which the TFP will ultimately be used in. For example, for use in humans, it may be beneficial for the antigen binding domain of the TFP to comprise human or humanized residues for the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-mesothelin binding domain comprises one or more (e.g., all three) light chain complementary determining region 1 (LC CDR1), light chain complementary determining region 2 (LC CDR2), and light chain complementary determining region 3 (LC CDR3) of a humanized or human anti-mesothelin binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-mesothelin binding domain described herein, e.g., a humanized or human anti-mesothelin binding domain comprising one or more, e.g., all three, LC CDRs and one or more, e.g., all three, HC CDRs. In one embodiment, the humanized or human anti-mesothelin binding domain comprises one or more (e.g., all three) heavy chain complementary determining region 1 (HC CDR1), heavy chain complementary determining region 2 (HC CDR2), and heavy chain complementary determining region 3 (HC CDR3) of a humanized or human anti-mesothelin binding domain described herein, e.g., the humanized or human anti-mesothelin binding domain has two variable heavy chain regions, each comprising a HC CDR1, a HC CDR2 and a HC CDR3 described herein. In one embodiment, the humanized or human anti-mesothelin binding domain comprises a humanized or human light chain variable region described herein and/or a humanized or human heavy chain variable region described herein. In one embodiment, the humanized or human anti-mesothelin binding domain comprises a humanized heavy chain variable region described herein, e.g., at least two humanized or human heavy chain variable regions described herein. In one embodiment, the anti-mesothelin binding domain is a scFv comprising a light chain and a heavy chain of an amino acid sequence provided herein. In an embodiment, the anti-mesothelin binding domain (e.g., a scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-mesothelin binding domain is a scFv, and a light chain variable region comprising an amino acid sequence described herein, is attached to a heavy chain variable region comprising an amino acid sequence described herein, via a linker, e.g., a linker described herein. In one embodiment, the humanized anti-mesothelin binding domain includes a $(Gly_4\text{-}Ser)_n$ linker, wherein n is 1, 2, 3, 4, 5, or 6, preferably 3 or 4. The light chain variable region and heavy chain variable region of a scFv can be, e.g., in any of the following orientations: light chain variable region-linker-heavy chain variable region or heavy chain variable region-linker-light chain variable region. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 93/017105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions (see, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference in their entirety). In such humanized antibodies and antibody fragments, substantially less than an intact human variable domain has been substituted by the corresponding sequence from a nonhuman species Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a $V_H$4-4-59 germline sequence. In one embodiment, the framework region can comprise, one, two, three, four or five modifications, e.g., substitutions, e.g., from the amino acid at the corresponding murine sequence.

In one embodiment, the framework region, e.g., all four framework regions of the light chain variable region are derived from a VK3-1.25 germline sequence. In one embodiment, the framework region can comprise, one, two, three, four or five modifications, e.g., substitutions, e.g., from the amino acid at the corresponding murine sequence.

In some aspects, the portion of a TFP composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human mesothelin. In some embodiments, a humanized antibody or antibody fragment may have improved affinity and/or specificity of binding to human mesothelin.

In one aspect, the anti-mesothelin binding domain is characterized by particular functional features or properties of an antibody or antibody fragment. For example, in one aspect, the portion of a TFP composition of the invention that comprises an antigen binding domain specifically binds human mesothelin. In one aspect, the antigen binding domain has the same or a similar binding specificity to human mesothelin as the FMC63 scFv described in Nicholson et al. Mol. Immun. 34 (16-17): 1157-1165 (1997). In one aspect, the invention relates to an antigen binding domain comprising an antibody or antibody fragment, wherein the antibody binding domain specifically binds to a mesothelin protein or fragment thereof, wherein the antibody or antibody fragment comprises a variable light chain and/or a variable heavy chain that includes an amino acid sequence provided herein. In certain aspects, the scFv is contiguous with and in the same reading frame as a leader sequence.

In one aspect, the anti-mesothelin binding domain is a fragment, e.g., a single chain variable fragment (scFv). In one aspect, the anti-mesothelin binding domain is a Fv, a Fab, a $(Fab')_2$, or a bi-functional (e.g. bi-specific) hybrid antibody (e.g., Lanzavecchia et al., Eur. J. Immunol. 17, 105 (1987)). In one aspect, the antibodies and fragments thereof disclosed herein bind a mesothelin protein with wild-type or enhanced affinity.

Also provided herein are methods for obtaining an antibody antigen binding domain specific for a target antigen (e.g., mesothelin or any target antigen described elsewhere herein for targets of fusion moiety binding domains), the method comprising providing by way of addition, deletion, substitution or insertion of one or more amino acids in the amino acid sequence of a $V_H$ domain set out herein a $V_H$ domain which is an amino acid sequence variant of the $V_H$ domain, optionally combining the $V_H$ domain thus provided with one or more $V_L$ domains, and testing the $V_H$ domain or $V_H/V_L$ combination or combinations to identify a specific binding member or an antibody antigen binding domain specific for a target antigen of interest (e.g., mesothelin) and optionally with one or more desired properties.

In some instances, $V_H$ domains and scFvs can be prepared according to method known in the art (see, for example, Bird et al., (1988) Science 242:423-426 and Huston et al., (1988) Proc. Natl. Acad. Sci. USA 85:5879-5883). scFv molecules can be produced by linking $V_H$ and $V_L$ regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intra-chain folding is prevented. Inter-chain folding is also required to bring the two variable regions together to form a functional epitope binding site. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3. For examples of linker orientation and size see, e.g., Hollinger et al. 1993 Proc. Natl. Acad. Sci. U.S.A. 90:6444-6448, U.S. Pat. No. 7,695, 936, U.S. Patent Application Publication Nos. 20050100543 and 20050175606, and PCT Publication Nos. WO2006/020258 and WO2007/024715, all of which are incorporated herein by reference.

A scFv can comprise a linker of about 10, 11, 12, 13, 14, 15 or greater than 15 residues between its $V_L$ and $V_H$ regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)_n$, where n is a positive integer equal to or greater than 1. In one embodiment, the linker can be $(Gly_4Ser)_4$ or $(Gly_4Ser)_3$. Variation in the linker length may retain or enhance activity, giving rise to superior efficacy in activity studies. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

Stability and Mutations

The stability of an anti-mesothelin binding domain, e.g., scFv molecules (e.g., soluble scFv) can be evaluated in reference to the biophysical properties (e.g., thermal stability) of a conventional control scFv molecule or a full length antibody. In one embodiment, the humanized or human scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a parent scFv in the described assays.

The improved thermal stability of the anti-mesothelin binding domain, e.g., scFv is subsequently conferred to the entire mesothelin-TFP construct, leading to improved therapeutic properties of the anti-mesothelin TFP construct. The thermal stability of the anti-mesothelin binding domain, e.g., scFv can be improved by at least about 2° C. or 3° C. as compared to a conventional antibody. In one embodiment, the anti-mesothelin binding domain, e.g., scFv has a 1° C. improved thermal stability as compared to a conventional antibody. In another embodiment, the anti-mesothelin binding domain, e.g., scFv has a 2° C. improved thermal stability as compared to a conventional antibody. In another embodiment, the scFv has a 4° C., 5° C., 6° C., 7° C., 8° C., 9° C., 10° C., 11° C., 12° C., 13° C., 14° C., or 15° C. improved thermal stability as compared to a conventional antibody. Comparisons can be made, for example, between the scFv molecules disclosed herein and scFv molecules or Fab fragments of an antibody from which the scFv $V_H$ and $V_L$ were derived. Thermal stability can be measured using methods known in the art. For example, in one embodiment, $T_M$ can be measured. Methods for measuring $T_M$ and other methods of determining protein stability are described below.

Mutations in scFv (arising through humanization or mutagenesis of the soluble scFv) alter the stability of the scFv and improve the overall stability of the scFv and the anti-mesothelin TFP construct. Stability of the humanized scFv is compared against the murine scFv using measurements such as $T_M$, temperature denaturation and temperature aggregation. In one embodiment, the anti-mesothelin binding domain, e.g., a scFv, comprises at least one mutation arising from the humanization process such that the mutated scFv confers improved stability to the anti-mesothelin TFP construct. In another embodiment, the anti-mesothelin binding domain, e.g., scFv comprises at least 1, 2, 3, 4, 5, 6, 7, 8, 9, 10 mutations arising from the humanization process such that the mutated scFv confers improved stability to the mesothelin-TFP construct.

In one aspect, the antigen binding domain of the TFP comprises an amino acid sequence that is homologous to an antigen binding domain amino acid sequence described herein, and the antigen binding domain retains the desired functional properties of the anti-mesothelin antibody fragments described herein. In one specific aspect, the TFP composition of the invention comprises an antibody fragment. In a further aspect, that antibody fragment comprises a scFv.

In various aspects, the antigen binding domain of the TFP is engineered by modifying one or more amino acids within one or both variable regions (e.g., $V_H$ and/or $V_L$), for example within one or more CDR regions and/or within one or more framework regions. In one specific aspect, the TFP composition of the invention comprises an antibody fragment. In a further aspect, that antibody fragment comprises a scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein. For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences refers to two or more sequences that are the same. Two sequences are "substantially identical" if two sequences have a specified percentage of amino acid residues or nucleotides that are the same (e.g., 60% identity, optionally 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology). Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

In one aspect, the present invention contemplates modifications of the starting antibody or fragment (e.g., scFv) amino acid sequence that generate functionally equivalent molecules. For example, the $V_H$ or $V_L$ of an anti-mesothelin binding domain, e.g., scFv, comprised in the TFP can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting $V_H$ or $V_L$ framework region of the anti-mesothelin binding domain, e.g., scFv. The present invention contemplates modifications of the entire TFP construct, e.g., modifications in one or more amino acid sequences of the various domains of the TFP construct in order to generate functionally equivalent molecules. The TFP construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity of the starting TFP construct.

Extracellular Domain

The extracellular domain may be derived either from a natural or from a recombinant source. Where the source is natural, the domain may be derived from any protein, but in particular a membrane-bound or transmembrane protein. In one aspect the extracellular domain is capable of associating with the transmembrane domain. An extracellular domain of particular use in this invention may include at least the extracellular region(s) of e.g., the alpha, beta or zeta chain of the T-cell receptor, or CD3 epsilon, CD3 gamma, or CD3 delta, or in alternative embodiments, CD28, CD45, CD4, CD5, CD8, CD9, CD16, CD22, CD33, CD37, CD64, CD80, CD86, CD134, CD137, CD154.

Transmembrane Domain

In general, a TFP sequence contains an extracellular domain and a transmembrane domain encoded by a single genomic sequence. In alternative embodiments, a TFP can be designed to comprise a transmembrane domain that is heterologous to the extracellular domain of the TFP. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region). In one aspect, the transmembrane domain is one that is associated with one of the other domains of the TFP is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another TFP on the TFP-T-cell surface. In a different aspect the amino acid sequence of the transmembrane domain may be modified or substituted so as to minimize interactions with the binding domains of the native binding partner present in the same TFP.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the TFP has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the TFP, e.g., the antigen binding domain of the TFP, via a hinge, e.g., a hinge from a human protein. For example, in one embodiment, the hinge can be a human immunoglobulin (Ig) hinge, e.g., an IgG4 hinge, or a CD8a hinge.

Linkers

Optionally, a short oligo- or polypeptide linker, between 2 and 10 amino acids in length may form the linkage between the transmembrane domain and the cytoplasmic region of the TFP. A glycine-serine doublet provides a particularly suitable linker. For example, in one aspect, the linker comprises the amino acid sequence of GGGGSGGGGS (SEQ ID NO. 53). In some embodiments, the linker is encoded by a nucleotide sequence of GGTGGCGGAGGTTCTGGAGGTGGAGGTTCC (SEQ ID NO. 54).

Cytoplasmic Domain

The cytoplasmic domain of the TFP can include an intracellular signaling domain, if the TFP contains CD3 gamma, delta or epsilon polypeptides; TCR alpha and TCR beta subunits are generally lacking in a signaling domain. An intracellular signaling domain is generally responsible for activation of at least one of the normal effector functions of the immune cell in which the TFP has been introduced. The term "effector function" refers to a specialized function of a cell. Effector function of a T-cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the TFP of the invention include the cytoplasmic sequences of the T-cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of naive T-cells and that a secondary and/or costimulatory signal is required. Thus, naïve T-cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs (ITAMs).

Examples of ITAMs containing primary intracellular signaling domains that are of particular use in the invention include those of CD3 zeta, FcR gamma, FcR beta, CD3 gamma, CD3 delta, CD3 epsilon, CD5, CD22, CD79a, CD79b, and CD66d. In one embodiment, a TFP of the invention comprises an intracellular signaling domain, e.g., a primary signaling domain of CD3-epsilon. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the TFP can comprise the CD3 zeta signaling domain by itself or it can be combined with any other desired intracellular signaling domain(s) useful in the context of a TFP of the invention. For example, the intracellular signaling domain of the TFP can comprise a CD3 epsilon chain portion and a costimulatory signaling domain. The costimulatory signaling domain refers to a portion of the TFP comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, DAP10, DAP12, CD30, CD40, PD1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human TFP-T-cells in vitro and augments human T-cell persistence and antitumor activity in vivo (Song et al. Blood. 2012; 119(3):696-706).

The intracellular signaling sequences within the cytoplasmic portion of the TFP of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequences.

In one embodiment, a glycine-serine doublet can be used as a suitable linker. In one embodiment, a single amino acid, e.g., an alanine, a glycine, can be used as a suitable linker.

In one aspect, the TFP-expressing cell described herein can further comprise a second TFP, e.g., a second TFP that includes a different antigen binding domain, e.g., to the same target (mesothelin) or a different target (e.g., CD123). In one embodiment, when the TFP-expressing cell comprises two or more different TFPs, the antigen binding domains of the different TFPs can be such that the antigen binding domains do not interact with one another. For example, a cell expressing a first and second TFP can have an antigen binding domain of the first TFP, e.g., as a fragment, e.g., a scFv, that does not associate with the antigen binding domain of the second TFP, e.g., the antigen binding domain of the second TFP is a $V_{HH}$.

In another aspect, the TFP-expressing cell described herein can further express another agent, e.g., an agent which enhances the activity of a TFP-expressing cell. For example, in one embodiment, the agent can be an agent which inhibits an inhibitory molecule. Inhibitory molecules, e.g., PD1, can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, LAG3, CTLA4, CD160, BTLA, LAIR1, TIM3, 2B4 and TIGIT, or a fragment of any of these (e.g., at least a portion of an extracellular domain of any of these), and a second polypeptide which is an intracellular signaling domain described herein (e.g., comprising a costimulatory domain (e.g., 4-1BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T-cells and myeloid cells (Agata et al. 1996 Int. Immunol 8:765-75). Two ligands for PD1, PD-L1 and PD-L2 have been shown to downregulate T-cell activation upon binding to PD1 (Freeman et al. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094) Immune suppression can be reversed by inhibiting the local interaction of PD1 with PD-L1.

In one embodiment, the agent comprises the extracellular domain (ECD) of an inhibitory molecule, e.g., Programmed Death 1 (PD1) can be fused to a transmembrane domain and optionally an intracellular signaling domain such as 41BB and CD3 zeta (also referred to herein as a PD1 TFP). In one embodiment, the PD1 TFP, when used in combinations with an anti-mesothelin TFP described herein, improves the persistence of the T-cell. In one embodiment, the TFP is a PD1 TFP comprising the extracellular domain of PD 1. Alternatively, provided are TFPs containing an antibody or antibody fragment such as a scFv that specifically binds to the Programmed Death-Ligand 1 (PD-L1) or Programmed Death-Ligand 2 (PD-L2).

In another aspect, the present invention provides a population of TFP-expressing T-cells, e.g., TFP-T-cells. In some embodiments, the population of TFP-expressing T-cells comprises a mixture of cells expressing different TFPs. For example, in one embodiment, the population of TFP-T-cells can include a first cell expressing a TFP having an anti-mesothelin binding domain described herein, and a second cell expressing a TFP having a different anti-mesothelin binding domain, e.g., an anti-mesothelin binding domain described herein that differs from the anti-mesothelin binding domain in the TFP expressed by the first cell. As another example, the population of TFP-expressing cells can include a first cell expressing a TFP that includes an anti-mesothelin binding domain, e.g., as described herein, and a second cell expressing a TFP that includes an antigen binding domain to a target other than mesothelin (e.g., another tumor-associated antigen).

In another aspect, the present invention provides a population of cells wherein at least one cell in the population expresses a TFP having an anti-mesothelin domain described herein, and a second cell expressing another agent, e.g., an agent which enhances the activity of a TFP-expressing cell. For example, in one embodiment, the agent can be an agent which inhibits an inhibitory molecule. Inhibitory molecules, e.g., can, in some embodiments, decrease the ability of a TFP-expressing cell to mount an immune effector response. Examples of inhibitory molecules include PD1, PD-L1, PD-L2, CTLA4, TIM3, LAG3, VISTA, BTLA, TIGIT, LAIR1, CD160, 2B4 and TGFR beta. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein.

Disclosed herein are methods for producing in vitro transcribed RNA encoding TFPs. The present invention also includes a TFP encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length. RNA so produced can efficiently transfect different kinds of cells. In one aspect, the template includes sequences for the TFP.

In one aspect, the anti-mesothelin TFP is encoded by a messenger RNA (mRNA). In one aspect the mRNA encoding the anti-mesothelin TFP is introduced into a T-cell for production of a TFP-T-cell. In one embodiment, the in vitro transcribed RNA TFP can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a TFP of the present invention. In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3,000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3'UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 Ts), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly (A) tail using poly (A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001);

Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Nucleic Acid Constructs Encoding a TFP

The present invention also provides nucleic acid molecules encoding one or more TFP constructs described herein. In one aspect, the nucleic acid molecule is provided as a messenger RNA transcript. In one aspect, the nucleic acid molecule is provided as a DNA construct.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired TFP of the invention is an adenoviral vector (A5/35). In another embodiment, the expression of nucleic acids encoding TFPs can be accomplished using of transposons such as sleeping beauty, crisper, CAS9, and zinc finger nucleases (See, June et al. 2009 Nature Reviews Immunol. 9.10: 704-716, incorporated herein by reference).

The expression constructs of the present invention may also be used for nucleic acid immunization and gene therapy, using standard gene delivery protocols. Methods for gene delivery are known in the art (see, e.g., U.S. Pat. Nos. 5,399,346, 5,580,859, 5,589,466, incorporated by reference herein in their entireties). In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, e.g., in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

A number of virally based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a TFP transgene in a mammalian T-cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving TFP expression from transgenes cloned into a lentiviral vector (see, e.g., Milone et al., Mol. Ther. 17(8): 1453-1464 (2009)). Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline-regulated promoter.

In order to assess the expression of a TFP polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art (see, e.g., Sambrook et al., 2012, Molecular Cloning: A Laboratory Manual, volumes 1-4, Cold Spring Harbor Press, NY). One method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like (see, e.g., U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable sub-micron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a TFP encoding nucleic acid molecule. In one aspect, a TFP vector can be directly transduced into a cell, e.g., a T-cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the TFP construct in mammalian T-cells. In one aspect, the mammalian T-cell is a human T-cell.

Sources of T-Cells

Prior to expansion and genetic modification, a source of T-cells is obtained from a subject. The term "subject" is intended to include living organisms in which an immune response can be elicited (e.g., mammals). Examples of subjects include humans, dogs, cats, mice, rats, and transgenic species thereof. T-cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T-cell lines available in the art, may be used. In certain aspects of the present invention, T-cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T-cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T-cells are isolated from peripheral blood lymphocytes by lysing the red blood cells and depleting the monocytes, for example, by centrifugation through a PERCOLL™ gradient or by counterflow centrifugal elutriation. A specific subpopulation of T-cells, such as CD3+, CD28+, CD4+, CD8+, CD45RA+, and CD45RO+ T-cells, can be further isolated by positive or negative selection techniques. For example, in one aspect, T-cells are isolated by incubation with anti-CD3/anti-CD28 (e.g., 3×28)-conjugated beads, such as DYNABEADS™ M-450 CD3/CD28 T, for a time period sufficient for positive selection of the desired T-cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T-cells in any situation where there are few T-cells as compared to other cell types, such in isolating tumor infiltrating lymphocytes (TIL) from tumor tissue or from immunocompromised individuals. Further, use of longer incubation times can increase the efficiency of capture of CD8+ T-cells. Thus, by simply shortening or lengthening the time T-cells are allowed to bind to the CD3/CD28 beads and/or by increasing or decreasing the ratio of beads to T-cells (as described further herein), subpopulations of T-cells can be preferentially selected for or against at culture initiation or at other time points during the process. Additionally, by increasing or decreasing the ratio of anti-CD3 and/or anti-CD28 antibodies on the beads or other surface, subpopulations of T-cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T-cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T-cells which typically express CD4+, CD25+, CD62Lhi, GITR+, and FoxP3+. Alternatively, in certain aspects, T regulatory cells are depleted by anti-C25 conjugated beads or other similar method of selection.

In one embodiment, a T-cell population can be selected that expresses one or more of IFN-γ, TNF-alpha, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/mL is used. In one aspect, a concentration of 1 billion cells/mL is used. In a further aspect, greater than 100 million cells/mL is used. In a further aspect, a concentration of cells of 10, 15, 20, 25, 30, 35, 40, 45, or 50 million cells/mL is used. In yet one aspect, a concentration of cells from 75, 80, 85, 90, 95, or 100 million cells/mL is used. In further aspects, concentrations of 125 or 150 million cells/mL can be used. Using high concentrations can result in increased cell yield, cell activation, and cell expansion. Further, use of high cell concentrations allows more efficient capture of cells that may weakly express target antigens of interest, such as CD28-negative T-cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T-cells that normally have weaker CD28 expression.

In a related aspect, it may be desirable to use lower concentrations of cells. By significantly diluting the mixture of T-cells and surface (e.g., particles such as beads), interactions between the particles and cells is minimized. This selects for cells that express high amounts of desired antigens to be bound to the particles. For example, CD4+ T-cells express higher levels of CD28 and are more efficiently captured than CD8+ T-cells in dilute concentrations. In one aspect, the concentration of cells used is $5\times10^6$/mL. In other aspects, the concentration used can be from about $1\times10^5$/mL to $1\times10^6$/mL, and any integer value in between. In other aspects, the cells may be incubated on a rotator for varying lengths of time at varying speeds at either 2-10° C. or at room temperature.

T-cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1 per minute and stored in the vapor phase of a liquid nitrogen storage tank. Other methods of controlled freezing may be used as well as uncontrolled freezing immediately at −20° C. or in liquid nitrogen. In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T-cells, isolated and frozen for later use in T-cell therapy for any number of diseases or conditions that would benefit from T-cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T-cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as alemtuzumab, anti-CD3 antibodies, cytoxan, fludarabine, cyclosporin, FK506, rapamycin, mycophenolic acid, steroids, FR901228, and irradiation.

In a further aspect of the present invention, T-cells are obtained from a patient directly following treatment that leaves the subject with functional T-cells. In this regard, it has been observed that following certain cancer treatments, in particular treatments with drugs that damage the immune system, shortly after treatment during the period when patients would normally be recovering from the treatment, the quality of T-cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T-cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T-cells, B cells, dendritic cells, and other cells of the immune system.

Activation and Expansion of T Cells

T-cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041, and 7,572,631.

Generally, the T-cells of the invention may be expanded by contact with a surface having attached thereto an agent that stimulates a CD3/TCR complex associated signal and a ligand that stimulates a costimulatory molecule on the surface of the T-cells. In particular, T-cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

T-cells that have been exposed to varied stimulation times may exhibit different characteristics. For example, typical blood or apheresed peripheral blood mononuclear cell products have a helper T-cell population (TH, CD4+) that is greater than the cytotoxic or suppressor T-cell population (TC, CD8+). Ex vivo expansion of T-cells by stimulating CD3 and CD28 receptors produces a population of T-cells that prior to about days 8-9 consists predominately of TH cells, while after about days 8-9, the population of T-cells comprises an increasingly greater population of TC cells.

Accordingly, depending on the purpose of treatment, infusing a subject with a T-cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T-cell product for specific purposes.

Once an anti-mesothelin TFP is constructed, various assays can be used to evaluate the activity of the molecule, such as but not limited to, the ability to expand T-cells following antigen stimulation, sustain T-cell expansion in the absence of re-stimulation, and anti-cancer activities in appropriate in vitro and animal models. Assays to evaluate the effects of an anti-mesothelin TFP are described in further detail below Western blot analysis of TFP expression in primary T-cells can be used to detect the presence of monomers and dimers (see, e.g., Milone et al., Molecular Therapy 17(8): 1453-1464 (2009)). Very briefly, T-cells (1:1 mixture of $CD4^+$ and $CD8^+$ T-cells) expressing the TFPs are expanded in vitro for more than 10 days followed by lysis and SDS-PAGE under reducing conditions. TFPs are detected by Western blotting using an antibody to a TCR chain. The same T-cell subsets are used for SDS-PAGE analysis under non-reducing conditions to permit evaluation of covalent dimer formation.

In vitro expansion of TFP T-cells following antigen stimulation can be measured by flow cytometry. For example, a mixture of $CD4^+$ and $CD8^+$ T-cells are stimulated with alphaCD3/alphaCD28 and APCs followed by transduction with lentiviral vectors expressing GFP under the control of the promoters to be analyzed. Exemplary promoters include the CMV IE gene, EF-1alpha, ubiquitin C, or phosphoglycerokinase (PGK) promoters. GFP fluorescence is evaluated on day 6 of culture in the CD4+ and/or CD8+ T-cell subsets by flow cytometry (see, e.g., Milone et al., Molecular Therapy 17(8): 1453-1464 (2009)). Alternatively, a mixture of CD4+ and CD8+ T-cells are stimulated with alphaCD3/alphaCD28 coated magnetic beads on day 0, and transduced with TFP on day 1 using a bicistronic lentiviral vector expressing TFP along with eGFP using a 2A ribosomal skipping sequence. Cultures are re-stimulated with either mesothelin+K562 cells (K562-mesothelin), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/mL. GFP+ T-cells are enumerated by flow cytometry using bead-based counting (see, e.g., Milone et al., Molecular Therapy 17(8): 1453-1464 (2009)).

Sustained TFP+ T-cell expansion in the absence of re-stimulation can also be measured (see, e.g., Milone et al., Molecular Therapy 17(8): 1453-1464 (2009)). Briefly, mean T-cell volume (fl) is measured on day 8 of culture using a Coulter Multisizer III particle counter following stimulation with alphaCD3/alphaCD28 coated magnetic beads on day 0, and transduction with the indicated TFP on day 1.

Animal models can also be used to measure a TFP-T activity. For example, xenograft model using human mesothelin-specific TFP+ T-cells to treat a cancer in immunodeficient mice (see, e.g., Milone et al., Molecular Therapy 17(8): 1453-1464 (2009)). Very briefly, after establishment of cancer, mice are randomized as to treatment groups. Different numbers of engineered T-cells are coinjected at a 1:1 ratio into NOD/SCID/γ−/− mice bearing cancer. The number of copies of each vector in spleen DNA from mice is evaluated at various times following T-cell injection. Animals are assessed for cancer at weekly intervals. Peripheral blood mesothelin+ cancer cell counts are measured in mice that are injected with alphamesothelin-zeta TFP+ T-cells or mock-transduced T-cells. Survival curves for the groups are compared using the log-rank test. In addition, absolute peripheral blood CD4+ and CD8+ T-cell counts 4 weeks following T-cell injection in NOD/SCID/γ−/− mice can also be analyzed. Mice are injected with cancer cells and 3 weeks later are injected with T-cells engineered to express TFP by a bicistronic lentiviral vector that encodes the TFP linked to eGFP. T-cells are normalized to 45-50% input GFP+ T-cells by mixing with mock-transduced cells prior to injection, and confirmed by flow cytometry. Animals are assessed for cancer at 1-week intervals. Survival curves for the TFP+ T-cell groups are compared using the log-rank test.

Dose dependent TFP treatment response can be evaluated (see, e.g., Milone et al., Molecular Therapy 17(8): 1453-1464 (2009)). For example, peripheral blood is obtained 35-70 days after establishing cancer in mice injected on day 21 with TFP T-cells, an equivalent number of mock-transduced T-cells, or no T-cells. Mice from each group are randomly bled for determination of peripheral blood mesothelin+ cancer cell counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of TFP-mediated proliferation is performed in microtiter plates by mixing washed T-cells with cells expressing mesothelin or CD32 and CD137 (KT32-BBL) for a final T-cell:cell expressing mesothelin ratio of 2:1. Cells expressing mesothelin cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8+ T-cell expansion ex vivo. T-cells are enumerated in cultures using CountBright™ fluorescent beads (Invitrogen) and flow cytometry as described by the manufacturer. TFP+ T-cells are identified by GFP expression using T-cells that are engineered with eGFP-2A linked TFP-expressing lentiviral vectors. For TFP+ T-cells not expressing GFP, the TFP+ T-cells are detected with biotinylated recombinant mesothelin protein and a secondary avidin-PE conjugate. CD4+ and CD8+ expression on T-cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences) according the manufacturer's instructions. Fluorescence is assessed using a FACScalibur flow cytometer, and data is analyzed according to the manufacturer's instructions.

Cytotoxicity can be assessed by a standard $^{51}$Cr-release assay (see, e.g., Milone et al., Molecular Therapy 17(8): 1453-1464 (2009)). Briefly, target cells are loaded with $^{51}$Cr (as $NaCrO_4$, New England Nuclear) at 37° C. for 2 hours with frequent agitation, washed twice in complete RPMI medium and plated into microtiter plates. Effector T-cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}Cr$ is then measured using a gamma particle counter (Packard Instrument Co., Waltham, Mass.). Each condition is performed in at least triplicate, and the percentage of lysis is calculated using the formula: % Lysis=(ER-SR)/(TR-SR), where ER represents the average $^{51}Cr$ released for each experimental condition.

Imaging technologies can be used to evaluate specific trafficking and proliferation of TFPs in tumor-bearing animal models. Such assays have been described, e.g., in Barrett et al., Human Gene Therapy 22:1575-1586 (2011). Briefly, NOD/SCID/γc−/− (NSG) mice are injected IV with cancer cells followed 7 days later with T-cells 4 hour after electroporation with the TFP constructs. The T-cells are stably transfected with a lentiviral construct to express firefly luciferase, and mice are imaged for bioluminescence. Alternatively, therapeutic efficacy and specificity of a single injection of TFP+ T-cells in a cancer xenograft model can be measured as follows: NSG mice are injected with cancer cells transduced to stably express firefly luciferase, followed by a single tail-vein injection of T-cells electroporated with mesothelin TFP 7 days later. Animals are imaged at various time points post injection. For example, photon-density heat maps of firefly luciferase positive cancer in representative mice at day 5 (2 days before treatment) and day 8 (24 hours post TFP+ PBLs) can be generated.

Other assays, including those described in the Example section herein as well as those that are known in the art can also be used to evaluate the anti-mesothelin TFP constructs of the invention.

Therapeutic Applications

Mesothelin Associated Diseases and/or Disorders

In one aspect, the invention provides methods for treating a disease associated with mesothelin expression. In one aspect, the invention provides methods for treating a disease wherein part of the tumor is negative for mesothelin and part of the tumor is positive for mesothelin. For example, the TFP of the invention is useful for treating subjects that have undergone treatment for a disease associated with elevated expression of mesothelin, wherein the subject that has undergone treatment for elevated levels of mesothelin exhibits a disease associated with elevated levels of mesothelin.

In one aspect, the invention pertains to a vector comprising anti-mesothelin TFP operably linked to promoter for expression in mammalian T-cells. In one aspect, the invention provides a recombinant T-cell expressing the mesothelin TFP for use in treating mesothelin-expressing tumors, wherein the recombinant T-cell expressing the mesothelin TFP is termed a mesothelin TFP-T. In one aspect, the mesothelin TFP-T of the invention is capable of contacting a tumor cell with at least one mesothelin TFP of the invention expressed on its surface such that the TFP-T targets the tumor cell and growth of the tumor is inhibited.

In one aspect, the invention pertains to a method of inhibiting growth of a mesothelin-expressing tumor cell, comprising contacting the tumor cell with a mesothelin TFP T-cell of the present invention such that the TFP-T is activated in response to the antigen and targets the cancer cell, wherein the growth of the tumor is inhibited.

In one aspect, the invention pertains to a method of treating cancer in a subject. The method comprises administering to the subject a mesothelin TFP T-cell of the present invention such that the cancer is treated in the subject. An example of a cancer that is treatable by the mesothelin TFP T-cell of the invention is a cancer associated with expression of mesothelin. In one aspect, the cancer is a mesothelioma. In one aspect, the cancer is a pancreatic cancer. In one aspect, the cancer is an ovarian cancer. In one aspect, the cancer is a stomach cancer. In one aspect, the cancer is a lung cancer. In one aspect, the cancer is an endometrial cancer. In some embodiments, mesothelin TFP therapy can be used in combination with one or more additional therapies.

The invention includes a type of cellular therapy where T-cells are genetically modified to express a TFP and the TFP-expressing T-cell is infused to a recipient in need thereof. The infused cell is able to kill tumor cells in the recipient. Unlike antibody therapies, TFP-expressing T-cells are able to replicate in vivo, resulting in long-term persistence that can lead to sustained tumor control. In various aspects, the T-cells administered to the patient, or their progeny, persist in the patient for at least one month, two month, three months, four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T-cell to the patient.

The invention also includes a type of cellular therapy where T-cells are modified, e.g., by in vitro transcribed RNA, to transiently express a TFP and the TFP-expressing T-cell is infused to a recipient in need thereof. The infused cell is able to kill tumor cells in the recipient. Thus, in various aspects, the T-cells administered to the patient, is present for less than one month, e.g., three weeks, two weeks, or one week, after administration of the T-cell to the patient.

Without wishing to be bound by any particular theory, the anti-tumor immunity response elicited by the TFP-expressing T-cells may be an active or a passive immune response, or alternatively may be due to a direct vs indirect immune response. In one aspect, the TFP transduced T-cells exhibit specific proinflammatory cytokine secretion and potent cytolytic activity in response to human cancer cells expressing the mesothelin antigen, resist soluble mesothelin inhibition, mediate bystander killing and/or mediate regression of an established human tumor. For example, antigen-less tumor cells within a heterogeneous field of mesothelin-expressing tumor may be susceptible to indirect destruction by mesothelin-redirected T-cells that has previously reacted against adjacent antigen-positive cancer cells.

In one aspect, the human TFP-modified T-cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a TFP to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a TFP disclosed herein. The TFP-modified cell can be administered to a mammalian recipient to provide a therapeutic benefit. The mammalian recipient may be a human and the TFP-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T-cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the TFP-modified T-cells of the invention are used in the treatment of diseases, disorders and conditions associated with expression of mesothelin. In certain aspects, the cells of the invention are used in the treatment of patients at risk for developing diseases, disorders and conditions associated with expression of mesothelin. Thus, the present invention provides methods for the treatment or prevention of diseases, disorders and conditions associated with expression of mesothelin comprising administering to a subject in need thereof, a therapeutically effective amount of the TFP-modified T-cells of the invention.

In one aspect the TFP-T-cells of the inventions may be used to treat a proliferative disease such as a cancer or malignancy or a precancerous condition. In one aspect, the cancer is a mesothelioma. In one aspect, the cancer is a pancreatic cancer. In one aspect, the cancer is an ovarian cancer. In one aspect, the cancer is a stomach cancer. In one aspect, the cancer is a lung cancer. In one aspect, the cancer is a endometrial cancer. Further a disease associated with mesothelin expression includes, but is not limited to, e.g., atypical and/or non-classical cancers, malignancies, precancerous conditions or proliferative diseases expressing mesothelin. Non-cancer related indications associated with expression of mesothelin include, but are not limited to, e.g., autoimmune disease, (e.g., lupus), inflammatory disorders (allergy and asthma) and transplantation.

The TFP-modified T-cells of the present invention may be administered either alone, or as a pharmaceutical composition in combination with diluents and/or with other components such as IL-2 or other cytokines or cell populations.

The present invention also provides methods for inhibiting the proliferation or reducing a mesothelin-expressing cell population, the methods comprising contacting a population of cells comprising a mesothelin-expressing cell with an anti-mesothelin TFP-T-cell of the invention that binds to the mesothelin-expressing cell. In a specific aspect, the present invention provides methods for inhibiting the proliferation or reducing the population of cancer cells expressing mesothelin, the methods comprising contacting the mesothelin-expressing cancer cell population with an anti-mesothelin TFP-T-cell of the invention that binds to the mesothelin-expressing cell. In one aspect, the present invention provides methods for inhibiting the proliferation or reducing the population of cancer cells expressing mesothelin, the methods comprising contacting the mesothelin-expressing cancer cell population with an anti-mesothelin TFP-T-cell of the invention that binds to the mesothelin-expressing cell. In certain aspects, the anti-mesothelin TFP-T-cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model a cancer associated with mesothelin-expressing cells relative to a negative control. In one aspect, the subject is a human.

The present invention also provides methods for preventing, treating and/or managing a disease associated with mesothelin-expressing cells (e.g., a cancer expressing mesothelin), the methods comprising administering to a subject in need an anti-mesothelin TFP-T-cell of the invention that binds to the mesothelin-expressing cell. In one aspect, the subject is a human Non-limiting examples of disorders associated with mesothelin-expressing cells include autoimmune disorders (such as lupus), inflammatory disorders (such as allergies and asthma) and cancers (such as pancreatic cancer, ovarian cancer, stomach cancer, lung cancer, or endometrial cancer. or atypical cancers expressing mesothelin).

The present invention also provides methods for preventing, treating and/or managing a disease associated with mesothelin-expressing cells, the methods comprising administering to a subject in need an anti-mesothelin TFP-T-cell of the invention that binds to the mesothelin-expressing cell. In one aspect, the subject is a human.

The present invention provides methods for preventing relapse of cancer associated with mesothelin-expressing cells, the methods comprising administering to a subject in need thereof an anti-mesothelin TFP-T-cell of the invention that binds to the mesothelin-expressing cell. In one aspect, the methods comprise administering to the subject in need thereof an effective amount of an anti-mesothelin TFP-T-cell described herein that binds to the mesothelin-bmcaexpressing cell in combination with an effective amount of another therapy.

Combination Therapies

A TFP-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the "at least one additional therapeutic agent" includes a TFP-expressing cell. Also provided are T-cells that express multiple TFPs, which bind to the same or different target antigens, or same or different epitopes on the same target antigen. Also provided are populations of T-cells in which a first subset of T-cells express a first TFP and a second subset of T-cells express a second TFP.

A TFP-expressing cell described herein and the at least one additional therapeutic agent can be administered simultaneously, in the same or in separate compositions, or sequentially. For sequential administration, the TFP-expressing cell described herein can be administered first, and the additional agent can be administered second, or the order of administration can be reversed.

In further aspects, a TFP-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as alemtuzumab, anti-CD3 antibodies or other antibody therapies, cytoxin, fludarabine, cyclosporin, FK506, rapamycin, mycophenolic acid, steroids, FR901228, cytokines, and irradiation. A TFP-expressing cell described herein may also be used in combination with a peptide vaccine, such as that described in Izumoto et al. 2008 J Neurosurg 108:963-971. In a further aspect, a TFP-expressing cell described herein may also be used in combination with a promoter of myeloid cell differentiation (e.g., all-trans retinoic acid), an inhibitor of myeloid-derived suppressor cell (MDSC) expansion (e.g., inhibitors of c-kit receptor or a VEGF inhibitor), an inhibition of MDSC function (e.g., COX2 inhibitors or phosphodiesterase-5 inhibitors), or therapeutic elimination of MDSCs (e.g., with a chemotherapeutic regimen such as treatment with doxorubicin and cyclophosphamide). Other therapeutic agents that may prevent the expansion of MDSCs include amino-biphosphonate, biphosphanate, sildenafil and tadalafil, nitroaspirin, vitamin D3, and gemcitabine. (See, e.g., Gabrilovich and Nagaraj, Nat. Rev. Immunol, (2009) v9(3): 162-174).

In one embodiment, the subject can be administered an agent which reduces or ameliorates a side effect associated with the administration of a TFP-expressing cell. Side effects associated with the administration of a TFP-expressing cell include, but are not limited to cytokine release syndrome (CRS), and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a TFP-expressing cell described herein to a subject and further administering an agent to manage elevated levels of a soluble factor resulting from treatment with a TFP-expressing cell. In one embodiment, the soluble factor elevated in the subject is one or more of IFN-γ, TNFα, IL-2, IL-6 and IL8. Therefore, an agent administered to treat this side effect can be an agent that neutralizes one or more of these soluble factors. Such agents include, but are not limited to a steroid, an inhibitor of TNFα, and an inhibitor of IL-6. An example of a TNFα inhibitor is entanercept. An example of an IL-6 inhibitor is tocilizumab (toc).

In one embodiment, the subject can be administered an agent which enhances the activity of a TFP-expressing cell. For example, in one embodiment, the agent can be an agent which inhibits an inhibitory molecule. Inhibitory molecules, e.g., Programmed Death 1 (PD1), can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can optimize a TFP-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the TFP-expressing cell. In an embodiment the inhibitor is a shRNA. In an embodiment, the inhibitory molecule is inhibited within a TFP-expressing cell. In these embodiments, a dsRNA molecule that inhibits expression of the inhibitory molecule is linked to the nucleic acid that encodes a component, e.g., all of the components, of the TFP. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy™; Bristol-Myers Squibb; tremelimumab (IgG2 monoclonal antibody available from Pfizer, formerly known as ticilimumab, CP-675,206)). In an embodiment, the agent is an antibody or antibody fragment that binds to TIM3. In an embodiment, the agent is an antibody or antibody fragment that binds to LAG3.

In some embodiments, the T cells may be altered (e.g., by gene transfer) in vivo via a lentivirus, e.g., a lentivirus specifically targeting a CD4+ or CD8+ T cell. (See, e.g., Zhou et al., J. Immunol. (2015) 195:2493-2501).

In some embodiments, the agent which enhances the activity of a TFP-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the TFP. In another embodiment, the fusion protein is expressed by a cell, e.g., a T-cell that does not express an anti-mesothelin TFP.

In some embodiments, the human or humanized antibody domain comprising an antigen binding domain that is an anti-mesothelin binding domain encoded by the nucleic acid, or an antibody comprising the anti-mesothelin binding domain, or a cell expressing the anti-mesothelin binding domain encoded by the nucleic acid has an affinity value of at most about 200 nM, 100 nM, 75 nM, a 50 nM, 25 nM, 20 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM; and/or at least about 100 nM, 75 nM, a 50 nM, 25 nM, 20 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM; and or about 200 nM, 100 nM, 75 nM, a 50 nM, 25 nM, 20 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM.

Pharmaceutical Compositions

Pharmaceutical compositions of the present invention may comprise a TFP-expressing cell, e.g., a plurality of TFP-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T-cells described herein may be administered at a dosage of $10^4$ to $10^9$ cells/kg body weight, in some instances $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T-cells to a subject and then subsequently redraw blood (or have an apheresis performed), activate T-cells therefrom according to the present invention, and reinfuse the patient with these activated and expanded T-cells. This process can be carried out multiple times every few weeks. In certain aspects, T-cells can be activated from blood draws of from 10 cc to 400 cc. In certain aspects, T-cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T-cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T-cells. These T-cell isolates may be expanded by methods known in the art and treated such that one or more TFP constructs of the invention may be introduced, thereby creating a TFP-expressing T-cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded TFP T-cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for alemtuzumab, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the TFP is introduced into T-cells, e.g., using in vitro transcription, and the subject (e.g., human) receives an initial administration of TFP T-cells of the invention, and one or more subsequent administrations of the TFP T-cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the TFP T-cells of the invention are administered to the subject (e.g., human) per week, e.g., 2, 3, or 4 administrations of the TFP T-cells of the invention are administered per week. In one embodiment, the subject (e.g., human subject) receives more than one administration of the TFP T-cells per week (e.g., 2, 3 or 4 administrations per week) (also referred to herein as a cycle), followed by a week of no TFP T-cells administrations, and then one or more additional administration of the TFP T-cells (e.g., more than one administration of the TFP T-cells per week) is administered to the subject. In another embodiment, the subject (e.g., human subject) receives more than one cycle of TFP T-cells, and the time between each cycle is less than 10, 9, 8, 7, 6, 5, 4, or 3 days. In one embodiment, the TFP T-cells are administered every other day for 3 administrations per week. In one embodiment, the TFP T-cells of the invention are administered for at least two, three, four, five, six, seven, eight or more weeks.

In one aspect, mesothelin TFP T-cells are generated using lentiviral viral vectors, such as lentivirus. TFP-T-cells generated that way will have stable TFP expression.

In one aspect, TFP T-cells transiently express TFP vectors for 4, 5, 6, 7, 8, 9, 10, 11, 12, 13, 14, 15 days after transduction. Transient expression of TFPs can be effected by RNA TFP vector delivery. In one aspect, the TFP RNA is transduced into the T-cell by electroporation.

A potential issue that can arise in patients being treated using transiently expressing TFP T-cells (particularly with murine scFv bearing TFP T-cells) is anaphylaxis after multiple treatments.

Without being bound by this theory, it is believed that such an anaphylactic response might be caused by a patient developing humoral anti-TFP response, i.e., anti-TFP antibodies having an anti-IgE isotype. It is thought that a patient's antibody producing cells undergo a class switch from IgG isotype (that does not cause anaphylaxis) to IgE isotype when there is a ten to fourteen-day break in exposure to antigen.

If a patient is at high risk of generating an anti-TFP antibody response during the course of transient TFP therapy (such as those generated by RNA transductions), TFP T-cell infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: TFP Constructs

Anti-mesothelin TFP constructs are engineered by cloning an anti-mesothelin scFv DNA fragment linked to a CD3 or TCR DNA fragment by either a DNA sequence encoding a short linker (SL): AAAGGGGSGGGGSGGGGSLE (SEQ ID NO:2) or a long linker (LL): AAAIEVMYPPPYLGGGGSGGGGSGGGGSLE (SEQ ID NO:3) into p510 vector ((System Biosciences (SBI)) at XbaI and EcoRI sites.

The anti-mesothelin TFP constructs generated are p510_antimesothelin_LL_TCRα (anti-mesothelin scFv-long linker-human full length T-cell receptor α chain), p510_antimesothelin_LL_TCR αC (anti-mesothelin scFv-long linker-human T-cell receptor α constant domain chain), p510_antimesothelin_LL_TCRβ (anti-mesothelin scFv-long linker-human full length T-cell receptor β chain), p510_antimesothelin_LL_TCRβC (anti-mesothelin scFv-long linker-human T-cell receptor β constant domain chain), p510_antimesothelin_LL_CD3γ (anti-mesothelin scFv-long linker-human CD3γ chain), p510_antimesothelin_LL_CD3δ (anti-mesothelin scFv-long linker-human CD36 chain), p510_antimesothelin_LL_CD3ε (anti-mesothelin scFv-long linker-human CD3ε chain), p510_antimesothelin_SL_TCRβ (anti-mesothelin scFv-short linker-human full length T-cell receptor β chain), p510_antimesothelin_SL_CD3γ (anti-mesothelin scFv-short linker-human CD3γ chain), p510_antimesothelin_SL_CD3δ (anti-mesothelin scFv-short linker-human CD3δ chain), p510_antimesothelin_SL_CD3ε (anti-mesothelin scFv-short linker-human CD3ε chain).

The anti-mesothelin CAR construct, p510_antimesothelin_28ζ is generated by cloning synthesized DNA encoding anti-mesothelin, partial CD28 extracellular domain, CD28 transmembrane domain, CD28 intracellular domain and CD3 zeta into p510 vector at XbaI and EcoRI sites.

Example 2: Antibody Sequences

Generation of Antibody Sequences

The human mesothelin polypeptide canonical sequence is UniProt Accession No. Q13421 (or Q13421-1). Provided are antibody polypeptides that are capable of specifically binding to the human mesothelin polypeptide, and fragments or domains thereof. Anti-mesothelin antibodies can be generated using diverse technologies (see, e.g., (Nicholson et al, 1997). Where murine anti-mesothelin antibodies are used as a starting material, humanization of murine anti-mesothelin antibodies is desired for the clinical setting, where the mouse-specific residues may induce a human-anti-mouse antigen (HAMA) response in subjects who receive T-cell receptor (TCR) fusion protein (TFP) treatment, i.e., treatment with T-cells transduced with the TFP.mesothelin construct. Humanization is accomplished by grafting CDR regions from murine anti-mesothelin antibody onto appropriate human germline acceptor frameworks, optionally including other modifications to CDR and/or framework regions. As provided herein, antibody and antibody fragment residue numbering follows Kabat (Kabat E. A. et al, 1991; Chothia et al, 1987).

Generation of scFvs

Human or humanized anti-mesothelin IgGs are used to generate scFv sequences for TFP constructs. DNA sequences coding for human or humanized $V_L$ and $V_H$ domains are obtained, and the codons for the constructs are, optionally, optimized for expression in cells from *Homo sapiens*. The order in which the $V_L$ and $V_H$ domains appear in the scFv is varied (i.e., $V_L$—$V_H$, or $V_H$—$V_L$ orientation), and three copies of the "G4S" or "$G_4S$" subunit $(G_4S)_3$ connect the variable domains to create the scFv domain. Anti-mesothelin scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of mesothelin-expressing cells.

Exemplary anti-mesothelin $V_L$ and $V_H$ domains, CDRs, and the nucleotide sequences encoding them, can be those described in U.S. Pat. Nos. 9,272,002; 8,206,710; 9,023,351; 7,081,518; 8,911,732; 9,115,197 and 9,416,190; and U.S. Patent Publication No. 20090047211. Other exemplary anti-mesothelin $V_L$ and $V_H$ domains, CDRs, and the nucleotide sequences encoding them, respectively, can be those of the following monoclonal antibodies: rat anti-mesothelin antibody 420411, rat anti-mesothelin antibody 420404, mouse anti-mesothelin antibody MN-1, mouse anti-mesothelin antibody MB-G10, mouse anti-mesothelin antibody ABIN233753, rabbit anti-mesothelin antibody FQS3796(3), rabbit anti-mesothelin antibody TQ85, mouse anti-mesothelin antibody TA307799, rat anti-mesothelin antibody 295D, rat anti-mesothelin antibody B35, mouse anti-mesothelin antibody 5G157, mouse anti-mesothelin antibody 129588, rabbit anti-mesothelin antibody 11C187, mouse anti-mesothelin antibody 5B2, rabbit anti-mesothelin antibody SP74, rabbit anti-mesothelin antibody D4X7M, mouse anti-mesothelin antibody C-2, mouse anti-mesothelin antibody C-3, mouse anti-mesothelin antibody G-1, mouse anti-mesothelin antibody G-4, mouse anti-mesothelin antibody K1, mouse anti-mesothelin antibody B-3, mouse anti-mesothelin antibody 200-301-A87, mouse anti-mesothelin antibody 200-301-A88, rabbit anti-mesothelin antibody EPR2685(2), rabbit anti-mesothelin antibody EPR4509, or rabbit anti-mesothelin antibody PPI-2e(IHC).

In some embodiments, single-domain ($V_{HH}$) binders are used such as those set forth in SEQ ID NOS 58, 59, and 55 (SD1, SD4, and SD6, respectively).

Source of TCR Subunits

Subunits of the human T Cell Receptor (TCR) complex all contain an extracellular domain, a transmembrane domain, and an intracellular domain. A human TCR complex contains the CD3-epsilon polypeptide, the CD3-gamma polypeptide, the CD3-delta polypeptide, the CD3-zeta polypeptide, the TCR alpha chain polypeptide and the TCR beta chain polypeptide. The human CD3-epsilon polypeptide canonical sequence is Uniprot Accession No. P07766. The human CD3-gamma polypeptide canonical sequence is Uniprot Accession No. P09693. The human CD3-delta polypeptide canonical sequence is Uniprot Accession No. P043234. The human CD3-zeta polypeptide canonical sequence is Uniprot Accession No. P20963. The human TCR alpha chain canonical sequence is Uniprot Accession No. Q6ISU1. The human TCR beta chain C region canonical sequence is Uniprot Accession No. P01850, a human TCR beta chain V region sequence is P04435.

The human CD3-epsilon polypeptide canonical sequence is:

```
                                              (SEQ ID NO: 4)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI.
```

The human CD3-gamma polypeptide canonical sequence is:

```
                                              (SEQ ID NO: 5)
MEQGKGLAVLILAIILLQGTLAQSIKGNHLVKVYDYQEDGSVLLTCDAEA

KNITWFKDGKMIGFLTEDKKKWNLGSNAKDPRGMYQCKGSQNKSKPLQVY

YRMCQNCIELNAATISGFLFAEIVSIFVLAVGVYFIAGQDGVRQSRASDK

QTLLPNDQLYQPLKDREDDQYSHLQGNQLRRN.
```

The human CD3-delta polypeptide canonical sequence is:

```
                                              (SEQ ID NO: 6)
MEHSTFLSGLVLATLLSQVSPFKIPIEELEDRVFVNCNTSITWVEGTVGT

LLSDITRLDLGKRILDPRGIYRCNGTDIYKDKESTVQVHYRMCQSCVELD

PATVAGIIVTDVIATLLLALGVFCFAGHETGRLSGAADTQALLRNDQVYQ

PLRDRDDAQYSHLGGNWARNKS.
```

The human CD3-zeta polypeptide canonical sequence is:

```
                                              (SEQ ID NO: 7)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR.
```

The human TCR alpha chain canonical sequence is:

```
                                              (SEQ ID NO: 8)
MAGTWLLLLLALGCPALPTGVGGTPFPSLAPPIMLLVDGKQQMVVVCLVL

DVAPPGLDSPIWFSAGNGSALDAFTYGPSPATDGTWTNLAHLSLPSEELA

SWEPLVCHTGPGAEGHSRSTQPMHLSGEASTARTCPQEPLRGTPGGALWL

GVLRLLLFKLLLFDLLLTCSCLCDPAGPLPSPATTTRLRALGSHRLHPAT

ETGGREATSSPRPQPRDRRWGDTPPGRKPGSPVWGEGSYLSSYPTCPAQA

WCSRSALRAPSSSLGAFFAGDLPPPLQAGAA.
```

The human TCR alpha chain C region canonical sequence is:

```
                                              (SEQ ID NO: 9)
PNIQNPDPAVYQLRDSKSSDKSVCLFTDFDSQTNVSQSKDSDVYITDKTV

LDMRSMDFKSNSAVAWSNKSDFACANAFNNSIIPEDTFFPSPESSCDVKL

VEKSFETDTNLNFQNLSVIGFRILLLKVAGFNLLMTLRLWSS.
```

The human TCR alpha chain V region CTL-L17 canonical sequence is:

```
                                              (SEQ ID NO: 10)
MAMLLGASVLILWLQPDWVNSQQKNDDQQVKQNSPSLSVQEGRISILNCD

YTNSMFDYFLWYKKYPAEGPTFLISISSIKDKNEDGRFTVFLNKSAKHLS

LHIVPSQPGDSAVYFCAAKGAGTASKLTFGTGTRLQVTL.
```

The human TCR beta chain C region canonical sequence is:

```
                                              (SEQ ID NO: 11)
EDLNKVFPPEVAVFEPSEAEISHTQKATLVCLATGFFPDHVELSWWVNGK

EVHSGVSTDPQPLKEQPALNDSRYCLSSRLRVSATFWQNPRNHFRCQVQF

YGLSENDEWTQDRAKPVTQIVSAEAWGRADCGFTSVSYQQGVLSATILYE

ILLGKATLYAVLVSALVLMAMVKRKDF.
```

The human TCR beta chain V region CTL-L17 canonical sequence is:

```
                                              (SEQ ID NO: 12)
MGTSLLCWMALCLLGADHADTGVSQNPRHNITKRGQNVTFRCDPISEHNR

LYWYRQTLGQGPEFLTYFQNEAQLEKSRLLSDRFSAERPKGSFSTLEIQR

TEQGDSAMYLCASSLAGLNQPQHFGDGTRLSIL.
```

The human TCR beta chain V region YT35 canonical sequence is:

```
                                            (SEQ ID NO: 13)
MDSWTFCCVSLCILVAKHTDAGVIQSPRHEVTEMGQEVTLRCKPISGHNS

LFWYRQTMMRGLELLIYFNNNVPIDDSGMPEDRFSAKMPNASFSTLKIQP

SEPRDSAVYFCASSFSTCSANYGYTFGSGTRLTVV.
```

Generation of TFPs from TCR Domains and scFvs

The mesothelin scFvs are recombinantly linked to CD3-epsilon or other TCR subunits (see 1C) using a linker sequence, such as $G_4S$, $(G_4S)_2$ $(G_4S)_3$ or $(G_4S)_4$. Various linkers and scFv configurations are utilized. TCR alpha and TCR beta chains were used for generation of TFPs either as full length polypeptides or only their constant domains. Any variable sequence of TCR alpha and TCR beta chains is allowed for making TFPs.

TFP Expression Vectors

Expression vectors are provided that include: a promoter (Cytomegalovirus (CMV) enhancer-promoter), a signal sequence to enable secretion, a polyadenylation signal and transcription terminator (Bovine Growth Hormone (BGH) gene), an element allowing episomal replication and replication in prokaryotes (e.g., SV40 origin and ColE1 or others known in the art) and elements to allow selection (ampicillin resistance gene and zeocin marker).

Preferably, the TFP-encoding nucleic acid construct is cloned into a lentiviral expression vector and expression validated based on the quantity and quality of the effector T-cell response of TFP.mesothelin-transduced T-cells ("mesothelin.TFP" or "mesothelin.TFP T-cells" or "TFP.mesothelin" or "TFP.mesothelin T-cells") in response to mesothelin+ target cells. Effector T-cell responses include, but are not limited to, cellular expansion, proliferation, doubling, cytokine production and target cell lysis or cytolytic activity (i.e., degranulation).

The TFP.mesothelin lentiviral transfer vectors are used to produce the genomic material packaged into the VSV-G pseudotyped lentiviral particles. Lentiviral transfer vector DNA is mixed with the three packaging components of VSV-G, gag/pol and rev in combination with Lipofectamine® reagent to transfect them together into HEK-293 (embryonic kidney, ATCC® CRL-1573™) cells. After 24 and 48 hours, the media is collected, filtered and concentrated by ultracentrifugation. The resulting viral preparation is stored at −80° C. The number of transducing units is determined by titration on Sup-T1 (T-cell lymphoblastic lymphoma, ATCC® CRL-1942™) cells. Redirected TFP.mesothelin T-cells are produced by activating fresh naïve T-cells with, e.g., anti-CD3 anti-CD28 beads for 24 hrs and then adding the appropriate number of transducing units to obtain the desired percentage of transduced T-cells. These modified T-cells are allowed to expand until they become rested and come down in size at which point they are cryopreserved for later analysis. The cell numbers and sizes are measured using a Coulter Multisizer™ III. Before cryopreserving, the percentage of cells transduced (expressing TFP.mesothelin on the cell surface) and the relative fluorescence intensity of that expression are determined by flow cytometric analysis. From the histogram plots, the relative expression levels of the TFPs are examined by comparing percentage transduced with their relative fluorescent intensity.

In some embodiments multiple TFPs are introduced by T-cell transduction with multiple viral vectors.

Evaluating Cytolytic Activity, Proliferation Capabilities and Cytokine Secretion of Humanized TFP Redirected T Cells The functional abilities of TFP.mesothelin T-cells to produce cell-surface expressed TFPs, and to kill target tumor cells, proliferate and secrete cytokines are determined using assays known in the art.

Human peripheral blood mononuclear cells (PBMCs, e.g., blood from a normal apheresed donor whose naïve T-cells are obtained by negative selection for T-cells, CD4+ and CD8+ lymphocytes) are treated with human interleukin-2 (IL-2) then activated with anti-CD3x anti-CD28 beads, e.g., in 10% RPMI at 37° C., 5% $CO_2$ prior to transduction with the TFP-encoding lentiviral vectors. Flow cytometry assays are used to confirm cell surface presence of a TFP, such as by an anti-FLAG antibody or an anti-murine variable domain antibody. Cytokine (e.g., IFN-γ) production is measured using ELISA or other assays.

Example 3: Human TFP T-Cell Efficacy in a Human ALL Mouse Model

Primary human ALL cells can be grown in immune compromised mice (e.g., NSG or NOD) without having to culture them in vitro. Likewise, cultured human ALL cell lines can induce leukemia in such mice. ALL-bearing mice can be used to test the efficacy of human TFP.mesothelin T-cells, for instance, in the model HALLX5447. The readout in this model is the survival of mice after intravenous (i.v.) infusion of ALL cells in the absence and presence of i.v. administered human TFP.mesothelin T-cells.

Example 4: Demonstration of Multiplexed TFP Polypeptides, and Use of Multiplexed Humanized TFP Redirected T-Cells The TFP polypeptides provided herein are capable of functionally associating with endogenous TCR subunit polypeptides to form functional TCR complexes. Here, multiple TFPs in lentiviral vectors are used to transduce T-cells in order to create a functional, multiplexed recombinant TCR complex. For example, provided is a T-cell containing i) a first TFP having an extracellular domain, a transmembrane domain, and an intracellular domain from the CD3-delta polypeptide and a mesothelin-specific scFv antibody fragment, and ii) a second TFP having an extracellular domain, a transmembrane domain, and an intracellular domain from the CD3-gamma polypeptide and a mesothelin-specific antibody fragment. The first TFP and second TFP are capable of interacting with each other and with endogenous TCR subunit polypeptides, thereby forming a functional TCR complex.

The use of these multiplexed humanized TFP.mesothelin T-cells can be demonstrated in liquid and solid tumors as provided in Examples 2 and 3 above.

Example 5: Preparation of T-Cells Transduced with TFPs Lentiviral Production

Lentivirus encoding the appropriate constructs are prepared as follows. $5\times10^6$ HEK-293FT-cells are seeded into a 100 mm dish and allowed to reach 70-90% confluency overnight. 2.5 μg of the indicated DNA plasmids and 20 at Lentivirus Packaging Mix (ALSTEM, cat #VP100) are diluted in 0.5 mL DMEM or Opti-MEMO I Medium without serum and mixed gently. In a separate tube, 30 μL of NanoFect® transfection reagent (ALSTEM, cat #NF100) is diluted in 0.5 mL DMEM or Opti-MEMO I Medium without serum and mixed gently. The NanoFect/DMEM and DNA/DMEM solutions are then mixed together and votrexed for 10-15 seconds prior to incubation of the DMEM-plasmid-NanoFect mixture at room temperature for 15 minutes. The complete transfection complex from the previous step is added dropwise to the plate of cells and rocked to disperse the transfection complex evenly in the plate. The plate is then incubated overnight at 37° C. in a humidified 5% $CO_2$ incubator. The following day, the supernatant is replaced with 10 mL fresh media and supplemented with 20 μL of ViralBoost (500×, ALSTEM, cat #VB100). The plates are then incubated at 37° C. for an additional 24 hours. The lentivirus containing supernatant is then collected into a 50 mL sterile, capped conical centrifuge tube and put on ice. After centrifugation at 3000 rpm for 15 minutes at 4° C., the cleared supernatant is filtered with a low-protein binding 0.45 μm sterile filter and virus is subsequently isolated by ultracentrifugation at 25,000 rpm (Beckmann, L8-70M) for 1.5 hours, at 4° C. The pellet is removed and re-suspended in DMEM media and lentivirus concentrations/titers are established by quantitative RT-PCR, using the Lenti-X qRT-PCR Titration kit (Clontech; catalog number 631235). Any residual plasmid DNA is removed by treatment with DNaseI. The virus stock preparation is either used for infection immediately or aliquoted and stored at −80° C. for future use.

PBMC Isolation

Peripheral blood mononuclear cells (PBMCs) are prepared from either whole blood or buffy coat. Whole blood is collected in 10 mL Heparin vacutainers and either processed immediately or stored overnight at 4° C. Approximately 10 mL of whole anti-coagulated blood is mixed with sterile phosphate buffered saline (PBS) buffer for a total volume of 20 mL in a 50 mL conical centrifuge tube (PBS, pH 7.4, without $Ca^{2+}/Mg^{2+}$). 20 mL of this blood/PBS mixture is then gently overlaid onto the surface of 15 mL of Ficoll-Paque® PLUS (GE Healthcare, 17-1440-03) prior to centrifugation at 400 g for 30-40 min at room temperature with no brake application.

Buffy coat is purchased from Research Blood Components (Boston, Mass.). LeucoSep® tubes (Greiner bio-one) are prepared by adding 15 mL Ficoll-Paque® (GE Health Care) and centrifuged at 1000 g for 1 minute. Buffy coat is diluted 1:3 in PBS (pH 7.4, without $Ca^{2+}$ or $Mg^{2+}$). The diluted buffy coat is transferred to Leucosep tube and centrifuged at 1000 g for 15 minutes with no brake application. The layer of cells containing PBMCs, seen at the diluted plasma/ficoll interface, is removed carefully to minimize contamination by ficoll. Residual ficoll, platelets, and plasma proteins are then removed by washing the PBMCs three times with 40 mL of PBS by centrifugation at 200 g for 10 minutes at room temperature. The cells are then counted with a hemocytometer. The washed PBMC are washed once with CAR-T media (AIM V-AlbuMAX® (BSA) (Life Technologies), with 5% AB serum and 1.25 μg/mL amphotericin B (Gemini Bioproducts, Woodland, Calif.), 100 U/mL penicillin, and 100 μg/mL streptomycin). Alternatively, the washed PBMC's are transferred to insulated vials and frozen at −80° C. for 24 hours before storing in liquid nitrogen for later use.

T-Cell Activation

PBMCs prepared from either whole blood or buffy coat are stimulated with anti-human CD28 and CD3 antibody-conjugated magnetic beads for 24 hours prior to viral transduction. Freshly isolated PBMC are washed once in CAR-T media (AIM V-AlbuMAX (BSA) (Life Technologies), with 5% AB serum and 1.25 μg/mL amphotericin B (Gemini Bioproducts), 100 U/mL penicillin, and 100 μg/mL streptomycin) without huIL-2, before being re-suspended at a final concentration of $1\times10^6$ cells/mL in CAR-T medium with 300 IU/mL human IL-2 (from a 1000× stock; Invitrogen). If the PBMCs had previously been frozen they are thawed and re-suspended at $1\times10^7$ cells/mL in 9 mL of pre-warmed (37° C.) cDMEM media (Life Technologies), in the presence of 10% FBS, 100 U/mL penicillin, and 100 μg/mL streptomycin, at a concentration of $1\times10^6$ cells/mL prior to washing once in CAR-T medium, re-suspension at $1\times10^6$ cells/mL in CAR-T medium, and addition of IL-2 as described above.

Prior to activation, anti-human CD28 and CD3 antibody-conjugated magnetic beads (available from, e.g., Invitrogen, Life Technologies) are washed three times with 1 mL of sterile 1×PBS (pH 7.4), using a magnetic rack to isolate beads from the solution, before re-suspension in CAR-T medium, with 300 IU/mL human IL-2, to a final concentration of $4\times10^7$ beads/mL. PBMC and beads are then mixed at a 1:1 bead-to-cell ratio, by transferring 25 μL ($1\times10^6$ beads) of beads to 1 mL of PBMC. The desired number of aliquots are then dispensed to single wells of a 12-well low-attachment or non-treated cell culture plate, and incubated at 37° C., with 5% $CO_2$, for 24 hours before viral transduction.

T-Cell Transduction/Transfection and Expansion

Following activation of PBMC, cells are incubated for 48 hours at 37° C., 5% $CO_2$. Lentivirus is thawed on ice and $5\times10^6$ lentivirus, along with 2 μL of TransPlus™ (Alstem) per mL of media (a final dilution of 1:500) is added to each well of $1\times10^6$ cells. Cells are incubated for an additional 24 hours before repeating addition of virus. Alternatively, lentivirus is thawed on ice and the respective virus is added at 5 or 50 MOI in presence of 5 μg/mL polybrene (Sigma). Cells are spinoculated at 100 g for 100 minutes at room temperature. Cells are then grown in the continued presence of 300 IU/mL of human IL-2 for a period of 6-14 days (total incubation time is dependent on the final number of CAR-T-cells required). Cell concentrations are analyzed every 2-3 days, with media being added at that time to maintain the cell suspension at $1\times10^6$ cells/mL.

In some instances, activated PBMCs are electroporated with in vitro transcribed (IVT) mRNA. In one embodiment, human PBMCs are stimulated with Dynabeads® (ThermoFisher) at 1-to-1 ratio for 3 days in the presence of 300 IU/ml recombinant human IL-2 (R&D Systems) (other stimulatory reagents such as TransAct T Cell Reagent from Milyeni Pharmaceuticals may be used). The beads are removed before electroporation. The cells are washed and re-suspended in OPTI-MEM medium (ThermoFisher) at the concentration of $2.5\times10^7$ cells/mL. 200 μL of the cell suspension ($5\times10^6$ cells) are transferred to the 2 mm gap Electroporation Cuvettes Plus™ (Harvard Apparatus BTX) and prechilled on ice. 10 μg of IVT TFP mRNA is added to the cell suspension. The mRNA/cell mixture is then electroporated at 200 V for 20 milliseconds using ECM830 Electro Square Wave Porator (Harvard Apparatus BTX) Immediately after the electroporation, the cells are transferred to fresh cell culture medium (AIM V AlbuMAX (BSA) serum free medium+5% human AB serum+300 IU/ml IL-2) and incubated at 37° C.

Verification of TFP Expression by Cell Staining

Following lentiviral transduction or mRNA electroporation, expression of anti-mesothelin TFPs is confirmed by flow cytometry, using an anti-mouse Fab antibody to detect the murine anti-mesothelin scFv. T-cells are washed three times in 3 mL staining buffer (PBS, 4% BSA) and re-suspended in PBS at 1×106 cells per well. For dead cell exclusion, cells are incubated with LIVE/DEAD® Fixable Aqua Dead Cell Stain (Invitrogen) for 30 minutes on ice. Cells are washed twice with PBS and re-suspended in 50 μL staining buffer. To block Fc receptors, 1 μL of 1:100 diluted normal goat lgG (BD Bioscience) is added to each tube and incubated in ice for 10 minutes. 1.0 mL FACS buffer is added to each tube, mixed well, and cells are pelleted by centrifugation at 300 g for 5 min. Surface expression of scFv TFPs is detected by Zenon® R-Phycoerythrin-labeled human MSLN IgG1 Fc or human IgG1 isotype control. 1 μg antibodies are added to the respective samples and incubated for 30 minutes on ice. Cells are then washed twice, and stained for surface markers using Anti-CD3 APC (clone, UCHT1), anti-CD4-Pacific blue (Clone RPA-T4), anti-CD8 APCCy7 (Clone SK1), from BD bioscience. Flow cytometry is performed using LSRFortessa™ X20 (BD Biosciences) and data is acquired using FACS diva software and is analyzed with FlowJo® (Treestar, Inc. Ashland, Oreg.).

Exemplary results are shown in FIG. 5A, which shows the surface expression analysis of activated PBMC cells stained for CD8 (anti-CD8 APCCy7, y-axes) and mesothelin ("MSLN") (Zenon® R-Phycoerythrin-labeled hMSLN IgG, x-axes). Shown from left to right are cells that were either non-transduced or transduced with anti-MSLN-CD3ε, anti-MSLN-CD28ζ, and anti-MSLN-41BBζ constructs. The proportion of CD8+, MSLN+ cells is shown in the top right corner of each panel.

FIG. 5B shows similar results from activated PBMC cells, stained for MSLN and GFP, that were transduced with TFP constructs comprising in-house single domain ("SD") mesothelin binders. The top row shows (from left to right) non-transduced cells, and cells transduced with a positive control anti-MSLN-CD3ε TFP ("SS1"). Rows 2-4 show the anti-MSLN binders SD1, SD4, and SD6, respectively, in cells transduced with GFP-tagged (from left to right) CD3ε TFP, CD3γTFP, TCRβ TFP, and CD28ζ CAR constructs. The proportion of GFP+, MSLN+ cells is shown in the top right corner of each panel.

Example 6: Cytotoxicity Assay by Flow Cytometry

Target cells that are either positive or negative for mesothelin are labelled with the fluorescent dye, carboxyfluorescein diacetate succinimidyl ester (CFSE). These target cells are mixed with effector T-cells that are either un-transduced, transduced with control CAR-T constructs, or transduced with TFPs. After the indicated incubation period, the percentage of dead to live CFSE-labeled target cells and negative control target cells is determined for each effector/target cell culture by flow cytometry. The percent survival of target cells in each T-cell-positive target cell culture is calculated relative to wells containing target cells alone.

The cytotoxic activity of effector T-cells is measured by comparing the number of surviving target cells in target cells without or with effector T-cells, following co-incubation of effector and target cells, using flow cytometry. In experiments with mesothelin TFPs or CAR-T-cells, the target cells are mesothelin-positive cells, while cells used as a negative control are mesothelin-negative cells.

Target cells are washed once, and re-suspended in PBS at $1\times10^6$ cells/mL. The fluorescent dye carboxyfluorescein diacetate succinimidyl ester (CFSE) (ThermoFisher) is added to the cell suspension at a concentration of 0.03 μM and the cells are incubated for 20 minutes at room temperature. The labeling reaction is stopped by adding to the cell suspension complete cell culture medium (RPMI-1640+10% HI-FBS) at the volume 5 times of the reaction volume, and the cells are incubated for an additional two minutes at room temperature. The cells are pelleted by centrifugation and re-suspended in cytotoxicity medium (Phenol red-free RPMI1640 (Invitrogen) plus 5% AB serum (Gemini Bio-products) at $2\times10^5$ cells/mL. Fifty microliters of CFSE labelled-target cell suspension (equivalent to 10,000 cells) are added to each well of the 96-well U-bottom plate (Corning).

Effector T-cells transduced with anti-mesothelin TFP constructs, together with non-transduced T-cells as negative controls, are washed and suspended at $2\times10^6$ cells/mL, or $1\times10^6$ cells/mL in cytotoxicity medium. 50 μL of effector T-cell suspensions (equivalent to 100,000 or 50,000 cells) are added to the plated target cells to reach the effector-to-target ratio of 10-to-1 or 5-to-1, respectively, in a total volume of 100 μL. The cultures are then mixed, spun down, and incubated for four hours at 37° C. and 5% $CO_2$. Immediately following this incubation, 7AAD (7-aminoactinomycin D) (BioLegend) is added to the cultured cells as recommended by the manufacturer, and flow cytometry is performed with a BD LSRFortessa™ X-20 (BD Biosciences). Analysis of flow cytometric data is performed using FlowJo® software (TreeStar, Inc.).

The percentage of survival for target cells is calculated by dividing the number of live target cells (CFSE+7-AAD-) in a sample with effector T-cells and target cells, by the number of live (CFSE+7-AAD-) cells in the sample with target cells alone. The cytotoxicity for effector cells is calculated as the percentage of killing for target cells=100%−percentage of survival for the cells.

T-cells transduced with an anti-MSLN 28ζ CAR construct may demonstrate cytotoxicity against mesothelin-expressing cells when compared to T-cells that are either non-transduced or are transduced with a non-mesothelin-specific CAR control. However, T-cells transduced with anti-mesothelin-CD3ε may induce more efficient cytotoxicity against the targets than the anti-mesothelin CAR control. Anti-mesothelin-CD3γ TFPs may also mediate robust cytotoxicity that is greater than that observed with anti-mesothelin-CAR at effector:target ratios between 5 and 10:1. Some cytotoxicity may be observed with anti-mesothelin-TCRα and anti-mesothelin-TCRβ TFPs. Similar results may be obtained with anti-mesothelin TFPs constructed with an alternative hinge region. Once again, cytotoxicity against mesothelin-expressing target cells may be greater with anti-mesothelin-CD3ε or anti-mesothelin-CD3γ TFP-transduced T-cells than with anti-mesothelin-CAR-transduced T-cells.

T-cells electroporated with mRNA encoding TFPs specific for mesothelin may also demonstrate robust cytotoxicity against mesothelin-expressing cells. While no significant killing of the mesothelin-negative cells may be seen with either control or anti-mesothelin TFP constructs, mesothelin-specific killing of mesothelin-expressing cells may be observed by T-cells transduced with either anti-mesothelin-CD3ε SL, or anti-mesothelin-CD3γ SL TFPs.

Example 8: Determining Cytotoxicity by Real Time Cytotoxicity Assay

Anti-mesothelin TFPs may also demonstrate superior cytotoxicity over anti-mesothelin CARs in the real-time cytotoxicity assay (RTCA) format. The RTCA assay measures the electrical impedance of an adherent target cell monolayer, in each well of a specialized 96-well plate, in real time and presents the final readout as a value called the cell index. Changes in cell index indicate disruption of the target cell monolayer as a result of killing of target cells by co-incubated T-cell effectors. Thus the cytotoxicity of the effector T-cells can be evaluated as the change in cell index of wells with both target cells and effector T-cells compared to that of wells with target cells alone.

Adherent target cells are cultured in DMEM, 10% FBS, 1% Antibiotic-Antimycotic (Life Technologies). To prepare the RTCA, 50 μL of, e.g., DMEM medium is added into the appropriate wells of an E-plate (ACEA Biosciences, Inc, Catalog #: JL-10-156010-1A). The plate is then placed into a RTCA MP instrument (ACEA Biosciences, Inc.) and the appropriate plate layout and assay schedule entered into the RTCA 2.0 software as described in the manufacturers manual. Baseline measurement is performed every 15 minutes for 100 measurements. $1\times10^4$ target cells in a 100 μL volume are then added to each assay well and the cells are allowed to settle for 15 minutes. The plate is returned to the reader and readings are resumed.

The next day, effector T-cells are washed and re-suspended in cytotoxicity media (Phenol red-free RPMI1640 (Invitrogen) plus 5% AB serum (Gemini Bioproducts; 100-318)). The plate is then removed from the instrument and the effector T-cells, suspended in cytotoxicity medium (Phenol red-free RPMI1640+5% AB serum), are added to each well at 100,000 cells or 50,000 cells to reach the effector-to-target ratio of 10-to-1 or 5-to-1, respectively. The plate is then placed back to the instrument. The measurement is carried out for every 2 minutes for 100 measurements, and then every 15 minutes for 1,000 measurements.

In the RTCA assay, killing of mesothelin-transduced cells may be observed by T-cells transduced with anti-mesothelin-28ζ CAR-transduced T-cells, as demonstrated by a time-dependent decrease in the cell index following addition of the effector cells relative to cells alone or cells co-incubated with T-cells transduced with a control CAR construct. However, target cell killing by anti-mesothelin-CD3ε TFP-expressing T-cells may be deeper and more rapid than that observed with the anti-mesothelin CAR. For example, within 4 hours of addition of T-cells transduced with anti-mesothelin-CD3ε TFP, killing of the mesothelin-expressing target cells may be essentially complete. Little or no killing may be observed with T-cells transduced with a number of TFP constructs comprising other CD3 and TCR constructs Similar results may be obtained with anti-mesothelin TFPs constructed with an alternative hinge region. Cytotoxicity against mesothelin-transduced target cells may be greater with anti-mesothelin-CD3ε or anti-mesothelin-CD3γ TFP-transduced T-cells than with anti-mesothelin-CAR-transduced T-cells.

The cytotoxic activity of TFP-transduced T-cells may be dose-dependent with respect to the amount of virus (MOI) used for transduction. Increased killing of mesothelin-positive cells may be observed with increasing MOI of anti-mesothelin-CD3ε TFP lentivirus, further reinforcing the relationship between TFP transduction and cytotoxic activity.

Exemplary results of the RTCA assay are shown in FIGS. 6A-C. An anti-MSLN TFP construct was engineered by cloning an anti-MSLN scFv DNA fragment linked to a CD3ε DNA fragment by a DNA sequence coding the linker: GGGGSGGGGSGGGGSLE (SEQ ID NO:1) into a p510 vector (from SBI) at XbaI and EcoRI sites. The anti-MSLN TFP construct generated was p510_antiMSLN_SS1_CD3ε (anti-MSLN SS1 scFv-linker-human CD3ε chain).

Full length mesothelin (NM_005823) was PCR amplified from pCMV6_XL4_Mesothelin (Origene) and cloned into XbaI and EcoRI restriction digested p527a (pCDH-EF1-MCS-T2A-Puro) (SBI) via Gibson Recombination reaction.

Target cells for the RTCA were mesothelin-positive HeLa cells (cervical adenocarcinoma, ATCC® CCL-2™) and mesothelin-negative PC-3 cells (prostate adenocarcinoma, ATCC® CRL-1435™) were used as negative controls. Adherent target cells were cultured in DMEM with 10% FBS and 1% Antibiotic-Antimycotic (Life Technologies).

The normalized cell index, indicative of cytotoxicity, was determined. Activated PBMCs were untreated (trace #1), non-transduced (trace #2), or transduced with empty vector (trace #3), an anti-MSLN TFP ("Anti-MSLN-CD3ε TRuC", trace #4), an anti-MSLN CAR with the CD28ζ (trace #5) or 41BBζ (trace #6) signaling domain ("Anti-MSLN-28ζ CAR" and "Anti-MSLN-41BBζ CAR," respectively).

As shown in FIG. 6A, the target MSLN-positive HeLa cells were efficiently killed by the anti-MSLN TFP-transduced T cells, compared to the negative controls. In contrast, the MSLN-negative PC-3 cells were not efficiently killed by any of the constructs (FIG. 6B).

A similar experiment was performed using in-house TFP constructs with single-domain anti-mesothelin binders. FIG. 6C shows killing of MSLN-positive cells in a high target density cell line (HeLa-(MSLN$^{high}$)) using T cells from two different human donors (top and bottom). Shown are the cell killing traces for TFP T cells with the anti-MSLN binders SD1 (left), SD4 (middle), and SD6 (right). Activated PBMCs were non-transduced (trace #1), or transduced with CD3ε TFP (trace #2), CD3γ TFP (trace #3), TCRβ TFP (trace #4), or CD28ζ CAR (trace #5). The normalized cell index, indicative of cytotoxicity, was determined in a real time cell analyzer (RTCA) assay. As shown in the Figure, all the T cells, except the non-transduced, were able to kill cancer cells.

Example 7: Luciferase-Based Cytotoxicity Assay in Cells with High or Low Target Density The luciferase-based cytotoxicity assay ("Luc-Cyto" assay) assesses the cytotoxicity of TFP T and CAR T cells by indirectly measuring the luciferase enzymatic activity in the residual live target cells after co-culture. The high target density cells used in Luc-Cyto assay were HeLa-MSLN$^{high}$ cells and the low target density cells used were PC3 cells expressing low levels of mesothelin (PC3-MSLN$^{low}$), each stably transduced to express firefly luciferase. The DNA encoding firefly luciferase was synthesized by GeneArt® (Thermo Fisher®) and inserted into the multiple cloning site of single-promoter lentiviral vector pCDH527A-1 (System Bioscience).

The lentivirus carrying the firefly luciferase was packaged as described above. The HeLa-MSLN$^{high}$ or PC3-MSLN$^{low}$ cells were then transduced with the firefly luciferase construct carrying lentivirus for 24 hours and then selected with puromycin (5 μg/mL). The generation of HeLa-luc-MSLN$^{high}$- and PC3-luc-MSLN$^{low}$-luciferase cells was confirmed by measuring the luciferase enzymatic activity in the cells with Bright-Glo™ Luciferase Assay System (Promega).

Separate populations from two different human donors were transduced with an empty expression vector ("NT"), or the following TFPs or CARs: anti-MSLN (positive control, "SS1", affinity 11 nM), anti-MSLN-SD1 (affinity 25 nM), anti-MSLN-SD4 (affinity 6 nM), or anti-MSLN SD6 (affinity 0.59 nM), each in the format of CD3ε TFP, CD3γ TFP, TCRβ TFP, and CD28ζ CAR. The two populations of transduced T cells were incubated with HeLa-MSLN$^{high}$ (FIGS. 7A-C) or PC3-MSLN$^{low}$ (FIGS. 8A-D).

The target cells were plated at 5000 cells per well in 96-well plate. The TFP T, the CAR T, or control cells were added to the target cells at effector-to-target ratios or 1:1 (black bars) or 1:5 (gray bars). The mixture of cells was then cultured for 24 hours at 37° C. with 5% $CO_2$ before the luciferase enzymatic activity in the live target cells was measured by the Bright-Glo® Luciferase Assay System. The cells were spun into a pellet and resuspended in medium containing the luciferase substrate. Luciferase is released by cell lysis, thus, higher luciferase activity corresponds to a greater percentage of cell death.

Results using cells expressing high levels of MSLN are shown in FIGS. 7A-C. Shown are the % of cells killed in samples with no T cells ("target only"), empty vector transduced ("NT"), anti-MSLN (positive control, "SS1"), or anti-mesothelin TFP T cells with in-house anti-mesothelin binders SD1 (FIG. 7A), SD4 (FIG. 7B), and SD6 (FIG. 7C), each in each in the format of CD3ε TFP, CD3γ TFP, TCRβ TFP, and CD28ζ CAR. In each graph, black bars represent a 1:1 ratio of T cells to target cells, and gray bars represent a 1:5 ratio of T cells to target cells. As can be seen in the Figures, all of the TFP-T cells, CAR-T cells, and positive control SS1 were efficient at killing the MSLN FIGS. 8A-D are a series of graphs showing the activity of anti-MSLN CAR T cells and TFP T cells against a target cell line expressing low levels of mesothelin (PC3-$MSLN^{low}$). Shown are the % of cells killed in samples with no T cells ("target only"), empty vector transduced ("NT"), anti-MSLN (positive control, "SS1"), or anti-mesothelin constructs SD1, SD4, and SD6 in the TFP formats CD3ε (FIG. 8A), CD3γ (FIG. 8B), TCRβ (FIG. 8C), and CD28ζ CAR (FIG. 8D). In each graph, black bars represent a 1:1 ratio of T cells to target cells, and gray bars represent a 1:5 ratio of T cells to target cells. Similar results were seen for a second T cell donor.

As shown in the FIG., a 1:1 ratio of T cells to target cells resulted in the highest level of killing of target cells, as was expected. In addition, all TFP T and CAR T cells showed similar activity in cells expressing high levels of MSLN.

Example 8: Measurement of Activation of T Cells by FACS

Activation of the T-cells expressing anti-MSLN CAR and TFP Constructs was performed using MSLN+ and MSLN− K562 cells, and is shown in FIGS. 9A-D. As described above, Activated PBMCs were transduced with 50 MOI LVs for two consecutive days and expanded. Day 8 post transduction, co-cultures of PBMCs were set up with target cells (K562 cells overexpressing MSLN) at E:T, 1:1 ratio ($0.2\times 10^6$ each cell type) in cytotoxicity medium (Phenol red-free RPMI1640 (Invitrogen) plus 5% AB serum (Gemini Bioproducts; 100-318). K562 cells overexpressing BCMA were used as negative controls. 24 hours after the beginning of co-culturing, cells were harvested, washed with PBS three times and stained with Live/Dead Aqua for 30 min on ice. To block Fc receptors, human Fc block (BD) was added and incubated for 10 minutes at room temperature. Cells were subsequently stained with anti-CD3 APC (clone, UCHT1), anti-CD8 APCcy7 (Clone SK1), anti-CD69-Alexa Fluor® 700 (clone FN50) from BD Biosciences and anti-CD25-PE (Clone BC96, eBioscience). Cells were washed twice and analyzed by BD LSRH-Fortessa. Data were analyzed as above using FlowJo® analysis software (Tree star, Inc.).

As shown in FIG. 9A, from left to right, T cells were either non-transduced, transduced with empty vector, transduced with anti-MSLN-CD3ε TFP, anti-MSLN-28ζ CAR, or anti-MSLN-41BBζ CAR. Cells co-cultured with MSLN− cells are shown in the top row, and those co-cultured with MSLN+ target cells are shown in the bottom row. The cells were then stained with antibodies specific for the surface activation markers CD69 and CD25. The numbers of cells stained with anti-CD69 correspond to the x-axes and those stained with anti-CD25 correspond to the y-axes. As shown, T-cells expressing anti-mesothelin CAR and TFP constructs were activated by culturing with MSLN+ cells, as demonstrated by elevated levels of CD69 and CD25 expression, relative to co-culturing with MSLN− cells (FIG. 9B). The percentage of CD25+ cells for each construct in MSLN− (white bars) and MSLN+ (black bars) cells is shown.

A similar experiment was done using K562 MSLN− cells (FIG. 9C, circles) and K562-MSLN+ cells (FIG. 9C, squares) in either non-transduced T cells or T cells transduced with anti-MSLN positive control binders ("510-SS1-CD3ε). Data represent the sum of CD25+, CD69+, and CD25+/CD69+ cells. In FIG. 9D, data are shown for the in-house anti-MSLN binders SD1 (squares), SD4 (circles), and SD6 (triangles) in K562 MSLN− target cells (left panel) and K562 MSLN+ cells (right panel) combined with donor T cells having TFP formats CD3ε, CD3γ, TCRβ, and CD28ζ CAR. Similar results were seen using cells from a second T cell donor.

Activation of T-cells may be similarly assessed by analysis of granzyme B production. T-cells are cultured and expanded as described above, and intracellular staining for granzyme B is done according to the manufacturer's kit instructions (Gemini Bioproducts; 100-318). cells were harvested, washed with PBS three times and blocked with human Fc block for 10 min. Cells were stained for surface antigens with anti-CD3 APC (clone, UCHT1), and anti-CD8 APCcy7 (Clone SK1) for 30 min at 4° C. Cells were then fixed with Fixation/Permeabilization solution (BD Cytofix/Cytoperm Fixation/Permealbilzation kit cat #554714) for 20 min at 4 C, flowed by washing with BD Perm/Wash buffer. Cells were subsequently stained with anti-Granzyme B Alexafluor700 (Clone GB11), washed with BD Perm/Wash buffer twice and resuspended in FACS buffer. Data was acquired on BD LSRII-Fortessa and analyzed using FlowJo® (Tree star Inc.).

As shown in FIG. 10A, from left to right, T cells were either non-transduced, transduced with empty vector, transduced with Anti-MSLN-CD3ε TFP, anti-MSLN-28ζ CAR, or anti-MSLN-41BBζ CAR. Cells co-cultured with MSLN− cells are shown in the top row, and those co-cultured with MSLN+ target cells are shown in the bottom row. The numbers of cells stained with anti-GrB correspond to the x-axes and those stained with anti-CD8 correspond to the y-axes. As shown, T-cells expressing anti-mesothelin CAR and TFP constructs were activated by culturing with MSLN+ cells, but not the MSLN-cells. These results are shown again in FIG. 10B, wherein the percentage of GrB+ cells for each construct in mesothelin negative ("MSLN−", white bars) and mesothelin positive ("MSLN+, black bars) cells is shown. These data demonstrate the ability of MSLN-expressing cells to specifically activate T-cells.

Example 9: IL-2 and IFN-γ Secretion by ELISA

Another measure of effector T-cell activation and proliferation associated with the recognition of cells bearing cognate antigen is the production of effector cytokines such as interleukin-2 (IL-2) and interferon-gamma (IFN-γ).

ELISA assays for human IL-2 (catalog #EH2IL2, Thermo Scientific) and IFN-γ catalog #KHC4012, Invitrogen) are performed as described in the product inserts. In one example, 50 μL of reconstituted standards or samples in duplicate are added to each well of a 96-well plate followed by 50 jut of Biotinylated Antibody Reagent. Samples are mixed by gently tapping the plate several times. 50 μL of Standard Diluent is then added to all wells that did not contain standards or samples and the plate is carefully sealed with an adhesive plate cover prior to incubation for 3 hours at room temperature (20-25° C.). The plate cover is then removed, plate contents are emptied, and each well is filled with Wash Buffer. This wash procedure is repeated a total of 3 times and the plate is blotted onto paper towels or other absorbent material. 100 μL of prepared Streptavidin-HRP Solution is added to each well and a new plate cover is attached prior to incubation for 30 minutes at room temperature. The plate cover is again removed, the plate contents are discarded, and 100 μL of TMB Substrate Solution is added into each well. The reaction is allowed to develop at room temperature in the dark for 30 minutes, after which 100 μL of Stop Solution is added to each well. Evaluate the plate. Absorbance is measured on an ELISA plate reader set at 450 nm and 550 nm within 30 minutes of stopping the reaction. 550 nm values are subtracted from 450 nm values and IL-2 amounts in unknown samples are calculated relative to values obtained from an IL-2 standard curve.

Alternatively, 2-Plex assays are performed using the Human Cytokine Magnetic Buffer Reagent Kit (Invitrogen, LHB0001M) with the Human IL-2 Magnetic Bead Kit (Invitrogen, LHC0021M) and the Human IFN-γ Magnetic Bead Kit (Invitrogen, LHC4031M). Briefly, 25 μL of Human IL-2 and IFN-γ antibody beads are added to each well of a 96-well plate and washed using the following guidelines: two washes of 200 μL 1× wash solution, placing the plate in contact with a Magnetic 96-well plate Separator (Invitrogen, A14179), letting the beads settle for 1 minute and decanting the liquid. Then, 50 μL of Incubation Buffer is added to each well of the plate with 100 μL of reconstituted standards in duplicates or 50 μL of samples (supernatants from cytotoxicity assays) and 50 μL of Assay Diluent, in triplicate, for a total volume of 150 μL. Samples are mixed in the dark at 600 rpm with an orbital shaker with a 3 mm orbital radius for 2 hours at room temperature. The plate is washed following the same washing guidelines and 100 μL of human IL-2 and IFN-γ biotinylated detector antibody is added to each well. Samples are mixed in the dark at 600 rpm with an orbital shaker with a 3 mm orbital radius for 1 hour at room temperature. The plate is washed following the same washing guidelines and 100 μL of Streptavidin-R-Phycoerythrin is added to each well. Samples are mixed in the dark at 600 rpm with an orbital shaker with a 3 mm orbital radius for 30 minutes at room temperature. The plate is washed 3 times using the same washing guidelines and after decanting the liquid the samples are re-suspended in 150 μL of 1× wash solution. The samples are mixed at 600 rpm with an orbital shaker with a 3 mm orbital radius for 3 minutes and stored over night at 4° C. Afterwards, the plate is washed following the same washing guidelines and the samples are re-suspended in 150 μL of 1× wash solution.

The plate is read using the MAGPIX System (Luminex) and xPONENT software. Analysis of the data is performed using MILLIPLEX Analyst software, which provides the standard curve and cytokine concentrations.

Relative to non-transduced or control CAR-transduced T-cells, T-cells transduced with anti-mesothelin TFPs may produce higher levels of both IL-2 and IFN-γ when co-cultured with either cells that endogenously express mesothelin or mesothelin-transduced cells. In contrast, co-culture with mesothelin negative cells or non-transduced cells, may result in little or no cytokine release from TFP-transduced T-cells. Consistent with the previous cytotoxicity data, anti-mesothelin TFPs constructed with an alternative hinge region may generate similar results upon co-culture with mesothelin-bearing target cells.

In agreement with the previous cytotoxicity data, anti-mesothelin-CD3ε and anti-mesothelin-CD3γ may produce the highest IL-2 and IFN-γ levels of the TFP constructs. However, cytokine production by T-cells transduced with anti-mesothelin-CD3ε and anti-mesothelin-CD3γ TFPs may be comparable to that of T-cells expressing anti-mesothelin-28ζ CAR, despite the TFPs demonstrating much higher levels of target cell killing. The possibility that TFPs may more efficiently kill target cells than CARs, but release comparable or lower levels of pro-inflammatory cytokines, represents a potential advantage for TFPs relative to CARs since elevated levels of these cytokines have been associated with dose-limiting toxicities for adoptive CAR-T therapies.

Exemplary results are shown in FIGS. 11A-B. As described above, activated PBMCs were transduced with 50 MOI lentiviruses for two consecutive days and expanded. Day 8 post transduction, co-cultures of PBMCs were set up with target cells (K562 cells overexpressing MSLN) at E:T, 1:1 ratio ($0.2\times10^6$ each cell type) in cytotoxicity medium (Phenol red-free RPMI1640 (Invitrogen) plus 5% AB serum (Gemini Bioproducts; 100-318). K562 cells overexpressing BCMA were used as negative controls. After 24 hours cells were analyzed for IFN-γ (FIG. 11A) and IL-2 (FIG. 11B) expression by ELISA as described above. In each FIG., from left to right, T cells were either non-transduced, transduced with empty vector, transduced with Anti-MSLN-CD3ε TFP, anti-MSLN-28ζ CAR, or anti-MSLN-41BBζ CAR. Cells co-cultured with MSLN− cells are represented by white bars, and those co-cultured with MSLN+ target cells are represented by black bars. As can be seen in the FIG., T-cells expressing anti-mesothelin CAR and TFP constructs were activated, as evidenced by both IFN-γ and IL-2 production, by co-culturing with MSLN+ cells, but not the MSLN− cells, further demonstrating the ability of MSLN-expressing cells to specifically activate T-cells.

Example 10: CD107a Exposure by Flow Cytometry

An additional assay for T-cell activation is surface expression of CD107a, a lysosomal associated membrane protein (also known as LAMP-1) that is located in the membrane of cytoplasmic cytolytic granules in resting cells. Degranulation of effector T-cells, a prerequisite for cytolytic activity, results in mobilization of CD107a to the cell surface following activation-induced granule exocytosis. Thus, CD107a exposure provides an additional measure of T-cell activation, in addition to cytokine production, that correlates closely with cytotoxicity.

Target and effector cells are separately washed and re-suspended in cytotoxicity medium (RPMI+5% human AB serum+1% antibiotic antimycotic). The assay is performed by combining $2\times10^5$ effectors cells with $2\times10^5$ target cells in a 100 μL final volume in U-bottom 96-well plates (Corning), in the presence of 0.5 μL/well of PE/Cy7-labelled anti-human CD107a (LAMP-1) antibody (Clone-H4A3, BD Biosciences). The cultures are then incubated for an hour at 37° C., 5% $CO_2$ Immediately following this incubation, 10 μL of a 1:10 dilution of the secretion inhibitor monensin (1000× solution, BD GolgiStop™) is carefully added to each well without disturbing the cells. The plates are then incubated for a further 2.5 hours at 37° C., 5% $CO_2$. Following this incubation, the cells are stained with APC anti-human CD3 antibody (Clone-UCHT1, BD Biosciences), PerCP/Cy5.5 anti-human CD8 antibody (Clone-SK1, BD Biosciences) and Pacific Blue anti-human CD4 antibody (Clone-RPA-T4, BD Biosciences) and then incubated for 30 minutes at 37° C., 5% $CO_2$. The cells are then washed 2× with FACS buffer (and resuspended in 100 μL FACS buffer and 100 ul IC fix buffer prior to analysis.

Exposure of CD107a on the surface of T-cells is detected by flow cytometry. Flow cytometry is performed with a LSRFortessa™ X20 (BD Biosciences) and analysis of flow cytometric data is performed using FlowJo software (Treestar, Inc. Ashland, Oreg.). The percentage of CD8+ effector cells, within the CD3 gate, that are CD107 +ve is determined for each effector/target cell culture.

Consistent with the previous cytotoxicity and cytokine data, co-culture of mesothelin-expressing target cells with effector T-cells transduced with anti-mesothelin-28ζ CAR may induce an increase in surface CD107a expression relative to effectors incubated with mesothelin negative target cells. In comparison, under the same conditions, anti-mesothelin-CD3ε LL or anti-mesothelin-CD3γ LL TFP-expressing effectors may exhibit a 5- to 7-fold induction of CD107a expression. Anti-mesothelin TFPs constructed with an alternative hinge region may generate similar results upon co-culture with mesothelin-bearing target cells.

Example 11: In Vivo Mouse Efficacy Studies

To assess the ability of effector T-cells transduced with anti-mesothelin TFPs to achieve anti-tumor responses in vivo, effector T-cells transduced with either anti-mesothelin-28ζ CAR, anti-mesothelin-CD3ε LL TFP or anti-mesothelin-CD3γ LL TFP are adoptively transferred into NOD/SCID/IL-2Rγ−/− (NSG-JAX) mice that had previously been inoculated with mesothelin+ human cancer cell lines.

Female NOD/SCID/IL-2Rγ−/− (NSG-JAX) mice, at least 6 weeks of age prior to the start of the study, are obtained from The Jackson Laboratory (stock number 005557) and acclimated for 3 days before experimental use. Human mesothelin-expressing cell lines for inoculation are maintained in log-phase culture prior to harvesting and counting with trypan blue to determine a viable cell count. On the day of tumor challenge, the cells are centrifuged at 300 g for 5 minutes and re-suspended in pre-warmed sterile PBS at either $0.5\text{-}1\times10^6$ cells/100 μL. T-cells for adoptive transfer, either non-transduced or transduced with anti-mesothelin-28ζ CAR, anti-mesothelin-CD3ε LL TFP or anti-CD3γ LL TFP constructs are prepared. On day 0 of the study, 10 animals per experimental group are challenged intravenously with $0.5\text{-}1\times10^6$ mesothelin-expressing cells. 3 days later, $5\times10^6$ of effector T-cell populations are intravenously transferred to each animal in 100 μL of sterile PBS. Detailed clinical observations on the animals are recorded daily until euthanasia. Body weight measurements are made on all animals weekly until death or euthanasia. All animals are euthanized 35 days after adoptive transfer of test and control articles. Any animals appearing moribund during the study are euthanized at the discretion of the study director in consultation with a veterinarian.

Relative to non-transduced T-cells, adoptive transfer of T-cell transduced with either anti-mesothelin-28ζ CAR, anti-mesothelin-CD3ε LL TFP or anti-mesothelin-CD3γ LL TFP may prolong survival mesolthelin-expressing cell line tumor-bearing mice, and may indicate that both anti-mesothelin CAR- and TFP-transduced T-cells are capable of mediating target cell killing with corresponding increased survival in these mouse models. Collectively, these data may indicate that TFPs represent an alternative platform for engineering chimeric receptors that demonstrate superior antigen-specific killing to first generation CARs both in vitro and in vivo.

Example 12: Human TFP T-Cell Treatment in an In Vivo Solid Tumor Xenograft Mouse Model The efficacy of treatment with human TFP.mesothelin T-cells can also be tested in immune compromised mouse models bearing subcutaneous solid tumors derived from human mesothelin-expressing ALL, CLL, NHL, or MSTO human cell lines. Tumor shrinkage in response to treatment with human TFP.mesothelin T-cells can be either assessed by caliper measurement of tumor size or by following the intensity of a green fluorescence protein (GFP) signal emitted by GFP-expressing tumor cells.

Primary human solid tumor cells can be grown in immune compromised mice without having to culture them in vitro. Exemplary solid cancer cells include solid tumor cell lines, such as provided in The Cancer Genome Atlas (TCGA) and/or the Broad Cancer Cell Line Encyclopedia (CCLE, see Barretina et al., Nature 483:603 (2012)). Exemplary solid cancer cells include primary tumor cells isolated from mesothelioma, renal cell carcinoma, stomach cancer, breast cancer, lung cancer, ovarian cancer, prostate cancer, colon cancer, cervical cancer, brain cancer, liver cancer, pancreatic cancer, kidney, endometrial, or stomach cancer. In some embodiments, the cancer to be treated is selected from the group consisting of mesotheliomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas. These mice can be used to test the efficacy of TFP.mesothelin T-cells in the human tumor xenograft models (see, e.g., Morton et al., Nat. Procol. 2:247 (2007)). Following an implant or injection of $1\times10^6\text{-}1\times10^7$ primary cells (collagenase-treated bulk tumor suspensions in EC matrix material) or tumor fragments (primary tumor fragments in EC matrix material) subcutaneously, tumors are allowed to grow to 200-500 $mm^3$ prior to initiation of treatment.

One such experiment was performed to test the efficacy of MSLN-specific single domain antibody (sdAb) activity in vivo in a mesothelioma xenograft mouse model as described above. Luciferase-labeled MSTO-211H-FL-MSLN-Luc) were inoculated at $1\times10^6$ cells per mouse, subcutaneously, as a 1:1 ratio with Matrigel®. Tumor volume was monitored by caliper measurement twice weekly. Fourteen days after tumor injection, when tumor volume was approximately 300 $mm^3$, $1\times10^7$ T cells were injected intravenously into each animal T cells used included those transduced with a CD3ε-SD1 TFP, a CD3γ-SD1 TFP, a CD3ε-SD4 TFP, a CD3γ-SD4 TFP, a CD28ζ SD1 CAR, and a CD28ζ SD1 CAR. A group of mice with no T cell injection was used as a negative control.

Results are shown in FIG. 12A. Mice injected with CD3ε-SD1 TFP and CD3γ-SD1 TFP T cells showed the greatest and fastest reduction in tumor volume, although mice injected with any but the no T cell control showed reductions in tumor volume after the injection of the T cells.

The persistent efficacy of SD1 ε- and γ-TFP T cells was tested in vivo by rechallenging the surviving mice in the mesothelioma xenograft mouse model.

The mice were inoculated with $1\times10^6$ tumor cells (MSTO 211H FL MSLN Luc) per mouse, subcutaneously, with Matrigel® (1to-1 ratio). One group of mice were injected with Raji cells as a negative control, and one group of mice was injected with MSTO cells alone, again as a negative control. Tumor volume was monitored by caliper measurement twice a week. Fourteen days after tumor injection (when tumor volume reached approximately 300 $mm^3$), $1\times10^7$ MSTO (MSLN+) or Raji (MSLN−, as a negative control) were injected intravenously into each animal Results are shown in FIG. 12B. Each line in the figure represents single animal. As shown in the FIG., mice that had previously been treated with anti-MSLN TFP T cells were able to again reduce tumor volume or eradicate the tumor, indicating that either the originally injected T cells persisted in the mice, or that the mice had developed an anti-MSLN memory response. In contrast, mice re-challenged with Raji (MSLN−) cells were not able to control the growth of the Raji tumors, thus illustrating the specificity of the TFP T-cell response.

Example 13. In Vivo Efficacy of Patients' Derived MSLN ε-TFP T Cells in MSLN Tumor Xenograft Mouse Model SD1 ε-TFP T cells from ovarian cancer patients were used to test the in vitro and in vivo anti-tumor efficacy of SD1 ε-TFP T cells against mesothelin expressing tumor cells (MSTO-MSLN-Luc).

Lentivirus was prepared as described above.

Preparation of $CD4^+$ and $CD8^+$ T Cells from Whole Blood of Ovarian Cancer Patients $CD4^+$ and $CD8^+$ T cells were purified from whole blood of ovarian cancer patients as follows (a schematic overview is shown in FIG. 13A). 40-50 mL of heparinized whole blood of ovarian cancer patients was collected and shipped overnight by Conversant Bio (Huntsville, Ala.). The blood was diluted with an equal volume of PBS and 35 mL of diluted whole blood was carefully layered over 15 mL of Ficoll-Paque® (GE healthcare, cat #: 17-5442-02) in a 50 mL conical tube. It was then centrifuged at 800×g for 20 min at RT in a swinging bucket rotor without brake. The upper layer was aspirated, leaving the mononuclear cell layer (lymphocytes, monocytes, and thrombocytes) undisturbed at the interphase. The mononuclear cell layer was transferred to a new 50 mL conical tube, add 30 mL of PBS and centrifuge at 300×g for 10 min at RT. 1-2 mL of ACK lysis buffer was added (ThermoFisher, cat #: A1049201) to the pellets, mixed thoroughly, and incubated at RT for 2 min, 20 mL of PBS was added, centrifuged at 300×g for 10 min at RT. Cell pellets were resuspended in 10 mL of ice cold MACs buffer and cells were counted via a Cellometer Auto 2000. CD4+ and CD8+ T cell isolation was performed using Miltenyi human CD4/8 microbeads (cat #: 130-045-101; 130-045-201) according to manufacturers' instructions.

TFP T cells were produced as described above, and transduction was determined by FACS. Mesothelin expression was confirmed on target cells ($MSLN^{high}$ cell line MSTO-211H-FL MSLN (generated in house from parental MSTO-211H, ATCC, CRL-2081)) and MSLN-Fc expression was confirmed SD1 ε-TFP T cells by flow cytometry on the same day as a luciferase assay. The single suspension of luciferase-labeled target cells (MSTO-211H-FL MSLN-Luc or the MSLN− cell line C30-Luc (A2780, Sigma)) was prepared in R10 medium. $1\times10^4$ of target cells in 100 μL was added to 96-well flat-bottom plate. TFP T cells were added in 100 μL at different effector-to-target ratio (E:T) as indicated.

FACS-Based Transduction Efficiency and T Cell Activation Determination

TFP T cells were thawed, debeaded (if ex vivo expanded in Dynabeads+IL-2 condition), washed, and then re-suspended in T cell culture media without cytokine. The desired number of T cells (in 100 μL) was added to reach effector-to-target ratio at 5-to-1, 1-to-1 and 1-to-5, respectively. Three replicates were prepared for each type of T cell at tested ratio. The cells were then cultured for 24 hours at 37° C. with 5% $CO_2$. After 24 hours' co-culture, the plate was centrifuged at 300×g for 2 minutes to pellet down the cells. 100 μL of culture supernatant from each well were removed carefully for Luminex assay. 100 μL of assay buffer from Bright-Glo™ Luciferase Assay System (Promega, #E2650) were added to each well. The content in each well was mixed by gently pipetting up and down. The cell-reagent mixture was left at room temperature in dark for 3 minutes for complete lysis of the cells. 200 μL of cell lysate from each well were transferred to Greiner-One white walled 96 well plate. The luminescence was measured relative luminescence unit (RLU) by SpectraMax M5 plate reader (Molecular devices).

The percent (%) of tumor lysis was calculated by the formula listed below:

$$\%\ \text{Tumor Lysis} = 100 * \left[1 - \frac{\text{Luminescence (Tumor} + T\ \text{cell)}}{\text{Luminescence(Tumor)}}\right]$$

Luminex® Assay

Supernatant from tumor-T cell co-culture was harvest and stored in −80° C. as described previously. Cytokine profiles were detected using Millipore Luminex kit (HCD8MAG-15K) as according to manufacturers' instructions. The supernatant was plated without any dilution and the reading was measured using a Magpix xMAP® Technology.

Subcutaneous Mesothelioma Xenograft Mouse Model and In Vivo Assessments

Female 6-week-old NSG mice (NOD.Cg-$Prkdc^{scid}$ $Il2rg^{tm1\,Wjl}$/SzJ, cat #: 005557, Jackson Laboratories) were used in this study. The animals were acclimated for minimum 3 days under the same condition as the study. The MSTO-211H-FLMSLN-Luc cells were suspended in sterile PBS at a concentration of $1\times10^6$ cells/100 μL. The PBS cell suspension was then mixed 1-to-1 with ice cold Matrigel® for a final injection volume of 200 μL for each mouse. The resulting PBS/Matrigel® cell suspension was kept on ice until subcutaneous administration in the dorsal hind flank of the mouse. Tumor growth was monitored as tumor volume with Caliper measurement. The volume of tumor was calculated as:

$$\text{Tumor volume} = \tfrac{1}{2}(\text{length} \times \text{width}^2)$$

Ten days after tumor cell injection, the animals were randomized according to tumor volume (200~300 $mm^3$) and divided into 10 groups to receive injection of SD1 ε-TFP T cells from different patients (number of mice per group varies depending on the number of SD1 ε-TFP T cells recovered on the day of injection). The T cell injection day was considered as the day 0 of the study. The T cells were prepared in sterile PBS at a concentration of $5\times10^6$ cells/100 μL. The cell suspension was then injected intravenously into the mouse via tail vein.

Ex Vivo Expansion of SD1 ε-TFP T Cells from Ovarian Cancer Patients

MSLN-specific sdAb TFP T cells were prepared with lentivirus encoding CDRε formats of the TFP with SD1 binders targeting MSLN. Fold expansion, determined by viable cell count on day 10, ranged from 8.58 to 28.2 fold (17.8+/−3.3) compared to day 0 in cells prepared with Dynabeads®+IL-2, and 10 to 33.6 fold (22.9+/−5.0) compared to day 0 in cells prepared with TransAct®+IL-7/15. The transduction efficiency for the SD1 ε-TFP T cells was determined on day 10 of expansion by surface stain for the presence of GFP and MSLN-Fc on $CD4^+$ and $CD8^+$ populations. Transduction efficiency ranged from 28.6% to 52.1% (40.9+/−4.0%) in cells prepared with Dynabeads+IL-2, and 5.7% to 46.9% (26.8+/−6.3%) in cells prepared with TransAct+IL-7/15; no significant differences were shown in fold expansion and transduction efficiency between Dynabeads+IL-2 and TransAct+IL-7/15 conditions. Vector copy number per cell was in line with transduction efficiency, with around 1-2 copy numbers per cell in either Dynabeads+IL-2 or TransAct+IL7/15 conditions, except for patient 1, which had 0.38 vector copy number per cell.

In Vitro Anti-Tumor Activity of SD1 ε-TFP T Cells from Ovarian Cancer Patients

The in vitro efficacy of SD1 ε-TFP T cells from ovarian cancer patients was tested using luciferase reporter tumor cell lysis assays. Mesothelin expression was confirmed on MSTO-211H-FLMSLN-Luc cell lines on the day of assay (FIG. 13B); all SD1 ε-TFP T cells showed different levels of tumor killing Robust tumor cell lysis was observed for patients 1, 2, 4, and 5 (75%-97%). MSLN ε-TFP T cells when co-cultured with MSTO-211H-FLMSLN-Luc (a MSLN high expresser) at 5-to-1 effector to target ratio, patient 3 shows ~35% of tumor lysis at 5-to-1 effector to target ratio, 4 out of 5 patients (patients 1, 2, 4, and 5) showed on average 50% of tumor lysis at 1-to-1 effector to target ratio, 2 out of 5 (patients 4 and 5) showed ~50% of tumor lysis even at 1-to-5 effector to target ratio. All T cells showed rapid killing of the tumor cell. No tumor lysis was observed for all MSLN ε-TFP™ T cells when co-cultured with mesothelin negative cell lines C30-Luc (FIG. 13C). The cytokine profile of MSLN ε-TFP from five patients were analyzed using a human CD8 Luminex® panel, cytolytic cytokines such as IFN-γ, GM-CSF, Granzyme-A/B, IL-2, MIP-1α/β, TNF-α, and perforin were significantly increased in MSLN ε-TFP™ T cells compared to non-transduced T cells (FIGS. 13D-L).

In Vivo Efficacy of MSLN ε-TFP T Cells in MSLN-Expressing Tumor Mouse Xenograft Model MSTO-211H-FLMSLN-Luc was used to establish a subcutaneous xenografted mesothelin-expressing tumor mouse model. Tumor volume was measured twice a week. On day 10 post tumor injection, the average tumor volume reached 200-300 $mm^3$, and day 10-expanded MSLN ε-TFP T cells from one normal donor (ND12, FIG. 14A) and patients 1-4 (FIGS. 14B-E) and were thawed and transduction efficiency was confirmed. $5\times10^6$ per mouse MSLN ε-TFP T cells or matching non-transduced T cells were i.v. injected and tumor volumes were monitored thereafter. MSLN ε-TFP T cells from 3 out of 4 patients (patients 1, 2, and 4) showed complete tumor clearance by day 20 post-T cell injection. Tumor clearance was maintained until day 40. Five out of six mice received MSLN ε-TFP T cells from patient 3, which showed partial protection. From all four patients who received MSLN ε-TFP T cells from ND12, one showed complete tumor clearance, two showed partial tumor clearance.

ENDNOTES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

APPENDIX A

SEQUENCE SUMMARY

| SEQ ID NO. | Name | Sequence |
|---|---|---|
| 1 | Short Linker 1 | GGGGSGGGGSCCGGSLE |
| 2 | Short Linker 2 | AAAGGGGSGGGGSGGGGSLE |
| 3 | Long Linker | AAAIEVMYPPPYLGGGGSGGGGSGGGGSLE |
| 4 | human CD3-ε | MQSGTHWRVLGLCLLSVGVWGQDGNEEMGGITQTPYKVSISGTTVILTCPQYPGSEILWQHNDK NIGGDEDDKNIGSDEDHLSLKEFSELEQSGYYVCYPRGSKPEDANFYLYLRARVCENCMEMDVM SVATIVIVDICITGGLLLLVYYWSKNRKAKAKPVTRGAGAGGRQRGQNKERPPPVPNPDYEPIR KGQRDLYSGLNQRRI |
| 5 | human CD3-γ | MEQGKGLAVLILAIILLQGTLAQSIKGNHLVKVYDYQEDGSVLLTCDAEAKNITWFKDGKMIGF LTEDKKKWNLGSNAKDPRGMYQCKGSQNKSKPLQVYYRMCQNCIELNAATISGFLFAEIVSIFV LAVGVYFIAGQDGVRQSRASDKQTLLPNDQLYQPLKDREDDQYSHLQGNQLRRN |
| 6 | human CD3-δ | MEHSTFLSGLVLATLLSQVSPFKIPIEELEDRVFVNCNTSITWVEGTVGTLLSDITRLDLGKRI LDPRGIYRCNGTDIYKDKESTVQVHYRMCQSCVELDPATVAGIIVTDVIATLLLALGVFCFAGH ETGRLSGAADTQALLRNDQVYQPLRDRDDAQYSHLGGNWARNKS |
| 7 | human CD3-ζ | MKWKALFTAAILQAQLPITEAQSFGLLDPKLCYLLDGILFIYGVILTALFLRVKFSRSADAPAY QQGQNQLYNELNLGRREEYDVLDKRRGRDPEMGGKPQRRKNPQEGLYNELQKDKMAEAYSEIGM KGERRRGKGHDGLYQGLSTATKDTYDALHMQALPPR |

APPENDIX A-continued

SEQUENCE SUMMARY

| SEQ ID NO. | Name | Sequence |
|---|---|---|
| 57 | human TCR α-chain | MAGTWLLLLLALGCPALPTGVGGTPFPSLAPPIMLLVDGKQQMVVVCLVLDVAPPGLDSPIWFS<br>AGNGSALDAFTYGPSPATDGTWTNLAHLSLPSEELASWEPLVCHTGPGAEGHSRSTQPMHLSGE<br>ASTARTCPQEPLRGTPGGALWLGVLRLLLFKLLLFDLLLTCSCLCDPAGPLPSPATTTRLRALG<br>SHRLHPATETGGREATSSPRPQPRDRRWGDTPPGRKPGSPVWGEGSYLSSYPTCPAQAWCSRSA<br>LRAPSSSLGAFFAGDLPPPLQAGA |
| 9 | human TCR α-chain C region | PNIQNPDPAVYQLRDSKSSDKSVCLFTDFDSQTNVSQSKDSDVYITDKTVLDMRSMDFKSNSAV<br>AWSNKSDFACANAFNNSIIPEDTFFPSPESSCDVKLVEKSFETDTNLNFQNLSVIGFRILLLKV<br>AGFNLLMTLRLWSS |
| 10 | human TCR α-chain V region CTL-L17 | MAMLLGASVLILWLQPDWVNSQQKNDDQQVKQNSPSLSVQEGRISILNCDYTNSMFDYFLWYKK<br>YPAEGPTFLISISSIKDKNEDGRFTVFLNKSAKHLSLHIVPSQPGDSAVYFCAAKGAGTASKLT<br>FGTGTRLQVTL |
| 11 | human TCR β-chain C region | EDLNKVFPPEVAVFEPSEAEISHTQKATLVCLATGFFPDHVELSWWVNGKEVHSGVSTDPQPLK<br>EQPALNDSRYCLSSRLRVSATFWQNPRNHFRCQVQFYGLSENDEWTQDRAKPVTQIVSAEAWGR<br>ADCGFTSVSYQQGVLSATILYEILLGKATLYAVLVSALVLMAMVKRKDF |
| 12 | human TCR β-chain V region CTL-L17 | MGTSLLCWMALCLLGADHADTGVSQNPRHNITKRGQNVTFRCDPISEHNRLYWYRQTLGQGPEF<br>LTYFQNEAQLEKSRLLSDRFSAERPKGSFSTLEIQRTEQGDSAMYLCASSLAGLNQPQHFGDGT<br>RLSIL |
| 13 | human TCR β-chain V region YT35 | MDSWTFCCVSLCILVAKHTDAGVIQSPRHEVTEMGQEVTLRCKPISGHNSLFWYRQTMMRGLEL<br>LIYFNNNVPIDDSGMPEDRFSAKMPNASFSTLKIQPSEPRDSAVYFCASSFSTCSANYGYTFGS<br>GTRLTVV |
| 14 | MSLN DNA Seq. | acgcgtgtagtcttatgcaatactcttgtagtcttgcaacatggtaacgatgagttagcaacat<br>gccttacaaggagagaaaaagcaccgtgcatgccgattggtggaagtaaggtggtacgatcgtg<br>ccttattaggaaggcaacagacgggtctgacatggattggacgaaccactgaattgccgcattg<br>cagagatattgtatttaagtgcctagctcgatacaataaacgggtctctctggttagaccagat<br>ctgagcctgggagctctctggctaactagggaacccactgcttaagcctcaataaagcttgcct<br>tgagtgcttcaagtagtgtgtgcccgtctgttgtgtgactctggtaactagagatccctcagac<br>ccttttagtcagtgtggaaaatctctagcagtggcgcccgaacagggacctgaaagcgaaaggg<br>aaaccagagctctctcgacgcaggactcggcttgctgaagcgcgcacggcaagaggcgaggggc<br>ggcgactggtgagtacgccaaaaattttgactagcggaggctagaaggagagagatgggtgcga<br>gagcgtcagtattaagcgggggagaattagatcgcgatgggaaaaaattcggttaaggccaggg<br>ggaaagaaaaaatataaattaaaacatatagtatgggcaagcagggagctagaacgattcgcag<br>ttaatcctggcctgttagaaacatcagaaggctgtagacaaatactgggacagctacaaccatc<br>ccttcagacaggatcagaagaacttagatcattatataatacagtagcaaccctctattgtgtg<br>catcaaaggatagagataaaagacaccaaggaagctttagacaagatagaggaagagcaaaaca<br>aaagtaagaccaccgcacagcaagcggccactgatcttcagacctggaggaggagatatgaggg<br>acaattggagaagtgaattatataaatataaagtagtaaaaattgaaccattaggagtagcacc<br>caccaaggcaaagagaagagtggtgcagagagaaaaaagagcagtgggaataggagctttgttc<br>cttgggttcttgggagcagcaggaagcactatgggcgcagcctcaatgacgctgacggtacagg<br>ccagacaattattgtctggtatagtgcagcagcagaacaatttgctgagggctattgaggcgca<br>acagcatctgttgcaactcacagtctggggcatcaagcagctccaggcaagaatcctggctgtg<br>gaaagatacctaaaggatcaacagctcctggggatttggggttgctctggaaaactcatttgca<br>ccactgctgtgccttggaatgctagttggagtaataaatctctggaacagattggaatcacacg<br>acctggatggagtgggacagagaaattaacaattacacaagcttaatacactccttaattgaag<br>aatcgcaaaaccagcaagaaaagaatgaacaagaattattggaattagataaatgggcaagttt<br>gtggaattggtttaacataacaaattggctgtggtatataaaattattcataatgatagtagga<br>ggcttggtaggtttaagaatagtttttgctgtactactatagtgaatagagttaggcagggata<br>ttcaccattatcgtttcagacccacctcccaaccccgaggggacccgacaggcccgaaggaata<br>gaagaagaaggtggagagagagacagagacagatccattcgattagtgaacggatctcgacggt<br>atcggttaacttttaaaagaaaaggggggattggggggtacagtgcaggggaaagaatagtaga<br>cataatagcaacagacatacaaactaaagaattacaaaaacaaattacaaaattcaaaatttta<br>tcgatactagtattatgcccagtacatgaccttatgggactttcctacttggcagtacatctac<br>gtattagtcatcgctattaccatggtgatgcggttttggcagtacatcaatgggcgtggatagc<br>ggtttgactcacggggatttccaagtctccaccccattgacgtcaatgggagtttgttttggca<br>ccaaaatcaacgggactttccaaaatgtcgtaacaactccgccccattgacgcaaatgggcggt<br>aggcgtgtacggtgggaggtttatataagcagagctcgtttagtgaaccgtcagatcgcctgga<br>gacgccatccacgctgttttgacctccatagaagattctagagccgccaccatgcttctcctgg<br>tgacaagccttctgctctgtgagttaccacacccagcattcctcctgatcccagacattcagca<br>ggtccagctccagcagtctggccctgaactcgaaaaacctggcgctagcgtgaaaatttcctgt<br>aaagcctccggctactcttttactggctacacaatgaattgggtgaaacagtctcacggcaaat<br>ccctcgaatggatcggactcatcacaccctacaatggcgcctcttcctacaaccagaaattccg<br>gggcaaggcaacactcactgtggacaaatcatcctctaccgcctacatggatctgctctccctc<br>acatctgaggactccgctgtctacttttgtgcccgaggaggatacgacggacgaggattcgatt<br>actggggacagggaacaactgtgaccgtgtctagtggcggcggagggagtggaggcggaggatc<br>ttctggcggggggatccgatattgaactcacacagtctcccgctatcatgtctgcttctcccggc<br>gagaaagtgactatgacttgctctgcttcctcttctgtgtcctacatgcactggtaccagcaga<br>aatctggcacatcccctaaacggtggatctacgatactagcaaactggcatccggcgtgcctgg<br>gcgattctctggctctggctctggcaactcttactctctcacaatctcatctgtcgaggctgag<br>gacgatgccacatactactgtcagcagtggtctaaacacccactcacattcggcgctggcacta<br>aactggaaataaaagcggccgcaggtggcggcggttctggtggcggcggttctggtggcggcgg |

APPENDIX A-continued

| SEQUENCE SUMMARY | |
|---|---|
| SEQ ID NO.Name | Sequence |
| | ttctctcgaggatggtaatgaagaaatgggtggtattacacagacaccatataaagtctccatc<br>tctggaaccacagtaatattgacatgccctcagtatcctggatctgaaatactatggcaacaca<br>atgataaaaacataggcggtgatgaggatgataaaaacataggcagtgatgaggatcacctgtc<br>actgaaggaattacagaattggagcaaagtggttattatgtctgctaccccagaggaagcaaac<br>cagaagatgcgaacttttatctctacctgagggcaagagtgtgtgagaactgcatggagatgga<br>tgtgatgtcggtggccacaattgtcatagtggacatctgcatcactgggggcttgctgctgctg<br>gtttactactggagcaagaatagaaaggccaaggccaagcctgtgacacgaggagcgggtgctg<br>gcggcaggcaaaggggacaaaacaaggagaggccaccacctgttcccaacccagactatgagcc<br>catccggaaaggccagcgggacctgtattctggcctgaatcagagacgcatctgataagaattc<br>gatccgcggccgcgaaggatctgcgatcgctccggtgcccgtcagtgggcagagcgcacatcgc<br>ccacagtccccgagaagttggggggaggggtcggcaattgaacgggtgcctagagaaggtggcg<br>cggggtaaactgggaaagtgatgtcgtgtactggctccgcctttttcccgagggtgggggagaa<br>ccgtatataagtgcagtagtcgccgtgaacgttctttttcgcaacgggtagccgccagaacaca<br>gctgaagcttcgaggggctcgcatctctccttcacgcgcccgccgccctacctgaggccgccat<br>ccacgccggttgagtcgcgttctgccgcctcccgcctgtggtgcctcctgaactgcgtccgccg<br>tctaggtaagtttaaagctcaggtcgagaccgggcctttgtccggcgctcccttggagcctacc<br>tagactcagccggctctccacgctttgcctgaccctgcttgctcaactctacgtctttgtttcg<br>ttttctgttctgcgccgttacagatccaagctgtgaccggcgcctacgctagatgaccgagtac<br>aagcccacggtgcgcctcgccacccgcgacgacgtccccagggccgtacgcaccctcgccgccg<br>cgttcgccgactaccccgccacgcgccacaccgtcgatccggaccgccacatcgagcgggtcac<br>cgagctgcaagaactcttcctcacgcgcgtcgggctcgacatcggcaaggtgtgggtcgcggac<br>gacggcgccgcggtggcggtctggaccacgccggagagcgtcgaagcgggggcggtgttcgccg<br>agatcggcccgcgcatggccgagttgagcggttcccggctggccgcgcagcaacagatggaagg<br>cctcctggcgccgcaccggcccaaggagcccgcgtggttcctggccaccgtcggcgtctcgccc<br>gaccaccagggcaagggtctgggcagcgccgtcgtgctccccggagtggaggcggccgagcgcg<br>ccggggtgcccgccttcctggagacctccgcgccccgcaacctccccttctacgagcggctcgg<br>cttcaccgtcaccgccgacgtcgaggtgcccgaaggaccgcgcacctggtgcatgacccgcaag<br>cccggtgcctgagtcgacaatcaacctctggattacaaaatttgtgaaagattgactggtattc<br>ttaactatgttgctccttttacgctatgtggatacgctgctttaatgcctttgtatcatgctat<br>tgcttcccgtatggctttcattttctcctccttgtataaatcctggttgctgtctctttatgag<br>gagttgtggcccgttgtcaggcaacgtggcgtggtgtgcactgtgtttgctgacgcaaccccca<br>ctggttggggcattgccaccacctgtcagctcctttccgggactttcgctttccccctccctat<br>tgccacggcggaactcatcgccgcctgccttgcccgctgctggacaggggctcggctgttgggc<br>actgacaattccgtggtgttgtcggggaaatcatcgtcctttccttggctgctcgcctgtgttg<br>ccacctggattctgcgcgggacgtccttctgctacgtcccttcggccctcaatccagcggacct<br>tccttcccgcggcctgctgccggctctgcggcctcttccgcgtcttcgccttcgccctcagacg<br>agtcggatctccctttgggccgcctccccgcctggtacctttaagaccaatgacttacaaggca<br>gctgtagatcttagccactttttaaaagaaaaggggggactggaagggctaattcactcccaac<br>gaaaataagatctgctttttgcttgtactgggtctctctggttagaccagatctgagcctggga<br>gctctctggctaactagggaacccactgcttaagcctcaataaagcttgccttgagtgcttcaa<br>gtagtgtgtgcccgtctgttgtgtgactctggtaactagagatccctcagacccttttagtcag<br>tgtggaaaatctctagcagtagtagttcatgtcatcttattattcagtatttataacttgcaaa<br>gaaatgaatatcagagagtgagaggaacttgtttattgcagcttataatggttacaaataaagc<br>aatagcatcacaaatttcacaaataaagcatttttttcactgcattctagttgtggtttgtcca<br>aactcatcaatgtatcttatcatgtctggctctagctatcccgcccctaactccgcccagaccg<br>cccattctccgccccatggctgactaattttttttatttatgcagaggccgaggccgcctcggc<br>ctctgagctattccagaagtagtgaggaggcttttttggaggcctagacttttgcagagacggc<br>ccaaattcgtaatcatggtcatagctgtttcctgtgtgaaattgttatccgctcacaattccac<br>acaacatacgagccggaagcataaagtgtaaagcctggggtgcctaatgagtgagctaactcac<br>attaattgcgttgcgctcactgcccgctttccagtcgggaaacctgtcgtgccagctgcattaa<br>tgaatcggccaacgcgcggggagaggcggtttgcgtattgggcgctcttccgcttcctcgctca<br>ctgactcgctgcgctcggtcgttcggctgcggcgagcggtatcagctcactcaaaggcggtaat<br>acggttatccacagaatcaggggataacgcaggaaagaacatgtgagcaaaaggccagcaaaag<br>gccaggaaccgtaaaaaggccgcgagctggcgtttttccataggctccgcccccctgacgagca<br>tcacaaaaatcgacgctcaagtcagaggtggcgaaacccgacaggactataaagataccaggcg<br>tttccccctggaagctccctcgtgcgctctcctgaccgaccctgccgcttaccggatacctgtc<br>cgcctactcccttcgggaagcgtggcgctactcatagctcacgctgtaggtatctcagttcggt<br>gtaggtcgttcgctccaagctgggctgtgtgcacgaaccccccgttcagcccgaccgctgcgcc<br>ttatccggtaactatcgtcttgagtccaacccggtaagacacgacttatcgccactggcagcag<br>ccactggtaacaggattagcagagcgaggtatgtaggcggtgctacagagttcttgaagtggtg<br>gcctaactacggctacactagaaggacagtatttggtatctgcgctctgctgaagccagttacc<br>ttcggaaaaagagaggtagctcttgatccggcaaacaaaccaccgctggtagcggtggtttttt<br>tgtagcaagcagcagattacgcgcagaaaaaaaggatctcaagaagatcctttgatcttttcta<br>cggggtctgacgctcagtggaacgaaaactcacgttaagggattttggtcatgagattatcaaa<br>aaggatcttcacctagatccttttaaattaaaaatgaagttttaaatcaatctaaagtatatat<br>gagtaaacttggtctgacagttaccaatgcttaatcagtgaggcacctatctcagcgatctgtc<br>tatttcgttcatccatagttgcctgactccccgtcgtgtagataactacgatacgggagggctt<br>accatctggccccagtgctgcaatgataccgcgagacccacgctcaccggctccagatttatca<br>gcaataaaccagccagccggaagggccgagcgcagaagtggtcctgcaactttatccgcctcca<br>tccagtctattaattgttgccgggaagctagagtaagtagttcgccagttaatagtttgcgcaa<br>cgttgttgccattgctacaggcatcgtggtgtcacgctcgtcgtttggtatggcttcattcagc<br>tccggttcccaacgatcaaggcgagttacatgatcccccatgttgtgcaaaaaagcggttagct<br>ccttcggtcctccgatcgttgtcagaagtaagttggccgcagtgttatcactcatggttatggc<br>agcactgcataattctcttactgtcatgccatccgtaagatgcttttctgtgactggtgagtac<br>tcaaccaagtcattctgagaatagtgtatgcggcgaccgagttgctcttgcccggcgtcaatac<br>gggataataccgcgccacatagcagaactttaaaagtgctcatcattggaaaacgttcttcggg |

APPENDIX A-continued

SEQUENCE SUMMARY

| SEQ ID NO. | Name | Sequence |
| --- | --- | --- |
| | | gcgaaaactctcaaggatcttaccgctgttgagatccagttcgatgtaacccactcgtgcaccc<br>aactgatcttcagcatcttttactttcaccagcgtttctgggtgagcaaaaacaggaaggcaaa<br>atgccgcaaaaaagggaataagggcgacacggaaatgttgaatactcatactcttcctttttca<br>atattattgaagcatttatcagggttattgtctcatgagcggatacatatttgaatgtatttag<br>aaaaataaacaaataggggttccgcgcacatttccccgaaaagtgccacctgacgtctaagaaa<br>ccattattatcatgacattaacctataaaaataggcgtatcacgaggccctttcgtctcgcgcg<br>tttcggtgatgacggtgaaaacctctgacacatgcagctcccggagacggtcacagcttgtctg<br>taagcggatgccgggagcagacaagcccgtcagggcgcgtcagcgggtgttggcgggtgtcggg<br>gctggcttaactatgcggcatcagagcagattgtactgagagtgcaccatatgcggtgtgaaat<br>accgcacagatgcgtaaggagaaaataccgcatcaggcgccattcgccattcaggctgcgcaac<br>tgttgggaagggcgatcggtgcgggcctcttcgctattacgccagctggcgaaagggggatgtg<br>ctgcaaggcgattaagttgggtaacgccagggttttcccagtcacgacgttgtaaaacgacggc<br>cagtgccaagctg |
| 15 | MSLN amino acid sequence: human mesothelin sequence (UniProt Accession No. Q13421) | MALPTARPLLGSCGTPALGSLLFLLFSLGWVQPSRTLAGETGQEAAPLDGVLANPPNISSLSPR<br>QLLGFPCAEVSGLSTERVRELAVALAQKNVKLSTEQLRCLAHRLSEPPEDLDALPLDLLLFLNP<br>DAFSGPQACTRFFSRITKANVDLLPRGAPERQRLLPAALACWGVRGSLLSEADVRALGGLACDL<br>PGRFVAESAEVLLPRLVSCPGPLDQDQQEAARAALQGGGPPYGPPSTWSVSTMDALRGLLPVLG<br>QPIIRSIPQGIVAAWRQRSSRDPSWRQPERTILRPRFRREVEKTACPSGKKAREIDESLIFYKK<br>WELEACVDAALLATQMDRVNAIPFTYEQLDVLKHKLDELYPQGYPESVIQHLGYLFLKMSPEDI<br>RKWNVTSLETLKALLEVNKGHEMSPQVATLIDRFVKGRGQLDKDTLDTLTAFYPGYLCSLSPEE<br>LSSVPPSSIWAVRPQDLDTCDPRQLDVLYPKARLAFQNMNGSEYFVKIQSFLGGAPTEDLKALS<br>QQNVSMDLATFMKLRTDAVLPLTVAEVQKLLGPHVEGLKAEERHRPVRDWILRQRQDDLDTLGL<br>GLQGGIPNGYLVLDLSMQEALSGTPCLLGPGPVLTVLALLLASTLA |
| 16 | p510_anti-MSLN_SS1_CD3ϵ DNA | acgcgtgtagtcttatgcaatactcttgtagtcttgcaacatggtaacgatgagttagcaacat<br>gccttacaaggagagaaaaagcaccgtgcatgccgattggtggaagtaaggtggtacgatcgtg<br>ccttattaggaaggcaacagacgggtctgacatggattggacgaaccactgaattgccgcattg<br>cagagatattgtatttaagtgcctagctcgatacaataaacgggtctctctggttagaccagat<br>ctgagcctgggagctctctggctaactagggaacccactgcttaagcctcaataaagcttgcct<br>tgagtgcttcaagtagtgtgtgcccgtctgagtgtgactctggtaactagagatccctcagacc<br>cttttagtcagtgtggaaaatctctagcagtggcgcccgaacagggacctgaaagcgaaaggga<br>aaccagagctctctcgacgcaggactcggcttgctgaagcgcgcacggcaagaggcgaggggcg<br>gcgactggtgagtacgccaaaaattttgactagcggaggctagaaggagagagatgggtgcgag<br>agcgtcagtattaagcgggggagaattagatcgcgatgggaaaaaattcggttaaggccagggg<br>gaaagaaaaaatataaattaaaacatatagtatgggcaagcagggagctagaacgattcgcagt<br>taatcctggcctgttagaaacatcagaaggctgtagacaaatactgggacagctacaaccatcc<br>cttcagacaggatcagaagaacttagatcattatataatacagtagcaaccctctattgtgtgc<br>atcaaaggatagagataaaagacaccaaggaagctttagacaagatagaggaagagcaaaacaa<br>aagtaagaccaccgcacagcaagcggccactgatcttcagacctggaggaggagatatgaggga<br>caattggagaagtgaattatataaatataaagtagtaaaaattgaaccattaggagtagcaccc<br>accaaggcaaagagaagagtggtgcagagagaaaaaagagcagtgggaataggagctttgttcc<br>ttgggttcttgggagcagcaggaagcactatgggcgcagcctcaatgacgctgacggtacaggc<br>cagacaattattgtctggtatagtgcagcagcagaacaatttgctgagggctattgaggcgcaa<br>cagcatctgttgcaactcacagtctggggcatcaagcagctccaggcaagaatcctggctgtgg<br>aaagatacctaaaggatcaacagctcctggggatttggggttgctctggaaaactcatttgcac<br>cactgctgtgccttggaatgctagttggagtaataaatctctggaacagattggaatcacacga<br>cctggatggagtgggacagagaaattaacaattacacaagcttaatacactccttaattgaaga<br>atcgcaaaaccagcaagaaaagaatgaacaagaattattggaattagataaatgggcaagtttg<br>tggaattggtttaacataacaaattggctgtggtatataaaattattcataatgatagtaggag<br>gcttggtaggtttaagaatagtttttgctgtactactatagtgaatagagttaggcagggatat<br>tcaccattatcgtttcagacccacctcccaaccccgaggggacccgacaggcccgaaggaatag<br>aagaagaaggtggagagagagacagagacagatccattcgattagtgaacggatctcgacggta<br>tcggttaacttttaaaagaaaaggggggattggggggtacagtgcaggggaaagaatagtagac<br>ataatagcaacagacatacaaactaaagaattacaaaaacaaattacaaaattcaaaattttat<br>cgatactagtattatgcccagtacatgaccttatgggactacctacttggcagtacatctacgt<br>attagtcatcgctattaccatggtgatgcggttaggcagtacatcaatgggcgtggatagcggt<br>ttgactcacggggatttccaagtctccaccccattgacgtcaatgggagtttgttttggcacca<br>aaatcaacgggactttccaaaatgtcgtaacaactccgccccattgacgcaaatgggcggtagg<br>cgtgtacggtgggaggtttatataagcagagctcgtttagtgaaccgtcagatcgcctggagac<br>gccatccacgctgttttgacctccatagaagattctagagccgccaccatgcttctcctggtga<br>caagccttctgctctgtgagttaccacacccagcattcctcctgatcccagacattcagcaggt<br>ccagctccagcagtctggccctgaactcgaaaaacctggcgctagcgtgaaaatttcctgtaaa<br>gcctccggctactcttttactggctacacaatgaattgggtgaaacagtctcacggcaaatccc<br>tcgaatggatcggactcatcacaccctacaatggcgcctcttcctacaaccagaaattccgggg<br>caaggcaacactcactgtggacaaatcatcctctaccgcctacatggatctgctctccctcaca<br>tctgaggactccgctgtctacttagtgcccgaggaggatacgacggacgaggattcgattactg<br>gggacagggaacaactgtgaccgtgtctagtggcggcggagggagtggaggcggaggatcttct<br>ggcgggggatccgatattgaactcacacagtctcccgctatcatgtctgcttctcccggcgaga<br>aagtgactatgacttgctctgcttcctcttctgtgtcctacatgcactggtaccagcagaaatc<br>tggcacatcccctaaacggtggatctacgatactagcaaactggcatccggcgtgcctgggcga<br>ttctctggctctggctctggcaactcttactctctcacaatctcatctgtcgaggctgaggacg<br>atgccacatactactgtcagcagtggtctaaacacccactcacattcggcgctggcactaaact<br>ggaaataaaagcggccgcaggtggcggcggttctggtggcggcggttctggtggcggcggttct<br>ctcgaggatggtaatgaagaaatgggtggtattacacagacaccatataaagtctccatctctg<br>gaaccacagtaatattgacatgccctcagtatcctggatctgaaatactatggcaacacaatga |

APPENDIX A-continued

SEQUENCE SUMMARY

| SEQ ID NO.Name | Sequence |
|---|---|
| | taaaaacataggcggtgatgaggatgataaaaacataggcagtgatgaggatcacctgtcactg aaggaattttcagaattggagcaaagtggttattatgtctgctaccccagaggaagcaaaccag aagatgcgaacttttatctctacctgagggcaagagtgtgtgagaactgcatggagatggatgt gatgtcggtggccacaattgtcatagtggacatctgcatcactggggggcttgctgctgctggtt tactactggagcaagaatagaaaggccaaggccaagcctgtgacacgaggagcgggtgctggcg gcaggcaaaggggacaaaacaaggagaggccaccacctgttcccaacccagactatgagcccat ccggaaaggccagcgggacctgtattctggcctgaatcagagacgcatctgataagaattcgat ccgcggccgcgaaggatctgcgatcgctccggtgcccgtcagtgggcagagcgcacatcgccca cagtccccgagaagttggggggaggggtcggcaattgaacgggtgcctagagaaggtggcgcgg ggtaaactgggaaagtgatgtcgtgtactggctccgcctttttcccgagggtgggggagaaccg tatataagtgcagtagtcgccgtgaacgttctttttcgcaacgggtagccgccagaacacagct gaagcttcgaggggctcgcatctctccttcacgcgcccgccgccctacctgaggccgccatcca cgccggttgagtcgcgttctgccgcctcccgcctgtggtgcctcctgaactgcgtccgccgtct aggtaagtttaaagctcaggtcgagaccgggcctttgtccggcgctcccttggagcctacctag actcagccggctctccacgctttgcctgaccctgcttgctcaactctacgtctagtacgttact gactgcgccgttacagatccaagctgtgaccggcgcctacgctagatgaccgagtacaagccca cggtgcgcctcgccacccgcgacgacgtccccagggccgtacgcaccctcgccgccgcgttcgc cgactaccccgccacgcgccacaccgtcgatccggaccgccacatcgagcgggtcaccgagctg caagaactcttcctcacgcgcgtcgggctcgacatcggcaaggtgtgggtcgcggacgacggcg ccgcggtggcggtctggaccacgccggagagcgtcgaagcgggggcggtgttcgccgagatcgg cccgcgcatggccgagttgagcggttcccggctggccgcgcagcaacagatggaaggcctcctg gcgccgcaccggcccaaggagcccgcgtggttcctggccaccgtcggcgtctcgcccgaccacc agggcaagggtctgggcagcgccgtcgtgctccccggagtggaggcggccgagcgcgccggggt gcccgccttcctggagacctccgcgccccgcaacctccccttctacgagcggctcggcttcacc gtcaccgccgacgtcgaggtgcccgaaggaccgcgcacctggtgcatgacccgcaagcccggtg cctgagtcgacaatcaacctctggattacaaaatttgtgaaagattgactggtattcttaacta tgttgctccttttacgctatgtggatacgctgctttaatgcctttgtatcatgctattgcttcc cgtatggctttcattttctcctccttgtataaatcctggttgctgtctctttatgaggagttgt ggcccgttgtcaggcaacgtggcgtggtgtgcactgtgtttgctgacgcaacccccactggttg gggcattgccaccacctgtcagctcctttccgggactttcgctttccccctccctattgccacg gcggaactcatcgccgcctgccttgcccgctgctggacaggggctcggctgttgggcactgaca attccgtggtgttgtcggggaaatcatcgtcctttccttggctgctcgcctgtgttgccacctg gattctgcgcgggacgtccttctgctacgtcccttcggccctcaatccagcggaccttccttcc cgcggcctgctgccggctctgcggcctcttccgcgtcttcgccttcgccctcagacgagtcgga tctccctttgggccgcctccccgcctggtacctttaagaccaatgacttacaaggcagctgtag atcttagccactttttaaaagaaaaggggggactggaagggctaattcactcccaacgaaaata agatctgctttttgcttgtactgggtctctctggttagaccagatctgagcctgggagctctct ggctaactagggaacccactgcttaagcctcaataaagcttgccttgagtgcttcaagtagtgt gtgcccgtctgttgtgtgactctggtaactagagatccctcagacccttttagtcagtgtggaa aatctctagcagtagtagttcatgtcatcttattattcagtatttataacttgcaaagaaatga atatcagagagtgagaggaacttgtttattgcagcttataatggttacaaataaagcaatagca tcacaaatttcacaaataaagcatttttttcactgcattctagttgtggtttgtccaaactcat caatgtatcttatcatgtctggctctagctatcccgcccctaactccgcccagaccgcccattc tccgccccatggctgactaattttttttatttatgcagaggccgaggccgcctcggcctctgag ctattccagaagtagtgaggaggcttttttggaggcctagacttttgcagagacggcccaaatt cgtaatcatggtcatagctgtttcctgtgtgaaattgttatccgctcacaattccacacaacat acgagccggaagcataaagtgtaaagcctggggtgcctaatgagtgagctaactcacattaatt gcgttgcgctcactgcccgctttccagtcgggaaacctgtcgtgccagctgcattaatgaatcg gccaacgcgcggggagaggcggtttgcgtattgggcgctcttccgcttcctcgctcactgactc gctgcgctcggtcgttcggctgcggcgagcggtatcagctcactcaaaggcggtaatacggtta tccacagaatcaggggataacgcaggaaagaacatgtgagcaaaaggccagcaaaaggccagga accgtaaaaaggccgcgttgctggcgtttttccataggctccgcccccctgacgagcatcacaa aaatcgacgctcaagtcagaggtggcgaaacccgacaggactataaagataccaggcgtttccc cctggaagctccctcgtgcgctctcctgttccgaccctgccgcttaccggatacctgtccgcct ttctcccttcgggaagcgtggcgctttctcatagctcacgctgtaggtatctcagttcggtgta ggtcgttcgctccaagctgggctgtgtgcacgaaccccccgttcagcccgaccgctgcgcctta tccggtaactatcgtcttgagtccaacccggtaagacacgacttatcgccactggcagcagcca ctggtaacaggattagcagagcgaggtatgtaggcggtgctacagagttcttgaagtggtggcc taactacggctacactagaaggacagtataggtatctgcgctctgctgaagccagttaccttcg gaaaaagagaggtagctcttgatccggcaaacaaaccaccgctggtagcggtggattatgtagc aagcagcagattacgcgcagaaaaaaaggatctcaagaagatcctttgatcttttctacggggt ctgacgctcagtggaacgaaaactcacgttaagggattttggtcatgagattatcaaaaaggat cttcacctagatccttttaaattaaaaatgaagttttaaatcaatctaaagtatatatgagtaa acttggtctgacagttaccaatgcttaatcagtgaggcacctatctcagcgatctgtctatttc gttcatccatagttgcctgactccccgtcgtgtagataactacgatacgggagggcttaccatc tggccccagtgctgcaatgataccgcgagacccacgctcaccggctccagatttatcagcaata aaccagccagccggaagggccgagcgcagaagtggtcctgcaactttatccgcctccatccagt ctattaattgttgccgggaagctagagtaagtagttcgccagttaatagtttgcgcaacgagtt gccattgctacaggcatcgtggtgtcacgctcgtcgtttggtatggcttcattcagctccggtt cccaacgatcaaggcgagttacatgatcccccatgttgtgcaaaaaagcggttagctccttcgg tcctccgatcgttgtcagaagtaagttggccgcagtgttatcactcatggttatggcagcactg cataattctcttactgtcatgccatccgtaagatgcttactgtgactggtgagtactcaaccaa gtcattctgagaatagtgtatgcggcgaccgagttgctcttgcccggcgtcaatacgggataat accgcgccacatagcagaactttaaaagtgctcatcattggaaaacgttcttcggggcgaaaac tctcaaggatcttaccgctgttgagatccagttcgatgtaacccactcgtgcacccaactgatc ttcagcatcttttactttcaccagcgtttctgggtgagcaaaaacaggaaggcaaaatgccgca |

APPENDIX A-continued

| SEQUENCE SUMMARY | | |
|---|---|---|
| SEQ ID NO. | Name | Sequence |
| | | aaaaagggaataagggcgacacggaaatgagaatactcatactcttcctattcaatattattga agcatttatcagggttattgtctcatgagcggatacatatttgaatgtatttagaaaaataaac aaataggggttccgcgcacatttccccgaaaagtgccacctgacgtctaagaaaccattattat catgacattaacctataaaaataggcgtatcacgaggccctttcgtctcgcgcgtttcggtgat gacggtgaaaacctctgacacatgcagctcccggagacggtcacagcttgtctgtaagcggatg ccgggagcagacaagcccgtcagggcgcgtcagcgggtgttggcgggtgtcggggctggcttaa ctatgcggcatcagagcagattgtactgagagtgcaccatatgcggtgtgaaataccgcacaga tgcgtaaggagaaaataccgcatcaggcgccattcgccattcaggctgcgcaactgttgggaag ggcgatcggtgcgggcctcttcgctattacgccagctggcgaaaggggggatgtgctgcaaggcg attaagttgggtaacgccagggttttcccagtcacgacgttgtaaaacgacggccagtgccaag ctg |
| 17 | p510_anti-MSLN_SS1_CD3ε amino acid | MLLLVTSLLLCELPHPAFLLIPDIQQVQLQQSGPELEKPGASVKISCKASGYSFTGYTMNWVKQ SHGKSLEWIGLITPYNGASSYNQKFRGKATLTVDKSSSTAYMDLLSLTSEDSAVYFCARGGYDG RGFDYWGQGTTVTVSSGGGGSGGGGSSGGGSDIELTQSPAIMSASPGEKVTMTCSASSSVSYMH WYQQKSGTSPKRWIYDTSKLASGVPGRFSGSGSGNSYSLTISSVEAEDDATYYCQQWSKHPLTF GAGTKLEIKAAAGGGGSGGGGSGGGGSLEDGNEEMGGITQTPYKVSISGTTVILTCPQYPGSEI LWQHNDKNIGGDEDDKNIGSDEDHLSLKEFSELEQSGYYVCYPRGSKPEDANFYLYLRARVCEN CMEMDVMSVATIVIVDICITGGLLLLVYYWSKNRKAKAKPVTRGAGAGGRQRGQNKERPPPVPN PDYEPIRKGQRDLYSGLNQRRI* |
| 18 | Anti-MSLN Light Chain amino acid (MHC1445LC.1) | DVVMTQTPLSLPVSLGDQASISCRSSQSLVHSNGNTYLHWYLQKPGQSPKLLIYKVSNRFSGVP DRFSGSGSGTDFTLKITRVEAEDLGVFFCSQSTHVPFTFGSGTKLEIK |
| 19 | Anti-MSLN Light Chain DNA (MHC1445LC.1) | gatgagtgatgacccaaactccactctccctgcctgtcagtcaggagatcaagcctccatctca gcagatctagtcagagccagtacacagtaatggaaacacctatttacattggtacctgcagaag ccaggccagtctccaaagctcctgatctacaaagtaccaaccgattactggggtcccagacagg acagtggcagtggatcagggactgatacacactcaagatcaccagagtggaggctgaggatctg ggagtattactgctctcaaagtacacatgaccattcacgttcggctcggggacaaagaggaaat aaaa |
| 20 | Anti-MSLN Heavy Chain amino acid (MHC1445HC.1) | QVQLQQSGAELVRPGASVTLSCKASGYTFFDYEMHWVKQTPVHGLEWIGAIDPEIDGTAYNQKF KGKAILTADKSSSTAYMELRSLTSEDSAVYYCTDYYGSSYWYFDVWGTGTTVTVSS |
| 21 | Anti-MSLN Heavy Chain DNA (MHC1445HC.1) | caggacaactgcagcagtctggggctgagctggtgaggcctggggcttcagtgacgctgtcctg caaggcttcgggctacacattattgactatgaaatgcactgggtgaagcagacacctgtgcatg gcctggaatggattggagctattgatcctgaaattgatggtactgcctacaatcagaagacaag ggcaaggccatactgactgcagacaaatcctccagcacagcctacatggagctccgcagcctga catctgaggactctgccgtctattactgtacagattactacggtagtagctactggtacttcga tgtctggggcacagggaccacggtcaccgtctcctc |
| 22 | Anti-MSLN Light Chain amino acid (MHC1446LC.1) | DVMMTQTPLSLPVSLGDQASISCRSSQSLVHSNGNTYLHWFLQKPGQSPKLLIYKVSNRFSGVP DRFSGSGSGTDFTLKISRVEAEDLGVYFCSQTTHVPLTFGAGTKLELK |
| 23 | Anti-MSLN Light Chain DNA (MHC1446LC.1) | gatgaatgatgacccaaactccactctccctgcctgtcagtcaggagatcaagcctccatctca gcagatctagtcagagccagtacacagtaatggaaacacctatttacattggacctgcagaagc caggccagtctccaaagctcctgatctacaaagtaccaaccgattactggggtcccagacagga cagtggcagtggatcagggacagatacacactcaagatcagcagagtggaggctgaggatctgg gagatatactgctctcaaactacacatgaccgctcacgttcggtgctgggaccaagctggagct gaaa |
| 24 | Anti-MSLN Heavy Chain amino acid (MHC1446HC.3) | QVQLQQSGAELVRPGASVTLSCKASGYTFTDYEMHWVKQTPVHGLEWIGAIDPEIAGTAYNQKF KGKAILTADKSSSTAYMELRSLTSEDSAVYYCSRYGGNYLYYFDYWGQGTTLTVSS |
| 25 | Anti-MSLN Heavy Chain DNA (MHC1446HC.3) | caggacaactgcagcagtctggggctgagctggtgaggcctggggcttcagtgacgctgtcctg caaggcttcgggctacacattactgactatgaaatgcactgggtgaagcagacacctgtccatg gcctggaatggattggagctattgatcctgaaattgctggtactgcctacaatcagaagttcaa gggcaaggccatactgactgcagacaaatcctccagcacagcctacatggagctccgcagcctg acatctgaggactctgccgtctattactgacaagatacggtggtaactaccatactactagact actggggccaaggcaccactctcacagtctcctca |
| 26 | Anti-MSLN Light Chain amino acid (MHC1447LC.5) | DVLMTQIPLSLPVSLGDQASISCRSSQNIVYSNGNTYLEWYLQKPGQSPKLLIYKVSNRFSGVP DRFSGSGSGTDFTLKISRVEAEDLGVYYCFQGSHVPFTFGSGTKLEIK |

APPENDIX A-continued

| SEQ ID NO. | Name | Sequence |
|---|---|---|
| 27 | Anti-MSLN Light Chain DNA (MHC1447LC.5) | gatgttttgatgacccaaattccactctccctgcctgtcagtcttggagatcaagcctccatctcttgcagatctagtcagaacattgtgtatagtaatggaaacacctatttagagtggtacctgcagaaaccaggccagtctccaaagctcctgatctacaaagtttccaaccgattttctggggtcccagacaggttcagtggcagtggatcagggacagatttcacactcaagatcagcagagtggaggctgaggatctgggagtttattactgctttcaaggttcacatgttccattcacgttcggctcggggacaaagttggaaataaaa |
| 28 | Anti-MSLN Heavy Chain amino acid (MHC1447HC.5) | QVQLQQSGAELVRPGASVTLSCKASGYTFTDYEMHWVKQTPVHGLEWIGAIDPEIGGSAYNQKFKGRAILTADKSSSTAYMELRSLTSEDSAVYYCTGYDGYFWFAYWGQGTLVTVSS |
| 29 | Anti-MSLN Heavy Chain DNA (MHC1447HC.5) | caggttcaactgcagcagtccggggctgagctggtgaggcctggggcttcagtgacgctgtcctgcaaggcttcgggctacacatttactgactatgaaatgcactgggtgaagcagacacctgtgcatggcctggaatggattggagctattgatcctgaaattggtggttctgcctacaatcagaagttcaagggcagggccatattgactgcagacaaatcctccagcacagcctacatggagctccgcagcctgacatctgaggactctgccgtctattattgtacgggctatgatggttacttttggtttgcttactggggccaagggactctggtcactgtctcttca |
| 30 | Anti-MSLN Light Chain amino acid (MHC1448LC.4) | ENVLTQSPAIMSASPGEKVTMTCSASSSVSYMHWYQQKSSTSPKLWIYDTSKLASGVPGRFSGSGSGNSYSLTISSMEAEDVATYYCFQGSGYPLTFGSGTKLEIK |
| 31 | Anti-MSLN Light Chain DNA (MHC1448LC.4) | gaaaatgttctcacccagtctccagcaatcatgtccgcatctccaggggaaaaggtcaccatgacctgcagtgctagctcaagtgtaagttacatgcactggtaccagcagaagtcaagcacctccccccaaactctggatttatgacacatccaaactggcttctggagtcccaggtcgcttcagtggcagtgggtctggaaactcttactctctcacgatcagcagcatggaggctgaagatgagccacttattactgttacaggggagtgggtacccactcacgttcggctcggggacaaagttggaaataaaa |
| 32 | Anti-MSLN Heavy Chain amino acid (MHC1448HC.3) | QVQLQQSGAELVRPGASVTLSCKASGYTFTDYEMHWVKQTPVHGLEWIGGIDPETGGTAYNQKFKGKAILTADKSSSTAYMELRSLTSEDSAVYYCTSYYGSRVFWGTGTTVTVSS |
| 33 | Anti-MSLN Heavy Chain DNA (MHC1448HC.3) | caggttcaactgcagcagtctggggctgagctggtgaggcctggggcttcagtgacgctgtcctgcaaggcttcgggctacacatttactgactatgaaatgcactgggtgaaacagacacctgtgcatggcctggaatggattggaggtattgatcctgaaactggtggtactgcctacaatcagaagttcaagggtaaggccatactgactgcagacaaatcctccagcacagcctacatggagctccgcagcctgacatctgaggactctgccgtctattactgtacaagttactatggtagtagagtcttctggggcacagggaccacggtcaccgtctcctca |
| 34 | Anti-MSLN Light Chain amino acid (MHC1449LC.3) | QIVLSQSPAILSAFPGEKVTMTCRASSSVSYMHWYQQKPGSSPKPWIYATSNLASGVPARFSGSGSGTSYSLTISSVEAEDAATYYCQQWSSNPPTLTFGAGTKLELK |
| 35 | Anti-MSLN Light Chain DNA (MHC1449LC. 3) | caaattgactctcccagtctccagcaatcctgtctgcataccaggggagaaggtcactatgacttgcagggccagctcaagtgtaagttacatgcactggtaccagcagaagccaggatcctcccccaaaccctggatttatgccacatccaacctggcttctggagtccctgctcgcttcagtggcagtgggtctgggacctcttactctctcacaatcagcagtgtggaggctgaagatgctgccacttattactgccagcagtggagtagtaacccacccacgctcacgttcggtgctgggaccaagctggagctgaaa |
| 36 | Anti-MSLN Heavy Chain amino acid (MHC1449HC.3) | QVQLQQSGAELARPGASVKLSCKASGYTFTSYGISWVKQRTGQGLEWIGEIYPRSGNTYYNESFKGKVTLTADKSSGTAYMELRSLTSEDSAVYFCARWGSYGSPPFYYGMDYWGQGTSVTVSS |
| 37 | Anti-MSLN Heavy Chain DNA (MHC1449HC.3) | caggttcagctgcagcagtctggagctgagctggcgaggcctggggcttcagtgaagctgtcctgcaaggcttctggctacaccttcacaagctatggtataagctgggtgaagcagaggactggacagggccttgagtggattggagagatttatcctagaagtggtaatacttactacaatgagagcttcaagggcaaggtcacactgaccgcagacaaatcttccggcacagcgtacatggagctccgcagcctgacatctgaggactctgcggtctatactgtgcaagatggggctcctacggtagtcccccctttt tactatggtatggactactggggtcaaggaacctcagtcaccgtctcctca |
| 38 | Anti-MSLN Light Chain amino acid (MHC1450LC.3) | DVLMTQTPLSLPVSLGNQASISCRSSQSIVHSSGSTYLEWYLQKPGQSPKLLIYKVSNRFSGVPDRFSGSGSGTDFTLKISRVEAEDLGVYYCFQGSHVPYTFGGGTKLEIK |
| 39 | Anti-MSLN Light Chain DNA (MHC1450LC.3) | gatgttagatgacccaaactccactctccctgcctgtcagtcttggaaatcaagcctccatctcttgcagatctagtcagagcattgtacatagtagtggaagcacctatttagaatggtacctgcagaaaccaggccagtctccaaagctcctgatctacaaagtaccaaccgattactggggtcccagacaggttcagtggcagtggatcagggacagatttcacactcaagatcagcagagtggaggctgagg |

APPENDIX A-continued

| SEQUENCE SUMMARY | | |
|---|---|---|
| SEQ ID NO. | Name | Sequence |
| | | atctgggagtttattactgctttcaaggctcacatgaccatacacgttcggaggggggaccaag ctggaaataaaa |
| 40 | Anti-MSLN Heavy Chain amino acid (MHC1450HC.5) | QVQLQQSGAELARPGTSVKVSCKASGYTFTSYGISWVKQRIGQGLEWIGEIHPRSGNSYYNEKI RGKATLTADKSSSTAYMELRSLISEDSAVYFCARLITTVVANYYAMDYWGQGTSVTVSS |
| 41 | Anti-MSLN Heavy Chain DNA (MHC1450HC.5) | caggttcagctgcagcagtctggagctgagctggcgaggcctgggacttcagtgaaggtgtcct gcaaggcttctggctataccttcacaagttatggtataagctgggtgaagcagagaattggaca gggccttgagtggattggagagattcatcctagaagtggtaatagttactataatgagaagatc aggggcaaggccacactgactgcagacaaatcctccagcacagcgtacatggagctccgcagcc tgatatctgaggactctgcggtctatttctgtgcaaggctgattactacggtagttgctaatta ctatgctatggactactggggtcaaggaacctcagtcaccgtctcctca |
| 42 | Anti-MSLN Light Chain amino acid (MHC1451LC.1) | DIVMSQSPSSLAVSAGEKVTMSCKSSQSLLNSRTRKNYLAWYQQKPGQSPKLLIYWASTRESGV PDRFTGSGSGTDFTLTISSVQAEDLAVYYCKQSYNLVTFGAGTKLELK |
| 43 | Anti-MSLN Light Chain DNA (MHC1451LC. 1) | gacattgtgatgtcacagtctccatcctccctggctgtgtcagcaggagagaaggtcactatga gctgcaaatccagtcagagtctgctcaacagtagaacccgaaagaactacttggcttggtacca gcagaaaccagggcagtctcctaaactgctgatctactgggcatccactagggaatctggggtc cctgatcgcttcacaggcagtggatctgggacagatttcactctcaccatcagcagtgtgcagg ctgaagacctggcagtttattactgcaaacaatcttataatctggtcacgttcggtgctgggac caagctggagctgaaa |
| 44 | Anti-MSLN Heavy Chain amino acid (MHC1451HC.2) | QVQLQQSGAELVRPGASVTLSCKASGYTFFDYEMHWVKQTPVHGLEWIGAIDPEIDGTAYNQKF KGKAILTADKSSSTAYMELRSLTSEDSAVYYCTDYYGSSYWYFDVWGTGTTVTVSS |
| 45 | Anti-MSLN Heavy Chain DNA (MHC1451HC.2) | caggttcaactgcagcagtctggggctgagctggtgaggcctggggcttcagtgacgctgtcct gcaaggcttcgggctacacatttttttgactatgaaatgcactgggtgaagcagacacctgtgca tggcctggaatggattggagctattgatcctgaaattgatggtactgcctacaatcagaagttc aagggcaaggccatactgactgcagacaaatcctccagcacagcctacatggagctccgcagcc tgacatctgaggactctgccgtctattactgtacagattactacggtagtagctactggtactt cgatgtctggggcacagggaccacggtcaccgtctcctc |
| 46 | Anti-MSLN Light Chain amino acid (MHC1452LC. 1) | QIVLTQSPAIMSASPGEKVTISCSASSSVSYMYWYQQKPGSSPKPWIYRTSNLASGVPARFSGS GSGTSYSLTISSMEAEDAATYYCQQYHSYPLTFGAGTKLELK |
| 47 | Anti-MSLN Light Chain DNA (MHC1452LC. 1) | caaattgttctcacccagtctccagcaatcatgtctgcatctccaggggagaaggtcaccatat cctgcagtgccagctcaagtgtaagttacatgtactggtaccagcagaagccaggatcctcccc caaaccctggatttatcgcacatccaacctggcttctggagtccctgctcgcttcagtggcagt gggtctgggacctcttactctctcacaatcagcagcatggaggctgaagatgctgccacttatt actgccagcagtatcatagttacccactcacgttcggtgctgggaccaagctggagctgaaa |
| 48 | Anti-MSLN Light Chain amino acid (MHC1452LC.6) | QIVLTQSPAIMSASPGERVTMTCSASSSVSSSYLYWYQQKSGSSPKLWIYSISNLASGVPARFS GSGSGTSYSLTINSMEAEDAATYYCQQWSSNPQLTFGAGTKLELK |
| 49 | Anti-MSLN Light Chain DNA (MHC1452LC.6) | caaattgttctcacccagtctccagcaatcatgtctgcatctcctggggaacgggtcaccatga cctgcagtgccagctcaagtgtaagttccagctacttgtactggtaccagcagaagtcaggatc ctcccccaaaactctggatttatagcatatccaacctggcttctggagtcccagctcgcttcagt ggcagtgggtctgggacctcttactctctcacaatcaacagcatggaggctgaagatgctgcca cttattactgccagcagtggagtagtaacccacagctcacgttcggtgctgggaccaagctgga gctgaaa |
| 56 | Anti-MSLN Heavy Chain amino acid (MHC1452HC.2) | QVQLKQSGAELVKPGASVKISCKASGYTFTDYYINWVKQRPGQGLEWIGKIGPGSGSTYYNEKF KGKATLTADKSSSTAYMQLSSLTSEDSAVYFCARTGYYVGYYAMDYWGQGTSVTVSS |
| 50 | Anti-MSLN Heavy Chain DNA (MHC1452HC.2) | caggtccagctgaagcagtctggagctgagctggtgaagcctggggcttcagtgaagatatcct gcaaggcttctggctacaccttcactgactactatataaactgggtgaagcagaggcctggaca gggccttgagtggattggaaagattggtcctggaagtggtagtacttactacaatgagaagttc aagggcaaggccacactgactgcagacaaatcctccagcacagcctacatgcagctcagcagcc tgacatctgaggactctgcagtctatactgtgcaagaactggttactacgaggttactatgcta tggactactggggtcaaggaacctcagtcaccgtctcctca |
| 51 | Anti-MSLN Heavy Chain | QVQLQQSGAELARPGASVKLSCKASGYTFTIYGISWVKQRTGQGLEWIGEIYPRSDNTYYNEKF KGKATLTADKSSSTAYMELRSLTSEDSAVYFCARWYSFYAMDYWGQGTSVTVSS |

APPENDIX A-continued

SEQUENCE SUMMARY

| SEQ ID NO. | Name | Sequence |
|---|---|---|
| | amino acid (MHC1452HC.4) | |
| 52 | Anti-MSLN Heavy Chain DNA (MHC1452HC.4) | caggttcagctgcagcagtctggagctgagctggcgaggcctggggcttcagtgaagctgtcct gcaaggcttctggctacaccttcacaatctatggtataagctgggtgaaacagagaactggaca gggccttgagtggattggagagatttatcctagaagtgataatacttactacaatgagaagttc aagggcaaggccacactgactgcagacaaatcctccagcacagcgtacatggagctccgcagcc tgacatctgaggactctgcggtctatactgtgcaagatggtactcgttctatgctatggactac tggggtcaaggaacctcagtcaccgtctcctca |
| 58 | Single domain anti-MSLN binder 1 (SD1) | EVQLVESGGGLVQPGGSLRLSCAASGGDWSANFMYWYRQAPGKQRELVARISGRGVVDYVESVK GRFTISRDNSKNTLYLQMNSLRAEDTAVYYCAVASYWGQGTLVTVSS |
| 59 | Single domain anti-MSLN binder 4 (SD4) | EVQLVESGGGLVQPGGSLRLSCAASGSTSSINTMYWYRQAPGKERELVAFISSGGSTNVRDSVK GRFTISRDNSKNTLYLQMNSLRAEDTAVYYCNTYIPYGGTLHDFWGQGTLVTVSS |
| 55 | Single domain anti-MSLN binder 6 (5D6) | QVQLVESGGGVVQAGGSLRLSCAASGSTFSIRAMRWYRQAPGTERDLVAVIYGSSTYYADAVKG RFTISRDNSKNTLYLQMNSLRAEDTAVYYCNADTIGTARDYWGQGTLVTVSS |

What is claimed is:

1. A method of treating mesothelin-expressing cancer in a human subject comprising administering to the human subject a therapeutically effective amount of (i) a recombinant nucleic acid encoding a T cell receptor (TCR) fusion protein (TFP) comprising (a) a TCR subunit comprising a full-length TCR extracellular domain and a TCR intracellular domain comprising a stimulatory domain from an intracellular signaling domain of CD3 epsilon or CD3 gamma, and (b) an antibody domain comprising an antigen binding domain that is an anti-mesothelin binding domain; or (ii) a human T cell expressing the TFP, wherein the TFP lacks (i) a costimulatory domain, (ii) a heterologous stimulatory domain, or (iii) a combination thereof, wherein the mesothelin-expressing cancer is selected from the group consisting of mesothelioma, ovarian cancer, papillary serous ovarian adenocarcinoma, clear cell ovarian carcinoma, mixed Mullerian ovarian carcinoma, endometroid mucinous ovarian carcinoma, pancreatic cancer, pancreatic adenocarcinoma, ductal pancreatic adenocarcinoma, uterine serous carcinoma, lung cancer, lung adenocarcinoma, extrahepatic bile duct carcinoma, gastric adenocarcinoma, esophageal adenocarcinoma, colorectal adeno-carcinoma, breast cancer, breast adenocarcinoma, cholangiocarcinoma, and combinations thereof.

2. The method of claim 1, wherein the T cell is a CD8+ T cell, a CD4+ T cell, a CD4+ and CD8+ T cell, a gamma delta T cell, or a natural killer T cell.

3. The method of claim 1, wherein the recombinant nucleic acid is a vector or a mRNA.

4. The method of claim 1, wherein the antigen binding domain is a human or humanized $V_{HH}$, a human or humanized single domain antibody, or a human or humanized scFv.

5. The method of claim 1, wherein the antigen binding domain is connected to the TCR extracellular domain by a linker sequence.

6. The method of claim 1, further comprising administering an agent that increases efficacy of the recombinant nucleic acid or the human T cell.

7. The method of claim 6, wherein the agent comprises an agent that inhibits PD1, PD-L1, PD-L2, CTLA4, TIM3, LAG3, VISTA, BTLA, TIGIT, LAIR1, CD160, 2B4, TGFR beta, or any combination thereof.

8. The method of claim 1, wherein the method comprises administering the human T cell expressing the TFP, and wherein production of a pro-inflammatory cytokine selected from the group consisting of TNFα, GM-CSF, IL-2 and combinations thereof by the T cell is lower compared to production of the pro-inflammatory cytokine by a T cell comprising a nucleic acid encoding a chimeric antigen receptor (CAR) comprising the antigen binding domain operatively linked to a either (i) an extracellular domain, a transmembrane domain, a CD28 intracellular domain, and a CD3 zeta intracellular domain (CD28-CAR) or (ii) an extracellular domain, a transmembrane domain, a 41-BB intracellular domain, and a CD3 zeta intracellular domain (41-BB CAR).

9. The method of claim 1, further comprising administering an agent that ameliorates one or more side effects associated with administration of the recombinant nucleic acid or the human T cell.

10. The method of claim 1, wherein the human subject exhibits a greater reduction in a size of a tumor compared to a reduction in a size of a tumor in a mammal administered a T cell comprising a nucleic acid encoding a CD28-CAR or 41-BB CAR.

11. The method of claim 1, wherein the TFP lacks a heterologous stimulatory domain.

12. The method of claim 1, wherein the therapeutically effective amount of the human T cell expressing the TFP is a dosage of $10^4$ to $10^9$ cells/kg body weight.

13. The method of claim 1, wherein the method comprises a treatment regimen comprising administering by transfusion to the human subject the human T cell expressing the TFP.

14. The method of claim 1, further comprising administering to the human subject cyclophosphamide, fludarabine, or a combination thereof.

15. The method of claim 1, wherein the method comprises administering the human T cell expressing the TFP for a first time and a second time, wherein the second time is administered less than 15 days of the first time.

16. The method of claim 1, wherein the method comprises administering the human T cell expressing the TFP, and wherein the human T cell, or its progeny, persists in the human subject for at least one month after administration of the human T cell.

17. The method of claim 1, wherein, prior to administering, the human subject has undergone leukapheresis.

18. The method of claim 1, wherein, prior to administering, the human subject has been treated with chemotherapy, peripheral blood stem cell transplantation, or a combination thereof.

19. The method of claim 1, wherein, prior to administering, the human subject has been treated with cyclophosphamide, fludarabine, or a combination thereof.

* * * * *

SEQUENCE LISTING

```
<160> NUMBER OF SEQ ID NOS: 72

<210> SEQ ID NO 1
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Gly Gly Gly Ser Gly Gly Gly Gly Ser Gly Gly Gly Gly Ser Leu
1               5                   10                  15

Glu


<210> SEQ ID NO 2
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Ala Ala Gly Gly Gly Gly Ser Gly Gly Gly Gly Ser Gly Gly Gly
1               5                   10                  15

Gly Ser Leu Glu
            20


<210> SEQ ID NO 3
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

```
Ala Ala Ala Ile Glu Val Met Tyr Pro Pro Pro Tyr Leu Gly Gly Gly
1               5                   10                  15

Gly Ser Gly Gly Gly Gly Ser Gly Gly Gly Gly Ser Leu Glu
            20                  25                  30


<210> SEQ ID NO 4
<211> LENGTH: 207
<212> TYPE: PRT
<213> ORGANISM: Homo sapiens

<400> SEQUENCE: 4

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205


<210> SEQ ID NO 5
<211> LENGTH: 182
<212> TYPE: PRT
<213> ORGANISM: Homo sapiens

<400> SEQUENCE: 5

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95
```

```
Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180


<210> SEQ ID NO 6
<211> LENGTH: 172
<212> TYPE: PRT
<213> ORGANISM: Homo sapiens

<400> SEQUENCE: 6

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys Ser
                165                 170


<210> SEQ ID NO 7
<211> LENGTH: 164
<212> TYPE: PRT
<213> ORGANISM: Homo sapiens

<400> SEQUENCE: 7

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60
```

```
Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 8
<211> LENGTH: 281
<212> TYPE: PRT
<213> ORGANISM: Homo sapiens

<400> SEQUENCE: 8

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Ala
                245                 250                 255

Leu Arg Ala Pro Ser Ser Ser Leu Gly Ala Phe Phe Ala Gly Asp Leu
            260                 265                 270
```

```
Pro Pro Pro Leu Gln Ala Gly Ala Ala
        275                 280


<210> SEQ ID NO 9
<211> LENGTH: 142
<212> TYPE: PRT
<213> ORGANISM: Homo sapiens

<400> SEQUENCE: 9

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140


<210> SEQ ID NO 10
<211> LENGTH: 139
<212> TYPE: PRT
<213> ORGANISM: Homo sapiens

<400> SEQUENCE: 10

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Lys Gly Ala Gly Thr Ala Ser Lys Leu Thr
        115                 120                 125

Phe Gly Thr Gly Thr Arg Leu Gln Val Thr Leu
    130                 135


<210> SEQ ID NO 11
<211> LENGTH: 177
<212> TYPE: PRT
<213> ORGANISM: Homo sapiens
```

<400> SEQUENCE: 11

Glu Asp Leu Asn Lys Val Phe Pro Pro Glu Val Ala Val Phe Glu Pro
1 5 10 15

Ser Glu Ala Glu Ile Ser His Thr Gln Lys Ala Thr Leu Val Cys Leu
20 25 30

Ala Thr Gly Phe Phe Pro Asp His Val Glu Leu Ser Trp Trp Val Asn
35 40 45

Gly Lys Glu Val His Ser Gly Val Ser Thr Asp Pro Gln Pro Leu Lys
50 55 60

Glu Gln Pro Ala Leu Asn Asp Ser Arg Tyr Cys Leu Ser Ser Arg Leu
65 70 75 80

Arg Val Ser Ala Thr Phe Trp Gln Asn Pro Arg Asn His Phe Arg Cys
85 90 95

Gln Val Gln Phe Tyr Gly Leu Ser Glu Asn Asp Glu Trp Thr Gln Asp
100 105 110

Arg Ala Lys Pro Val Thr Gln Ile Val Ser Ala Glu Ala Trp Gly Arg
115 120 125

Ala Asp Cys Gly Phe Thr Ser Val Ser Tyr Gln Gln Gly Val Leu Ser
130 135 140

Ala Thr Ile Leu Tyr Glu Ile Leu Leu Gly Lys Ala Thr Leu Tyr Ala
145 150 155 160

Val Leu Val Ser Ala Leu Val Leu Met Ala Met Val Lys Arg Lys Asp
165 170 175

Phe

<210> SEQ ID NO 12
<211> LENGTH: 133
<212> TYPE: PRT
<213> ORGANISM: Homo sapiens

<400> SEQUENCE: 12

Met Gly Thr Ser Leu Leu Cys Trp Met Ala Leu Cys Leu Leu Gly Ala
1 5 10 15

Asp His Ala Asp Thr Gly Val Ser Gln Asn Pro Arg His Asn Ile Thr
20 25 30

Lys Arg Gly Gln Asn Val Thr Phe Arg Cys Asp Pro Ile Ser Glu His
35 40 45

Asn Arg Leu Tyr Trp Tyr Arg Gln Thr Leu Gly Gln Gly Pro Glu Phe
50 55 60

Leu Thr Tyr Phe Gln Asn Glu Ala Gln Leu Glu Lys Ser Arg Leu Leu
65 70 75 80

Ser Asp Arg Phe Ser Ala Glu Arg Pro Lys Gly Ser Phe Ser Thr Leu
85 90 95

Glu Ile Gln Arg Thr Glu Gln Gly Asp Ser Ala Met Tyr Leu Cys Ala
100 105 110

Ser Ser Leu Ala Gly Leu Asn Gln Pro Gln His Phe Gly Asp Gly Thr
115 120 125

Arg Leu Ser Ile Leu
130

<210> SEQ ID NO 13
<211> LENGTH: 135
<212> TYPE: PRT
<213> ORGANISM: Homo sapiens

<400> SEQUENCE: 13

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Phe Ser Thr Cys Ser Ala Asn Tyr Gly Tyr Thr Phe Gly Ser
        115                 120                 125

Gly Thr Arg Leu Thr Val Val
    130                 135
```

<210> SEQ ID NO 14
<211> LENGTH: 8791
<212> TYPE: DNA
<213> ORGANISM: Homo sapiens

<400> SEQUENCE: 14

```
acgcgtgtag tcttatgcaa tactcttgta gtcttgcaac atggtaacga tgagttagca     60

acatgcctta caaggagaga aaaagcaccg tgcatgccga ttggtggaag taaggtggta    120

cgatcgtgcc ttattaggaa ggcaacagac gggtctgaca tggattggac gaaccactga    180

attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780

atcagaagaa cttagatcat tatataatac agtagcaacc ctctattgtg tgcatcaaag    840

gatagagata aaagacacca aggaagcttt agacaagata gaggaagagc aaaacaaaag    900

taagaccacc gcacagcaag cggccactga tcttcagacc tggaggagga gatatgaggg    960

acaattggag aagtgaatta tataaatata aagtagtaaa aattgaacca ttaggagtag   1020

cacccaccaa ggcaaagaga agagtggtgc agagagaaaa aagagcagtg ggaataggag   1080

ctttgttcct tgggttcttg ggagcagcag gaagcactat gggcgcagcc tcaatgacgc   1140

tgacggtaca ggccagacaa ttattgtctg gtatagtgca gcagcagaac aatttgctga   1200

gggctattga ggcgcaacag catctgttgc aactcacagt ctggggcatc aagcagctcc   1260
```

```
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga cattcagcag gtccagctcc agcagtctgg ccctgaactc   2400
gaaaaacctg gcgctagcgt gaaaatttcc tgtaaagcct ccggctactc ttttactggc   2460
tacacaatga attgggtgaa acagtctcac ggcaaatccc tcgaatggat cggactcatc   2520
acaccctaca atggcgcctc ttcctacaac cagaaattcc ggggcaaggc aacactcact   2580
gtggacaaat catcctctac cgcctacatg gatctgctct ccctcacatc tgaggactcc   2640
gctgtctact tttgtgcccg aggaggatac gacggacgag gattcgatta ctggggacag   2700
ggaacaactg tgaccgtgtc tagtggcggc ggagggagtg gaggcggagg atcttctggc   2760
gggggatccg atattgaact cacacagtct cccgctatca tgtctgcttc tcccggcgag   2820
aaagtgacta tgacttgctc tgcttcctct tctgtgtcct acatgcactg gtaccagcag   2880
aaatctggca catcccctaa acggtggatc tacgatacta gcaaactggc atccggcgtg   2940
cctgggcgat tctctggctc tggctctggc aactcttact ctctcacaat ctcatctgtc   3000
gaggctgagg acgatgccac atactactgt cagcagtggt ctaaacaccc actcacattc   3060
ggcgctggca ctaaactgga aataaaagcg gccgcaggtg gcggcggttc tggtggcggc   3120
ggttctggtg gcggcggttc tctcgaggat ggtaatgaag aaatgggtgg tattacacag   3180
acaccatata aagtctccat ctctggaacc acagtaatat tgacatgccc tcagtatcct   3240
ggatctgaaa tactatggca acacaatgat aaaaacatag gcggtgatga ggatgataaa   3300
aacataggca gtgatgagga tcacctgtca ctgaaggaat tttcagaatt ggagcaaagt   3360
ggttattatg tctgctaccc cagaggaagc aaaccagaag atgcgaactt ttatctctac   3420
ctgagggcaa gagtgtgtga gaactgcatg gagatggatg tgatgtcggt ggccacaatt   3480
gtcatagtgg acatctgcat cactgggggc ttgctgctgc tggtttacta ctggagcaag   3540
aatagaaagg ccaaggccaa gcctgtgaca cgaggagcgg gtgctggcgg caggcaaagg   3600
ggacaaaaca aggagaggcc accacctgtt cccaacccag actatgagcc catccggaaa   3660
```

```
ggccagcggg acctgtattc tggcctgaat cagagacgca tctgataaga attcgatccg   3720
cggccgcgaa ggatctgcga tcgctccggt gcccgtcagt gggcagagcg cacatcgccc   3780
acagtccccg agaagttggg gggaggggtc ggcaattgaa cgggtgccta gagaaggtgg   3840
cgcggggtaa actgggaaag tgatgtcgtg tactggctcc gcctttttcc cgagggtggg   3900
ggagaaccgt atataagtgc agtagtcgcc gtgaacgttc tttttcgcaa cgggtttgcc   3960
gccagaacac agctgaagct tcgaggggct cgcatctctc cttcacgcgc ccgccgccct   4020
acctgaggcc gccatccacg ccggttgagt cgcgttctgc cgcctcccgc ctgtggtgcc   4080
tcctgaactg cgtccgccgt ctaggtaagt ttaaagctca ggtcgagacc gggcctttgt   4140
ccggcgctcc cttggagcct acctagactc agccggctct ccacgctttg cctgaccctg   4200
cttgctcaac tctacgtctt tgtttcgttt tctgttctgc gccgttacag atccaagctg   4260
tgaccggcgc ctacgctaga tgaccgagta caagcccacg gtgcgcctcg ccacccgcga   4320
cgacgtcccc agggccgtac gcaccctcgc cgccgcgttc gccgactacc ccgccacgcg   4380
ccacaccgtc gatccggacc gccacatcga gcgggtcacc gagctgcaag aactcttcct   4440
cacgcgcgtc gggctcgaca tcggcaaggt gtgggtcgcg gacgacggcg ccgcggtggc   4500
ggtctggacc acgccggaga gcgtcgaagc gggggcggtg ttcgccgaga tcggcccgcg   4560
catggccgag ttgagcggtt cccggctggc cgcgcagcaa cagatggaag gcctcctggc   4620
gccgcaccgg cccaaggagc ccgcgtggtt cctggccacc gtcggcgtct cgcccgacca   4680
ccagggcaag ggtctgggca gcgccgtcgt gctccccgga gtggaggcgg ccgagcgcgc   4740
cggggtgccc gccttcctgg agacctccgc gccccgcaac ctccccttct acgagcggct   4800
cggcttcacc gtcaccgccg acgtcgaggt gcccgaagga ccgcgcacct ggtgcatgac   4860
ccgcaagccc ggtgcctgag tcgacaatca acctctggat tacaaaattt gtgaaagatt   4920
gactggtatt cttaactatg ttgctccttt tacgctatgt ggatacgctg ctttaatgcc   4980
tttgtatcat gctattgctt cccgtatggc tttcattttc tcctccttgt ataaatcctg   5040
gttgctgtct ctttatgagg agttgtggcc cgttgtcagg caacgtggcg tggtgtgcac   5100
tgtgtttgct gacgcaaccc ccactggttg gggcattgcc accacctgtc agctcctttc   5160
cgggactttc gctttccccc tccctattgc cacggcggaa ctcatcgccg cctgccttgc   5220
ccgctgctgg acaggggctc ggctgttggg cactgacaat tccgtggtgt tgtcggggaa   5280
atcatcgtcc tttccttggc tgctcgcctg tgttgccacc tggattctgc gcgggacgtc   5340
cttctgctac gtcccttcgg ccctcaatcc agcggacctt ccttcccgcg gcctgctgcc   5400
ggctctgcgg cctcttccgc gtcttcgcct tcgccctcag acgagtcgga tctccctttg   5460
ggccgcctcc ccgcctggta cctttaagac caatgactta caaggcagct gtagatctta   5520
gccacttttt aaaagaaaag gggggactgg aagggctaat tcactcccaa cgaaaataag   5580
atctgctttt tgcttgtact gggtctctct ggttagacca gatctgagcc tgggagctct   5640
ctggctaact agggaaccca ctgcttaagc ctcaataaag cttgccttga gtgcttcaag   5700
tagtgtgtgc ccgtctgttg tgtgactctg gtaactagag atccctcaga cccttttagt   5760
cagtgtggaa aatctctagc agtagtagtt catgtcatct tattattcag tatttataac   5820
ttgcaaagaa atgaatatca gagagtgaga ggaacttgtt tattgcagct tataatggtt   5880
acaaataaag caatagcatc acaaatttca caaataaagc atttttttca ctgcattcta   5940
gttgtggttt gtccaaactc atcaatgtat cttatcatgt ctggctctag ctatcccgcc   6000
```

```
cctaactccg cccagttccg cccattctcc gccccatggc tgactaattt tttttattta   6060
tgcagaggcc gaggccgcct cggcctctga gctattccag aagtagtgag gaggcttttt   6120
tggaggccta gacttttgca gagacggccc aaattcgtaa tcatggtcat agctgtttcc   6180
tgtgtgaaat tgttatccgc tcacaattcc acacaacata cgagccggaa gcataaagtg   6240
taaagcctgg ggtgcctaat gagtgagcta actcacatta attgcgttgc gctcactgcc   6300
cgctttccag tcgggaaacc tgtcgtgcca gctgcattaa tgaatcggcc aacgcgcggg   6360
gagaggcggt ttgcgtattg ggcgctcttc cgcttcctcg ctcactgact cgctgcgctc   6420
ggtcgttcgg ctgcggcgag cggtatcagc tcactcaaag gcggtaatac ggttatccac   6480
agaatcaggg gataacgcag gaaagaacat gtgagcaaaa ggccagcaaa aggccaggaa   6540
ccgtaaaaag gccgcgttgc tggcgttttt ccataggctc cgcccccctg acgagcatca   6600
caaaaatcga cgctcaagtc agaggtggcg aaacccgaca ggactataaa gataccaggc   6660
gtttccccct ggaagctccc tcgtgcgctc tcctgttccg accctgccgc ttaccggata   6720
cctgtccgcc tttctccctt cgggaagcgt ggcgctttct catagctcac gctgtaggta   6780
tctcagttcg gtgtaggtcg ttcgctccaa gctgggctgt gtgcacgaac cccccgttca   6840
gcccgaccgc tgcgccttat ccggtaacta tcgtcttgag tccaacccgg taagacacga   6900
cttatcgcca ctggcagcag ccactggtaa caggattagc agagcgaggt atgtaggcgg   6960
tgctacagag ttcttgaagt ggtggcctaa ctacggctac actagaagga cagtatttgg   7020
tatctgcgct ctgctgaagc cagttacctt cggaaaaaga gttggtagct cttgatccgg   7080
caaacaaacc accgctggta gcggtggttt ttttgtttgc aagcagcaga ttacgcgcag   7140
aaaaaaagga tctcaagaag atcctttgat cttttctacg gggtctgacg ctcagtggaa   7200
cgaaaactca cgttaaggga ttttggtcat gagattatca aaaaggatct tcacctagat   7260
ccttttaaat taaaaatgaa gttttaaatc aatctaaagt atatatgagt aaacttggtc   7320
tgacagttac caatgcttaa tcagtgaggc acctatctca gcgatctgtc tatttcgttc   7380
atccatagtt gcctgactcc ccgtcgtgta gataactacg atacgggagg gcttaccatc   7440
tggccccagt gctgcaatga taccgcgaga cccacgctca ccggctccag atttatcagc   7500
aataaaccag ccagccggaa gggccgagcg cagaagtggt cctgcaactt tatccgcctc   7560
catccagtct attaattgtt gccgggaagc tagagtaagt agttcgccag ttaatagttt   7620
gcgcaacgtt gttgccattg ctacaggcat cgtggtgtca cgctcgtcgt ttggtatggc   7680
ttcattcagc tccggttccc aacgatcaag gcgagttaca tgatccccca tgttgtgcaa   7740
aaaagcggtt agctccttcg gtcctccgat cgttgtcaga agtaagttgg ccgcagtgtt   7800
atcactcatg gttatggcag cactgcataa ttctcttact gtcatgccat ccgtaagatg   7860
cttttctgtg actggtgagt actcaaccaa gtcattctga gaatagtgta tgcggcgacc   7920
gagttgctct tgcccggcgt caatacggga taataccgcg ccacatagca gaactttaaa   7980
agtgctcatc attggaaaac gttcttcggg gcgaaaactc tcaaggatct taccgctgtt   8040
gagatccagt tcgatgtaac ccactcgtgc acccaactga tcttcagcat cttttacttt   8100
caccagcgtt tctgggtgag caaaaacagg aaggcaaaat gccgcaaaaa agggaataag   8160
ggcgacacgg aaatgttgaa tactcatact cttccttttt caatattatt gaagcattta   8220
tcagggttat tgtctcatga gcggatacat atttgaatgt atttagaaaa ataaacaaat   8280
aggggttccg cgcacatttc cccgaaaagt gccacctgac gtctaagaaa ccattattat   8340
catgacatta acctataaaa ataggcgtat cacgaggccc tttcgtctcg cgcgtttcgg   8400
```

```
tgatgacggt gaaaacctct gacacatgca gctcccggag acggtcacag cttgtctgta   8460

agcggatgcc gggagcagac aagcccgtca gggcgcgtca gcgggtgttg gcgggtgtcg   8520

gggctggctt aactatgcgg catcagagca gattgtactg agagtgcacc atatgcggtg   8580

tgaaataccg cacagatgcg taaggagaaa ataccgcatc aggcgccatt cgccattcag   8640

gctgcgcaac tgttgggaag ggcgatcggt gcgggcctct tcgctattac gccagctggc   8700

gaaaggggga tgtgctgcaa ggcgattaag ttgggtaacg ccagggtttt cccagtcacg   8760

acgttgtaaa acgacggcca gtgccaagct g                                  8791
```

<210> SEQ ID NO 15
<211> LENGTH: 622
<212> TYPE: PRT
<213> ORGANISM: Homo sapiens

<400> SEQUENCE: 15

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300
```

```
Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620
```

<210> SEQ ID NO 16
<211> LENGTH: 8791
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
acgcgtgtag tcttatgcaa tactcttgta gtcttgcaac atggtaacga tgagttagca      60

acatgcctta caaggagaga aaaagcaccg tgcatgccga ttggtggaag taaggtggta     120

cgatcgtgcc ttattaggaa ggcaacagac gggtctgaca tggattggac gaaccactga     180
```

-continued

```
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga cattcagcag gtccagctcc agcagtctgg ccctgaactc   2400
gaaaaacctg gcgctagcgt gaaaatttcc tgtaaagcct ccggctactc ttttactggc   2460
tacacaatga attgggtgaa acagtctcac ggcaaatccc tcgaatggat cggactcatc   2520
acaccctaca atggcgcctc ttcctacaac cagaaattcc ggggcaaggc aacactcact   2580
```

```
gtggacaaat catcctctac cgcctacatg gatctgctct ccctcacatc tgaggactcc   2640
gctgtctact tttgtgcccg aggaggatac gacggacgag gattcgatta ctggggacag   2700
ggaacaactg tgaccgtgtc tagtggcggc ggagggagtg gaggcggagg atcttctggc   2760
gggggatccg atattgaact cacacagtct cccgctatca tgtctgcttc tcccggcgag   2820
aaagtgacta tgacttgctc tgcttcctct tctgtgtcct acatgcactg gtaccagcag   2880
aaatctggca catcccctaa acggtggatc tacgatacta gcaaactggc atccggcgtg   2940
cctgggcgat tctctggctc tggctctggc aactcttact ctctcacaat ctcatctgtc   3000
gaggctgagg acgatgccac atactactgt cagcagtggt ctaaacaccc actcacattc   3060
ggcgctggca ctaaactgga aataaaagcg gccgcaggtg gcggcggttc tggtggcggc   3120
ggttctggtg gcggcggttc tctcgaggat ggtaatgaag aaatgggtgg tattacacag   3180
acaccatata aagtctccat ctctggaacc acagtaatat tgacatgccc tcagtatcct   3240
ggatctgaaa tactatggca acacaatgat aaaaacatag gcggtgatga ggatgataaa   3300
aacataggca gtgatgagga tcacctgtca ctgaaggaat tttcagaatt ggagcaaagt   3360
ggttattatg tctgctaccc cagaggaagc aaaccagaag atgcgaactt ttatctctac   3420
ctgagggcaa gagtgtgtga gaactgcatg gagatggatg tgatgtcggt ggccacaatt   3480
gtcatagtgg acatctgcat cactgggggc ttgctgctgc tggtttacta ctggagcaag   3540
aatagaaagg ccaaggccaa gcctgtgaca cgaggagcgg gtgctggcgg caggcaaagg   3600
ggacaaaaca aggagaggcc accacctgtt cccaacccag actatgagcc catccggaaa   3660
ggccagcggg acctgtattc tggcctgaat cagagacgca tctgataaga attcgatccg   3720
cggccgcgaa ggatctgcga tcgctccggt gcccgtcagt gggcagagcg cacatcgccc   3780
acagtccccg agaagttggg gggaggggtc ggcaattgaa cgggtgccta gagaaggtgg   3840
cgcggggtaa actgggaaag tgatgtcgtg tactggctcc gcctttttcc cgagggtggg   3900
ggagaaccgt atataagtgc agtagtcgcc gtgaacgttc tttttcgcaa cgggtttgcc   3960
gccagaacac agctgaagct tcgaggggct cgcatctctc cttcacgcgc ccgccgccct   4020
acctgaggcc gccatccacg ccggttgagt cgcgttctgc cgcctcccgc ctgtggtgcc   4080
tcctgaactg cgtccgccgt ctaggtaagt ttaaagctca ggtcgagacc gggcctttgt   4140
ccggcgctcc cttggagcct acctagactc agccggctct ccacgctttg cctgaccctg   4200
cttgctcaac tctacgtctt tgtttcgttt tctgttctgc gccgttacag atccaagctg   4260
tgaccggcgc ctacgctaga tgaccgagta caagcccacg gtgcgcctcg ccacccgcga   4320
cgacgtcccc agggccgtac gcaccctcgc cgccgcgttc gccgactacc ccgccacgcg   4380
ccacaccgtc gatccggacc gccacatcga gcgggtcacc gagctgcaag aactcttcct   4440
cacgcgcgtc gggctcgaca tcggcaaggt gtgggtcgcg gacgacggcg ccgcggtggc   4500
ggtctggacc acgccggaga gcgtcgaagc gggggcggtg ttcgccgaga tcggcccgcg   4560
catggccgag ttgagcggtt cccggctggc cgcgcagcaa cagatggaag gcctcctggc   4620
gccgcaccgg cccaaggagc ccgcgtggtt cctggccacc gtcggcgtct cgcccgacca   4680
ccagggcaag ggtctgggca gcgccgtcgt gctccccgga gtggaggcgg ccgagcgcgc   4740
cggggtgccc gccttcctgg agacctccgc gccccgcaac ctccccttct acgagcggct   4800
cggcttcacc gtcaccgccg acgtcgaggt gcccgaagga ccgcgcacct ggtgcatgac   4860
ccgcaagccc ggtgcctgag tcgacaatca acctctggat tacaaaattt gtgaaagatt   4920
```

-continued

```
gactggtatt cttaactatg ttgctccttt tacgctatgt ggatacgctg ctttaatgcc   4980
tttgtatcat gctattgctt cccgtatggc tttcattttc tcctccttgt ataaatcctg   5040
gttgctgtct ctttatgagg agttgtggcc cgttgtcagg caacgtggcg tggtgtgcac   5100
tgtgtttgct gacgcaaccc ccactggttg gggcattgcc accacctgtc agctcctttc   5160
cgggactttc gctttccccc tccctattgc cacggcggaa ctcatcgccg cctgccttgc   5220
ccgctgctgg acaggggctc ggctgttggg cactgacaat tccgtggtgt tgtcggggaa   5280
atcatcgtcc tttccttggc tgctcgcctg tgttgccacc tggattctgc gcgggacgtc   5340
cttctgctac gtcccttcgg ccctcaatcc agcggacctt ccttcccgcg gcctgctgcc   5400
ggctctgcgg cctcttccgc gtcttcgcct tcgccctcag acgagtcgga tctccctttg   5460
ggccgcctcc ccgcctggta cctttaagac caatgactta caaggcagct gtagatctta   5520
gccacttttt aaaagaaaag gggggactgg aagggctaat tcactcccaa cgaaaataag   5580
atctgctttt tgcttgtact gggtctctct ggttagacca gatctgagcc tgggagctct   5640
ctggctaact agggaaccca ctgcttaagc ctcaataaag cttgccttga gtgcttcaag   5700
tagtgtgtgc ccgtctgttg tgtgactctg gtaactagag atccctcaga cccttttagt   5760
cagtgtggaa aatctctagc agtagtagtt catgtcatct tattattcag tatttataac   5820
ttgcaaagaa atgaatatca gagagtgaga ggaacttgtt tattgcagct tataatggtt   5880
acaaataaag caatagcatc acaaatttca caaataaagc atttttttca ctgcattcta   5940
gttgtggttt gtccaaactc atcaatgtat cttatcatgt ctggctctag ctatcccgcc   6000
cctaactccg cccagttccg cccattctcc gccccatggc tgactaattt tttttattta   6060
tgcagaggcc gaggccgcct cggcctctga gctattccag aagtagtgag gaggcttttt   6120
tggaggccta gacttttgca gagacggccc aaattcgtaa tcatggtcat agctgtttcc   6180
tgtgtgaaat tgttatccgc tcacaattcc acacaacata cgagccggaa gcataaagtg   6240
taaagcctgg ggtgcctaat gagtgagcta actcacatta attgcgttgc gctcactgcc   6300
cgctttccag tcgggaaacc tgtcgtgcca gctgcattaa tgaatcggcc aacgcgcggg   6360
gagaggcggt ttgcgtattg ggcgctcttc cgcttcctcg ctcactgact cgctgcgctc   6420
ggtcgttcgg ctgcggcgag cggtatcagc tcactcaaag gcggtaatac ggttatccac   6480
agaatcaggg gataacgcag gaaagaacat gtgagcaaaa ggccagcaaa aggccaggaa   6540
ccgtaaaaag gccgcgttgc tggcgttttt ccataggctc cgcccccctg acgagcatca   6600
caaaaatcga cgctcaagtc agaggtggcg aaacccgaca ggactataaa gataccaggc   6660
gtttccccct ggaagctccc tcgtgcgctc tcctgttccg accctgccgc ttaccggata   6720
cctgtccgcc tttctccctt cgggaagcgt ggcgctttct catagctcac gctgtaggta   6780
tctcagttcg gtgtaggtcg ttcgctccaa gctgggctgt gtgcacgaac cccccgttca   6840
gcccgaccgc tgcgccttat ccggtaacta tcgtcttgag tccaacccgg taagacacga   6900
cttatcgcca ctggcagcag ccactggtaa caggattagc agagcgaggt atgtaggcgg   6960
tgctacagag ttcttgaagt ggtggcctaa ctacggctac actagaagga cagtatttgg   7020
tatctgcgct ctgctgaagc cagttacctt cggaaaaaga gttggtagct cttgatccgg   7080
caaacaaacc accgctggta gcggtggttt ttttgtttgc aagcagcaga ttacgcgcag   7140
aaaaaaagga tctcaagaag atcctttgat cttttctacg gggtctgacg ctcagtggaa   7200
cgaaaactca cgttaaggga ttttggtcat gagattatca aaaggatctt cacctagat    7260
ccttttaaat taaaaatgaa gttttaaatc aatctaaagt atatatgagt aaacttggtc   7320
```

```
tgacagttac caatgcttaa tcagtgaggc acctatctca gcgatctgtc tatttcgttc   7380

atccatagtt gcctgactcc ccgtcgtgta gataactacg atacgggagg gcttaccatc   7440

tggccccagt gctgcaatga taccgcgaga cccacgctca ccggctccag atttatcagc   7500

aataaaccag ccagccggaa gggccgagcg cagaagtggt cctgcaactt tatccgcctc   7560

catccagtct attaattgtt gccgggaagc tagagtaagt agttcgccag ttaatagttt   7620

gcgcaacgtt gttgccattg ctacaggcat cgtggtgtca cgctcgtcgt ttggtatggc   7680

ttcattcagc tccggttccc aacgatcaag gcgagttaca tgatccccca tgttgtgcaa   7740

aaaagcggtt agctccttcg gtcctccgat cgttgtcaga agtaagttgg ccgcagtgtt   7800

atcactcatg gttatggcag cactgcataa ttctcttact gtcatgccat ccgtaagatg   7860

cttttctgtg actggtgagt actcaaccaa gtcattctga gaatagtgta tgcggcgacc   7920

gagttgctct tgcccggcgt caatacggga taataccgcg ccacatagca gaactttaaa   7980

agtgctcatc attggaaaac gttcttcggg gcgaaaactc tcaaggatct taccgctgtt   8040

gagatccagt tcgatgtaac ccactcgtgc acccaactga tcttcagcat cttttacttt   8100

caccagcgtt tctgggtgag caaaaacagg aaggcaaaat gccgcaaaaa agggaataag   8160

ggcgacacgg aaatgttgaa tactcatact cttccttttt caatattatt gaagcattta   8220

tcagggttat tgtctcatga gcggatacat atttgaatgt atttagaaaa ataaacaaat   8280

aggggttccg cgcacatttc cccgaaaagt gccacctgac gtctaagaaa ccattattat   8340

catgacatta acctataaaa ataggcgtat cacgaggccc tttcgtctcg cgcgtttcgg   8400

tgatgacggt gaaaacctct gacacatgca gctcccggag acggtcacag cttgtctgta   8460

agcggatgcc gggagcagac aagcccgtca gggcgcgtca gcgggtgttg gcgggtgtcg   8520

gggctggctt aactatgcgg catcagagca gattgtactg agagtgcacc atatgcggtg   8580

tgaaataccg cacagatgcg taaggagaaa ataccgcatc aggcgccatt cgccattcag   8640

gctgcgcaac tgttgggaag ggcgatcggt gcgggcctct tcgctattac gccagctggc   8700

gaaaggggga tgtgctgcaa ggcgattaag ttgggtaacg ccagggtttt cccagtcacg   8760

acgttgtaaa acgacggcca gtgccaagct g                                 8791
```

```
<210> SEQ ID NO 17
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Leu Leu Leu Val Thr Ser Leu Leu Leu Cys Glu Leu Pro His Pro
1               5                   10                  15

Ala Phe Leu Leu Ile Pro Asp Ile Gln Gln Val Gln Leu Gln Gln Ser
            20                  25                  30

Gly Pro Glu Leu Glu Lys Pro Gly Ala Ser Val Lys Ile Ser Cys Lys
        35                  40                  45

Ala Ser Gly Tyr Ser Phe Thr Gly Tyr Thr Met Asn Trp Val Lys Gln
    50                  55                  60

Ser His Gly Lys Ser Leu Glu Trp Ile Gly Leu Ile Thr Pro Tyr Asn
65                  70                  75                  80

Gly Ala Ser Ser Tyr Asn Gln Lys Phe Arg Gly Lys Ala Thr Leu Thr
```

```
                85                  90                  95

Val Asp Lys Ser Ser Ser Thr Ala Tyr Met Asp Leu Leu Ser Leu Thr
            100                 105                 110

Ser Glu Asp Ser Ala Val Tyr Phe Cys Ala Arg Gly Gly Tyr Asp Gly
        115                 120                 125

Arg Gly Phe Asp Tyr Trp Gly Gln Gly Thr Thr Val Thr Val Ser Ser
    130                 135                 140

Gly Gly Gly Gly Ser Gly Gly Gly Gly Ser Ser Gly Gly Gly Ser Asp
145                 150                 155                 160

Ile Glu Leu Thr Gln Ser Pro Ala Ile Met Ser Ala Ser Pro Gly Glu
                165                 170                 175

Lys Val Thr Met Thr Cys Ser Ala Ser Ser Ser Val Ser Tyr Met His
            180                 185                 190

Trp Tyr Gln Gln Lys Ser Gly Thr Ser Pro Lys Arg Trp Ile Tyr Asp
        195                 200                 205

Thr Ser Lys Leu Ala Ser Gly Val Pro Gly Arg Phe Ser Gly Ser Gly
    210                 215                 220

Ser Gly Asn Ser Tyr Ser Leu Thr Ile Ser Ser Val Glu Ala Glu Asp
225                 230                 235                 240

Asp Ala Thr Tyr Tyr Cys Gln Gln Trp Ser Lys His Pro Leu Thr Phe
                245                 250                 255

Gly Ala Gly Thr Lys Leu Glu Ile Lys Ala Ala Ala Gly Gly Gly Gly
            260                 265                 270

Ser Gly Gly Gly Gly Ser Gly Gly Gly Gly Ser Leu Glu Asp Gly Asn
        275                 280                 285

Glu Glu Met Gly Gly Ile Thr Gln Thr Pro Tyr Lys Val Ser Ile Ser
    290                 295                 300

Gly Thr Thr Val Ile Leu Thr Cys Pro Gln Tyr Pro Gly Ser Glu Ile
305                 310                 315                 320

Leu Trp Gln His Asn Asp Lys Asn Ile Gly Gly Asp Glu Asp Asp Lys
                325                 330                 335

Asn Ile Gly Ser Asp Glu Asp His Leu Ser Leu Lys Glu Phe Ser Glu
            340                 345                 350

Leu Glu Gln Ser Gly Tyr Tyr Val Cys Tyr Pro Arg Gly Ser Lys Pro
        355                 360                 365

Glu Asp Ala Asn Phe Tyr Leu Tyr Leu Arg Ala Arg Val Cys Glu Asn
    370                 375                 380

Cys Met Glu Met Asp Val Met Ser Val Ala Thr Ile Val Ile Val Asp
385                 390                 395                 400

Ile Cys Ile Thr Gly Gly Leu Leu Leu Leu Val Tyr Tyr Trp Ser Lys
                405                 410                 415

Asn Arg Lys Ala Lys Ala Lys Pro Val Thr Arg Gly Ala Gly Ala Gly
            420                 425                 430

Gly Arg Gln Arg Gly Gln Asn Lys Glu Arg Pro Pro Pro Val Pro Asn
        435                 440                 445

Pro Asp Tyr Glu Pro Ile Arg Lys Gly Gln Arg Asp Leu Tyr Ser Gly
    450                 455                 460

Leu Asn Gln Arg Arg Ile
465                 470
```

<210> SEQ ID NO 18
<211> LENGTH: 112
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 18

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Val Phe Phe Cys Ser Gln Ser
                85                  90                  95

Thr His Val Pro Phe Thr Phe Gly Ser Gly Thr Lys Leu Glu Ile Lys
            100                 105                 110


<210> SEQ ID NO 19
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

gatgttgtga tgacccaaac tccactctcc ctgcctgtca gtcttggaga tcaagcctcc      60

atctcttgca gatctagtca gagccttgta cacagtaatg gaaacaccta tttacattgg     120

tacctgcaga agccaggcca gtctccaaag ctcctgatct acaaagtttc caaccgattt     180

tctggggtcc cagacaggtt cagtggcagt ggatcaggga ctgatttcac actcaagatc     240

accagagtgg aggctgagga tctgggagtt tttttctgct ctcaaagtac acatgttcca     300

ttcacgttcg gctcggggac aaagttggaa ataaaa                               336


<210> SEQ ID NO 20
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Phe Asp Tyr
            20                  25                  30

Glu Met His Trp Val Lys Gln Thr Pro Val His Gly Leu Glu Trp Ile
        35                  40                  45

Gly Ala Ile Asp Pro Glu Ile Asp Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80
```

```
Met Glu Leu Arg Ser Leu Thr Ser Glu Asp Ser Ala Val Tyr Tyr Cys
                85                  90                  95

Thr Asp Tyr Tyr Gly Ser Ser Tyr Trp Tyr Phe Asp Val Trp Gly Thr
            100                 105                 110

Gly Thr Thr Val Thr Val Ser Ser
        115                 120
```

<210> SEQ ID NO 21
<211> LENGTH: 359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
caggttcaac tgcagcagtc tggggctgag ctggtgaggc ctggggcttc agtgacgctg     60

tcctgcaagg cttcgggcta cacatttttt gactatgaaa tgcactgggt gaagcagaca    120

cctgtgcatg gcctggaatg gattggagct attgatcctg aaattgatgg tactgcctac    180

aatcagaagt tcaagggcaa ggccatactg actgcagaca aatcctccag cacagcctac    240

atggagctcc gcagcctgac atctgaggac tctgccgtct attactgtac agattactac    300

ggtagtagct actggtactt cgatgtctgg ggcacaggga ccacggtcac cgtctcctc     359
```

<210> SEQ ID NO 22
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Asp Val Met Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Leu Thr Phe Gly Ala Gly Thr Lys Leu Glu Leu Lys
            100                 105                 110
```

<210> SEQ ID NO 23
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
gatgttatga tgacccaaac tccactctcc ctgcctgtca gtcttggaga tcaagcctcc     60
```

```
atctcttgca gatctagtca gagccttgta cacagtaatg gaaacaccta tttacattgg    120

ttcctgcaga agccaggcca gtctccaaag ctcctgatct acaaagtttc caaccgattt    180

tctggggtcc cagacaggtt cagtggcagt ggatcaggga cagatttcac actcaagatc    240

agcagagtgg aggctgagga tctgggagtt tatttctgct ctcaaactac acatgttccg    300

ctcacgttcg gtgctgggac caagctggag ctgaaa                              336


<210> SEQ ID NO 24
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Ile Ala Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ser Arg Tyr Gly Gly Asn Tyr Leu Tyr Tyr Phe Asp Tyr Trp Gly Gln
            100                 105                 110

Gly Thr Thr Leu Thr Val Ser Ser
        115                 120


<210> SEQ ID NO 25
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25

caggttcaac tgcagcagtc tggggctgag ctggtgaggc ctggggcttc agtgacgctg     60

tcctgcaagg cttcgggcta cacttttact gactatgaaa tgcactgggt gaagcagaca    120

cctgtccatg gcctggaatg gattggagct attgatcctg aaattgctgg tactgcctac    180

aatcagaagt tcaagggcaa ggccatactg actgcagaca aatcctccag cacagcctac    240

atggagctcc gcagcctgac atctgaggac tctgccgtct attactgttc aagatacggt    300

ggtaactacc tttactactt tgactactgg ggccaaggca ccactctcac agtctcctca    360


<210> SEQ ID NO 26
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 26

Asp Val Leu Met Thr Gln Ile Pro Leu Ser Leu Pro Val Ser Leu Gly
1 5 10 15

Asp Gln Ala Ser Ile Ser Cys Arg Ser Ser Gln Asn Ile Val Tyr Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Phe Thr Phe Gly Ser Gly Thr Lys Leu Glu Ile Lys
100 105 110

<210> SEQ ID NO 27
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 27
gatgttttga tgacccaaat tccactctcc ctgcctgtca gtcttggaga tcaagcctcc 60
atctcttgca gatctagtca gaacattgtg tatagtaatg gaaacaccta tttagagtgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tattactgct ttcaaggttc acatgttcca 300
ttcacgttcg gctcggggac aaagttggaa ataaaa 336

<210> SEQ ID NO 28
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 28

Gln Val Gln Leu Gln Gln Ser Gly Ala Glu Leu Val Arg Pro Gly Ala
1 5 10 15

Ser Val Thr Leu Ser Cys Lys Ala Ser Gly Tyr Thr Phe Thr Asp Tyr
20 25 30

Glu Met His Trp Val Lys Gln Thr Pro Val His Gly Leu Glu Trp Ile
35 40 45

Gly Ala Ile Asp Pro Glu Ile Gly Gly Ser Ala Tyr Asn Gln Lys Phe
50 55 60

Lys Gly Arg Ala Ile Leu Thr Ala Asp Lys Ser Ser Ser Thr Ala Tyr
65 70 75 80

Met Glu Leu Arg Ser Leu Thr Ser Glu Asp Ser Ala Val Tyr Tyr Cys
85 90 95

```
Thr Gly Tyr Asp Gly Tyr Phe Trp Phe Ala Tyr Trp Gly Gln Gly Thr
            100                 105                 110

Leu Val Thr Val Ser Ser
        115


<210> SEQ ID NO 29
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

caggttcaac tgcagcagtc cggggctgag ctggtgaggc ctggggcttc agtgacgctg      60

tcctgcaagg cttcgggcta cacatttact gactatgaaa tgcactgggt gaagcagaca     120

cctgtgcatg gcctggaatg gattggagct attgatcctg aaattggtgg ttctgcctac     180

aatcagaagt tcaagggcag ggccatattg actgcagaca aatcctccag cacagcctac     240

atggagctcc gcagcctgac atctgaggac tctgccgtct attattgtac gggctatgat     300

ggttactttt ggtttgctta ctggggccaa gggactctgg tcactgtctc ttca           354


<210> SEQ ID NO 30
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ser Gly Thr Lys Leu Glu Ile Lys
            100                 105


<210> SEQ ID NO 31
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

gaaaatgttc tcacccagtc tccagcaatc atgtccgcat ctccagggga aaaggtcacc      60

atgacctgca gtgctagctc aagtgtaagt tacatgcact ggtaccagca gaagtcaagc     120
```

```
acctccccca aactctggat ttatgacaca tccaaactgg cttctggagt cccaggtcgc    180

ttcagtggca gtgggtctgg aaactcttac tctctcacga tcagcagcat ggaggctgaa    240

gatgttgcca cttattactg ttttcagggg agtgggtacc cactcacgtt cggctcgggg    300

acaaagttgg aaataaaa                                                  318


<210> SEQ ID NO 32
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Ser Tyr Tyr Gly Ser Arg Val Phe Trp Gly Thr Gly Thr Thr Val
            100                 105                 110

Thr Val Ser Ser
        115


<210> SEQ ID NO 33
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33

caggttcaac tgcagcagtc tggggctgag ctggtgaggc ctggggcttc agtgacgctg     60

tcctgcaagg cttcgggcta cacatttact gactatgaaa tgcactgggt gaaacagaca    120

cctgtgcatg gcctggaatg gattggaggt attgatcctg aaactggtgg tactgcctac    180

aatcagaagt tcaagggtaa ggccatactg actgcagaca aatcctccag cacagcctac    240

atggagctcc gcagcctgac atctgaggac tctgccgtct attactgtac aagttactat    300

ggtagtagag tcttctgggg cacagggacc acggtcaccg tctcctca                 348


<210> SEQ ID NO 34
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34
```

```
Gln Ile Val Leu Ser Gln Ser Pro Ala Ile Leu Ser Ala Phe Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Trp Ser Ser Asn Pro Pro Thr
                85                  90                  95

Leu Thr Phe Gly Ala Gly Thr Lys Leu Glu Leu Lys
            100                 105


<210> SEQ ID NO 35
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35

caaattgttc tctcccagtc tccagcaatc ctgtctgcat ttccagggga gaaggtcact      60

atgacttgca gggccagctc aagtgtaagt tacatgcact ggtaccagca gaagccagga     120

tcctccccca aaccctggat ttatgccaca tccaacctgg cttctggagt ccctgctcgc     180

ttcagtggca gtgggtctgg gacctcttac tctctcacaa tcagcagtgt ggaggctgaa     240

gatgctgcca cttattactg ccagcagtgg agtagtaacc cacccacgct cacgttcggt     300

gctgggacca agctggagct gaaa                                            324


<210> SEQ ID NO 36
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Ser Phe
    50                  55                  60

Lys Gly Lys Val Thr Leu Thr Ala Asp Lys Ser Ser Gly Thr Ala Tyr
65                  70                  75                  80

Met Glu Leu Arg Ser Leu Thr Ser Glu Asp Ser Ala Val Tyr Phe Cys
                85                  90                  95

Ala Arg Trp Gly Ser Tyr Gly Ser Pro Pro Phe Tyr Tyr Gly Met Asp
            100                 105                 110
```

```
Tyr Trp Gly Gln Gly Thr Ser Val Thr Val Ser Ser
        115                 120


<210> SEQ ID NO 37
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

caggttcagc tgcagcagtc tggagctgag ctggcgaggc ctggggcttc agtgaagctg     60

tcctgcaagg cttctggcta caccttcaca agctatggta taagctgggt gaagcagagg    120

actggacagg gccttgagtg gattggagag atttatccta gaagtggtaa tacttactac    180

aatgagagct tcaagggcaa ggtcacactg accgcagaca aatcttccgg cacagcgtac    240

atggagctcc gcagcctgac atctgaggac tctgcggtct atttctgtgc aagatggggc    300

tcctacggta gtcccccctt ttactatggt atggactact ggggtcaagg aacctcagtc    360

accgtctcct ca                                                        372


<210> SEQ ID NO 38
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Val Leu Met Thr Gln Thr Pro Leu Ser Leu Pro Val Ser Leu Gly
1               5                   10                  15

Asn Gln Ala Ser Ile Ser Cys Arg Ser Ser Gln Ser Ile Val His Ser
            20                  25                  30

Ser Gly Ser Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110


<210> SEQ ID NO 39
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39

gatgttttga tgacccaaac tccactctcc ctgcctgtca gtcttggaaa tcaagcctcc     60

atctcttgca gatctagtca gagcattgta catagtagtg gaagcaccta tttagaatgg    120

tacctgcaga aaccaggcca gtctccaaag ctcctgatct acaaagtttc caaccgattt    180
```

tctggggtcc cagacaggtt cagtggcagt ggatcaggga cagatttcac actcaagatc 240
agcagagtgg aggctgagga tctgggagtt tattactgct ttcaaggctc acatgttcca 300
tacacgttcg gaggggggac caagctggaa ataaaa 336

<210> SEQ ID NO 40
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

Gln Val Gln Leu Gln Gln Ser Gly Ala Glu Leu Ala Arg Pro Gly Thr
1 5 10 15

Ser Val Lys Val Ser Cys Lys Ala Ser Gly Tyr Thr Phe Thr Ser Tyr
20 25 30

Gly Ile Ser Trp Val Lys Gln Arg Ile Gly Gln Gly Leu Glu Trp Ile
35 40 45

Gly Glu Ile His Pro Arg Ser Gly Asn Ser Tyr Tyr Asn Glu Lys Ile
50 55 60

Arg Gly Lys Ala Thr Leu Thr Ala Asp Lys Ser Ser Ser Thr Ala Tyr
65 70 75 80

Met Glu Leu Arg Ser Leu Ile Ser Glu Asp Ser Ala Val Tyr Phe Cys
85 90 95

Ala Arg Leu Ile Thr Thr Val Val Ala Asn Tyr Tyr Ala Met Asp Tyr
100 105 110

Trp Gly Gln Gly Thr Ser Val Thr Val Ser Ser
115 120

<210> SEQ ID NO 41
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 41
caggttcagc tgcagcagtc tggagctgag ctggcgaggc ctgggacttc agtgaaggtg 60
tcctgcaagg cttctggcta taccttcaca agttatggta taagctgggt gaagcagaga 120
attggacagg gccttgagtg gattggagag attcatccta gaagtggtaa tagttactat 180
aatgagaaga tcaggggcaa ggccacactg actgcagaca aatcctccag cacagcgtac 240
atggagctcc gcagcctgat atctgaggac tctgcggtct atttctgtgc aaggctgatt 300
actacggtag ttgctaatta ctatgctatg gactactggg gtcaaggaac ctcagtcacc 360
gtctcctca 369

<210> SEQ ID NO 42
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Val Thr Phe Gly Ala Gly Thr Lys Leu Glu Leu Lys
            100                 105                 110
```

<210> SEQ ID NO 43
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43

```
gacattgtga tgtcacagtc tccatcctcc ctggctgtgt cagcaggaga gaaggtcact     60

atgagctgca aatccagtca gagtctgctc aacagtagaa cccgaaagaa ctacttggct    120

tggtaccagc agaaaccagg gcagtctcct aaactgctga tctactgggc atccactagg    180

gaatctgggg tccctgatcg cttcacaggc agtggatctg ggacagattt cactctcacc    240

atcagcagtg tgcaggctga agacctggca gtttattact gcaaacaatc ttataatctg    300

gtcacgttcg gtgctgggac caagctggag ctgaaa                              336
```

<210> SEQ ID NO 44
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Phe Asp Tyr
            20                  25                  30

Glu Met His Trp Val Lys Gln Thr Pro Val His Gly Leu Glu Trp Ile
        35                  40                  45

Gly Ala Ile Asp Pro Glu Ile Asp Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Asp Tyr Tyr Gly Ser Ser Tyr Trp Tyr Phe Asp Val Trp Gly Thr
            100                 105                 110
```

```
Gly Thr Thr Val Thr Val Ser Ser
        115                 120


<210> SEQ ID NO 45
<211> LENGTH: 359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45

caggttcaac tgcagcagtc tggggctgag ctggtgaggc ctggggcttc agtgacgctg     60

tcctgcaagg cttcgggcta cacatttttt gactatgaaa tgcactgggt gaagcagaca    120

cctgtgcatg gcctggaatg gattggagct attgatcctg aaattgatgg tactgcctac    180

aatcagaagt tcaagggcaa ggccatactg actgcagaca aatcctccag cacagcctac    240

atggagctcc gcagcctgac atctgaggac tctgccgtct attactgtac agattactac    300

ggtagtagct actggtactt cgatgtctgg ggcacaggga ccacggtcac cgtctcctc     359


<210> SEQ ID NO 46
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Leu Thr
                85                  90                  95

Phe Gly Ala Gly Thr Lys Leu Glu Leu Lys
            100                 105


<210> SEQ ID NO 47
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

caaattgttc tcacccagtc tccagcaatc atgtctgcat ctccagggga gaaggtcacc     60

atatcctgca gtgccagctc aagtgtaagt tacatgtact ggtaccagca gaagccagga    120

tcctccccca aaccctggat ttatcgcaca tccaacctgg cttctggagt ccctgctcgc    180
```

ttcagtggca gtgggtctgg gacctcttac tctctcacaa tcagcagcat ggaggctgaa 240
gatgctgcca cttattactg ccagcagtat catagttacc cactcacgtt cggtgctggg 300
accaagctgg agctgaaa 318

<210> SEQ ID NO 48
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

Gln Ile Val Leu Thr Gln Ser Pro Ala Ile Met Ser Ala Ser Pro Gly
1 5 10 15

Glu Arg Val Thr Met Thr Cys Ser Ala Ser Ser Ser Val Ser Ser Ser
20 25 30

Tyr Leu Tyr Trp Tyr Gln Gln Lys Ser Gly Ser Ser Pro Lys Leu Trp
35 40 45

Ile Tyr Ser Ile Ser Asn Leu Ala Ser Gly Val Pro Ala Arg Phe Ser
50 55 60

Gly Ser Gly Ser Gly Thr Ser Tyr Ser Leu Thr Ile Asn Ser Met Glu
65 70 75 80

Ala Glu Asp Ala Ala Thr Tyr Tyr Cys Gln Gln Trp Ser Ser Asn Pro
85 90 95

Gln Leu Thr Phe Gly Ala Gly Thr Lys Leu Glu Leu Lys
100 105

<210> SEQ ID NO 49
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 49
caaattgttc tcacccagtc tccagcaatc atgtctgcat ctcctgggga acgggtcacc 60
atgacctgca gtgccagctc aagtgtaagt tccagctact tgtactggta ccagcagaag 120
tcaggatcct ccccaaaact ctggatttat agcatatcca acctggcttc tggagtccca 180
gctcgcttca gtggcagtgg gtctgggacc tcttactctc tcacaatcaa cagcatggag 240
gctgaagatg ctgccactta ttactgccag cagtggagta gtaacccaca gctcacgttc 300
ggtgctggga ccaagctgga gctgaaa 327

<210> SEQ ID NO 50
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50
caggtccagc tgaagcagtc tggagctgag ctggtgaagc ctggggcttc agtgaagata 60
tcctgcaagg cttctggcta caccttcact gactactata taaactgggt gaagcagagg 120

```
cctggacagg gccttgagtg gattggaaag attggtcctg gaagtggtag tacttactac    180

aatgagaagt tcaagggcaa ggccacactg actgcagaca aatcctccag cacagcctac    240

atgcagctca gcagcctgac atctgaggac tctgcagtct atttctgtgc aagaactggt    300

tactacgttg gttactatgc tatggactac tggggtcaag gaacctcagt caccgtctcc    360

tca                                                                  363


<210> SEQ ID NO 51
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ile Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Asp Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Trp Tyr Ser Phe Tyr Ala Met Asp Tyr Trp Gly Gln Gly Thr
            100                 105                 110

Ser Val Thr Val Ser Ser
        115


<210> SEQ ID NO 52
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

caggttcagc tgcagcagtc tggagctgag ctggcgaggc ctggggcttc agtgaagctg     60

tcctgcaagg cttctggcta caccttcaca atctatggta taagctgggt gaaacagaga    120

actggacagg gccttgagtg gattggagag atttatccta gaagtgataa tacttactac    180

aatgagaagt tcaagggcaa ggccacactg actgcagaca aatcctccag cacagcgtac    240

atggagctcc gcagcctgac atctgaggac tctgcggtct atttctgtgc aagatggtac    300

tcgttctatg ctatggacta ctggggtcaa ggaacctcag tcaccgtctc ctca          354


<210> SEQ ID NO 53
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 53

```
Gly Gly Gly Gly Ser Gly Gly Gly Gly Ser
1               5                   10
```

<210> SEQ ID NO 54
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 54

```
ggtggcggag gttctggagg tggaggttcc                                      30
```

<210> SEQ ID NO 55
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

```
Gln Val Gln Leu Val Glu Ser Gly Gly Gly Val Val Gln Ala Gly Gly
1               5                   10                  15

Ser Leu Arg Leu Ser Cys Ala Ala Ser Gly Ser Thr Phe Ser Ile Arg
            20                  25                  30

Ala Met Arg Trp Tyr Arg Gln Ala Pro Gly Thr Glu Arg Asp Leu Val
        35                  40                  45

Ala Val Ile Tyr Gly Ser Ser Thr Tyr Tyr Ala Asp Ala Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Asp Thr Ile Gly Thr Ala Arg Asp Tyr Trp Gly Gln Gly Thr Leu Val
            100                 105                 110

Thr Val Ser Ser
        115
```

<210> SEQ ID NO 56
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Gln Val Gln Leu Lys Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Lys Ile Gly Pro Gly Ser Gly Ser Thr Tyr Tyr Asn Glu Lys Phe
    50                  55                  60
```

```
Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Thr Gly Tyr Tyr Val Gly Tyr Tyr Ala Met Asp Tyr Trp Gly
            100                 105                 110

Gln Gly Thr Ser Val Thr Val Ser Ser
        115                 120


<210> SEQ ID NO 57
<211> LENGTH: 280
<212> TYPE: PRT
<213> ORGANISM: Homo sapiens

<400> SEQUENCE: 57

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Ala
                245                 250                 255

Leu Arg Ala Pro Ser Ser Ser Leu Gly Ala Phe Phe Ala Gly Asp Leu
            260                 265                 270

Pro Pro Pro Leu Gln Ala Gly Ala
        275                 280


<210> SEQ ID NO 58
<211> LENGTH: 111
<212> TYPE: PRT
```

<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Asp Trp Ser Ala Asn
            20                  25                  30

Phe Met Tyr Trp Tyr Arg Gln Ala Pro Gly Lys Gln Arg Glu Leu Val
        35                  40                  45

Ala Arg Ile Ser Gly Arg Gly Val Val Asp Tyr Val Glu Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Ala Ser Tyr Trp Gly Gln Gly Thr Leu Val Thr Val Ser Ser
            100                 105                 110
```

<210> SEQ ID NO 59
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 59

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Ser Ser Ile Asn
            20                  25                  30

Thr Met Tyr Trp Tyr Arg Gln Ala Pro Gly Lys Glu Arg Glu Leu Val
        35                  40                  45

Ala Phe Ile Ser Ser Gly Gly Ser Thr Asn Val Arg Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Thr Tyr Ile Pro Tyr Gly Gly Thr Leu His Asp Phe Trp Gly Gln Gly
            100                 105                 110

Thr Leu Val Thr Val Ser Ser
        115
```

<210> SEQ ID NO 60
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MISC_FEATURE
<222> LOCATION: (1)..(20)
<223> OTHER INFORMATION: /note="This sequence may encompass 1-4 'Gly Gly
Gly Gly Ser' repeating units"

<400> SEQUENCE: 60

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 61
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 61

```
Gly Gly Gly Gly Ser Gly Gly Gly Gly Ser Gly Gly Gly Gly Ser
1               5                   10                  15
```

<210> SEQ ID NO 62
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MISC_FEATURE
<222> LOCATION: (1)..(20)
<223> OTHER INFORMATION: /note="This sequence may encompass 2-4 'Gly Gly Gly Gly Ser' repeating units"

<400> SEQUENCE: 62

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 63
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MISC_FEATURE
<222> LOCATION: (1)..(15)
<223> OTHER INFORMATION: /note="This sequence may encompass 1-3 'Gly Gly Gly Gly Ser' repeating units"

<400> SEQUENCE: 63

```
Gly Gly Gly Gly Ser Gly Gly Gly Gly Ser Gly Gly Gly Gly Ser
1               5                   10                  15
```

<210> SEQ ID NO 64
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 64

Gly Gly Gly Ser
1

<210> SEQ ID NO 65
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 65

Gly Gly Gly Gly Ser Gly Gly Gly Gly Ser Gly Gly Gly Gly Ser Gly
1 5 10 15

Gly Gly Gly Ser
20

<210> SEQ ID NO 66
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 50-5000 nucleotides"
<220> FEATURE:
<221> NAME/KEY: source
<223> OTHER INFORMATION: /note="See specification as filed for detailed description of substitutions and preferred embodiments"

<400> SEQUENCE: 66
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140

-continued

```
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
```

```
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
aaaaaaaaaa aaaaaaaaaa aaaaaaaaaa aaaaaaaaaa aaaaaaaaaa aaaaaaaaaa   4140
aaaaaaaaaa aaaaaaaaaa aaaaaaaaaa aaaaaaaaaa aaaaaaaaaa aaaaaaaaaa   4200
aaaaaaaaaa aaaaaaaaaa aaaaaaaaaa aaaaaaaaaa aaaaaaaaaa aaaaaaaaaa   4260
aaaaaaaaaa aaaaaaaaaa aaaaaaaaaa aaaaaaaaaa aaaaaaaaaa aaaaaaaaaa   4320
aaaaaaaaaa aaaaaaaaaa aaaaaaaaaa aaaaaaaaaa aaaaaaaaaa aaaaaaaaaa   4380
aaaaaaaaaa aaaaaaaaaa aaaaaaaaaa aaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
aaaaaaaaaa aaaaaaaaaa aaaaaaaaaa aaaaaaaaaa aaaaaaaaaa aaaaaaaaaa   4560
aaaaaaaaaa aaaaaaaaaa aaaaaaaaaa aaaaaaaaaa aaaaaaaaaa aaaaaaaaaa   4620
aaaaaaaaaa aaaaaaaaaa aaaaaaaaaa aaaaaaaaaa aaaaaaaaaa aaaaaaaaaa   4680
aaaaaaaaaa aaaaaaaaaa aaaaaaaaaa aaaaaaaaaa aaaaaaaaaa aaaaaaaaaa   4740
aaaaaaaaaa aaaaaaaaaa aaaaaaaaaa aaaaaaaaaa aaaaaaaaaa aaaaaaaaaa   4800
aaaaaaaaaa aaaaaaaaaa aaaaaaaaaa aaaaaaaaaa aaaaaaaaaa aaaaaaaaaa   4860
aaaaaaaaaa aaaaaaaaaa aaaaaaaaaa aaaaaaaaaa aaaaaaaaaa aaaaaaaaaa   4920
aaaaaaaaaa aaaaaaaaaa aaaaaaaaaa aaaaaaaaaa aaaaaaaaaa aaaaaaaaaa   4980
aaaaaaaaaa aaaaaaaaaa                                               5000
```

<210> SEQ ID NO 67
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MISC_FEATURE
<222> LOCATION: (1)..(30)
<223> OTHER INFORMATION: /note="This sequence may encompass 1-6 'Gly Gly Gly Gly Ser' repeating units"
<220> FEATURE:
<221> NAME/KEY: source
<223> OTHER INFORMATION: /note="See specification as filed for detailed description of substitutions and preferred embodiments"

<400> SEQUENCE: 67

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 68
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68
tttttttttt tttttttttt tttttttttt tttttttttt tttttttttt tttttttttt 60
tttttttttt tttttttttt tttttttttt tttttttttt 100

<210> SEQ ID NO 69
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 50-5000 nucleotides"

<400> SEQUENCE: 69
tttttttttt tttttttttt tttttttttt tttttttttt tttttttttt tttttttttt 60
tttttttttt tttttttttt tttttttttt tttttttttt tttttttttt tttttttttt 120
tttttttttt tttttttttt tttttttttt tttttttttt tttttttttt tttttttttt 180
tttttttttt tttttttttt tttttttttt tttttttttt tttttttttt tttttttttt 240
tttttttttt tttttttttt tttttttttt tttttttttt tttttttttt tttttttttt 300
tttttttttt tttttttttt tttttttttt tttttttttt tttttttttt tttttttttt 360
tttttttttt tttttttttt tttttttttt tttttttttt tttttttttt tttttttttt 420
tttttttttt tttttttttt tttttttttt tttttttttt tttttttttt tttttttttt 480
tttttttttt tttttttttt tttttttttt tttttttttt tttttttttt tttttttttt 540
tttttttttt tttttttttt tttttttttt tttttttttt tttttttttt tttttttttt 600
tttttttttt tttttttttt tttttttttt tttttttttt tttttttttt tttttttttt 660
tttttttttt tttttttttt tttttttttt tttttttttt tttttttttt tttttttttt 720
tttttttttt tttttttttt tttttttttt tttttttttt tttttttttt tttttttttt 780
tttttttttt tttttttttt tttttttttt tttttttttt tttttttttt tttttttttt 840
tttttttttt tttttttttt tttttttttt tttttttttt tttttttttt tttttttttt 900
tttttttttt tttttttttt tttttttttt tttttttttt tttttttttt tttttttttt 960
tttttttttt tttttttttt tttttttttt tttttttttt tttttttttt tttttttttt 1020
tttttttttt tttttttttt tttttttttt tttttttttt tttttttttt tttttttttt 1080
tttttttttt tttttttttt tttttttttt tttttttttt tttttttttt tttttttttt 1140
tttttttttt tttttttttt tttttttttt tttttttttt tttttttttt tttttttttt 1200
tttttttttt tttttttttt tttttttttt tttttttttt tttttttttt tttttttttt 1260
tttttttttt tttttttttt tttttttttt tttttttttt tttttttttt tttttttttt 1320
tttttttttt tttttttttt tttttttttt tttttttttt tttttttttt tttttttttt 1380

-continued

```
tttttttttt tttttttttt tttttttttt tttttttttt tttttttttt tttttttttt   1440
tttttttttt tttttttttt tttttttttt tttttttttt tttttttttt tttttttttt   1500
tttttttttt tttttttttt tttttttttt tttttttttt tttttttttt tttttttttt   1560
tttttttttt tttttttttt tttttttttt tttttttttt tttttttttt tttttttttt   1620
tttttttttt tttttttttt tttttttttt tttttttttt tttttttttt tttttttttt   1680
tttttttttt tttttttttt tttttttttt tttttttttt tttttttttt tttttttttt   1740
tttttttttt tttttttttt tttttttttt tttttttttt tttttttttt tttttttttt   1800
tttttttttt tttttttttt tttttttttt tttttttttt tttttttttt tttttttttt   1860
tttttttttt tttttttttt tttttttttt tttttttttt tttttttttt tttttttttt   1920
tttttttttt tttttttttt tttttttttt tttttttttt tttttttttt tttttttttt   1980
tttttttttt tttttttttt tttttttttt tttttttttt tttttttttt tttttttttt   2040
tttttttttt tttttttttt tttttttttt tttttttttt tttttttttt tttttttttt   2100
tttttttttt tttttttttt tttttttttt tttttttttt tttttttttt tttttttttt   2160
tttttttttt tttttttttt tttttttttt tttttttttt tttttttttt tttttttttt   2220
tttttttttt tttttttttt tttttttttt tttttttttt tttttttttt tttttttttt   2280
tttttttttt tttttttttt tttttttttt tttttttttt tttttttttt tttttttttt   2340
tttttttttt tttttttttt tttttttttt tttttttttt tttttttttt tttttttttt   2400
tttttttttt tttttttttt tttttttttt tttttttttt tttttttttt tttttttttt   2460
tttttttttt tttttttttt tttttttttt tttttttttt tttttttttt tttttttttt   2520
tttttttttt tttttttttt tttttttttt tttttttttt tttttttttt tttttttttt   2580
tttttttttt tttttttttt tttttttttt tttttttttt tttttttttt tttttttttt   2640
tttttttttt tttttttttt tttttttttt tttttttttt tttttttttt tttttttttt   2700
tttttttttt tttttttttt tttttttttt tttttttttt tttttttttt tttttttttt   2760
tttttttttt tttttttttt tttttttttt tttttttttt tttttttttt tttttttttt   2820
tttttttttt tttttttttt tttttttttt tttttttttt tttttttttt tttttttttt   2880
tttttttttt tttttttttt tttttttttt tttttttttt tttttttttt tttttttttt   2940
tttttttttt tttttttttt tttttttttt tttttttttt tttttttttt tttttttttt   3000
tttttttttt tttttttttt tttttttttt tttttttttt tttttttttt tttttttttt   3060
tttttttttt tttttttttt tttttttttt tttttttttt tttttttttt tttttttttt   3120
tttttttttt tttttttttt tttttttttt tttttttttt tttttttttt tttttttttt   3180
tttttttttt tttttttttt tttttttttt tttttttttt tttttttttt tttttttttt   3240
tttttttttt tttttttttt tttttttttt tttttttttt tttttttttt tttttttttt   3300
tttttttttt tttttttttt tttttttttt tttttttttt tttttttttt tttttttttt   3360
tttttttttt tttttttttt tttttttttt tttttttttt tttttttttt tttttttttt   3420
tttttttttt tttttttttt tttttttttt tttttttttt tttttttttt tttttttttt   3480
tttttttttt tttttttttt tttttttttt tttttttttt tttttttttt tttttttttt   3540
tttttttttt tttttttttt tttttttttt tttttttttt tttttttttt tttttttttt   3600
tttttttttt tttttttttt tttttttttt tttttttttt tttttttttt tttttttttt   3660
tttttttttt tttttttttt tttttttttt tttttttttt tttttttttt tttttttttt   3720
tttttttttt tttttttttt tttttttttt tttttttttt tttttttttt tttttttttt   3780
```

tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

<210> SEQ ID NO 70
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 100-5000 nucleotides"

<400> SEQUENCE: 70
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600

```
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
```

aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 71
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 71

Gly Gly Gly Gly Ser
1               5


<210> SEQ ID NO 72
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gly Gly Gly Gly Ser Gly Gly Gly Gly Ser
1               5                   10
```